US012806632B2

(12) United States Patent
Allard et al.

(10) Patent No.: US 12,806,632 B2
(45) Date of Patent: Nov. 24, 2026

(54) PORTABLE CENTRIFUGE APPARATUS AND METHODS

(71) Applicant: ABC Med Tech Corp., Golden, CO (US)

(72) Inventors: Randall Allard, Golden, CO (US); Polly Allard, Golden, CO (US); Thomas J. Mcleer, Laguna Niguel, CA (US)

(73) Assignee: ABC Med Tech Corp., Golden, CO (US)

( * ) Notice: Subject to any disclaimer, the term of this patent is extended or adjusted under 35 U.S.C. 154(b) by 463 days.

(21) Appl. No.: 18/231,941

(22) Filed: Aug. 9, 2023

(65) Prior Publication Data

US 2023/0381792 A1 Nov. 30, 2023

Related U.S. Application Data

(63) Continuation-in-part of application No. 17/695,650, filed on Mar. 15, 2022, and a continuation of (Continued)

(51) Int. Cl.

| | |
|---|---|
| ***B04B 5/04*** | (2006.01) |
| ***A61M 1/36*** | (2006.01) |

(Continued)

(52) U.S. Cl.

CPC ......... *B04B 5/0414* (2013.01); *A61M 1/3693* (2013.01); *B01L 3/502753* (2013.01); (Continued)

(58) Field of Classification Search

CPC ........... B04B 5/0421; B04B 1/02; B04B 7/02; B04B 9/04; B04B 9/08; B04B 15/00; (Continued)

(56) References Cited

U.S. PATENT DOCUMENTS 866,844 A * 9/1907 Cottrell ................. B04B 5/0442 494/900
937,986 A * 10/1909 Carlsson ................... B04B 1/00 494/76

(Continued)

FOREIGN PATENT DOCUMENTS

CN 107824344 A 3/2018
RU 2182525 C1 5/2002

(Continued)

OTHER PUBLICATIONS

Giuseppe Marano et al., Convalescent Plasma: New Evidence for an Old Therapeutic Tool?, Blood Transfer, (2016), vol. 14, pp. 152-157.

(Continued)

*Primary Examiner* — Charles Cooley
(74) *Attorney, Agent, or Firm* — BrainSpark Associates, LLC

(57) ABSTRACT

A portable centrifuge comprising a base, which includes a rotational mechanism contained within. A sequester wheel having a plurality of concentric rings, forming at least one channel and a central container. The at least one channel comprising a second volume and the central container comprising a first volume. A first cover is disposed over the sequester wheel to create a seal. A second cover is disposed over the first cover and is rotatable to engage with the rotational mechanism to initiate rotation at a predetermined RPM. The whole blood, tissue or other cell types are separated into its constituent components and deposited into the at least one channel and the central container. Specific volumes of the constituent components, tissue and/or cell types may be calculated to match or substantially match the first and second volumes for predetermined volume control and ease of access.

20 Claims, 111 Drawing Sheets

Related U.S. Application Data application No. PCT/US2022/015937, filed on Feb. 10, 2022, said application No. 17/695,650 is a continuation of application No. PCT/US2020/050014, filed on Sep. 9, 2020, which is a continuation-in-part of application No. 16/815,430, filed on Mar. 11, 2020, now Pat. No. 11,964,092, application No. 18/231,941 is a continuation-in-part of application No. 16/815, 430, filed on Mar. 11, 2020, now Pat. No. 11,964,092.

(60) Provisional application No. 63/237,039, filed on Aug. 25, 2021, provisional application No. 63/147,908, filed on Feb. 10, 2021, provisional application No. 63/026,624, filed on May 18, 2020, provisional application No. 62/904,896, filed on Sep. 24, 2019, provisional application No. 62/816,873, filed on Mar. 11, 2019.

(51) Int. Cl.
*B01L 3/00* (2006.01)
*B04B 7/02* (2006.01)
*B04B 15/02* (2006.01)
*G01N 33/49* (2006.01)

(52) U.S. Cl.
CPC ................ *B04B 7/02* (2013.01); *B04B 15/02* (2013.01); *G01N 33/4905* (2013.01); *B01L 2200/16* (2013.01); *B01L 2300/0803* (2013.01); *B01L 2300/0832* (2013.01); *B01L 2300/1827* (2013.01); *B01L 2400/0409* (2013.01); *B04B 2005/0478* (2013.01); *B04B 2007/025* (2013.01)

(58) Field of Classification Search
CPC ....... B04B 5/0414; B04B 15/06; B04B 15/02; B04B 2005/0478; B04B 2007/025; A61M 1/3693; A61M 2202/0427; A61M 1/0272; B01F 2101/20; B01F 27/88; B01F 27/90; B01F 35/32005; A61L 2/10; A61L 2202/16; B01L 3/502; B01L 2300/0681; B01L 2300/0803; B01L 2400/0409; B01L 3/502753; B01L 2200/16; B01L 2300/0832; B01L 2300/1827; G01N 33/4905
USPC .............. 494/10, 20, 83–85, 76–78; 422/24; 210/360.1–380.3
See application file for complete search history.

(56) References Cited

U.S. PATENT DOCUMENTS 1,048,846 A * 12/1912 Mattern .................... B04B 1/20 494/52
1,126,247 A * 1/1915 Mason ...................... B04B 1/06 494/67
2,588,716 A * 3/1952 Gochenour ............... A61L 2/10 424/257.1
2,885,145 A * 5/1959 Folke ........................ B04B 5/04 D24/219
3,077,106 A 2/1963 Fink
3,707,354 A * 12/1972 Goodman ............. B04B 5/0407 435/286.7
4,030,897 A * 6/1977 Pelzer ....................... B04B 1/06 494/900
4,086,924 A 5/1978 Latham, Jr.
4,111,355 A 9/1978 Ishimaru
4,204,537 A 5/1980 Latham, Jr.
4,226,669 A * 10/1980 Vilardi ...................... B04B 7/06 200/61.7
4,228,951 A * 10/1980 Berber ...................... B04B 1/04 494/65
4,300,717 A 11/1981 Latham, Jr.
4,734,089 A 3/1988 Cullis
4,738,655 A * 4/1988 Brimhall ............... B04B 5/0414 494/84
5,242,370 A * 9/1993 Silver ..................... B04B 13/00 422/918
5,344,382 A * 9/1994 Pelzer ................ B01D 19/0052 96/216
5,368,386 A 11/1994 Murray
5,487,719 A * 1/1996 Houston ................... B04B 9/08 494/38
5,665,047 A * 9/1997 Brimhall ............... B04B 5/0414 494/37
5,924,972 A * 7/1999 Turvaville ............ B04B 5/0414 494/12
5,935,053 A * 8/1999 Strid ........................ D21D 5/00 494/77
6,361,518 B1 3/2002 Brierton et al.
7,077,799 B2 * 7/2006 Gorham .................. C02F 1/385 494/52
8,317,672 B2 11/2012 Nash et al.
8,394,006 B2 3/2013 Nash et al.
8,469,871 B2 6/2013 Nash et al.
8,556,794 B2 10/2013 Nash et al.
8,632,678 B2 * 1/2014 Carew .................... B01D 29/23 422/186
8,633,454 B2 * 1/2014 Durkin ...................... A61L 2/10 248/102
8,932,542 B2 1/2015 Schaefer et al.
8,974,362 B2 3/2015 Nash et al.
9,839,921 B2 * 12/2017 Yarina ....................... B04B 9/08
10,335,803 B2 * 7/2019 Yarina ....................... B04B 9/00
10,792,675 B2 * 10/2020 Yarina ....................... B04B 9/08
D907,796 S * 1/2021 Allard .......................... D24/219
12,558,463 B2 * 2/2026 Allard ................ A61M 1/0272
2004/0112824 A1 * 6/2004 Gorham .................. C02F 1/385 210/409
2009/0107903 A1 * 4/2009 Dassa .................. B01L 3/5021 210/206
2010/0267539 A1 * 10/2010 Emerson ............... B04B 5/0414 494/60
2012/0309636 A1 * 12/2012 Gibbons ............... B01L 3/0275 435/6.12
2013/0265417 A1 * 10/2013 Rust .................... A61M 1/3693 494/20
2014/0057770 A1 * 2/2014 Holmes ................... B04B 15/02 494/10
2015/0218506 A1 8/2015 Nash et al.
2016/0030952 A1 * 2/2016 Yarina ....................... B04B 9/02 435/5
2018/0065128 A1 * 3/2018 Yarina ................... B04B 5/0421
2019/0314829 A1 * 10/2019 Yarina ................... B04B 5/0421
2020/0289738 A1 * 9/2020 Allard ............... B01F 35/32005
2021/0316317 A1 * 10/2021 Schaff ....................... B04B 7/02
2022/0257841 A1 * 8/2022 Allard ....................... A61L 2/10
2023/0381792 A1 * 11/2023 Allard ....................... B04B 7/02

FOREIGN PATENT DOCUMENTS

RU 159947 U1 2/2016
SU 776644 A 7/1980
SU 1509114 A1 9/1989
TW 201006450 A 2/2010
WO 199848938 A1 11/1998
WO 2007076832 A1 7/2007
WO 2009037361 A1 3/2009
WO 2017062260 A2 4/2017
WO 2021/061406 A1 4/2021

OTHER PUBLICATIONS

Terumo BCT, Terumo BCT's Mirasol Shows Efficacy Against Virus Causing COVID-19 in Plasma and Platelets, Apr. 17, 2020, pp. 1-4.

(56) References Cited

OTHER PUBLICATIONS

International Search Authority—Russia, PCT International Search Report and Written Opinion for Appl. No. PCT/US2020/050014, dated Nov. 5, 2020, pp. 1-7.
Harris, Leanne F. et al., Coagulation Monitoring Devices: Past, Present, and Future at the Point of Care, Trends in Analytical Chemistry (2013) vol. 50, pp. 85-95.
Yeo, Joo Chan et al., Microfluidic Size Separation of Cells and Particles Using a Swinging Bucket Centrifuge, Biomicrofluidics (2015) doi:10.1063/1.4931953, paras. II, III, IV.
Shih Chih-Hsin et al., Prothrombin time tests on a microfluidic disc analyzer. Sensors and Actuators B: Chemical, 2012, 161, 1184-1190, abstract, pp. 1185-1187, paragraphs 2.2, 2.3, 2.5, 3.5, figure 2.
Raposio E. et al. How to isolate a ready-to-use adipose-derived stem cells pellet for clinical application. European Review for Medical and Pharmacological Sciences (2017), 21:4252-4260, fig. 1.
Pavlov Valentin N. et al. Stromal Vascular Fraction: Biology and Application Outlook. Creative Surgery and Oncology, vol. 11, No. 1, 2021 https://doi.org/10.24060/2076-3093-2021-11-1-92-99.
International Search Authority—Russia, PCT International Search Report and Written Opinion for Appl. No. PCT/US2022/015937, dated May 12, 2022, pp. 1-14.
European Patent Office, European Search Report for EP Appl. No. 20867420.0, dated Nov. 21, 2022, pp. 1-7.

* cited by examiner

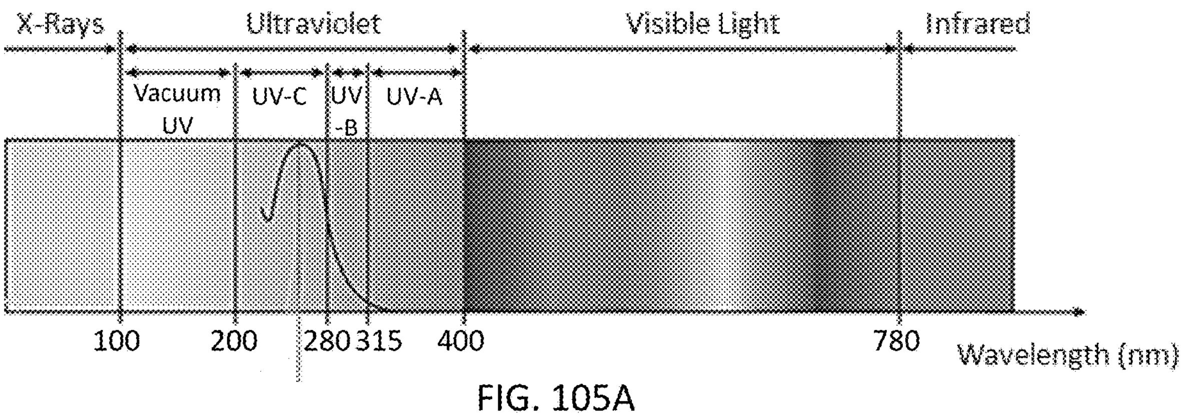

FIG. 105A

| GERMICIDAL IRRADIATION, BENEFITS AND DIFFERENCES OF ULTRAVIOLET LIGHT | | | | |
|---|---|---|---|---|
| **UV Type** | **Wavelength (nm)** | **Safe for Skin & Eyes** | **Rapid Degradation on Materials like Plastic or Rubber** | **Practical Uses** |
| VUV Far-UV | 100-200 | YES | YES | Medical Equipment |
| Far-UVC | 207-222 | YES | YES | Germicidal, Most Effective for Disinfecting, Sensing |
| UV-C | 200-280 | NO | YES | Germicidal, Most Effective for Disinfecting, Sensing |
| UV-B | 280-315 | NO | YES | Curing, Tanning, Medical Applications |
| UV-A | 315-400 | NO | NOT TYPICALLY | Curing, Printing, Lithography, Sensing, Medical Applications |

FIG. 105B

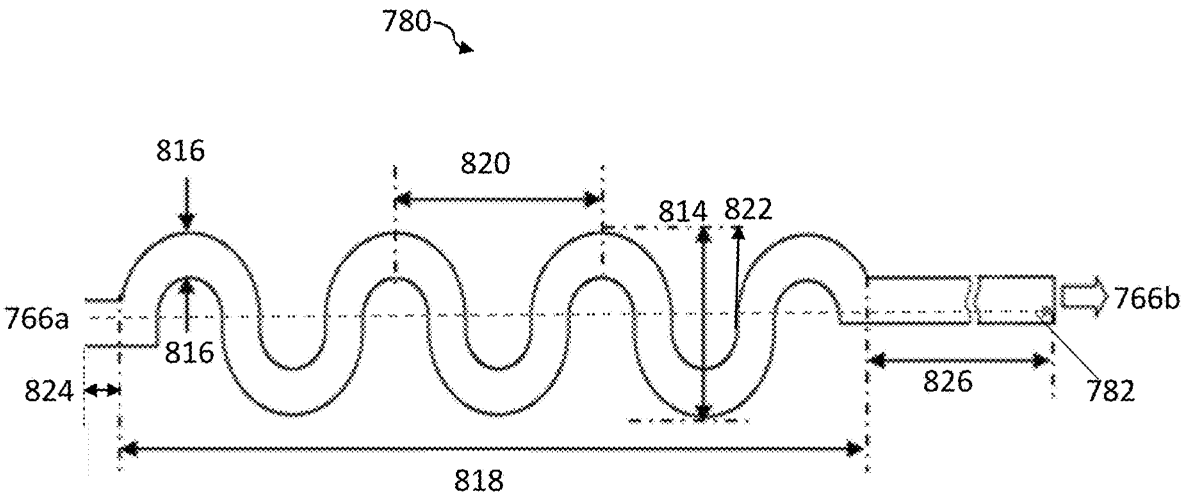
FIG. 116A
784
| RECTANGULAR SHAPE | CIRCULAR SHAPE |
|---|---|
| 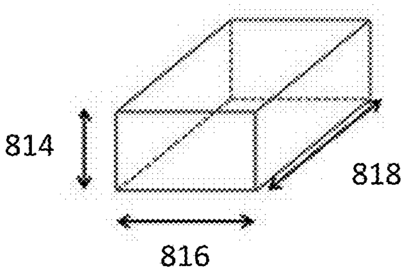  | 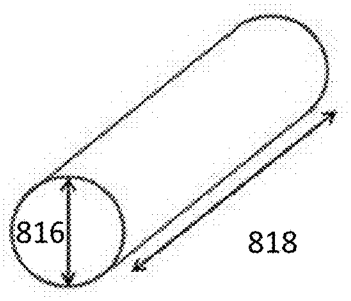  |
| L(m): length of the microchannel (L>w) | L(m): length of the microchannel (L>d) |
| H(m): height of microchannel | D(m) or W(m) : diameter of microchannel |
| W(m): width of microchannel (w>h) | Not Applicable |
| Formula: $R=12\mu L/H^2W$ | Formula: $R=128\mu L/D^4\pi$ |
FIG. 116B

PORTABLE CENTRIFUGE APPARATUS AND METHODS

CROSS-REFERENCE TO RELATED APPLICATIONS

This application is a continuation of PCT Appl. No. PCT/US22/15937, entitled "Portable Centrifuge Apparatus & Methods," filed on Feb. 10, 2022, which claims benefit to Prov. Appl. No. 63/147,908, filed on Feb. 10, 2021 entitled "Microfluidic Centrifuge Device and Method of Use", and Prov. Appl. No. 63/237,039, filed on Aug. 25, 2021, entitled "Isolation of Stem Cells Using Portable Centrifuge," which are incorporated herein by reference in their entireties.

This application is a continuation-in-part of U.S. application Ser. No. 17/695,650, entitled "Centrifuge Device and Method of Use," filed on Mar. 15, 2022, which is a continuation application of PCT Appl. No. PCT/US2020/050014, filed Sep. 9, 2020, entitled "Centrifuge Device and Method of Use," which claims priority to U.S. patent application Ser. No. 16/815,430, filed on Mar. 11, 2020, entitled "Centrifuge and Method of Use," and claims benefit to Prov. Appl. No. 62/904,896, filed on Sep. 24, 2019, entitled "Centrifuge Device and Method of Use", and Prov. Appl. No. 63/026,624, filed on May 18, 2020, entitled "Centrifuge Device and Method of Use," which are all incorporated herein by reference in their entireties.

This application is a continuation-in-part of U.S. patent application Ser. No. 16/815,430, filed on Mar. 11, 2020, entitled "Centrifuge and Method of Use," which claims benefit to Prov. Appl. No. 62/816,873, filed on Mar. 11, 2019, entitled "PRP Centrifuge and Method of Use, which are all incorporated herein by reference in their entireties.

TECHNICAL FIELD

This invention generally relates to centrifugal systems used to separate and/or isolate substances based on their density, size, viscosity, or shape for use in a variety of applications. More specifically, the invention relates to portable centrifugal systems used to separate blood into its blood components, including platelet poor plasma (PPP), platelet rich plasma (PRP) and red blood cells (RBC), as well as other different types of tissues, such as stem cells and its stem cell derivatives.

BACKGROUND INFORMATION

Currently systems used to separate blood to produce or separate into specific blood components, such as platelet poor plasma (PPP), platelet rich plasma (PRP) and red blood cells (RBC) commonly involve a centrifuge. Traditional blood separation centrifuges are based on three basic rotor designs: 1) the swinging bucket centrifuge; 2) the fixed angle centrifuge; and 3) the vertical tube centrifuge, where blood is injected into test tubes and spun within a chamber to induce a stacked or "cake-tier" separations.

Problems exist with current commercially available or traditional centrifuges. First, the conventional centrifuges are difficult to sterilize with the electrical components, in particular circuitry and power components and prevent them from being used in-situ in sterile environments requiring pre-processing or post-processing of a patient's blood. Secondly, cell damage may occur due to excessive steps with handling of the blood. Thirdly, extraction of blood components after centrifugation becomes exceedingly difficult and requires skilled personnel. The centrifugation process positions the blood components within the test tube in a stacked or layered configuration and requires specialized tools to properly extract the blood components without cross-contamination. Finally, the separation of the blood components usually results in at least 3 specific stacked layers of PPP, PRP, and RBCs, and if optimization of the concentrations of these blood components are desired, it requires multiple centrifugation cycles and excessive time to acquire the ideal concentration of each blood component.

SUMMARY OF THE INVENTION

Thus, a need exists for a blood separation system and process that (1) can be used in a sterile and/or non-sterile environment; (2) minimizes the number of handling and processing steps; (3) greatly simplifies the extraction of the blood components; and (4) allows automatic separation of different concentrations of PRP, tissue and/or stem cells with a single centrifugation cycle and/or reduced centrifuge cycles.

The present disclosure is directed towards instruments, systems, and related methods for apheresis. The instruments, systems, and related methods may facilitate blood separation, bone marrow separation, or tissue separation while minimizing handling and exposure to non-sterile environments. The instrument, systems, and related methods include a portable centrifuge system with a self-contained power source.

In one aspect, a centrifuge is provided, having a base container having a rotational mechanism contained within. Included is a centrifuge container having a bottom plate and a top plate joined by a circumferential sidewall, and with a coiled spring connected to the bottom plate. The centrifuge further includes a sequester wheel having a plurality of concentric rings, forming at least one channel, connected to a hub. The sequester wheel is engaged with the bottom plate, the coiled spring positioned therebetween, with the hub centered with the bottom plate and the top plate within the centrifuge container, defining an axis. The sequester wheel engagement may comprise a permanent fixation (not removable) or temporary fixation (removably connected or engaged). The centrifuge container is engaged with the rotational mechanism and rotatable about the axis.

In another aspect, a centrifuge is provided having, a base container having a rotational mechanism contained within. The centrifuge may further comprise a sequester device having a first center, a circumferential outer ring concentric with a plurality of inner tiered concentric rings forming at least one channel, and a container. The sequester device is engaged with the base container defining an axis. The sequester device engagement may comprise a permanent fixation (not removable) or temporary fixation (removably connected or engaged). The centrifuge further includes a centrifuge cover having a top side with a second center and a circumferential sidewall. The centrifuge cover is connected to the sequester device and forming a cylindrical container having an internal space with an outer channel, with the cylindrical container coupled to the rotational mechanism and rotatable about an axis defined by the first center and the second center. Furthermore, the base container further comprises at least one light, an activation switch, and/or any combination thereof.

In yet another aspect, a centrifuge is provided having a base container having a rotational mechanism contained within. Also included is at lease on cap having a cylindrically shaped container having a top side with a first center, a bottom side with a second center, a sidewall, and an interior having an anti-coagulant and a thixotropic separation gel within, where the cylindrical container is coupled to the rotational mechanism and is rotatable about an axis defined by the first center and the second center.

In still another aspect, a centrifuge is provided having a base container having a rotational mechanism connected to an activation switch. Included is a cap assembly having a cap at a first end of an articulated arm, an activation tab at a second end, and an activation handle protruding from the articulated arm. The centrifuge further includes an activation armature, a conical first member positioned within a conical second member having a plurality of openings and positioned within a conical third member, and a base ring. The first member engages the base ring and the base container, the activation armature extends from the base ring to the activation switch within the base container. The second member engages the rotation mechanism above the first member and the third member is positioned above the second member to engage the first member, the second member being rotatable between the first member and the second member. The cap engages the third member, and the activation tab engages the activation armature, providing a connection between the activation handle and the activation switch for activation of the rotational mechanism.

In another embodiment, the portable centrifuge comprising a base, a sequester device, a container cover, at least one light, and a protective cover. The base comprising a rotational mechanism; the sequester device being disposed onto the base, the sequester device including a plurality of concentric rings that are spaced apart to form at least one channel and a central container; the container cover including at least one injection tube and at least one extraction region, the at least one extraction region including a plurality of extraction holes, the container cover being disposed over a portion of the sequester device; and a protective cover, the protective being disposed over the container cover. The at least one light may comprise a UV light. The UV light includes a wavelength emission within the UV-C wavelength range. At least a portion of the sequester device, at least a portion of the plurality of concentric rings, and/or at least a portion of the central container comprising a coating. The coating is selected from a group consisting of anticoagulants, preservatives, germicidal agents, sterilants, antiseptics, clot activators, separator gels. The germicidal agents comprise amotosalen or riboflavin. The UV-C wavelength range comprises a range of 200 to 280 nanometers.

In another embodiment, the portable centrifuge comprising a base, a sequester device, a container cover and a protective cover. The base comprising a rotational mechanism, a first light and a second light; the sequester device being disposed onto the base, the sequester device including a plurality of concentric rings that are spaced apart to form at least one channel and a central container; the container cover including at least one injection tube and at least one extraction region, the at least one extraction region including a plurality of extraction holes, the container cover being disposed over a portion of the sequester device; and a protective cover, the protective being disposed over the container cover. The first light or the second light may comprise a UV-A light. The UV light includes a wavelength emission with the UV-A wavelength range. At least a portion of the sequester device, at least a portion of the plurality of concentric rings, and/or at least a portion of the central container comprising a coating. The coating comprises a germicidal agent, the germicidal agent comprises amotosalen or riboflavin. The UV-A wavelength range comprises a range of 315 to 400 nanometers.

In another embodiment, a microfluidic portable centrifuge comprising a base, a sequester device, a container cover, a protective cover, and at least one coagulation module; the base comprising a rotational mechanism, the sequester device being disposed onto the base, the sequester device including a plurality of concentric rings that are spaced apart to form at least one channel and a central container. The container cover including at least one injection tube, at least one extraction region, the at least one extraction region including a plurality of extraction holes. The at least one coagulation module disposed onto the container cover, the at least one coagulation module comprising a top surface, a bottom surface, and a microfluidic mechanism, the microfluidic mechanism disposed between the top surface and the bottom surface, the bottom surface including a blood communication port, the container cover being disposed over a portion of the sequester device; and a protective cover, the protective being disposed over the container cover. The microfluidic mechanism comprises at least one serpentine microchannel or the microfluidic mechanism comprises a plurality of serpentine microchannels. The microfluidic mechanism comprises at least one serpentine microchannel and a metering mechanism. The microfluidic portable centrifuge further comprises a first light and a second light, the first light or second light comprises a UV light, the UV light comprises a wavelength emission within the UV-C wavelength range for a germicidal effect. The at least one serpentine microchannel comprises a coating.

In yet another aspect, a method is provided including removing a protective cover from a centrifuge, introducing blood into a centrifuge container, replacing the protective cover of the centrifuge, turning the protective cover to activate the centrifuge, separating the blood into constituent components by rotation of the centrifuge, removing the protective cover from the centrifuge, and removing the blood constituent components.

In another embodiment, a microfluidic coagulation centrifuge comprising: a centrifuge, the centrifuge comprises a longitudinal axis, the centrifuge adapted to receive a fluid; and at least one coagulation module, the at least one coagulation module disposed onto the centrifuge, the coagulation module comprising a fluid chamber, an inlet and an outlet, the inlet and outlet are in fluid communication with the fluid chamber, fluid being in fluid communication with the inlet of the coagulation module to allow the fluid to flow through the fluid chamber towards the outlet at a set time to measure a coagulation potential. The fluid chamber comprises a serpentine shape. The inlet is adjacent to the longitudinal axis and the outlet is away from the longitudinal axis. The at least one coagulation module comprises clotting indicators. The centrifuge is rotatable about the longitudinal axis to create a pressure differential. The flow of the fluid is directed by the pressure differential. The flow of the fluid that is directed by the pressure differential flows toward the longitudinal axis. The fluid is blood. The fluid chamber is planar. The at least coagulation module comprises a translucent material.

In another embodiment, the microfluidic coagulation centrifuge comprising: a centrifuge, the centrifuge comprising a longitudinal axis, the centrifuge is adapted to receive a fluid, centrifuge is rotatable about the central axis forcing the fluid to be movable from a first radial distance with a first centrifugal force to a second radial distance with a second centrifugal force to create a pressure differential therebetween and a first fluid flow direction; at least one coagulation module, the at least one coagulation module disposed onto the centrifuge, the coagulation module comprising a fluid chamber, an inlet and an outlet, the inlet and outlet are in fluid communication with the fluid chamber, the movable fluid being directed to the inlet through the fluid chamber towards the outlet in a second flow direction by the pressure differential of the centrifuge to measure a coagulation potential at a set time. The fluid chamber comprises a serpentine shape. The second centrifugal force is higher than the first centrifugal force. The inlet is adjacent to or within the second radial distance. The inlet and the outlet comprise an axially alignment. The at least one coagulation module comprises clotting indicators. The second fluid flow direction is towards the longitudinal axis of the centrifuge. The first fluid flow direction is opposite to the second fluid flow direction. The fluid chamber is planar. The at least coagulation module comprises a translucent material. The centrifuge further comprises a sequester wheel, the sequester wheel comprises a first ring that defines the inner container, and a second ring, the second ring is concentric with the first ring, the second ring is spaced apart from the first ring to create a channel.

In another embodiment, the portable centrifuge comprises: a base, the base comprises a rotational mechanism and a longitudinal axis; a sequester wheel, the sequester wheel disposed onto the base, the sequester wheel comprising a first ring, a second ring, a third ring, a first channel and a second channel, each of the first, second and third rings are concentric to each other, the first channel is disposed between a first ring and a second ring, the second channel is disposed between a second ring and a third ring, the first ring forms the inner container; a heating mechanism; one or more disaggregation elements; and a cover, the cover comprising an injection port, and at least one extraction region, the at least extraction region including one or more extraction openings, the one or more extraction openings are aligned with each of the first and second channels, the cover disposed over the sequester wheel. The heating mechanism comprises an electrical heater or a chemical heater. The heating mechanism is disposed onto the base or the sequester wheel. The first ring or second ring comprises a filtration ring, the filtration ring includes a filtration mesh size of at least 40 micrometers or greater. The one or more disaggregation elements disposed onto the third ring, the one or more disaggregation elements includes a plurality of facets that disaggregates different medium types. The cover further comprises at least one blister module, the at least one blister module comprises a chamber, a frangible base and a reagent, the chamber is movable from a first position that is uncompressed with the chamber filled with the at least one reagent to a second position that is compressed breaking the frangible base to dispense the at least one reagent into the sequester wheel. The at least one blister modules are removably connected to the cover. The portable centrifuge further comprises a filtration mechanism, the filtration mechanism coupled to the injection port of the cover, the filtration mechanism includes a filtration mesh size of at least 40 micrometer or greater. The inner container of the sequester wheel comprises a reagent, the reagent includes a separation gel. The first or second channel comprises a reagent, the reagent includes a separation gel.

In a further aspect, a method is provided including removing a protective cover, introducing blood into a centrifuge container, replacing the protective cover, turning the protective cover to activate the centrifuge, having the blood interact with a thixotropic separation gel and an anti-coagulant, separating the blood into constituent components by activation of the centrifuge, removing the protective cover, and removing the blood constituent components.

In another aspect, a method is provided including removing a protective cover from a centrifuge, introducing blood into a centrifuge container, replacing the protective cover on the centrifuge, turning the protective cover to activate the centrifuge, separating the blood into constituent components, removing the protective cover, and removing the blood constituent components.

In a yet another aspect, a method is provided including removing a cap assembly, introducing blood into test-tubes, replacing the cap assembly, pressing the activation handle to activate the centrifuge, separating the blood into constituent components by activation of the centrifuge, removing the cap assembly, and removing blood constituent components from the test-tubes.

These, and other objects, features and advantages of this invention will become apparent from the following detailed description of the various aspects of the invention taken in conjunction with the accompanying drawings.

BRIEF DESCRIPTION OF THE DRAWINGS

The present invention will be understood more fully from the detailed description given hereinafter and from the accompanying drawings of certain embodiment of the present invention, which, however, should not be taken to limit the invention, but are for explanation and understanding only.

FIGS. 102A-1021 depicts various views of an alternate embodiment of a sequester device;

FIGS. 105A-105B illustrates tables that describes using UV light wavelengths as a germicidal agent;

FIGS. 116A-116B depict one embodiment of design factors for a microfluidic mechanism;

FIGS. 117A-117B depict different embodiments of the different operations of a microfluidic mechanism;

FIG. 118 depicts a cross-sectional view of one embodiment of a portable centrifuge comprising a disaggregation mechanism;

FIGS. 119A-119C depict isometric views of different embodiments of disaggregation mechanism central element;

FIGS. 120A-120C depict different views of different embodiments of a nano-fat emulsifier disaggregation mechanism;

FIGS. 121A-121B depict one embodiment of a portable centrifuge comprising a blister module;

FIG. 121C depicts a cross-sectional view of a blister module being movable from a first position to a second position for dispensing;

FIG. 122A-122E depict an isometric and top view of a sequester device comprising one or more filtration rings;

FIG. 123 depicts n isometric top view of one embodiment of a portable centrifuge comprising separation gel;

FIGS. 124A-124E depict isometric views of different embodiments of incubators;

FIGS. 125A-125B illustrate different methods of enzymatic isolation of MSCs from adipose tissue;

FIGS. 126A-126B illustrate different methods of non-enzymatic isolation of MSCs from adipose tissue; and FIGS. 127A-17B illustrate different methods of MNC isolation from bone marrow.

DETAILED DESCRIPTION OF THE INVENTION

Figure 1:
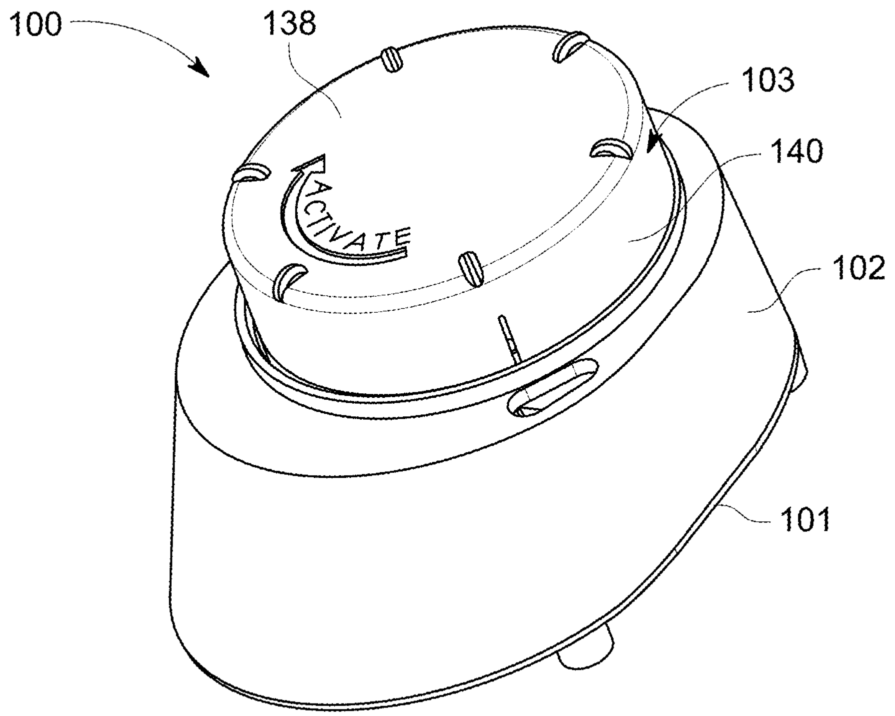
FIG. 1 is a top perspective view of a centrifuge.
Figure 2:
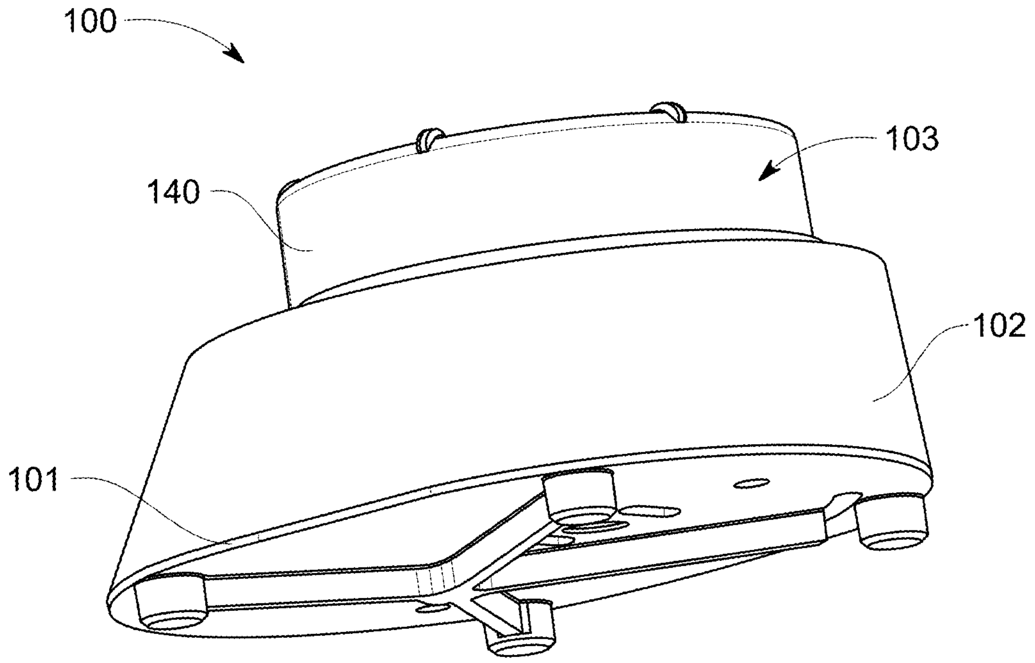
FIG. 2 is a bottom perspective view of the centrifuge of FIG. 1.
Figure 4:
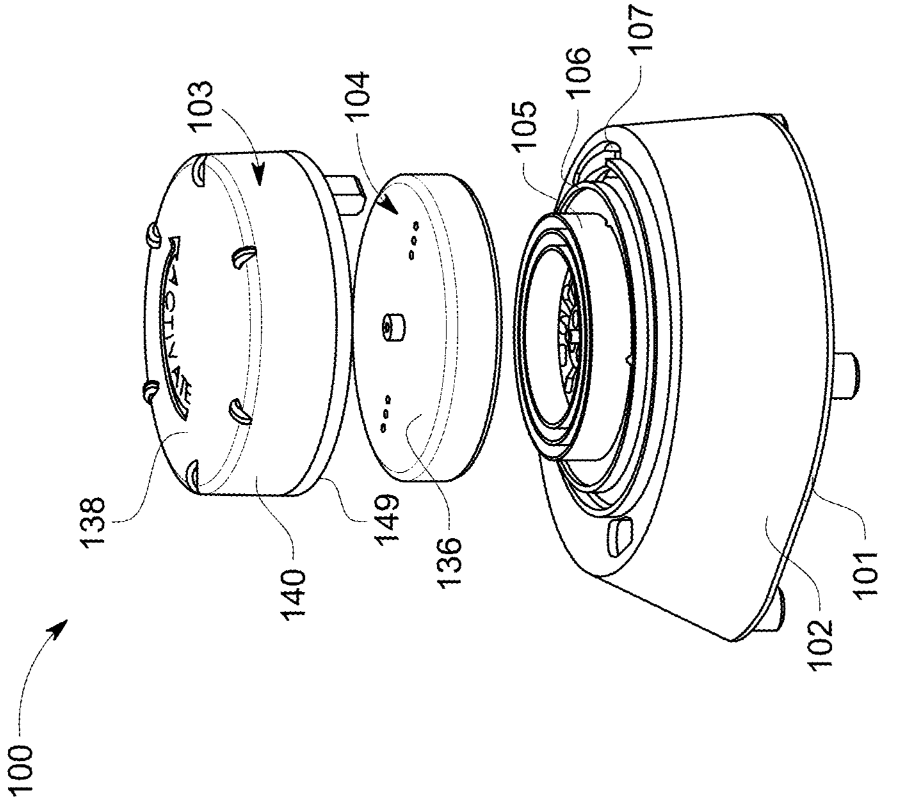
FIG. 4 is another top perspective exploded view of the centrifuge of FIG. 1.
Figure 3:
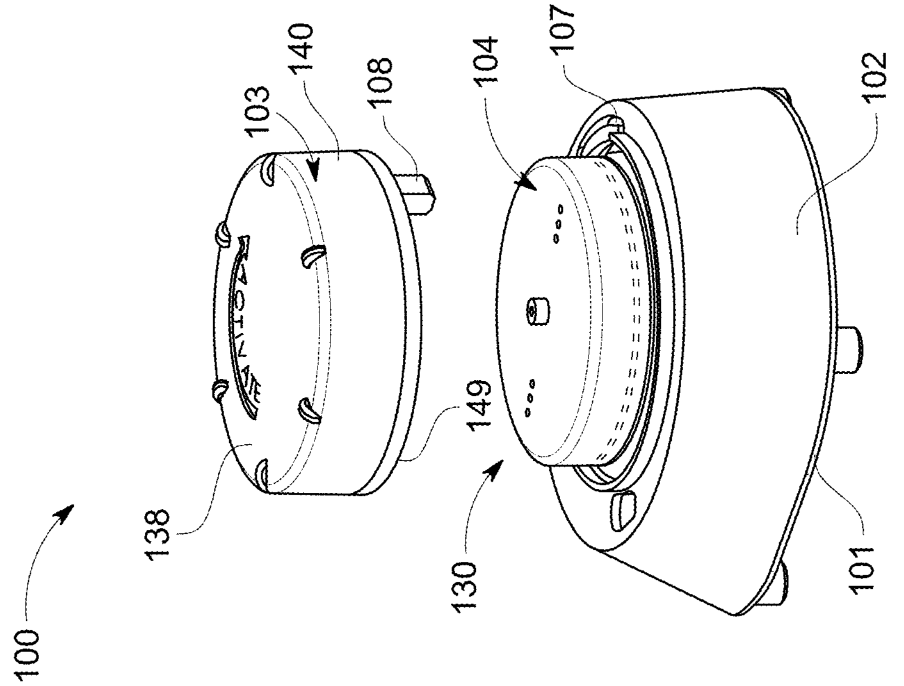
FIG. 3 is a top perspective exploded view of the centrifuge of FIG. 1.
Figure 6:
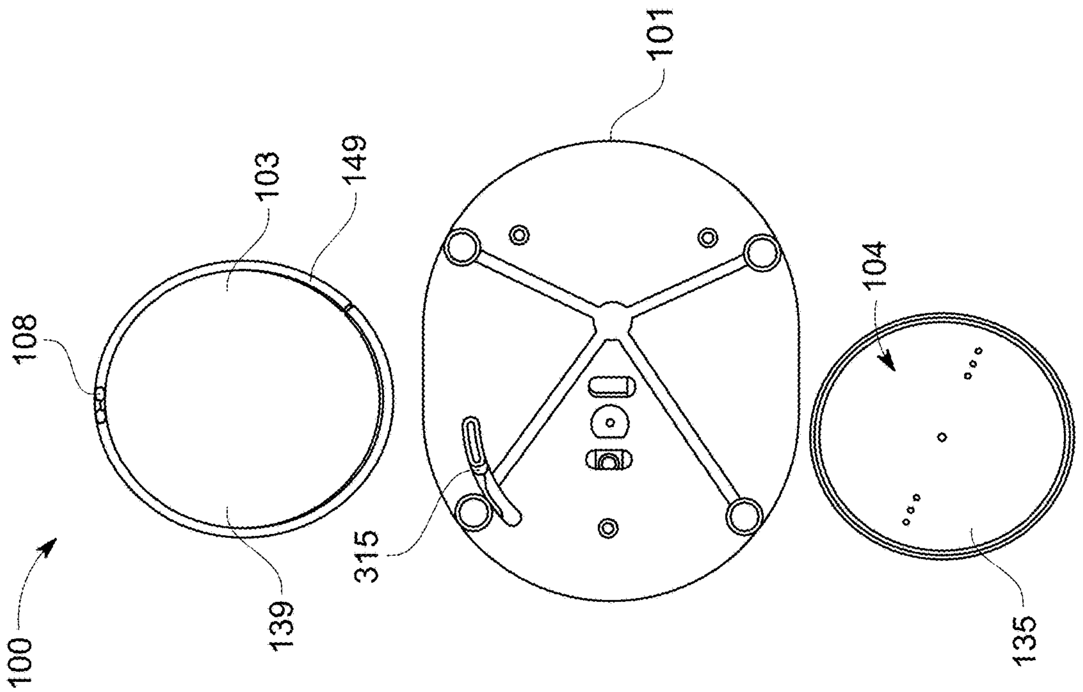
FIG. 6 is an exploded bottom view of the centrifuge of FIG. 1, the protective cover, and the centrifuge cover.
Figure 5:
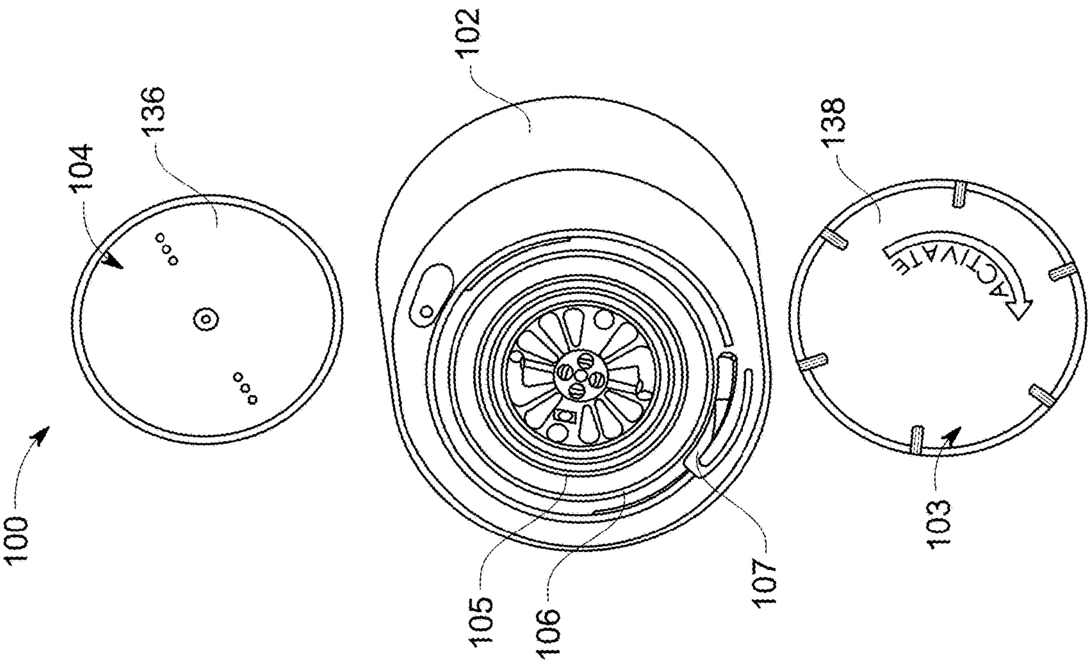
FIG. 5 is an exploded top view of the centrifuge of FIG. 1, a protective cover, and a centrifuge cover.
Figure 8:
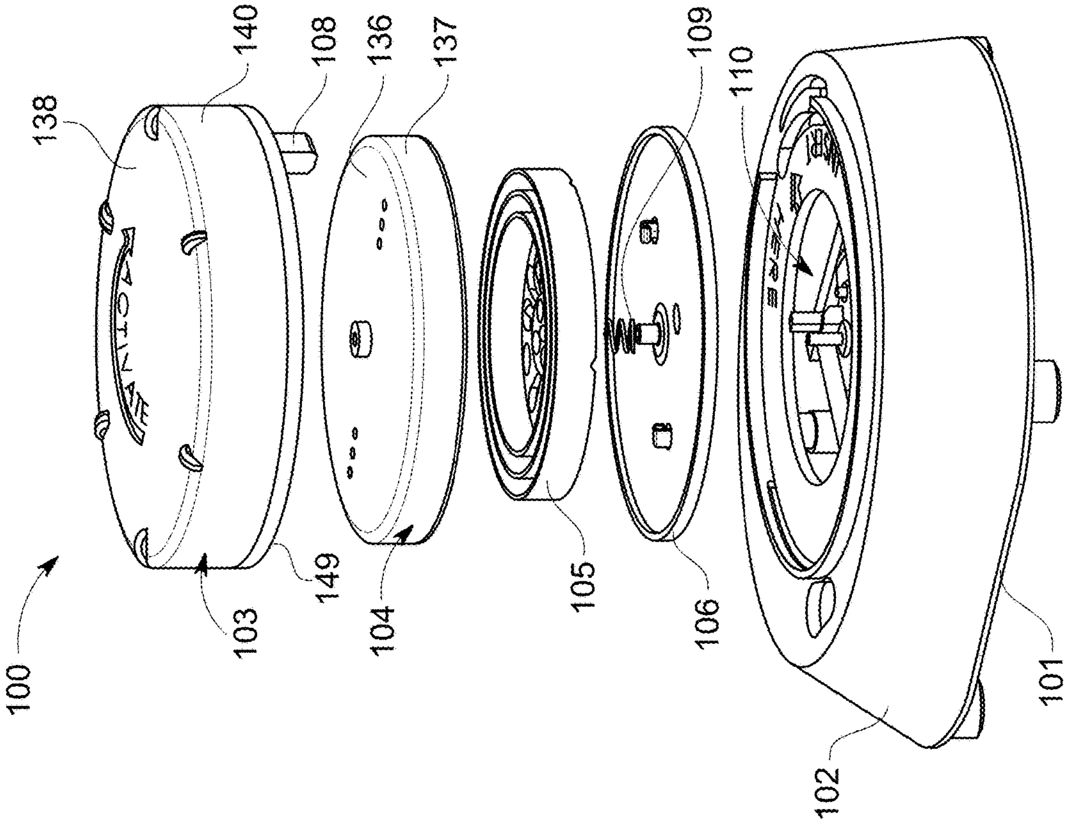
FIG. 8 is a side exploded perspective view of the centrifuge of FIG. 1.
Figure 7:
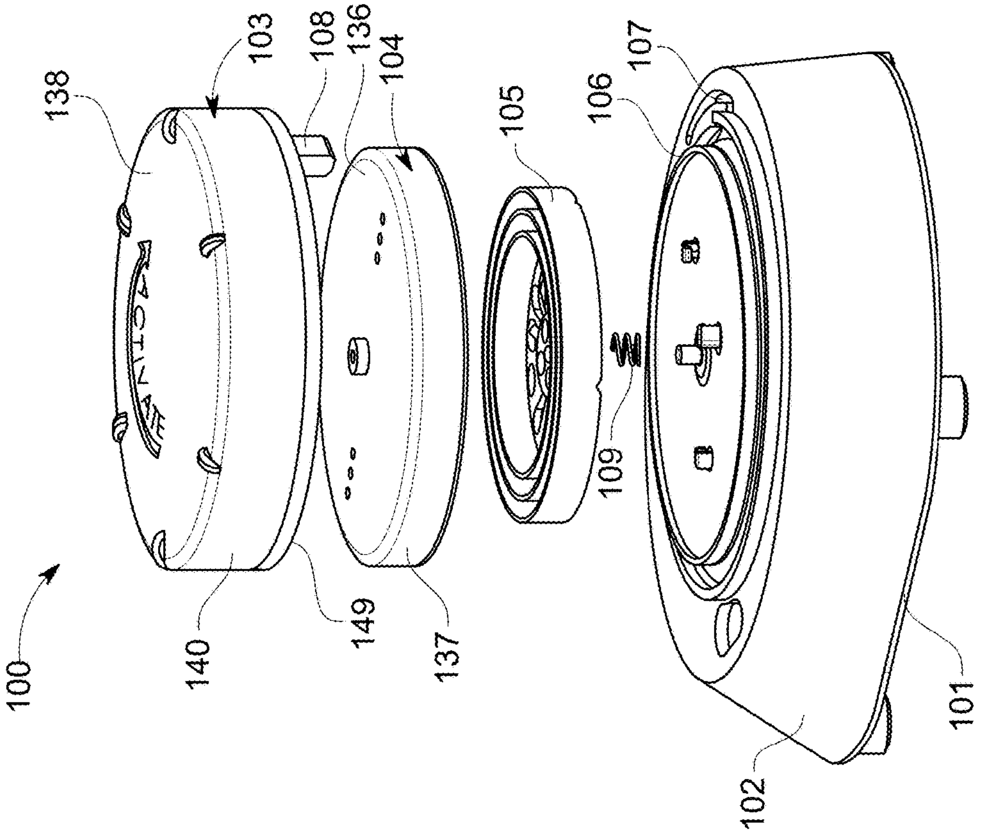
FIG. 7 is a side exploded perspective view of the centrifuge of FIG. 1.
Figure 9:
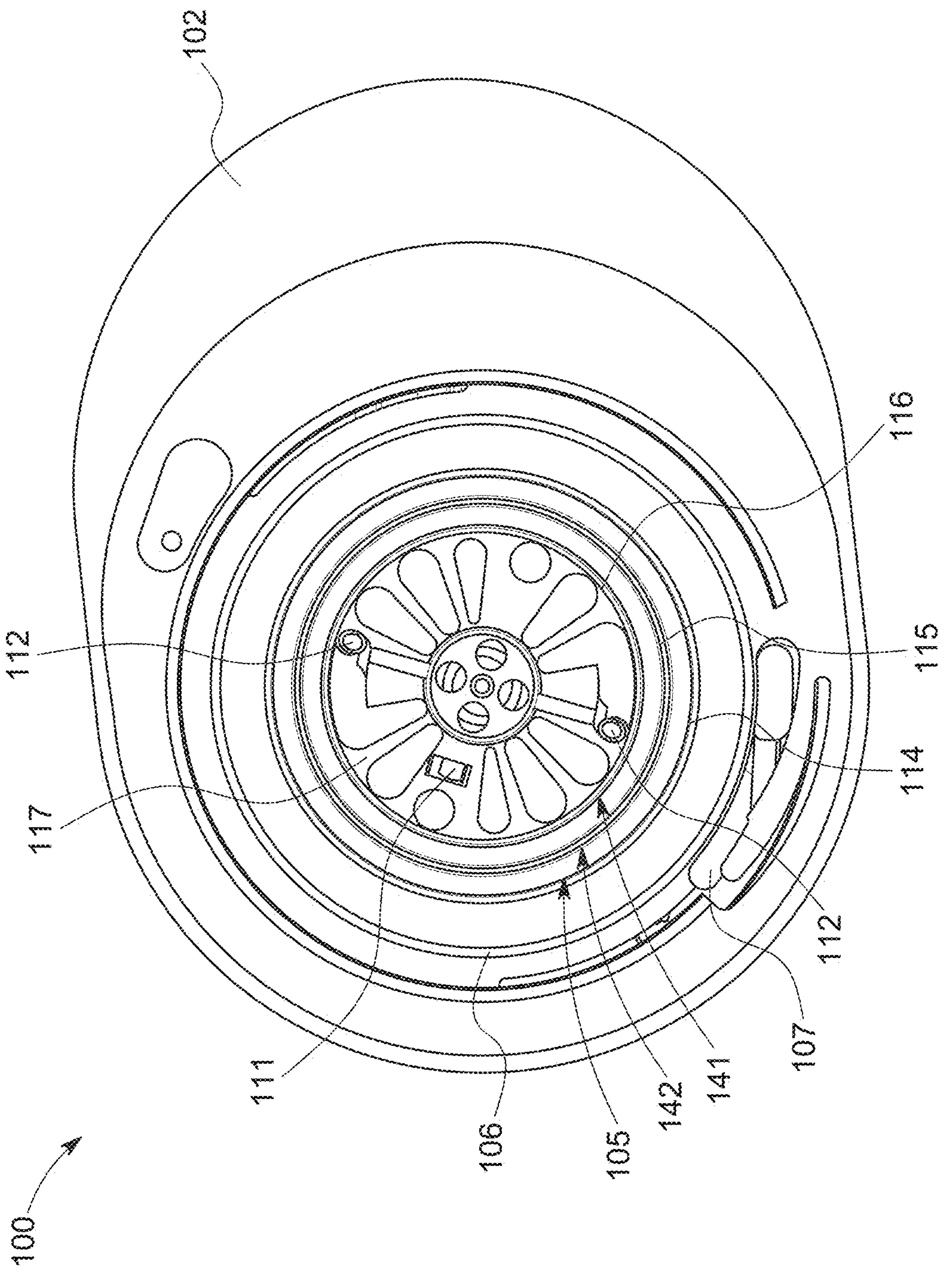
FIG. 9 is a top view of the centrifuge of FIG. 1 without a protective cover and centrifuge cover.
Figure 10:
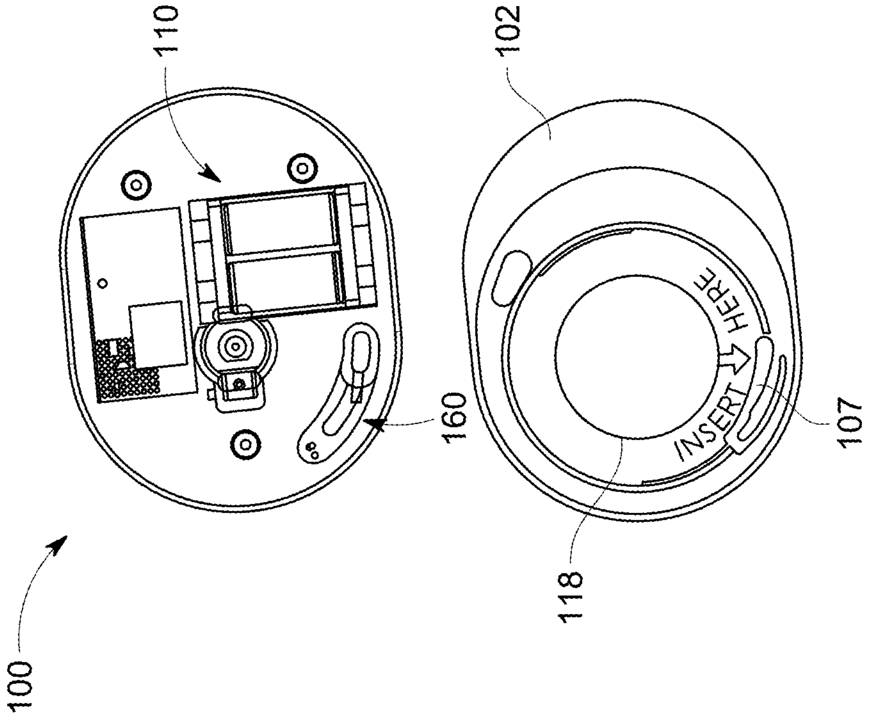
FIG. 10 is a top view of a centrifuge motor and a base cover of the centrifuge of FIG. 1.
Figure 11:
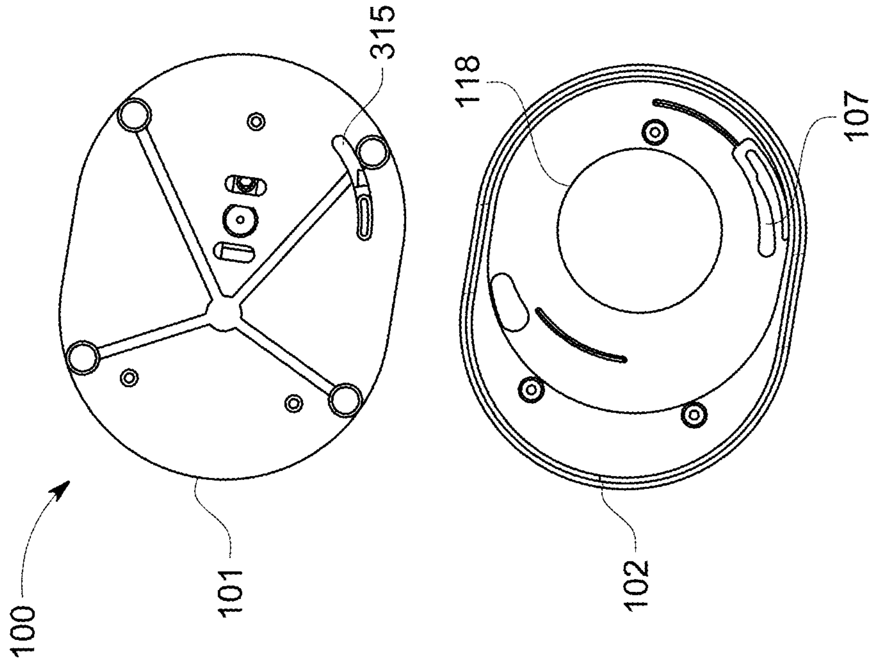
FIG. 11 is a bottom view of a base and the base cover of the centrifuge of FIG. 1.
Figure 12:
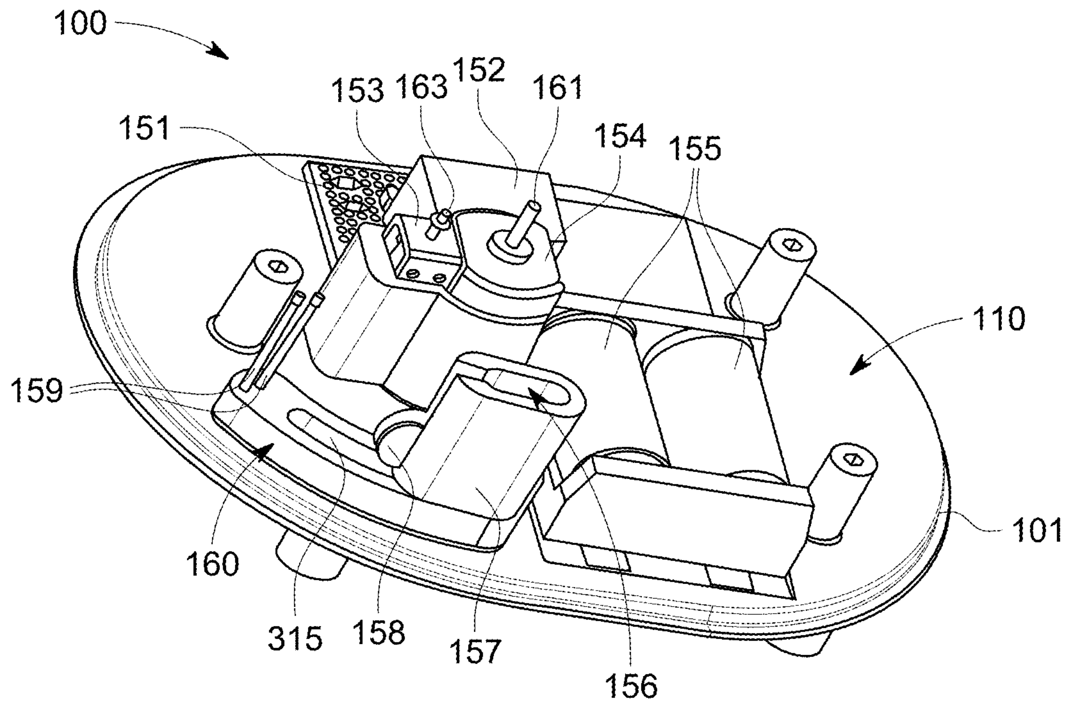
FIG. 12 is a top perspective view of the centrifuge motor of the centrifuge of FIG. 1.
Figure 13:
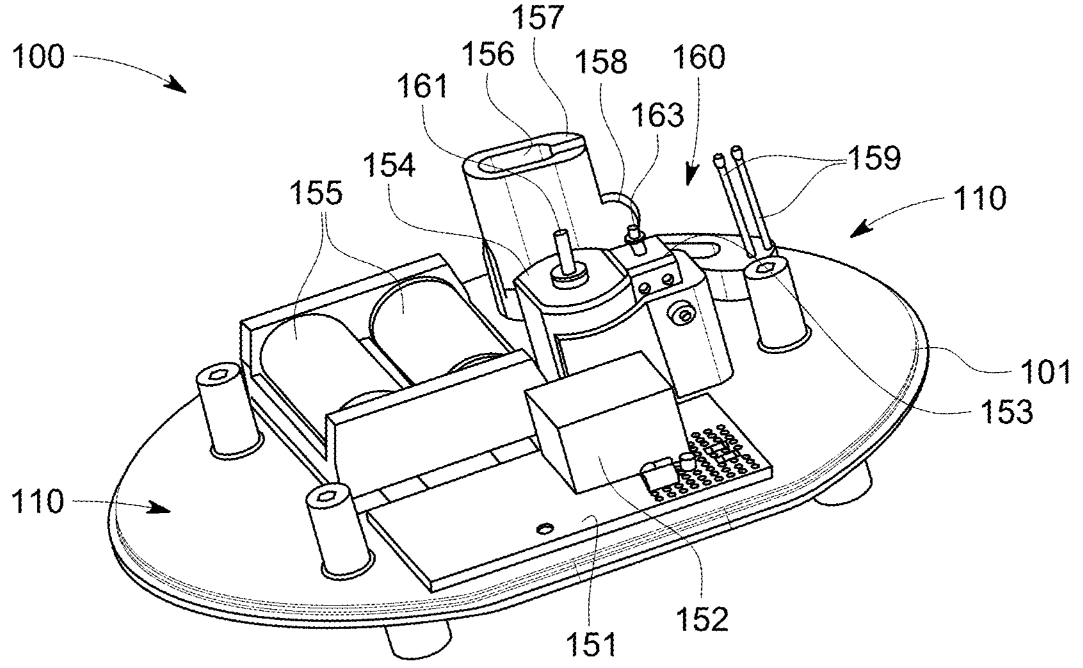
FIG. 13 is a top perspective view of the centrifuge motor of the centrifuge of FIG. 1.
Figure 14:
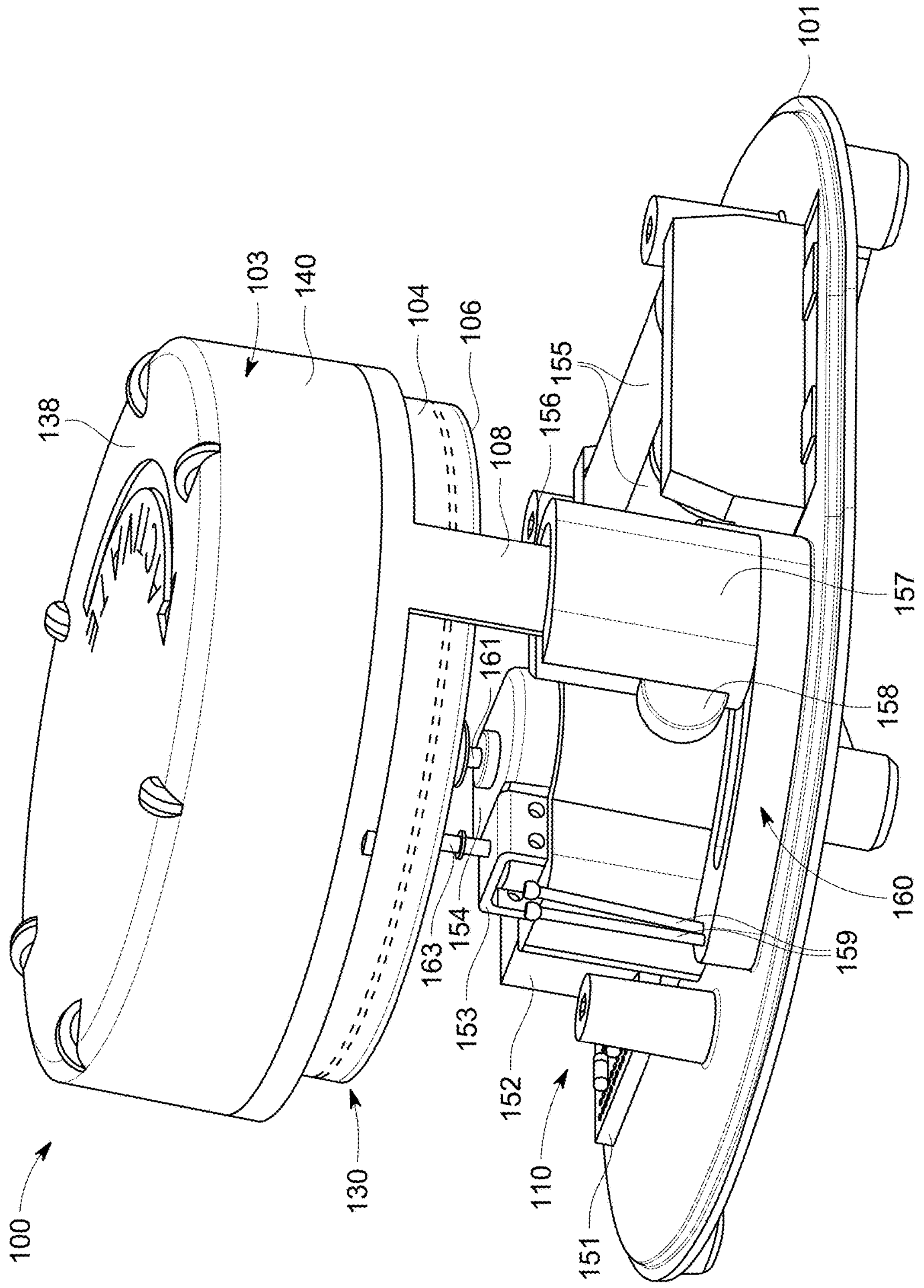
FIG. 14 is a side perspective view of the centrifuge of FIG. 1 without a base cover.
Figure 15:
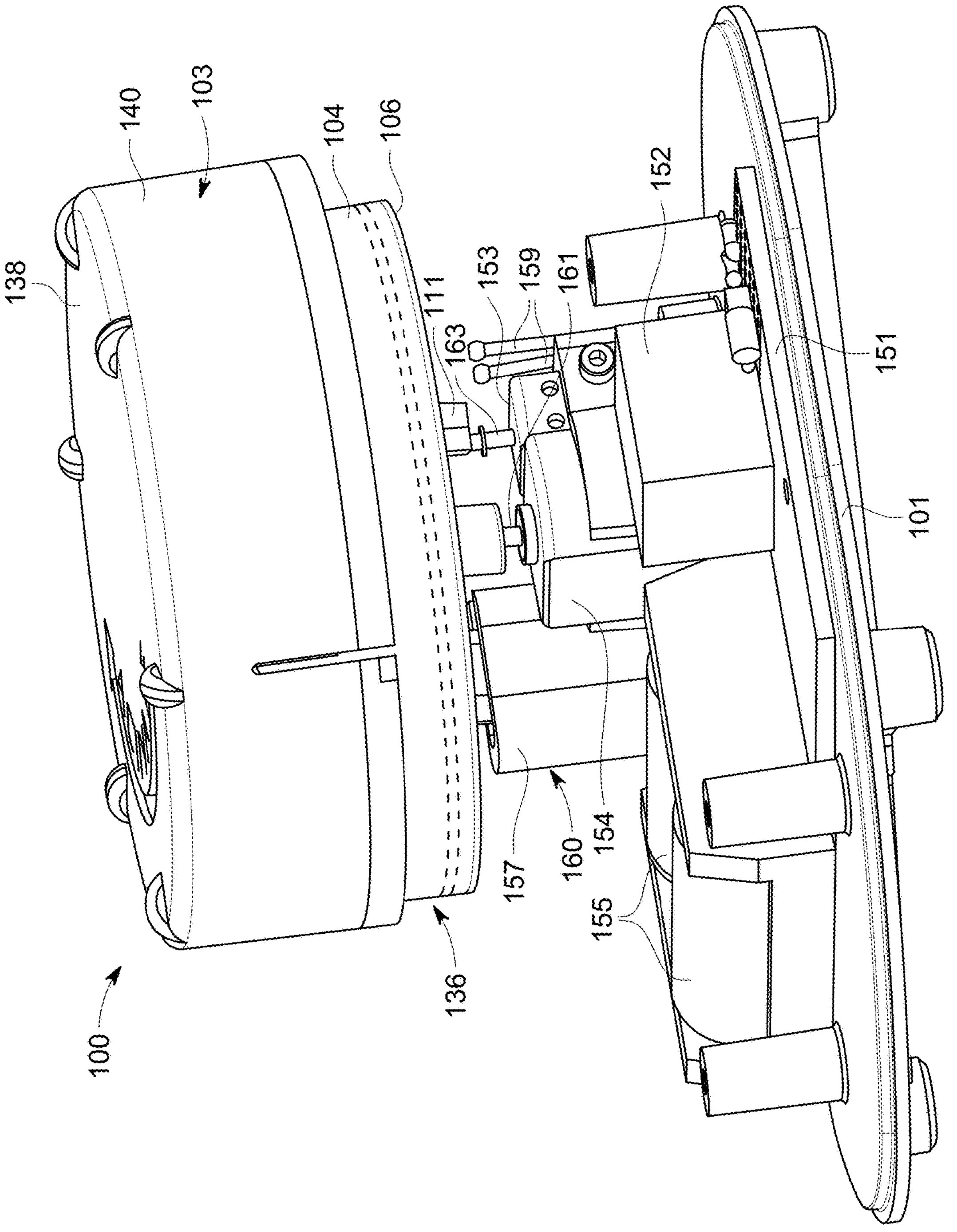
FIG. 15 is a side perspective cut-away view of the centrifuge of FIG. 1.

There is no intention to be bound by any expressed or implied theory presented in the preceding technical field, background, brief summary, or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The following description references systems, methods, and apparatuses for a cordless centrifugal device, or one with an internal power source, for separating blood (e.g. venous blood) into mesenchymal stem cells (MSCs), blood plasma, platelet rich plasma (PRP), platelet poor plasma (PPP), and/or red blood cells (RBC). Other aspects of the invention include systems, method, and apparatuses for a centrifugal device with an internal power source for separating bone marrow into bone marrow aspirate concentrate (BMAC), separating stem cells and/or mononuclear cells, stromal vascular fraction and other components, hemopoetic cells from tissue (e.g. adipose 'fat' tissue, periosteum, muscles, synovial membrane, skin, bone or trabecular bone, etc.), bone marrow, and whole blood. Still other aspects of the invention include systems, methods, and apparatuses for a centrifugal device for use with animal blood, bone marrow, and tissue. The following description also references systems, methods, and apparatuses for a centrifugal device with an internal power source for blood, bone marrow, or tissue preparation without having to leave the surgical environment. However, those possessing an ordinary level of skill in the relevant art will appreciate that other fluids, mixtures, slurries, tissue preparations, and liquids are suitable for use with the foregoing systems, methods, and apparatuses. Furthermore, those possessing an ordinary level of skill in the relevant art will appreciate that this device may be used outside the surgical environment, in sterile and non-sterile environments, and in veterinary surgical environments. Likewise, the various figures, steps, procedures, and workflows are presented only as an example and in no way limit the systems, methods or apparatuses described to perform their respective tasks and/or outcomes in different timeframes or orders. The teachings of the present invention may be applied to medical processes for viruses, cell cultures, proteins, nucleic acids, and polymers, and may be implemented in other processes that have similar separation considerations.

Aspects of the present disclosure and certain embodiment, features, advantages, and details thereof, are explained more fully below with reference to the non-limiting examples illustrated in the accompanying drawings. Descriptions of well-known materials, fabrication tools, processing techniques, etc., are omitted so as not to unnecessarily obscure the relevant details. It should be understood, however, that the detailed description and the specific examples, while indicating aspects of the disclosure, are given by way of illustration only, and are not by way of limitation. Various substitutions, modifications, additions, and/or arrangements, within the spirit and/or scope of the underlying inventive concepts will be apparent to those skilled in the art from this disclosure.

Approximating language, as used herein throughout disclosure, may be applied to modify any quantitative representation that could permissibly vary without resulting in a change in the basic function to which it is related. Accordingly, a value modified by a term or terms, such as "about" or "substantially," is not limited to the precise value specified. In some instances, the approximating language may correspond to the precision of an instrument for measuring the value.

Terminology used herein is for the purpose of describing particular examples only and is not intended to be limiting. As used herein, the singular forms "a", "an" and "the" are intended to include the plural forms as well, unless the context clearly indicates otherwise. Furthermore, references to "one embodiment" are not intended to be interpreted as excluding the existence of additional embodiments that also incorporate the recited features. Moreover, unless explicitly stated to the contrary, the terms "comprising" (and any form of "comprise," such as "comprises" and "comprising"), "have" (and any form of "have," such as "has" and "having"), "include" (and any form of "include," such as "includes" and "including"), and "contain" (and any form of "contain," such as "contains" and "containing") are used as open-ended linking verbs. As a result, any embodiments that "comprises," "has," "includes" or "contains" one or more step or element possesses such one or more step or element, but is not limited to possessing only such one or more step or element. As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable. For example, in some circumstances, an event or capacity can be expected, while in other circumstances the event or capacity cannot occur—this distinction is captured by the terms "may" and "may be."

As used herein, the term "portion" is not limited to a single continuous body of material unless otherwise noted. A "portion" may include multiple sub-portions that may be the same or differing materials, and/or may include coatings, adhesives, and the like, and may be a separate and distinct component or may be an integral section, segment, or fragment of a larger component. As used herein, the term "coupled" is not limited to a direct coupling of two separate and distinct components. Two "coupled portions" may include indirectly coupled portions or directly coupled portions.

The systems, methods, and apparatus described are directed to a cordless and/or portable centrifugal device for use in a sterile and/or a non-sterile environment. The cordless and/or portable centrifugal device overcomes many of the disadvantages of the conventional centrifugal machines. The portable centrifuge (1) can be used in a sterile and/or non-sterile environment; (2) minimizes the number of handling and processing steps; (3) eliminates the need for test tubes and thus eliminates spills or breakage within the portable centrifuge; (4) greatly simplifies the extraction of the blood components; and (5) reduces or eliminates the need to balance the portable centrifuge with a "dummy" test tube(s); (6) allows automatic separation of different concentrations of PRP with a single centrifugation cycle; (7) fewer moving parts and fewer mechanical failures.

Figure 104A:
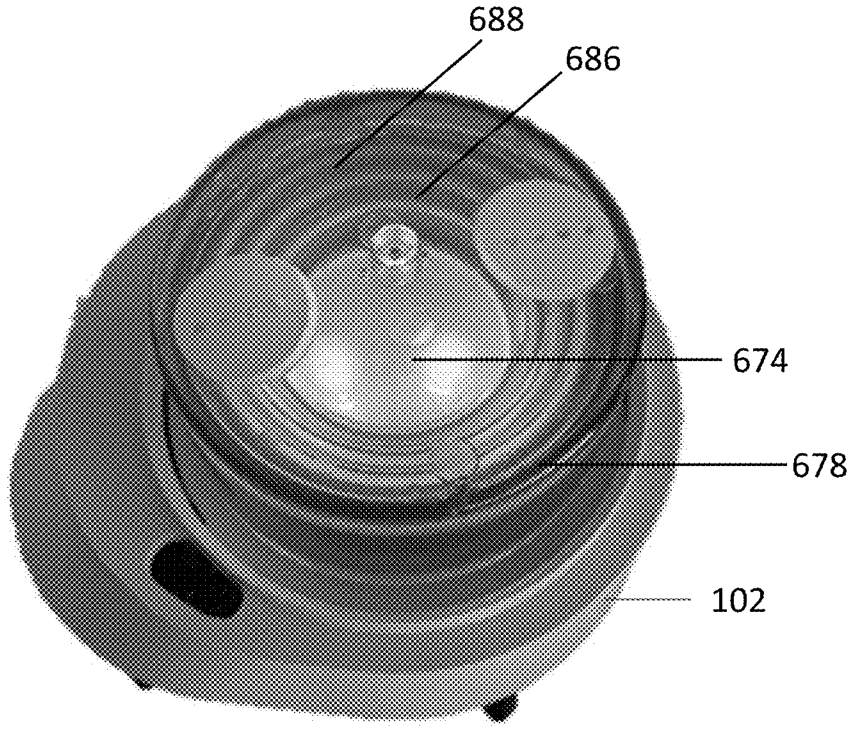
FIGS. 104A-104B depicts an isometric and top view of one embodiment of the portable centrifuge device.
Figure 104B:
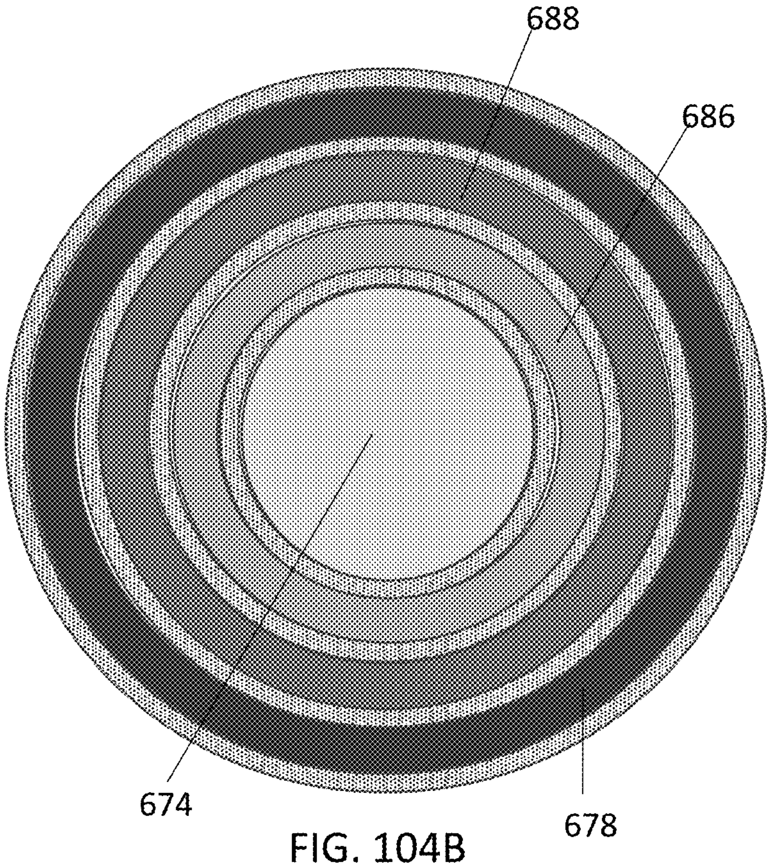
Figure 104C:
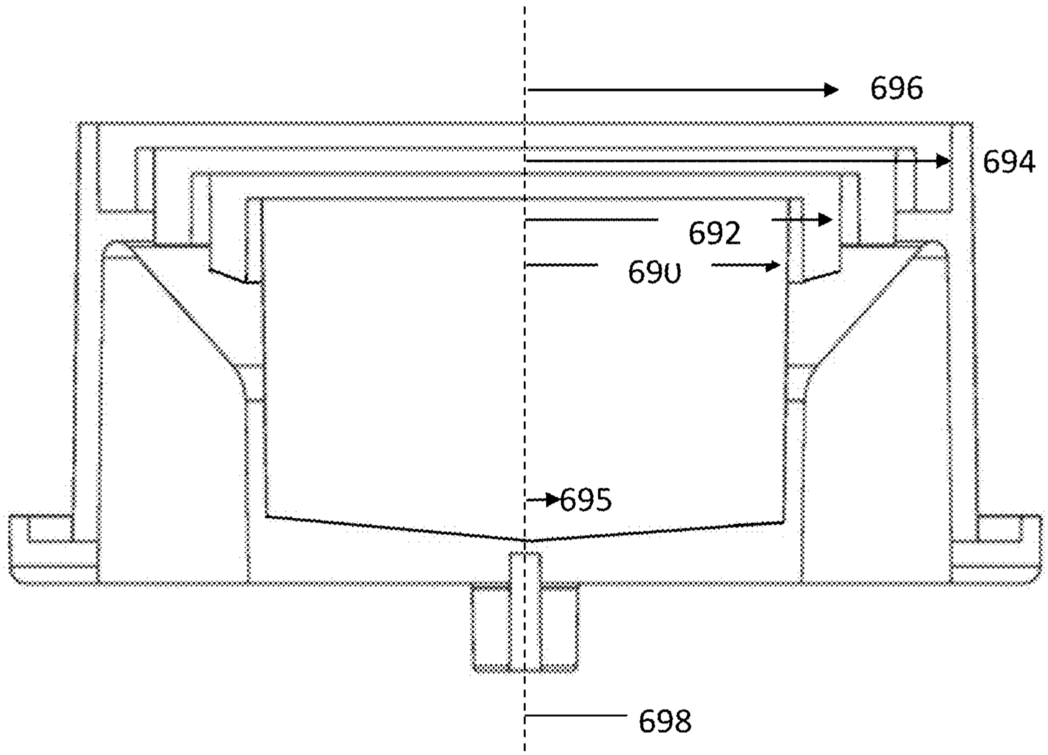
FIGS. 104C-104F illustrates the centrifugal fields (G forces) of one embodiment of the portable centrifuge device and traditional rotor centrifuges.
Figure 104D:
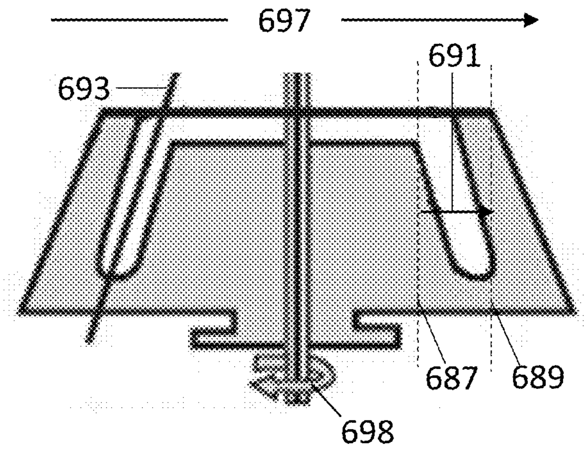
Figure 104E:
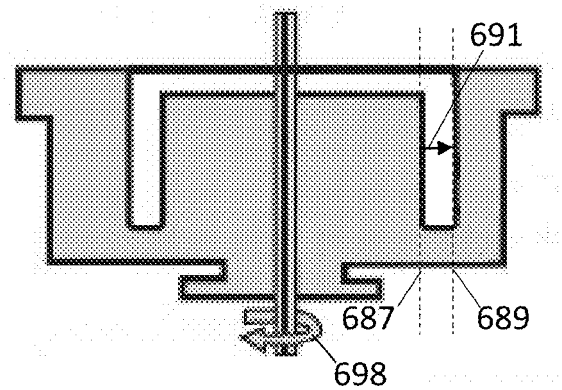
Figure 104F:
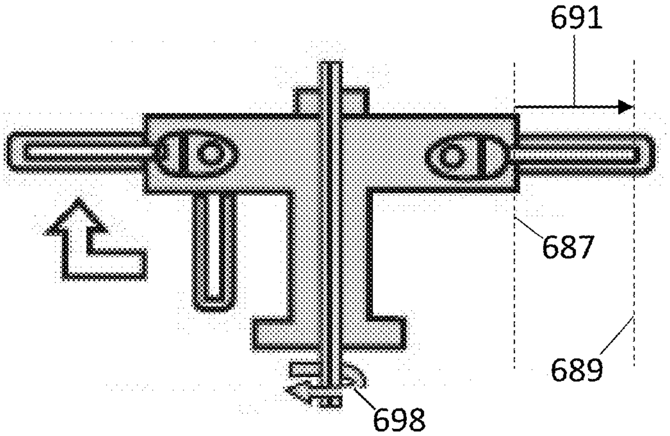

The portable centrifuge leverages the centrifugation principles to simplify extraction. The portable centrifuge is a device that is used to separate components of a mixture according to density, shape, viscosity, and/or particle size by depositing the separate components into their respective channels (see FIG. 104A-104B) rather than stacked-tiered layers or vertical layers via conventional rotor centrifuges. The portable centrifuge spins the mixture or whole blood in rotation using a fixed speed (RPM) around a fixed axis (spins it in a circle), which the whole blood or mixture is subjected to centrifugal forces. These centrifugal forces apply a force perpendicular to the axis of rotation (outward or horizontally) and/or parallel to the centrifugal force onto the mixture or whole blood causing the dense particles to migrate away from the axis of rotation (e.g. or move outward in the radial direction) and the lighter particles to move toward the axis of rotation. Once the components are deposited into each of the respective channels, each of the channels aligns with an extraction hole for easy visualization and extraction of the separated particles of a mixture or separated blood components of whole blood. Thus, eliminating the need for highly skilled personnel to extract the different components.

The portable centrifuge can exhibit a wide range of centrifugal forces or G-forces than compared to traditional rotor centrifuges. The portable centrifuge system exhibits a G-force or centrifugal force that comprises substantially zero and/or zero gravitational forces (or G forces) at the axis of rotation 698 and/or proximate to the axis of rotation 698. Accordingly, the G-forces progressively increases linearly in the radial direction from the smallest radius 695 (e.g. potentially smallest ring) towards the largest radius or largest ring on the sequester wheel, radius 1 690, radius 2 692, and/or radius 3 695 within the sequester wheel. The portable centrifuge may comprise G-forces from 0 to 10,000 Gs. This is highly contrasted by the traditional rotor centrifuges, which the traditional rotor centrifuges will never reach substantially zero or zero G-forces at and/or proximate to the axis of rotation 698. Each of the traditional centrifuges have substantially greater G-force due its minimum radius 687 and maximum radius 689 based on its design, which may be 2000 Gs and greater.

Figure 103:
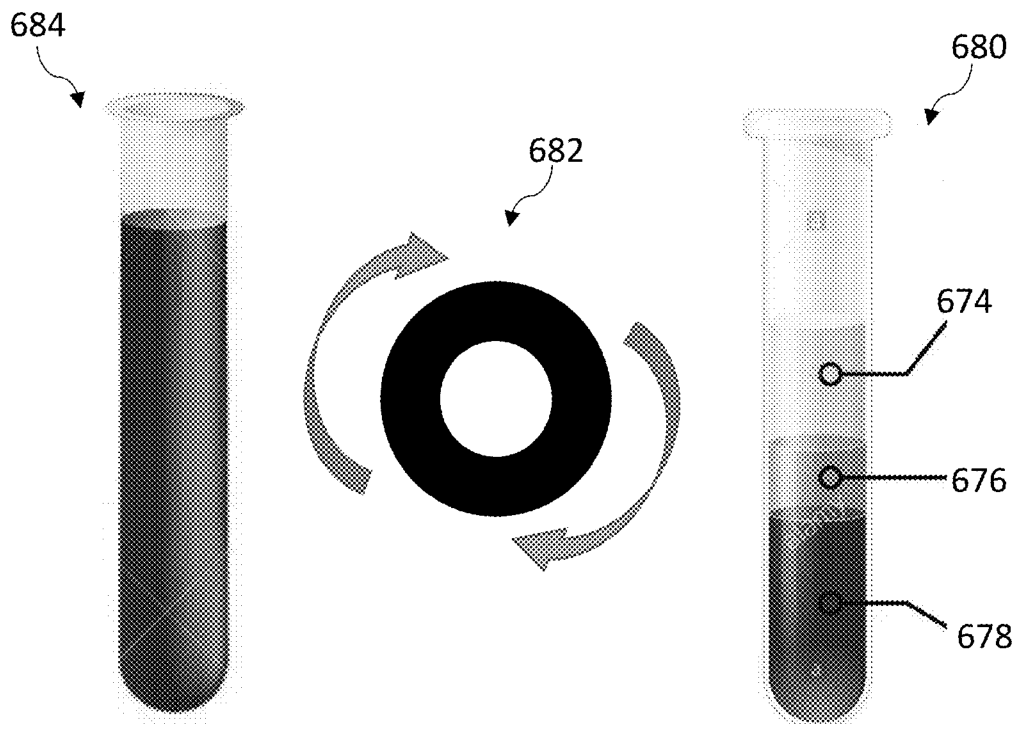
FIG. 103 depicts one embodiment of a conventional centrifuge process.

The portable centrifuge may desirably reduce or eliminate mechanical failures. The portable centrifuge does not include swinging parts (e.g., swinging bucket), nor does it require balancing prior to centrifugation. This is highly contrasted by conventional or traditional centrifuges. Conventional rotor centrifuges require the mixture or whole blood be placed into test tubes (see FIG. 103) and if there are an unequal amount of test tubes, the conventional centrifuge must be balanced to achieve uniformity of G-forces. G-forces may change dramatically by any slight differences in the uneven distribution of weight within the conventional rotor centrifuges. Furthermore, the conventional centrifuges, like the swinging bucket centrifuge, exhibit high metal stress due to the swinging of the bucket to a 90-degree angle when centripetal force is applied and can exhibit frequent mechanical failures. Accordingly, the length of time to stop the centrifugation process is delayed or slow to reduce the risk of contaminating or mixing the separated gradient layers.

In one exemplary embodiment, the portable centrifuge may minimize the number of handling and processing steps compared to conventional centrifugation techniques. The portable centrifuge provides for reduced handling and transferring of blood because the steps may be performed in a single location, thus reducing potential cross-contamination to extracted blood components and ensuring chain of title or chain of custody of the patient's blood. The portable centrifuge may comprise the steps of withdrawing the blood from a patient; injecting blood into portable centrifuge; activating centrifuge; and extracting blood components from the portable centrifuge; and injecting the extracted blood components into the patient. This contrasts with conventional techniques. Some conventional techniques involve a blood draw in a non-sterile separate location, which the blood is stored in a treated or non-treated test tube. The test tube is sent to a different lab for centrifugation cycle to separate the patient's blood into its separate components and then the specific components must be extracted and stored in second container for use or injection (e.g. syringe). The extracted components are then injected into the patient subcutaneously in a non-sterile environment potentially using visual guidance (e.g. ultrasound or fluoroscopy imaging). This conventional process is a time-consuming process.

In another embodiment, the portable centrifuge may comprise immediate separation of different concentrations of PRP's with a single centrifugation cycle. The PRP can be used "as-is" or it can be further separated into concentration 1 PRP and/or concentration 2 PRP. The PRP may be separated further into leukocyte-rich PRP (LR-PRP), defined as having a neutrophil concentration above baseline, and leukocyte-poor (LP-PRP) preparations, defined as having a leukocyte (neutrophil) concentration below baseline. In one embodiment, the PRP may comprise PRP concentration 1 and PRP concentration 2, the concentration 1 and/or 2 may comprise PRP, LP-PRP, LR-PRP, and/or any combination thereof. Such separation of the different concentrations of the PRP allows physicians to have specific recommendations for each separate concentration (PRP, LR-PRP and/or LP-PRP) for each musculoskeletal indication. Accordingly, the portable centrifuge may comprise a first blood component, a second blood component, and a third blood component. Alternatively, the portable centrifuge may comprise a first blood, component, a second blood component, a third blood component, and a fourth blood component, and/or any combination thereof. The portable centrifuge may comprise a first blood, component, a second blood component, a third blood component, a fourth blood component, a fifth blood component and/or any combination thereof. The blood components may include PPP, PRP, LR PRP, LP-PRP, RBC, and/or any combination thereof.

Applications

In another exemplary embodiment, the portable centrifuge may be used as an in-situ preparation for PPP and/or PRP therapies for musculoskeletal injuries and/or inflammation. Platelet-rich plasma (PRP) is a preparation of autologous human plasma with an increased platelet concentration produced by centrifuging a larger volume of a patient's own blood. Platelets contain a plethora of growth factors and mediators in their alpha granules (TGF-β1, PDGF, bFGF, VEGF, EGF, IGF-1), which are concentrated through the centrifugation process to release supraphysiologic amounts of these growth factors and cytokines to an injury site and augment the natural healing process. Platelet-rich plasma (PRP) therapy requires an injection of a concentration of a patient's own "active" platelets (e.g., the platelets may be activated with the addition of calcium chromide or thrombin) into injured or diseased body tissue to accelerate the healing of injured or inflamed tendons, ligaments, muscles, and joints. Then, the PRP releases the growth factors that stimulate and increase the number of reparative cells that a patient's body produces. PRP therapy can reduce the need for the administration of anti-inflammatories or stronger medications like opioids. In addition, the side effects of PRP injections are very limited because the injections are created from the patient's own blood, and the patient's body will not reject or react negatively to them.

In another embodiment, the portable centrifuge may be used as an in-situ preparation for convalescent plasma therapy that treats a disease condition where the pathogenesis is linked or associated to a specific toxic biologic substance and/or an infectious disease. Convalescent plasma therapy or plasmapheresis is the removal, and the return or exchange of blood components that contain antibodies into the patient for treatment of infectious diseases (e.g. COVID-19) and/or other toxic biologic substances. It can be used as a current or reactive treatment modality and/or used prophylactically to prevent infection. The portable centrifuge may allow for autologous plasma therapy, plasma exchange (PE, PLEX or PEX) or plasma exchange therapy (PET), and/or by donation. The portable centrifuge may further allow for single use, discontinuous flow centrifugation, continuous flow centrifugation, and plasma filtration. Discontinuous flow centrifugation requires a venous catheter line, and removal of 300 ml of blood at a time and centrifuged to separate plasma from blood cells. Continuous flow centrifugation may require two venous lines and requires slightly less blood volume out of the body at any one time, as it is able to continuously spin out plasma. Plasma filtration may require two venous lines and the plasma is filtered using standard hemodialysis equipment. This continuous process requires that less than 100 ml of blood be outside the body at one time. Single-use process comprises an injection of autologous or non-autologous (e.g. donation) blood to be centrifuged, which the centrifuged blood components, namely plasma, will be extracted and administered directly to the patient.

In another embodiment, the portable centrifuge may be used for treatment of various ocular or ophthalmological disorders, including, but not limited to dry eye syndrome, persistent epithelial defects (PEDs), neurotropic ulcerations, limbal deficiency and/or corneal dystrophies. The use of blood derivatives or blood components is highly desirable as a therapeutic approach to stimulate and accelerate tissue healing within the eye. The coagulated or anticoagulated blood may be centrifuged to separate into its constituent blood components, including plasma or serum (30% to 55%) and formed elements (70% to 45%) (e.g., formed elements includes RBCs, platelets and WBCs). Plasma and/or serum may be further filtered using a standard filtration media and administered using a variety of eye dispensing mechanisms. The eye dispensing mechanisms may comprise a pipette, a syringe, an eye dropper, and eye dropper with integral filter, a mechanical dispenser, and/or any dispensing mechanisms known in the art. The serum or plasma eye drops may be used as a reactive treatment modality and/or be used prophylactically. The serum or plasma eye drops may comprise autologous or non-autologous blood components.

In another embodiment, the portable centrifuge may be used for rapid and accurate assessment of blood hemostasis via microfluidic technology in conjunction with centrifugation (e.g., separation of blood into its blood constituent components). Rapid, quantitative and accurate hemostasis monitoring is critical in many clinical settings (for example, surgery, trauma, sepsis, anticoagulation and anti-platelet therapies) to anticipate, avoid and direct the management of serious disorders due to bleeding or thrombosis. An increasing number of patients are diagnosed with COVID-19 require precise and personalized anticoagulation dose monitoring on as close to real-time basis as possible to maintain homeostasis in-vivo to prevent any serious health effects from COVID-19 coagulopathies. Therefore, the lack of managing anticoagulation dosage precisely and continuously is a common cause of catastrophic hemorrhage and mortality in patients. Moreover, the requirement for monitoring homeostasis reliably at the bedside using low blood volumes is even more critical in pediatric patients with acute coagulopathy (acquired or congenital), as they are more vulnerable than adults. As a result, the portable centrifuge may comprise a simple microfluidic device for real-time monitoring of hemostasis and platelet function that permits rapid determination of a clotting time for native whole blood as it is perfused through a network of channels. The network of channels may be configured in such a way to potentially mimic local physiologically relevant changes in hemodynamics flow conditions experienced in living stenosed arterioles.

In another embodiment, the portable centrifuge may be used for isolation of different types of stem cells from embryonic and/or adult tissues for use in stem cell therapies (e.g., regenerative medicine) and research. Stem cells are characterized as cells endowed with continuous self-renewal ability and pluri- or multipotentiality and could consequently give rise to a large panel of cell types. Isolation of a large volume of stem cells with purity and viability must be completed to be useful for treatment purposes, thus leading to the development of stem cell separation technologies. The portable centrifuge may offer isolation of embryonic or adult stem cells via density gradient and/or differential centrifugation techniques without the complexity of steps of standard techniques, thereby minimizing sample variability, meeting the purity and viability standards and delivering more efficient on-site isolation.

Portable Centrifuge

Referring to the drawings, wherein like reference numerals are used to indicate like or analogous components throughout the several views, and with particular reference to FIGS. 1-43, there is illustrated a centrifuge 100 comprising a base, the base including a baseplate 101 and a rotational mechanism housing or a base cover 102, a centrifuge drive or a rotational mechanism, a centrifuge motor 110, an activation switch 160. The centrifuge 100 may further comprise a removable protective cover or an activation cover 103, and a centrifuge container or a sealed container 130, at least one light and/or any combination thereof. The baseplate 101 and the base cover 102 connect to form a base container. The centrifuge container 130 has a centrifuge cover 104, a sequester wheel or a sequester device 105, a centrifuge baseplate 106, a spring 109, a toggle switch 111, and a plurality of tabs or wheel lock tabs 112.

With reference to FIGS. 10 and 12-17, the rotational mechanism 110 is shown with an electric motor 154, a solenoid 153, a circuit board 151, a control relay 152, at least one battery 155, and an activation switch 160. The components, for example, the electric motor 154, the solenoid 153, the circuit board 151, the control relay 152, the at least one battery 155, and the activation switch 160 are connected to form an open circuit. The rotational mechanism 110 is shown connected to the baseplate 101 and covered by the base cover 102 such that an armature 161 of the electric motor 154 engages the centrifuge container 130 through the housing opening 118 and a solenoid armature or plunger 163 engages the toggle switch 111 through the housing opening 118. The baseplate 101 may, for example, have an approximate length of 130 mm and an approximate width of 100 mm.

With continued reference for FIGS. 1-8, 14, 15, 42, and 43, the protective cover 103 has a top side 138, a bottom side 139, a cover rim 149, and a sidewall 140. The protective cover 103 further has an activation tab 108 for engagement with the activation switch 160 through an activation slot 107 when the protective cover 103 engages with the centrifuge 100. The top side 138 and the bottom side form a circular disk, with the sidewall 140 extending circumferentially from the disk and away from bottom side 139 in a tubular form, towards the cover rim 149. The cover rim 149, forms a ring with an opening extending to the bottom side 139. The activation tab 108 is an elongated member, extending away from the cover rim 149. The protective cover 103 may, for example, be fabricated from a clear plastic polymer material or a material through which blood separation columns may be visible.

With reference to FIGS. 4, 7-9, 14-31, and 37-39, the centrifuge baseplate 106 has a bottom side 132 opposite a top side 131 and may be, for example, circular or cylindrical. The centrifuge baseplate 106 has a centrifuge base motor connector 120 which may, for example, be centered about a center of the centrifuge baseplate 106. The centrifuge base motor connector 120 may, for example, extend out from the top side 131 as a freestanding structure to connect with the armature 161 of the electric motor 154. the bottom side 132 of the baseplate 106 has a protrusion or axle 126 extending from the approximate center of baseplate 106. The motor armature 161, the base motor connector 120, the baseplate 106, and the axle 126 are connected for coaxial alignment and rotation about the common axis 165. The common axis 165 may be, for example, the rotational axis of the armature 161. The plurality of wheel lock tabs 112 extend out from the top of the bottom side 132. The tabs 112 have a first section extending out from the bottom side 132 and second section that curves or angles from the first section, with the first section and second section being angled at approximately 60° to 90°, and more specifically at approximately 90°. The centrifuge baseplate 106 further has a toggle switch 111 extending through the centrifuge baseplate 106 and pivotally connected to at least one toggle support 119. As further shown in FIGS. 30, and 36-37, the toggle switch 111 is pivotally connected to two toggle supports 119 and protrudes through the baseplate 106 through a toggle hole 127. The toggle hole 127 may be, for example a square or rectangular boss hole into which the toggle switch 111 may be, for example, press-fitted. The toggle hole 127 may also have a canted member 148.

With reference to FIGS. 4, 5, 7-9, 16-17, and 24-35, the sequester device 105 has a circular shape or wheel structure, with a first surface or sequester wheel top 134 and a second surface or sequester wheel bottom 133, a plurality of concentric rings 114, 115, 116 extending away from the top surface 134 as freestanding structures and forming at least one channel 141, 142. There may be, for example, a first ring or outer sequester ring 114, a second ring or middle sequester ring 115, and a third ring or inner sequester ring 116. There may also be, for example, a first channel 141 between the third ring 116 and second ring 115, and a second channel between the second ring 115 and the first ring 114. The top surface of the sequester ring 134, forms the bottom of the channels 141, 142. The sequester wheel 105 further has an inner section 144 within the third ring 116 and an axle hole or a hub 147 through the top and bottom surfaces 133, 134 and centered on the center of the sequester wheel 105 The motor armature 161, the base motor connector 120, the baseplate 106, the axle 126, and the sequester wheel hub 147 are connected for coaxial alignment and rotation about the common axis 165. The common axis 165 may be, for example, the rotational axis of the armature 161. The inner section 144, has a plurality of spokes 117 with holes in between, a sequester wheel toggle hole or slot 123 and a plurality of sequester wheel tab slots 125. The sequester wheel engages or couples with the base of the centrifuge 100, defining an axis. The sequester wheel engagement or coupling may comprise permanent fixation (not removable) or temporary fixation (removably connected or engaged). Such permanent fixation or temporary fixation may comprise fixation mechanisms known in the art. For example, temporary fixation may include quick release mechanism, set screw mechanism, dove tail mechanisms, frictional mechanisms and/or any combination thereof.

Each of the plurality of rings having at least one surface, at least one surface comprising a coating. Accordingly, each of the plurality of rings having a first surface and a second surface, the first surface and second surface having a coating. Accordingly, each of the plurality of rings having a first surface, a second surface and a third surface, the first surface, second surface and third surface having a coating. The coating may comprise anticoagulants, preservatives, disinfectants or germicidal agents or pathogen reduction agents or pathogen inactivation agents, sterilants, antiseptics, clot activators, separator gels. The at least one first surface, first surface, second surface or third surface may be surface directly in contact with the patient's whole blood or its separated blood components.

A shown in FIGS. 29-35, the inner sequester ring 116 has a diameter range of approximately 39 mm to 42 mm, the middle sequester ring has a diameter range of approximately 47 mm to 49 mm, and the outer sequester ring 114 has a diameter range of approximately 54 mm to 56 mm. More specifically, the first ring has a diameter of approximately 41 mm, the second ring has a diameter of approximately 47 mm, and the third ring has a diameter of approximately 56 mm. The height of the sequester wheel 105 may range from approximately, 8.5 mm to 1.0 cm and more specifically have a height of 9.8 mm, from the bottom surface 132 to the top of a ring (e.g. the first ring 116, the second ring 115, and the third ring 114). More specifically, the height of the rings (e.g. the first ring 114, the second ring 115, and the third ring 116) may be, approximately 8 mm. Each of the heights may be the same or they may be different.

With continued reference to FIGS. 29-35, the first channel 141 and the second channel 142 may each have as an example, an approximate volume of 2.5 ml. Additional channels may be included in other aspects of the centrifuge, however there may be, for example, a minimum practical volume for a channel of approximately 1 ml. The bottom surface 133 of the sequester wheel has a plurality of channels 124, extending from the bottom surface 133 towards the top surface 134 and from the outer wall of the exterior ring 116 to the inner section 144. The plurality of channels 124, may be, for example, semi-circular shaped. The sequester device or wheel 105 may comprise a total volume, the total volume includes less than or equal to 1000 cc of whole blood; the total volume includes less than or equal to 800 cc of whole blood; the total volume includes less than or equal to 600 cc of whole blood; and the total volume includes less than or equal to 400 cc of whole blood. The total volume is defined as the total blood volume extracted from the patient that can be processed by the centrifuge 100. Alternatively, the total volume may include 100 cc to 300 cc; the total volume may include 150 cc to 300 cc; the total volume may include 200 cc to 300 cc; the total volume may include 150 cc to 250 cc.

With reference to FIGS. 3-8, 17-27, and 40-41, the centrifuge cover 104 has a circular, top side 136, a circular bottom side 135, and a sidewall or centrifuge cover ring 137 extending away from the bottom side 135 and forming a ring about the circumference with an open interior space between an interior circumference of the sidewall 137. Several holes exist between the top surface 136 and the bottom surface 135, including a plurality of extraction holes 121 and at least one insertion hole 122. The centrifuge cover 104 may, for example, be fabricated from a clear polymer plastic material or a material through which blood separation columns may be visible.

As shown in FIGS. 3, 4, 7, 8, and 23-27, the centrifuge container 130 has a coil spring 109 positioned about the axle 126 between the baseplate 106 and the sequester wheel 105. The sequester wheel 105 may be, for example, positioned on the baseplate 106, with the baseplate axle 126 passing through hub 147, toggle switch 111 passing through toggle slot 123, and the plurality of tabs 112 positioned through the plurality of sequester wheel tab slots 125. The sequester wheel 105 may be, for example, engaged with the baseplate 106, with the spring 109 compressed between the sequester wheel 105 and the baseplate 106. The spokes 117 are engaged with the sequester wheel tabs 112 holding the sequester wheel 105 in position against the spring 109 and maintaining compression. The centrifuge cover 104 may be, for example, placed onto the baseplate 106 and sealed to create a liquid impermeable connection. Polymer barriers may be used to, for example, seal openings in the baseplate 106 (e.g. the plurality of tabs 112 and the toggle hole 127) and openings in the centrifuge cover (e.g. the plurality of extraction holes 121 and the at least one insertion hole 122) to create a sealed, liquid impermeable container.

With reference to FIGS. 18-23, the internal chamber of the centrifuge container 130 may have, for example, a height of approximately 10.5 mm to 13.5 mm and an internal diameter, for example, of approximately 60 mm to 70 mm. More specifically, the dimensions may, for example, be sized to accommodate 30 ml of fluid in addition to the internal components (e.g. the spring 109, the toggle 111, the plurality of tabs 112, and the sequester wheel 105) resulting in an internal chamber of approximately, 12.5 mm between the baseplate topside 132 and the centrifuge cover bottom side 135 and having a diameter of approximately 68 mm (e.g. total volume of approximately 45 ml). For the centrifuge container 104, separation may be, for example, performed on approximately 27 ml to 30 ml of blood, and more specifically, 30 ml.

The clearance between the top of the rings (e.g. the first ring 114, the second ring 115, and the third ring 116) and the bottom surface 135 of the centrifuge cover 104 may be, for example, approximately 1 mm to 3 mm, and more specifically, approximately 1 mm. The sequester wheel 105 may be, for example, positioned within the centrifuge container 130 resulting in a third channel 143 between the third ring 114 and the sidewall 137 of the centrifuge cover 104. The spacing of the plurality of extraction holes 121 align with a hole above each of the third channel 143, the second channel 142, the first channel 141, and the inner section 144.

With reference to FIGS. 1, 2, 7, 8, 14-17, and 28-31, the centrifuge motor base connector 120 of the centrifuge container 130 is connected to the motor armature 161, with a clearance between centrifuge baseplate 106 and the base cover, ranging from 1 mm to 5 mm, and more specifically, approximately 2 mm. The protective cover 103 is placed over the centrifuge container 130 and onto the base cover 102, such that the activation tab 108 is inserted through activation slot 107 and an activation slider slot 156 of the activation switch 160. The protective cover 103 may be sized to, for example, cover the centrifuge container and allowing the centrifuge container 130 to rotate without making contact with the inner surface of sidewall 140 or the bottom side 139. There may be, for example, a clearance of approximately 1 mm to 5 mm, and more specifically, approximately 3 mm between the bottom side 139 of the cover 103 and the top side 136 of the centrifuge container 130. There is a clearance of approximately 1 mm to 5 mm, and more specifically, approximately 3 mm between the sidewall 137 and the sidewall 140. The activation switch 160 has the activation slider slot 156 within the activation slider or sliding switch 157, a conductive member or magnetic member 158 connected to the activation slider 157, and a plurality of circuit members 159.

Referring to FIGS. 1-43 and 87, the centrifuge may be sealed and sterilized prior to use and introduction to a sterilized environment, such as, for example, a surgical operating room. A method of using centrifuge 100 may include, removing the protective cover 170 and introducing blood into the centrifuge container 171 through the insertion hole 122 using a sharp object, such as, for example, a syringe (not shown). The introduced blood may, for example, flow from the inner section 144 and through the spokes 117 and the channels 124 to accommodate the full volume of blood.

Still referring to FIGS. 1, 2, 7, 8, 14-17, 28-31, and 87, the method may also include replacing the protective cover 103, and turning or twisting the protective cover to activate the centrifuge 100. Turning the protective cover 103 may, for example, cause the activation tab 108 to move the activation slider 157, connecting the conductive member 158 with the plurality of circuit members 159 and completing a circuit to activate the rotational mechanism 110. The centrifuge container 130 may be, for example, rotated under the protective cover 103 by the motor 154 at, for example, approximately 10,000 rpm to 25,000 rpm, and more specifically at 20,000 rpm. The blood may separate into constituent components 174. The blood may, for example, separate into constituent columns and/or channels, with the RBC in a column approximately towards the sidewall 137 and above the third channel 143, the PRP in a column approximately above the first channel 141 and the second channel 142, and PPP remaining approximately within the inner section 144. There PRP column may be, for example, in a gradient of concentration between the PPP and RBC columns. The plurality of spokes 117 and the plurality sequester wheel channels 124 may also, for example, allow for blood to flow through and around during centrifugation, aiding to lessen a fluid path and shear on the cells. By constraining the volume of blood (e.g. 30 ml) introduced into a centrifuge container having a slightly greater volume (e.g. approximately 45 ml), thick columns of PPP, PRP, and RBC may be created and visible during centrifugation. A timer within the circuit board 151 may send a signal to activate the toggle switch 175. The timer within the circuit board 151 may be, for example, triggered upon rotational mechanism 110 activation. Upon reaching a threshold time, the circuit board 151 may, for example, trigger the solenoid 153, extending the solenoid armature 163 to make contact with the toggle switch 111. The toggle switch may activate the sequester wheel 176. The toggle switch 111 may, for example, pivot within the toggle supports 119, pushing or rotating against the canted member 148, pushing or rotating the sequester wheel 130, and freeing the sequester wheel 105 from the plurality of tabs 112. The sequester wheel may then capture the PRP 177. The compressed spring 109 may, for example, project the freed sequester wheel 105 in an approximately perpendicular direction to the baseplate 106. The projection may be, for example, with sufficient force for the top of the sequester wheel 105 to strike the centrifuge cover bottom side 135. However, the toggle switch 111 may, for example, be positioned through the baseplate 106 and the sequester wheel 105 to inhibit the sequester wheel 105 from rotating independently from the baseplate 106 after release from the plurality of tabs 112. The projected sequester wheel 105 may, for example, capture the PRP within the channels (e.g. the first channel 141 and the second channel 142). The timer on the circuit board 151 may send a stop signal to the electrical motor 178 and the centrifuge container may stop rotating 179. At a second threshold time, the circuit board 151 may, for example, open the circuit, and the centrifuge container 130 rotation slows until stopping. The RBC column may, for example, approximately fall into or remains within the third channel 143, with the PRP column falling within the second and first channels 142, 141, and the PPP column falling into within the inner section 144. The PRP may, for example, have a gradient of PRP concentrations between the first and second channels 141, 142. Within the first channel 141 and the second channel 142, the volume of PRP accumulation may be, for example, from approximately 3 ml to 5 ml, based on 30 ml of blood. The protective cover may be removed 180 and the blood constituent components may be removed 181. After the protective cover 103 is removed, the separated blood elements may, for example, be withdrawn from the plurality of extractions holes 121. The blood constituent components may be, for example, withdrawn by inserting a syringe needle (not shown) through one of the pluralities of extraction holes 121 aligned with the desired blood component. Removing PRP may include, inserting a syringe needle through one of the plurality of extraction holes 121 that are aligned with the first channel 141 or second channel 142, and then pulling the plunger to withdraw the constituent component into the syringe (not shown). Removing PPP may include, for example, inserting a syringe into insertion hole 122. While a syringe has been described for use in extracting blood from centrifuge 100, one having ordinary skill in the art would understand that other tools that may be used.

In other aspects of the centrifuge 100, the number of channels in a sequester wheel 105 may range from a single channel to five channels, with an inner ring and an outer ring having approximately the same dimensions to the first ring 114 and the third ring 116. In other aspects of the centrifuge 100, the centrifuge container 130 may be sized to, for example, hold 60 ml of fluid and internal components (e.g. the spring 109 and the sequester wheel 105), with the internal diameter of the centrifuge container 130 remaining approximately 60 mm to 70 mm, but having a height to accommodate the greater volume. In still other aspects of the centrifuge 100 for holding 60 ml of fluid, the height of the sequester wheel 105 may range from, approximately 21 mm to 25 mm. In other aspects of the centrifuge 100, rotation of the centrifuge container 130 may be slowed by the presence of a brake button on the protective container 103 to frictionally slow the centrifuge container 130. In still other aspects, the solenoid armature 163 may remain extended and contacting the toggle switch 111, aiding with braking the centrifuge container 130.

Referring now to FIGS. 45-73, an alternate embodiment for centrifuge 300 is shown. The centrifuge 300 has a protective cover or third member 302, a base frame, first member, or base ring 303, a base frame cover 304, and a cap assembly 310. The centrifuge 300 has a conical frustrum shape, with the base ring 303, the base frame cover 304, and the protective cover 302 having a large diameter at the bottom of the centrifuge 300, and the protective cover 302 narrowing towards the region at the top of the centrifuge 300 where a cap 301 of the cap assembly 310 is engaged as shown in FIGS. 45-51. The base frame cover 304 is connected to and above the base ring 303. The protective cover 302, is engaged with and above the base frame cover 304. The cap 301 is engaged at the top of the protective cover 302 and at the top of centrifuge 300.

With continuing reference to FIGS. 45-51 and 65-68, the cap assembly 310 is shown with the cap 301, a cap arm 305, an activation handle 306, an activation tab 307, and a cap connector 324. The cap assembly 310 may be, for example, constructed from a rigid plastic polymer material. The protective cover 302 has a protective cover opening or first opening 309, that is approximately circular, at a top end and extending at an approximately 45° to 50° angle to a protective cover base opening or second opening 327. The angle of the protective cover 302 may be, for example, more specifically be approximately 45°. The second opening may be, for example, approximately circular. The circumference of the first opening 309 may be, for example, smaller than the circumference of the second opening 327, with the openings being sufficiently large to cover the inner components of the centrifuge 300. The protective cover 302 has a first connector 326 along the circumference of the first opening 309 and a second connector 328 along the circumference of the second opening 327. The cap 301 may be, for example, circular with a diameter of approximately 75 mm. The cap 301 may, for example, engage with the protective cover 302, such that the cap connector 324 engages with the first connector 326 within the first opening 309. The cap arm 305 extends away from cap 301 at, for example, approximately 45° to 50° and more specifically at approximately 45°, extending towards the first connector 326. The cap arm 305 may, for example, have a length of approximately 70 mm to 80 mm, or more specifically, approximately 75 mm. The cap arm 305 may, for example, extend away from cap 301 and have an articulated section 325 distal to cap 301. The articulated section 325 may, for example, be at an angle to the rest of cap arm 305. The activation tab 307, extends from the second end of the articulated section 325 at an angle, and may be, for example, approximately perpendicular to the articulated section 325. The activation tab 307, may for example, have an approximately triangular shape.

Referring to FIGS. 52-56 and 69-71, the protective cover 302 may be, for example, removable from the centrifuge 300. The first connector 326 is configured (e.g. shaped and dimensioned) to engage with the base frame cover 304 when placed onto the centrifuge 300. Below the protective cover 302, centrifuge 300 has a rotating test-tube holder, test-tube armature, second member, or rotor 312, engaged with the motor 154. The rotor 312 may be, for example, conical frustrum shaped, having a circular top surface 319 with, for example, a diameter of approximately 113 mm. A circumferential sidewall 335 extends away from the top surface 319 at, for example, an approximate angle of 45° to 50° to a circular rotor bottom or ring 336, and more specifically, at approximately 45°. The rotor bottom 336 has an opening that extends to the top surface 319, with the rotor bottom 336 having a diameter of, for example, approximately 212 mm. The height of the rotor 312 may be, for example, approximately 65 mm.

Still referring to FIGS. 52-56 and 69-71, the rotor 312 holds a plurality of test-tubes 350, with each test-tube sized to, for example, 10 ml to 30 ml of fluid, and more specifically hold 15 ml of fluid. The test-tube may have, for example, a stoppered or a sealed opening. The top surface 319 has a plurality of test-tube slots 320, having openings at the top surface 319 and extending along an inner wall 316 of the rotor 312. The test-tube slots 320 have side walls extending from the inner wall 316, forming a channel with a curved bottom support 313, for engagement with a test-tube of the plurality of test-tubes 350, and providing approximately 0.5 mm of clearance between test-tube slot side walls and the test-tubes 350. Two test-tubes 350 are shown, however aspects of centrifuge 300 may, for example, hold up to and including eight test-tubes 350.

Continuing to refer to FIGS. 52-56 and 69-71, the underside of the rotor 312, may have, for example a plurality of buttresses or member 318 positioned as diametrically opposed pairs extending from the inner wall 316 toward a motor engagement support 317, axially aligned with the approximate center of top surface 319 and the approximate center of the bottom opening 327.

With reference to FIGS. 56-58 and 72-73, the base frame cover 304 has a top side 332, a bottom ring 329, an outer rim 331, and a plurality of protrusions 321. The base frame cover 304 may be, for example, also conical frustrum shaped, having a hole 323 extending from the top side 332 to an inner circumference of the bottom ring 329. The plurality of protrusions 321 extend from a bottom side of the bottom ring 329 for engagement with a plurality of connection holes 322, extending from an upper surface to a bottom surface of the base ring 303.

With reference to FIGS. 58-62, the base ring 303 is shown with a rotational mechanism or a centrifuge motor or centrifuge drive 330 and an activation armature 308 extending from the base ring 303 to the base plate 101 of the centrifuge motor 330. An activation armature slot 314 may be a channel following, for example, an arc of the base ring 303. A first end 333 of the activation armature 308 slot is movable within the armature slot 314, for example, along the arc of the base ring 303. A second end 334 of the activation armature 308 passes through an activation slot 315 through the baseplate 101 and connecting to the rotational mechanism 330.

Referring to FIGS. 1, 2, 64A, 59, and 64B, the rotational mechanism 330 is shown with the electric motor 154, the circuit board 151, the control relay 152, the at least one battery 155, and the activation switch 160 connected to form an open circuit. The rotational mechanism 330 is connected to the baseplate 101 and is covered by the base cover 102 such that the armature 161 of the electric motor 154 extends through the housing opening 118. The rotational mechanism 110 has been explained above in detail and the rotational mechanism 330 will not be described further for brevity sake, except to note that the rotational mechanism 110 has the solenoid 153 whereas rotational mechanism 330 does not. All other internal components are the same.

Figure 57:
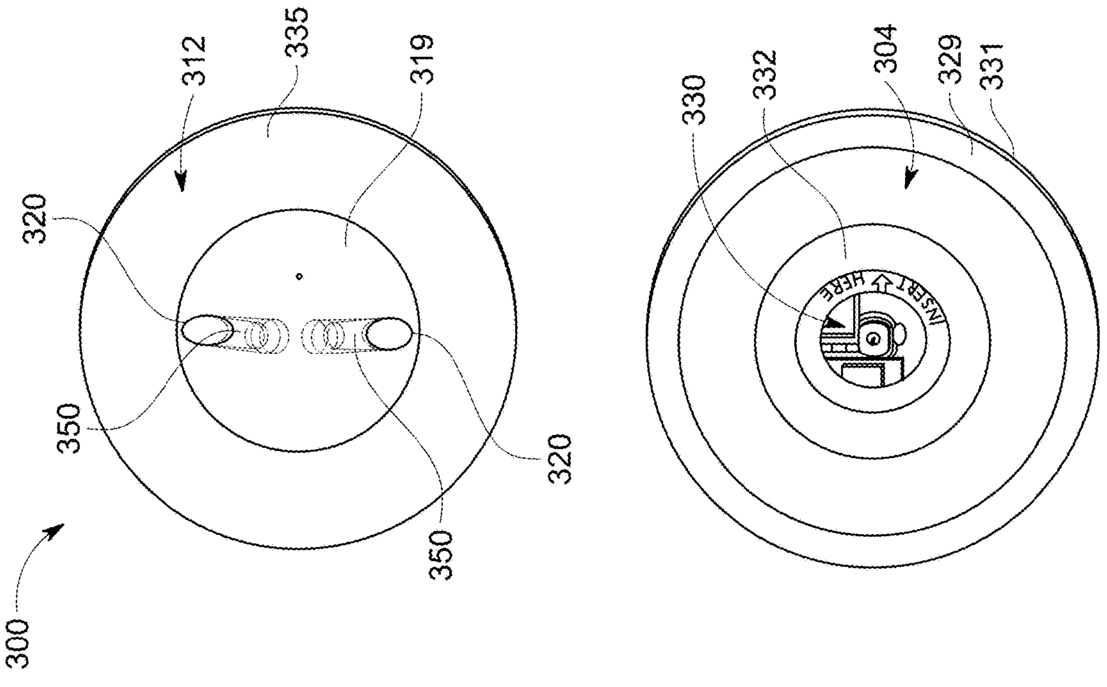
FIG. 57 is a top view of the centrifuge of FIG. 45 and the test-tube armature removed.
Figure 58:
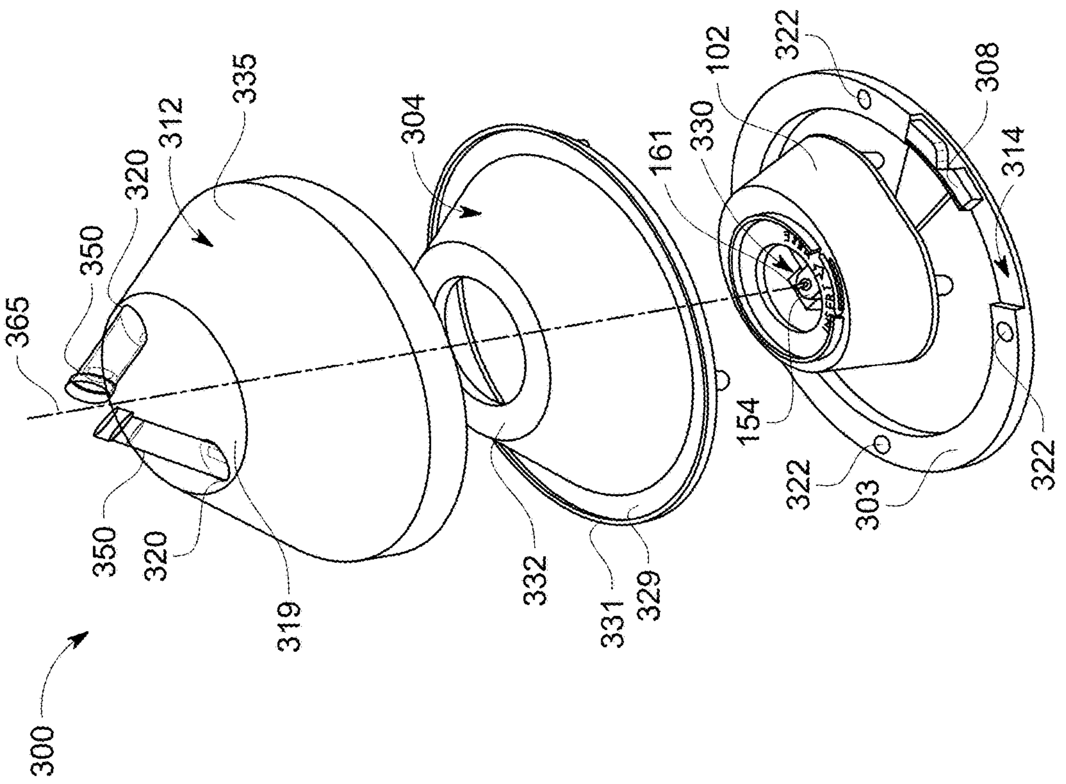
FIG. 58 is a top perspective view of the centrifuge of FIG. 45 with the test-tube cover and a base frame cover removed.
Figure 59:
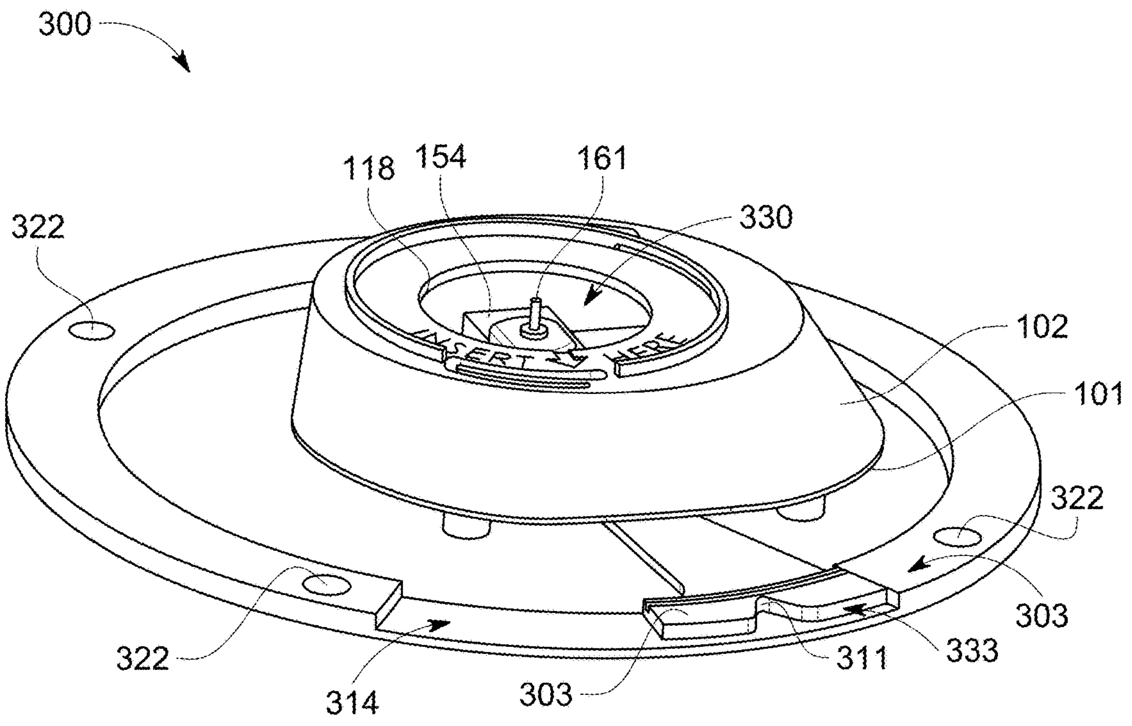
FIG. 59 is a top perspective view of the base container and base ring of the centrifuge of FIG. 45.
Figure 60:
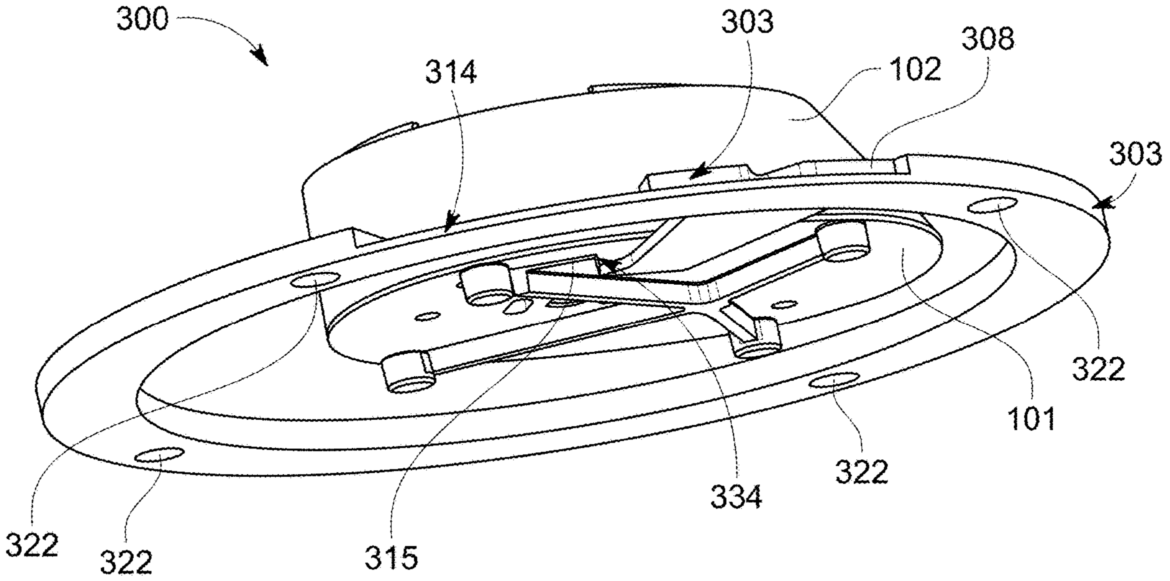
FIG. 60 is a bottom perspective view of the view of the base container and base ring of the centrifuge of FIG. 45.
Figure 61:
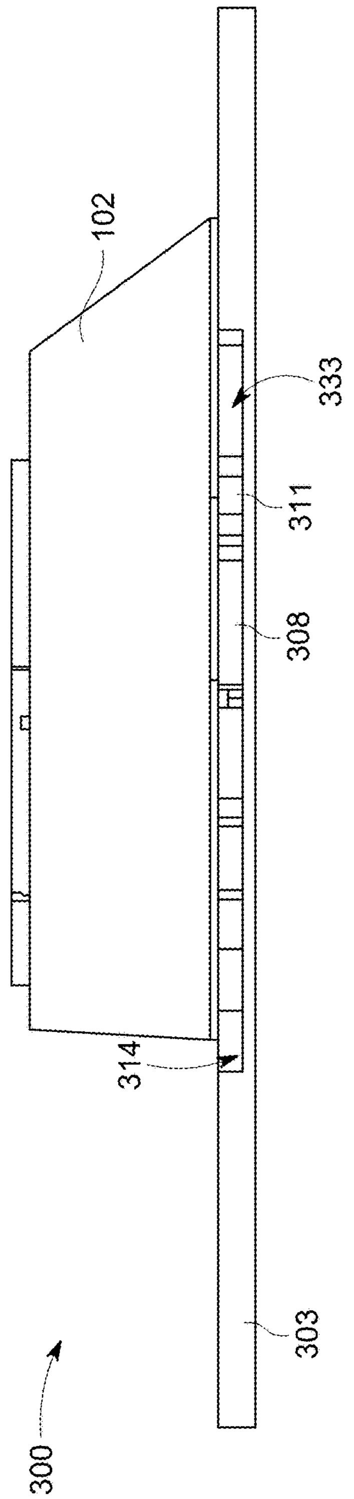
FIG. 61 is a side view of the view of the base container and base ring of the centrifuge of FIG. 45.
Figure 62:
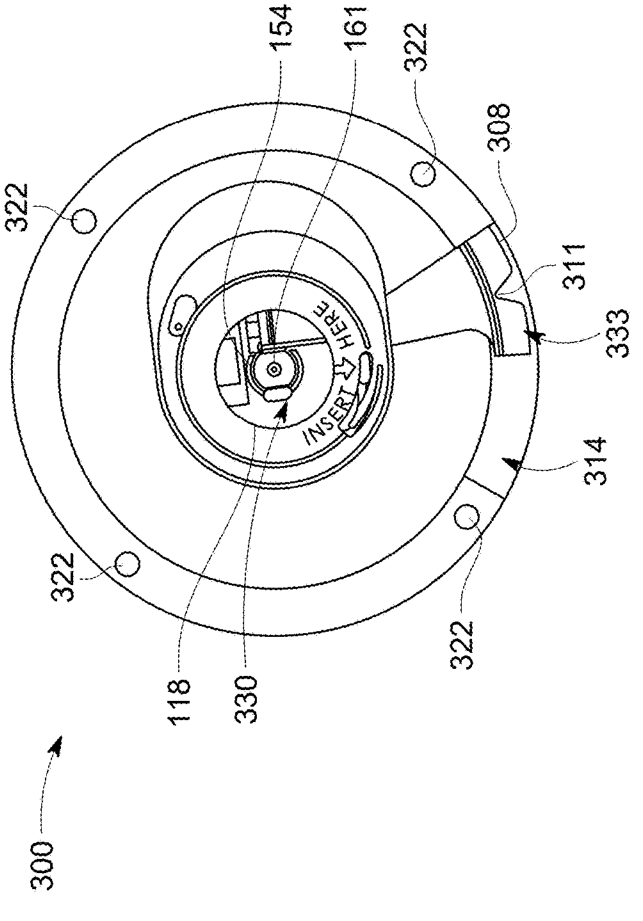
FIG. 62 is a top view of the view of the base container and base ring of the centrifuge of FIG. 45.
Figure 63:
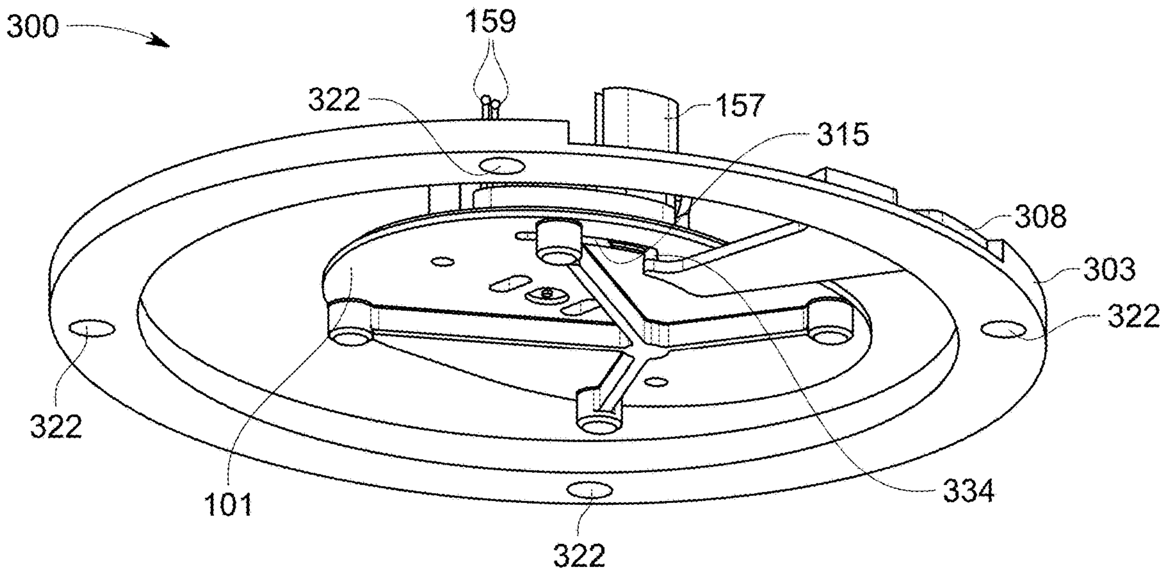
FIG. 63 is a bottom perspective view of the rotational mechanism of the centrifuge of FIG. 45.

As shown in FIGS. 57-58, the base frame cover 304 may be, for example, connected to the base ring 303 with the plurality of protrusions 321 engaged with the connection holes 322. The base frame cover 304 may be, for example, further engaged with the rotational mechanism housing or base cover 102 with the housing opening 118 aligned with the hole 323. The activation armature slot 314 may be, for example, covered by the base frame cover 304, forming, for example, a transverse slot covered with a top and a bottom and with the activation armature 308 remaining laterally movable within the slot 314 along the arc of the base ring 303.

With reference FIGS. 60, 63-64B, the second end 334 of the activation armature 308 may be, for example, connected to the activation switch 160 through the activation slot 315. The activation armature 308 further has a cap-arm engagement slot 311 on the first end 333, with the cap-arm engagement slot 311 shown as a triangular slot, extending from the first end 333 towards the second end 334. Moving the first end 333 of the activation armature 308 along the activation armature slot 314, moves the armature second end 334 along the activation slot 316, thus moving the sliding switch 157 along the activation slider slot, to activate the rotational mechanism 330.

With reference to FIGS. 56, 58, 70, and 71, the base frame cover 304 may be, for example, engaged with the base ring 303 and with the centrifuge cover 104, with the housing opening 118 aligned with the hole 323. The motor engagement support 317 of the rotor 312 may be, for example, connected to the armature 161 of the motor 154, such that the armature 161 is axially aligned with the motor engagement support 317. The rotor 312 connected to the armature 161 is configured (e.g. sized and dimensioned) and positioned above the base frame cover 304 with a clearance of approximately 1 mm to 3 mm. More specifically, there may be, for example, a clearance of approximately 3 mm. The motor armature 161, the base motor connector 120, the baseplate 106, the axle 126, and the sequester wheel hub 147 are all connected for coaxial alignment and rotation about the common axis 365. The common axis 165 may be, for example, the rotational axis of the armature 161.

Figure 52:
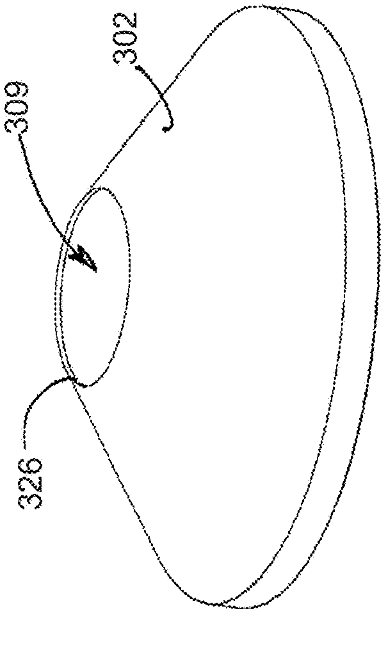
FIG. 52 is a top perspective view of the protective cover of the centrifuge of FIG. 45.
Figure 53:
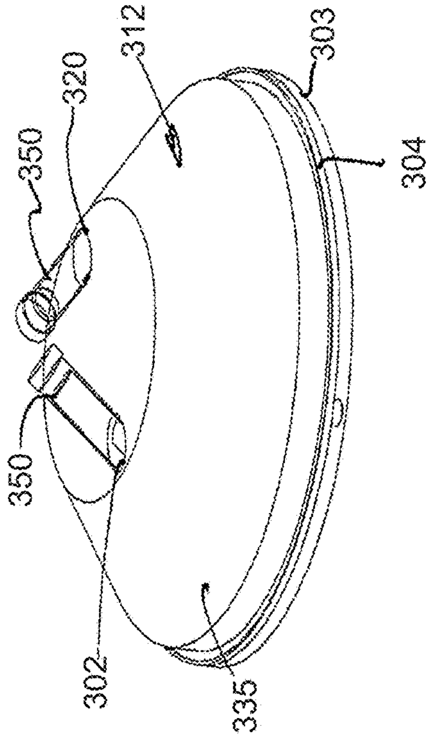
FIG. 53 is a top exploded perspective view of the centrifuge of FIG. 45 with the protective cover removed.
Figure 54:
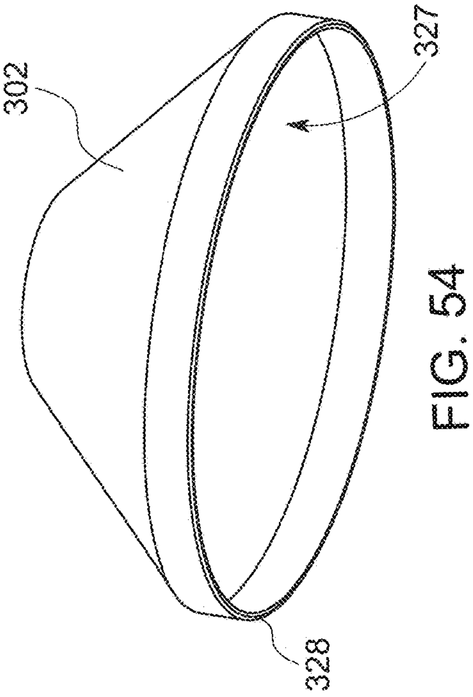
FIG. 54 is a bottom exploded perspective view of the centrifuge of FIG. 45 with the protective cover removed.
Figure 55:
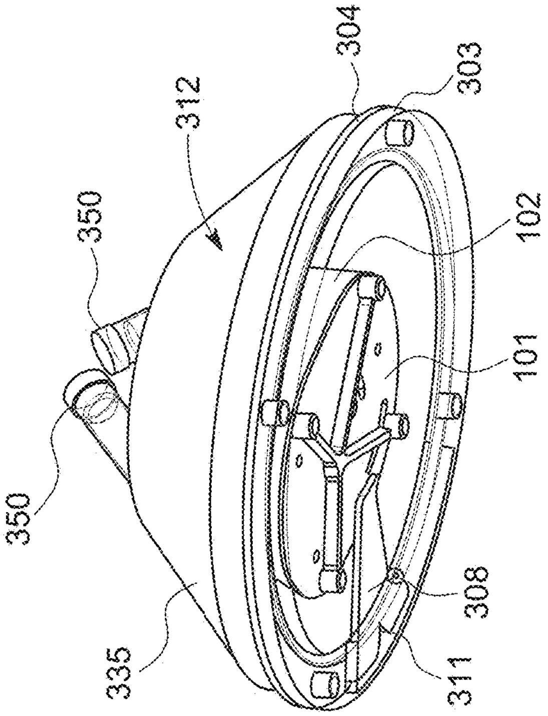
FIG. 55 is a bottom perspective view of the centrifuge of FIG. 45 with the protective cover removed.
Figure 56:
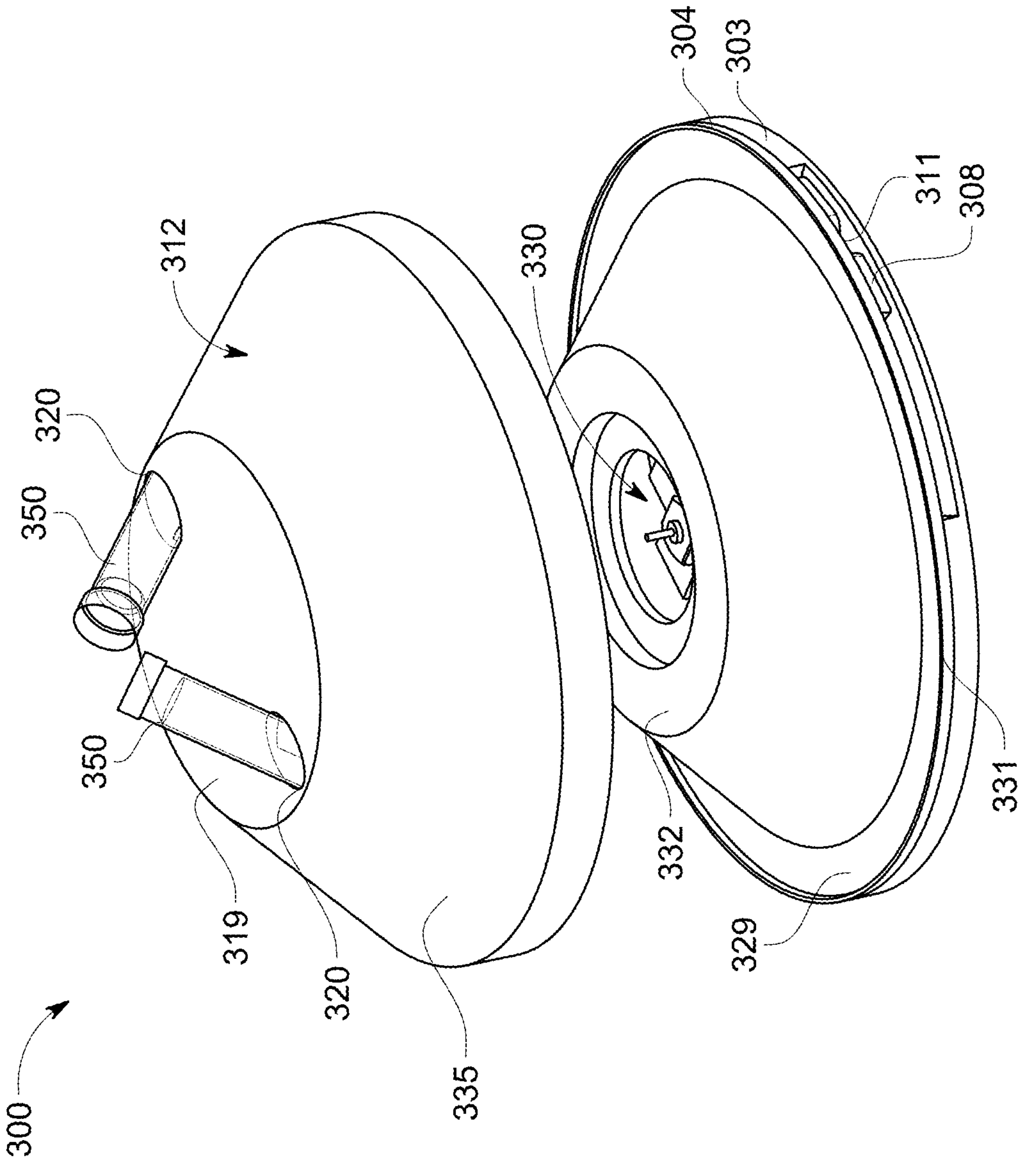
FIG. 56 is a top perspective view the centrifuge of FIG. 45 with a test-tube armature removed.

Referring to FIGS. 52-54, the protective cover 302 may be, for example, positioned onto the base frame cover 304 such that the outer rim 331 and the second connector 328 are engaged. The protective cover 302, covers the rotor 312 however, the test-tubes 350 may extend out through the cover opening. The protective cover 302 is configured (e.g. sized and dimensioned) such that rotor 312 may be, for example, rotatable under the protective cover 302, there being a clearance of, for example, approximately 1 mm to 3 mm, and more specifically, a clearance of approximately 3 mm. Thus, rotor 312 may be, for example, rotatable by the electric motor 154, having clearance from both the base frame cover 304 and the protective cover 302.

Figure 45:
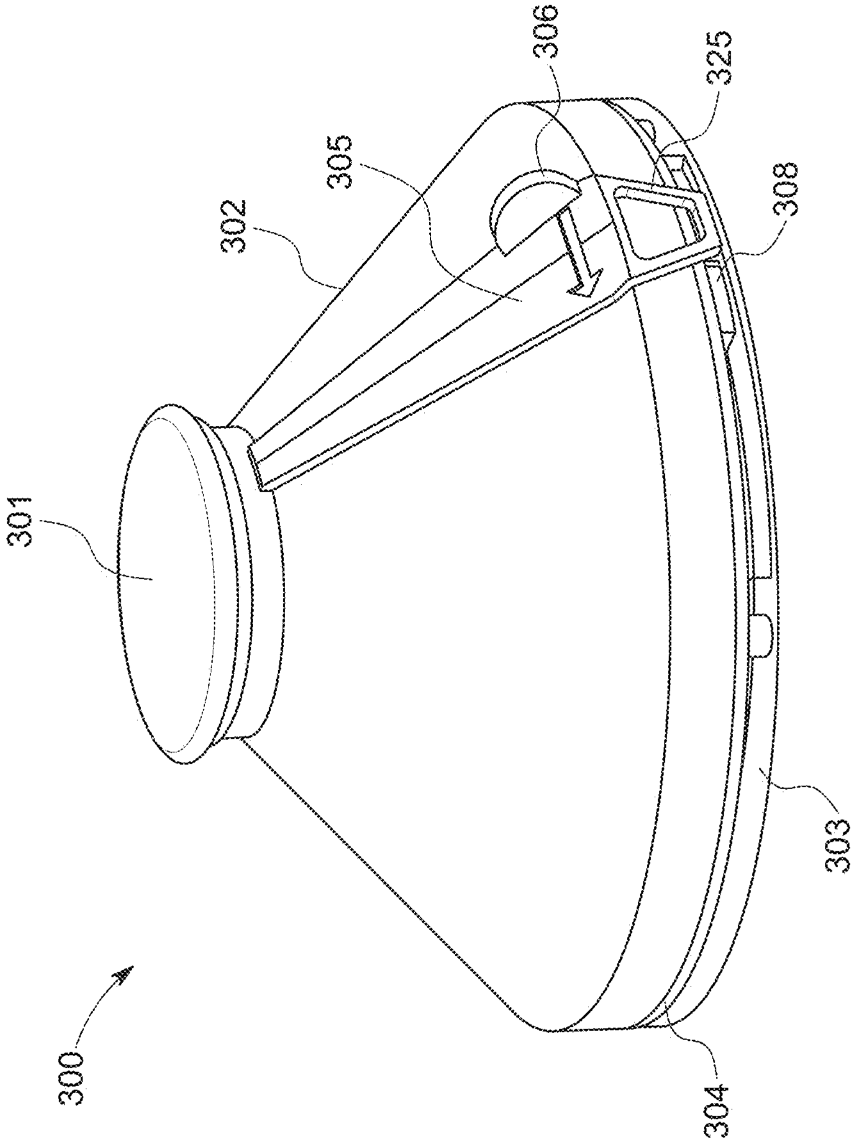
FIG. 45 is a top perspective view of another alternate embodiment of a centrifuge.
Figure 46:
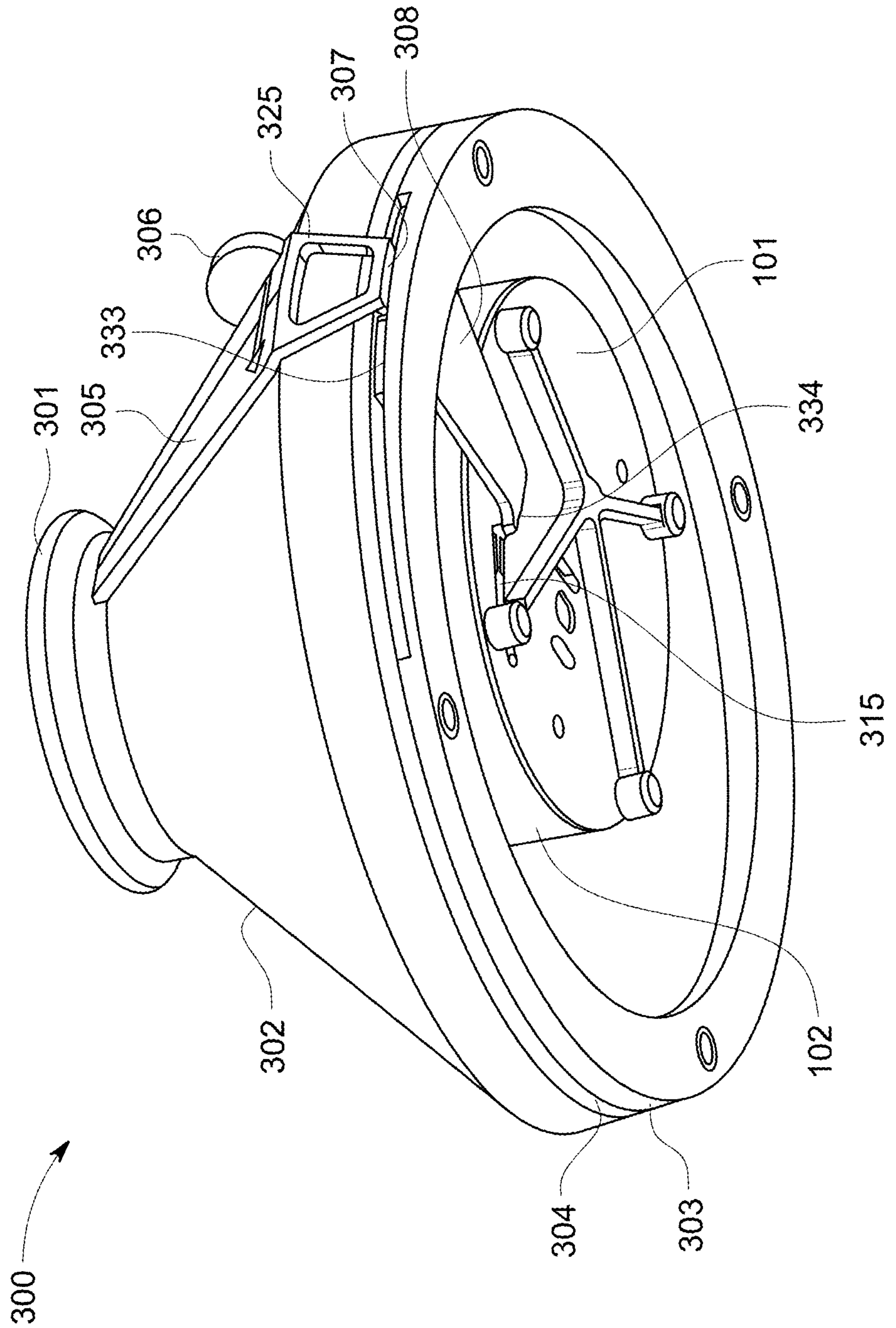
FIG. 46 is a bottom perspective view of the centrifuge of FIG. 45.
Figure 47:
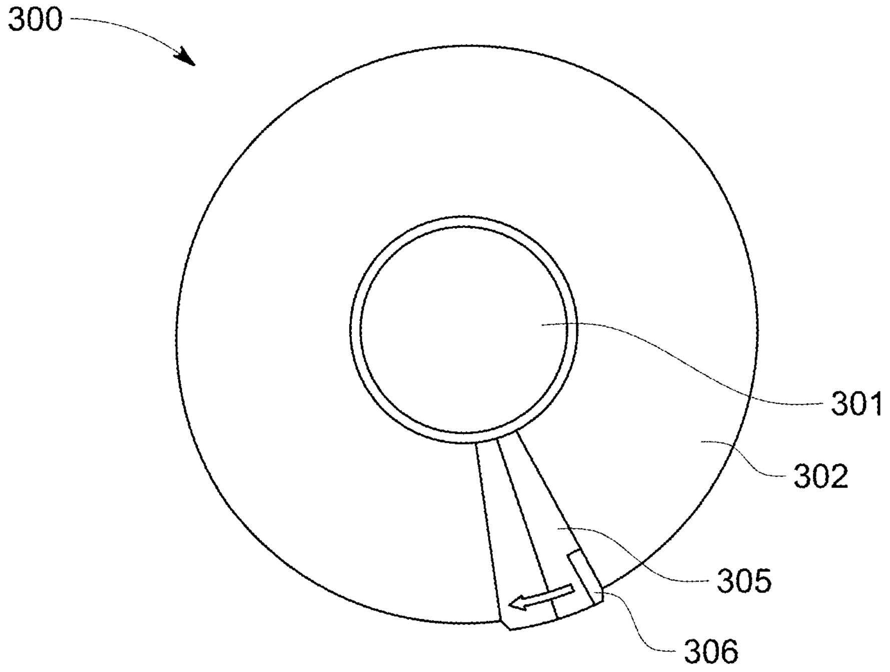
FIG. 47 is a top view of the centrifuge of FIG. 45.
Figure 48:
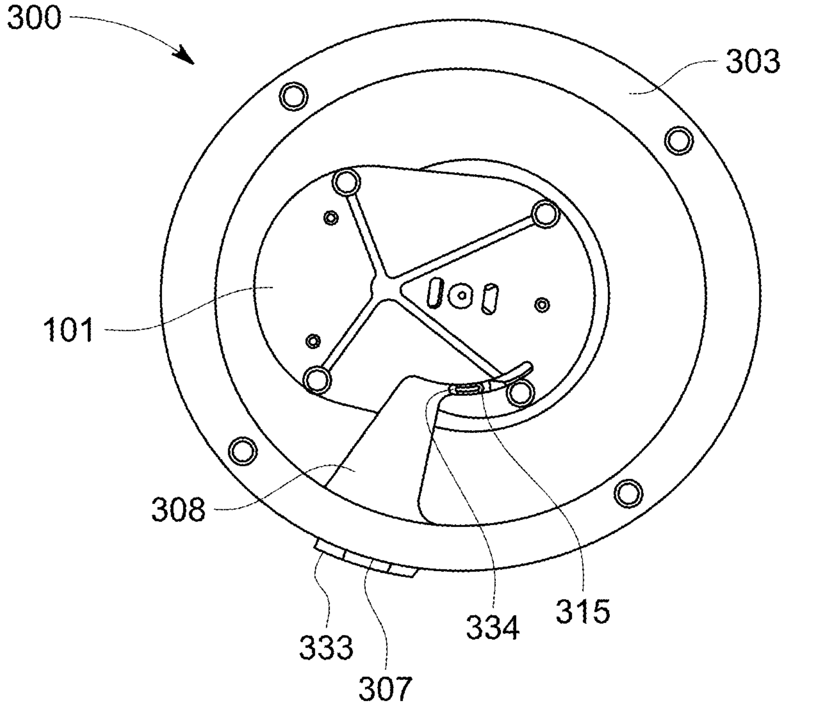
FIG. 48 is a bottom view of the centrifuge of FIG. 45.
Figure 49:
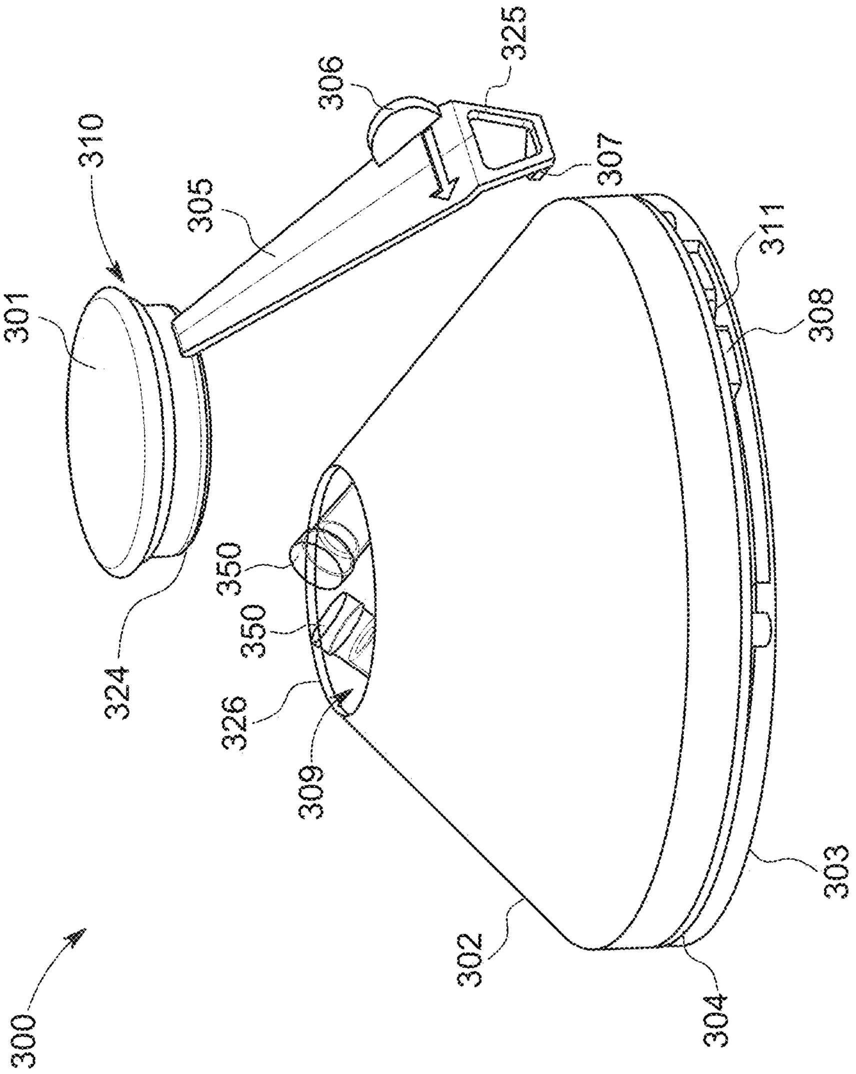
FIG. 49 is a top view of the centrifuge of FIG. 45 with a cap assembly removed.
Figure 50:
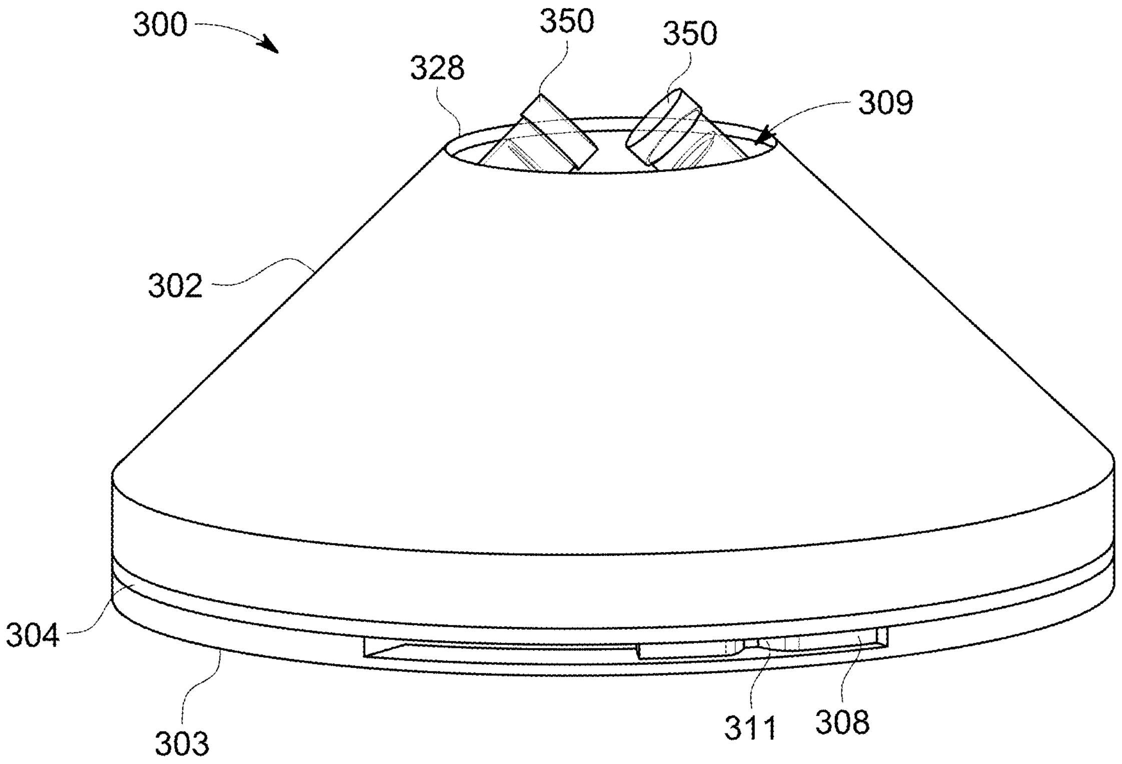
FIG. 50 is a side perspective view of the centrifuge of FIG. 45 with the cap assembly removed.
Figure 51:
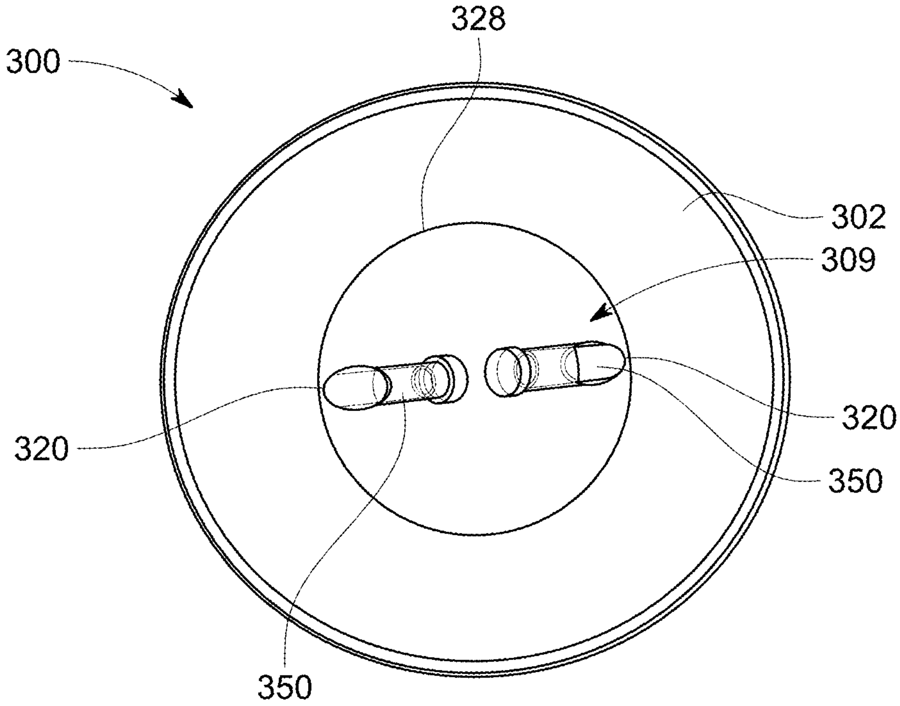
FIG. 51 is a top view of the centrifuge of FIG. 45 with the cap assembly removed.

With reference to FIGS. 45, 46, and 49, the cap assembly 310, may be, placed onto the protective cover 302 with the cap connector 324 engaged with the protective cover top rim 326. The cap 301 covers the cover opening 309 with a clearance provided between the test-tubes and the cap, ranging from 1 mm to 3 mm. The cap arm 305 extends along the cap 301 from approximately the cover opening 309 towards the protective cover bottom rim 328. The articulated section 325 is shown extending past the protective cover bottom rim 328 and towards the base ring 303, such that activation tab 307 is engaged with the cap-arm engagement slot 311. The cap arm slot 311 and the activation tab 307 are shown having a triangular shape, however other shapes and configurations may be used. The activation handle 306 extends from the cap arm 305 such that it may be, for example, grasped, pressed, pulled, or pushed to activate the centrifuge 300.

With reference to FIGS. 45-79 and 90, the centrifuge 300 may be sealed and sterilized, with the test-tubes 350 also being sterilized and included with the centrifuge 300. The test-tubes 350 may further have, for example, a thixotropic separation gel and an anti-coagulant included within, to aid in blood separation during and after centrifugation. The method for centrifugation includes removing the cap assembly 370. Blood may be introduced into the test-tubes 371. With test-tubes 350 already inserted into the test-tube slots 320 of rotor 312, blood may be, for example, introduced into the test-tubes 350 using a syringe (not shown). The cap assembly 310 may then be replaced 372. The cap 301 my, for example, cover the cover opening 308, with the cap connector 324 being engaged with the protective cover top rim 326, and the activation tab 307 inserted into the cap-arm engagement slot 311. The activation handle 306 may be pressed 373. For example, pressing or grasping and moving the activation handle rotate the cap assembly 310, with the cap 301 rotating within and along the circumference of protective cover top rim 326, the cap arm 305 rotating along the outer surface of the protective cover 302, and the activation tab 307, engaged with cap-arm engagement slot 311, rotating along the arc of the activation arm slot 314. As the activation tab 307 and the cap-arm engagement slot 311 are engaged, the activation armature first end 333 may be, for example, slid along the activation arm slot 314 and the activation armature second end 334, through the activation slot 315, moves the sliding switch 157 along the activation slider slot 156. When the conductive member 158 on the sliding switch 157 makes contact with the circuit members 159, the circuit may be, for example, closed and the motor 154 is activated. The blood may interact with the thixotropic separation gel and the anti-coagulant 374 and the blood may separate into constituent components 375. The separation gel may create a barrier for the RBCs, while the anti-coagulant may inhibit PRP and PPP from coagulating. The timer sends a signal to the motor 376. The motor 154 may, for example, continue rotating the rotor 312 until a timer on circuit board 151 opens the circuit, suspending power to the motor 154. The rotor 312 may continue to rotate until stopped 377. The cap assembly 310 may be removed 378. Removing the cap assembly 310 provides access to the test-tubes 350 and the blood, separated into RBC, PRP, and PPP. The blood constituent components may be removed from the test-tubes 379. Blood may be removing using a sharp object like, for example, a syringe.

With reference to FIGS. 74-86, yet another alternate embodiment of centrifuge 400 is shown. The centrifuge 400 has the rotational mechanism 330 on the baseplate 101 which is enclosed within base cover 102. As the rotational mechanism 330 has already been described herein, for the sake of brevity, further description will not be repeated. The centrifuge 400 further has a protective cover 403 and a centrifuge container or sealed container 430.

As shown in FIGS. 77-82, the protective cover 403 has a top side 409, a bottom side 410, a sidewall 411, an activation tab 408, a cover rim 449, and a brake 401. The protective cover has, for example, an approximately circular top side 409 that extends to the bottom side 410 and with a circumferential sidewall 411 extending away from the top side 409 and/or bottom side 410 to a cover rim 449. The cover rim 449 has an opening extending to the bottom side 410. The activation tab 408 extends from the cover rim 449 of the sidewall as a freestanding member. The protective cover 403 is configured (e.g. shaped and dimensioned) to cover the centrifuge container 430, while providing clearance between an interior surface of the protective cover 403 and the centrifuge container 430, and with the activation tab 408 inserted into the activation slot 107. The brake 401 may, for example, be a button of a flexible plastic material or from a plastic living hinge, and having a first and second position. The brake 401, when pressed, extends from the first position to the second position to make contact with the centrifuge container 430. The brake 401, may, for example, return to the first position when no longer depressed. In another aspect, the brake 401 may remain extended in the second position even after no longer being depressed.

Figure 86:
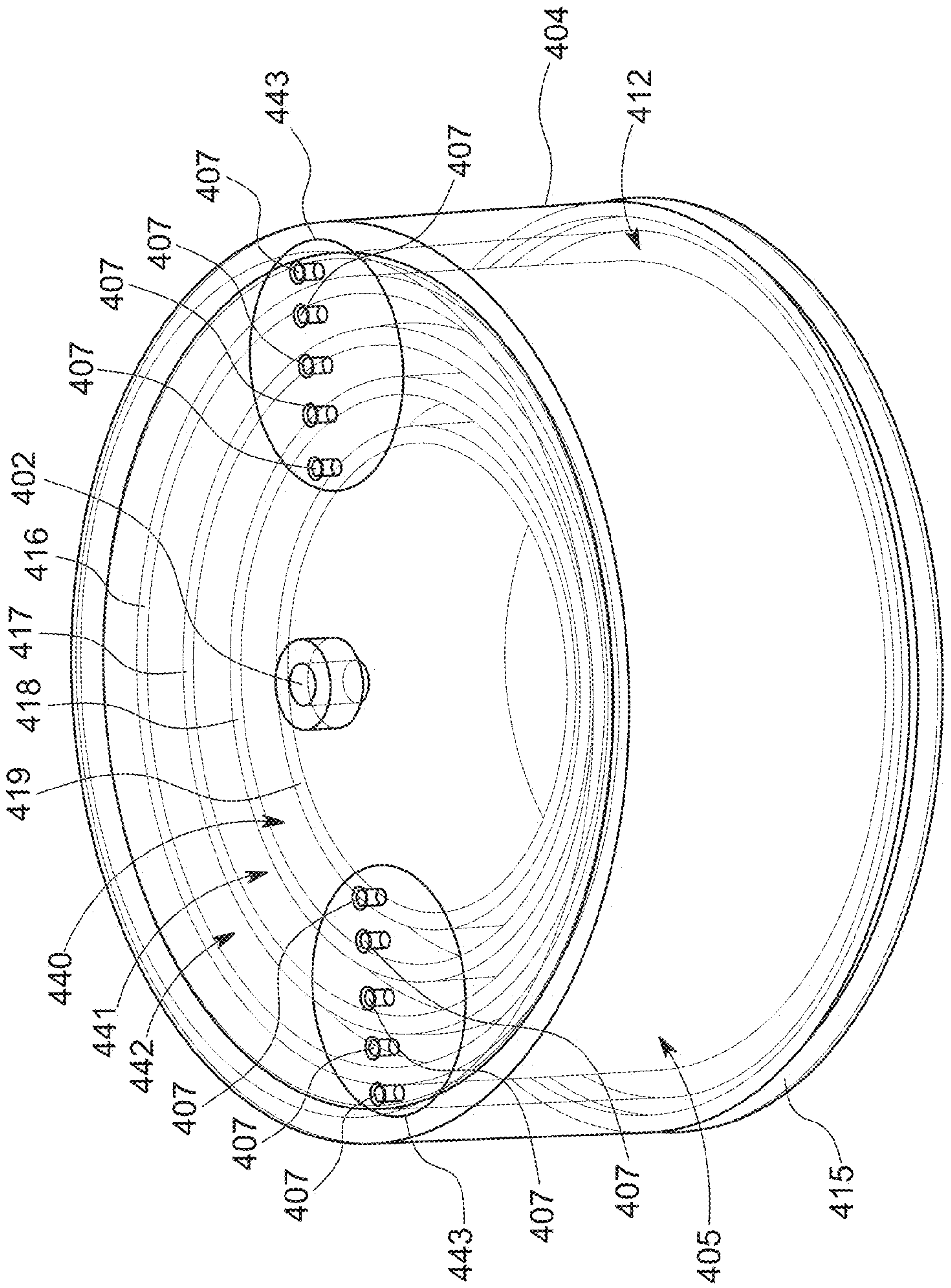
FIG. 86 is a cut-away perspective view of the centrifuge container with extraction barriers of the centrifuge of FIG. 74.
Figure 87:
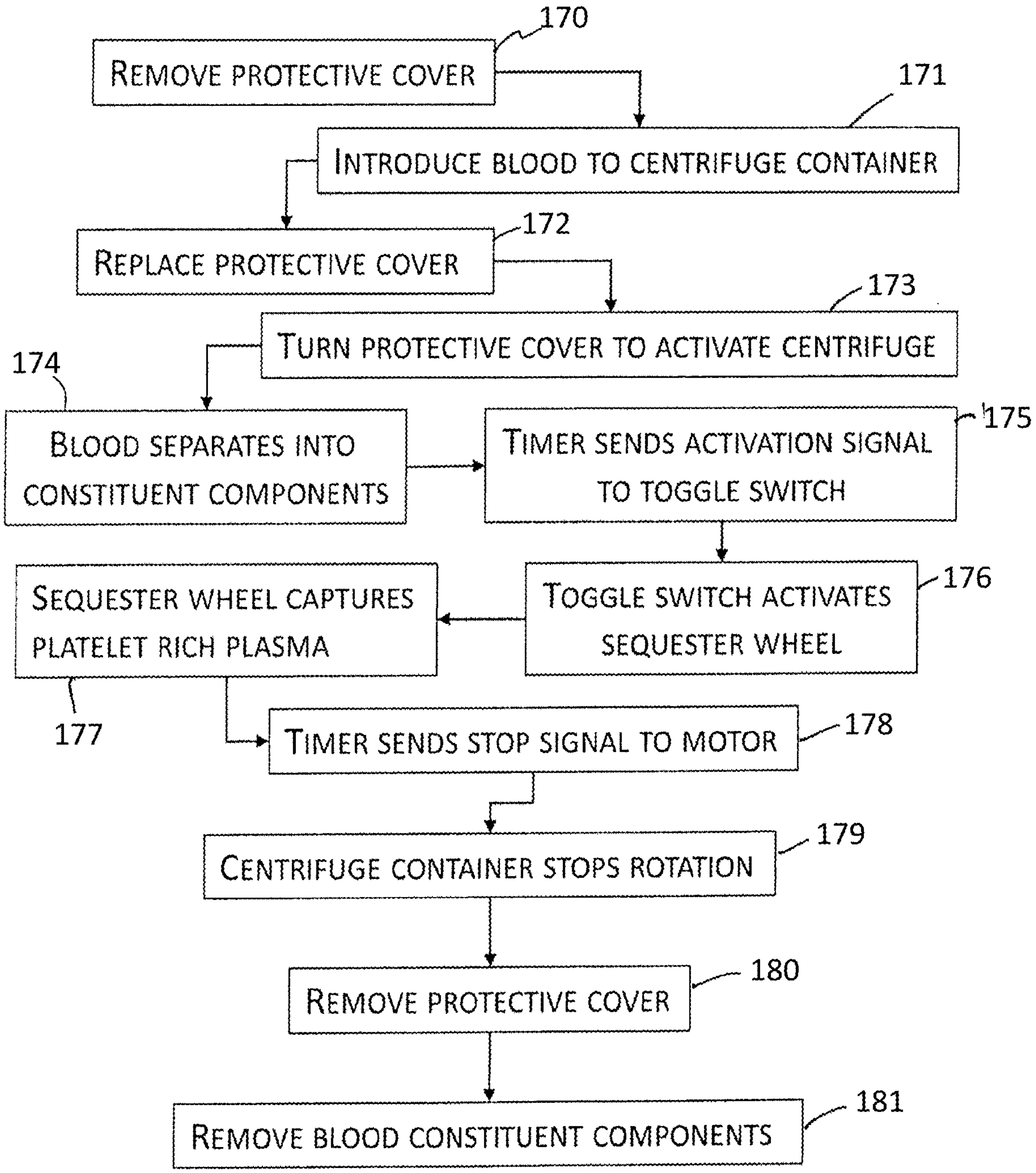
FIG. 87 depicts a method of blood centrifugation using the centrifuge of FIG. 1.
Figure 88:
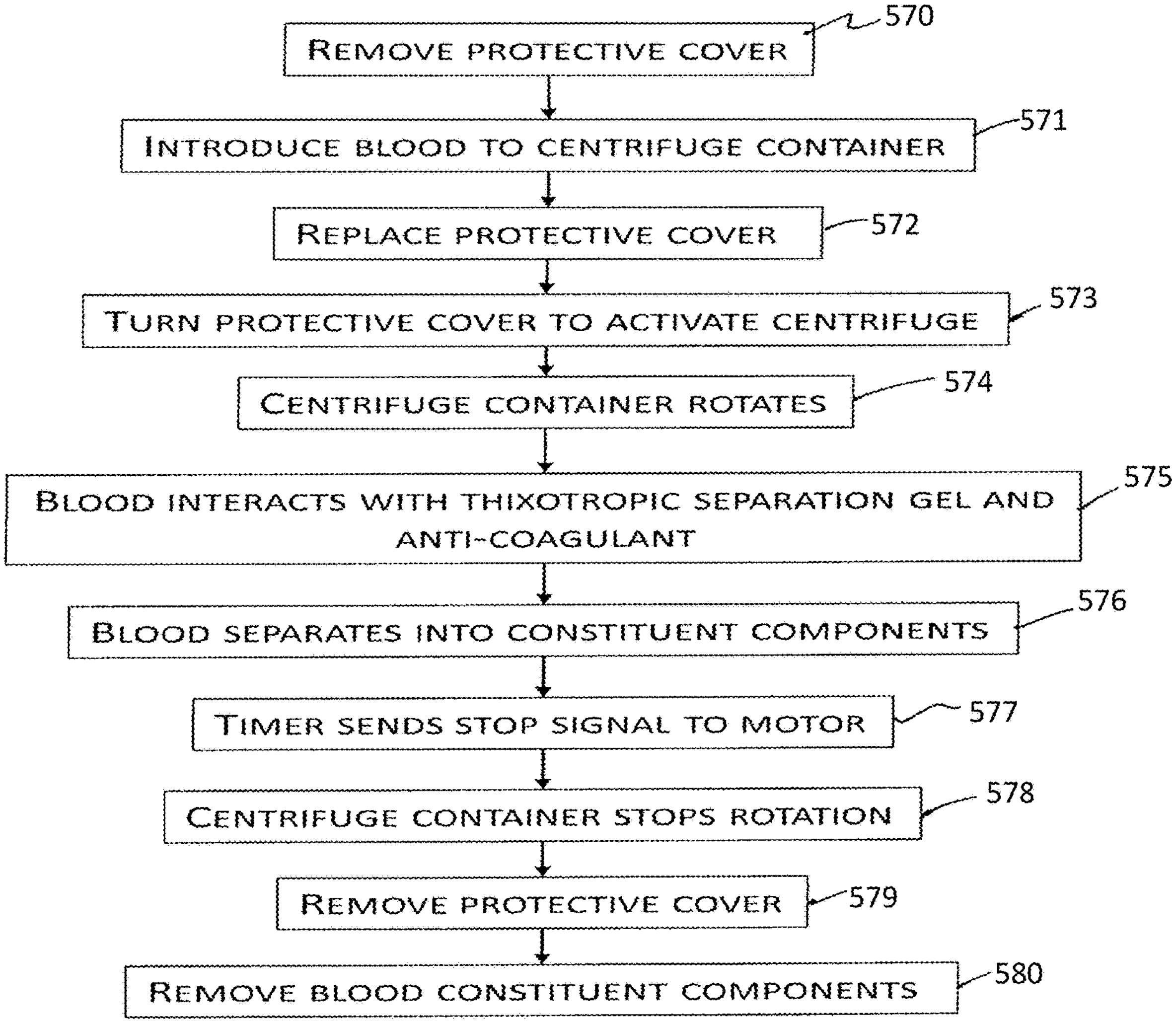
FIG. 88 depicts a method of blood centrifugation using the centrifuge of FIG. 44.
Figure 89:
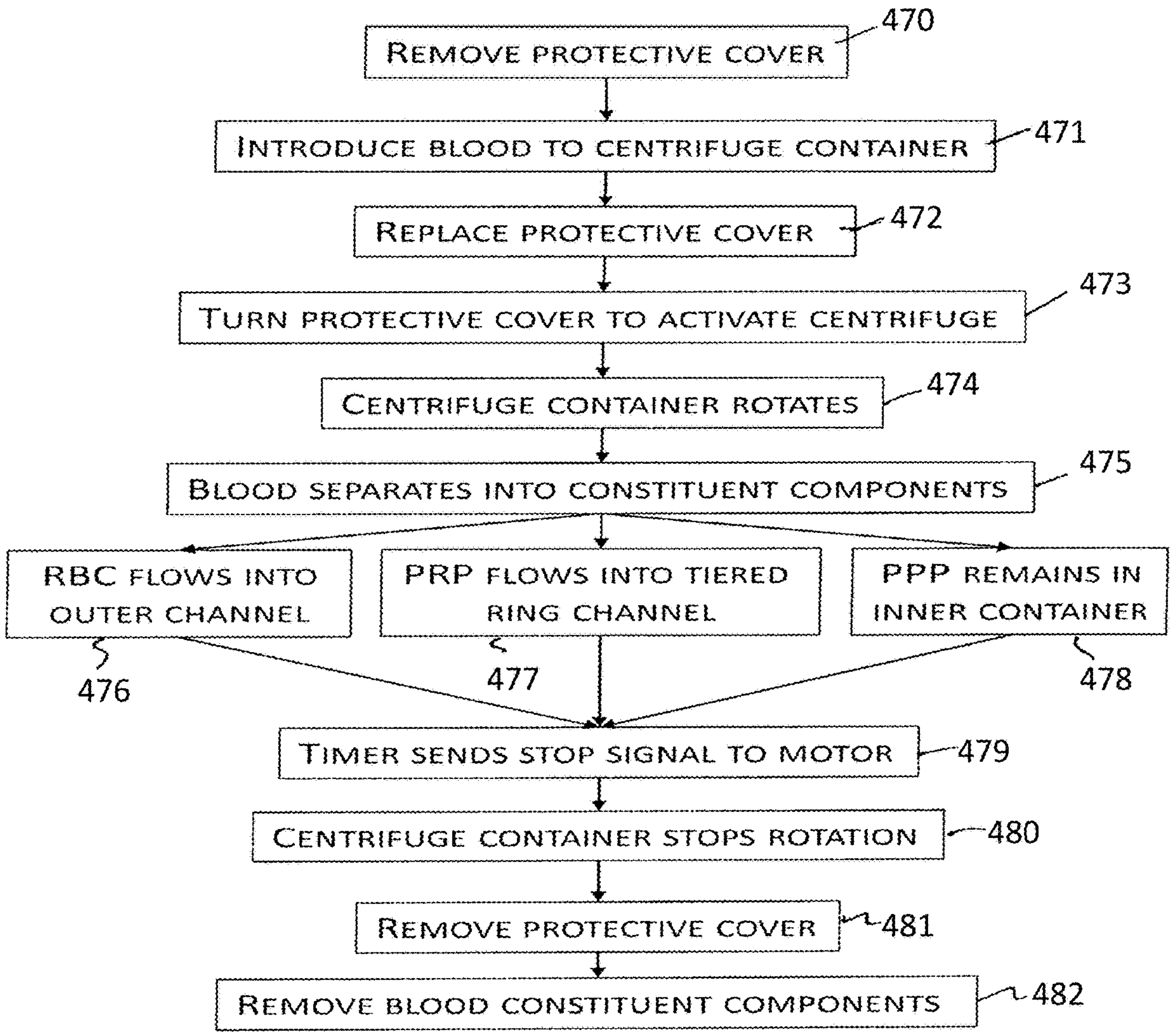
FIG. 89 depicts a method of blood centrifugation using the centrifuge of FIG. 74.
Figure 90:
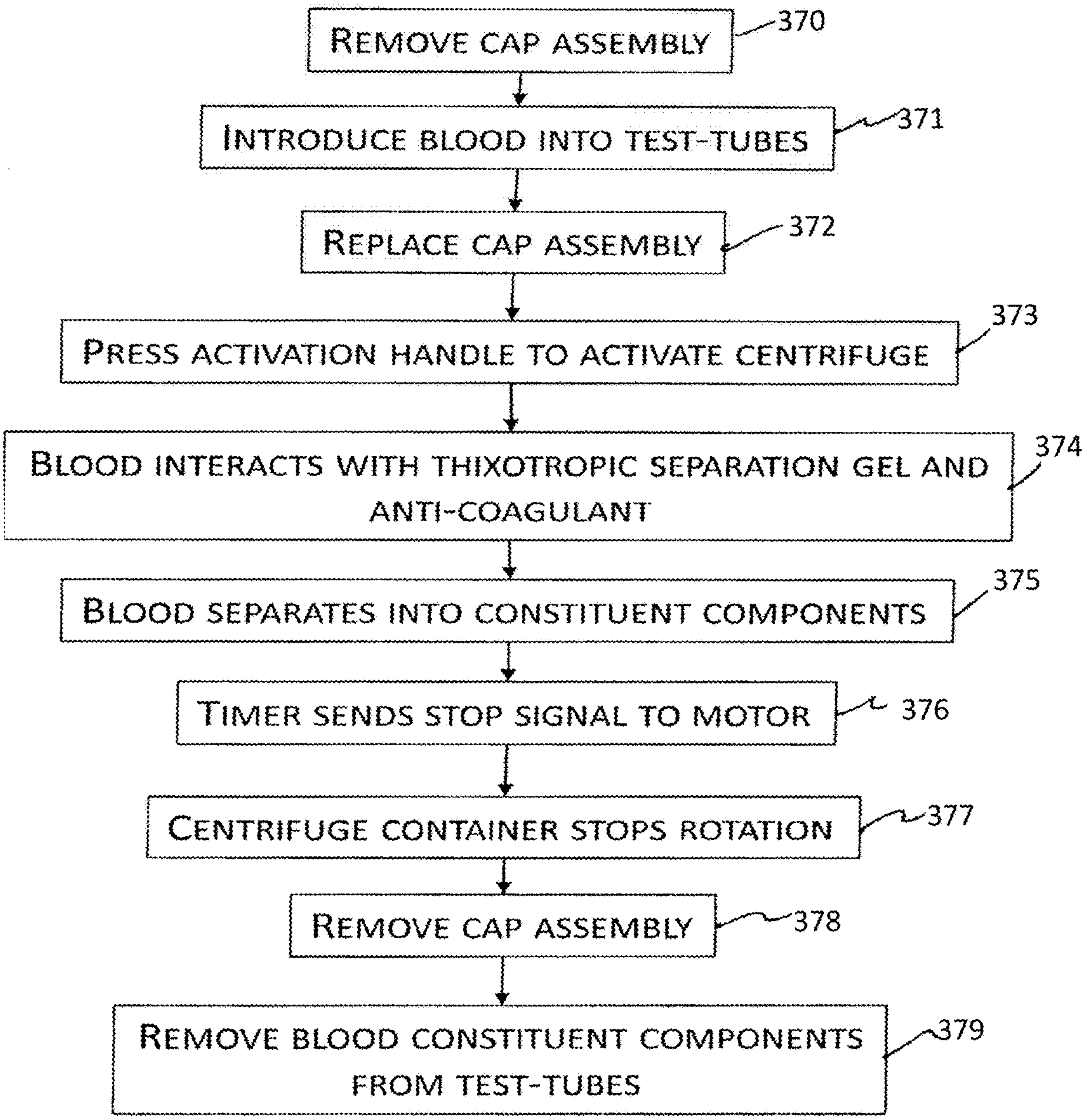
FIG. 90 depicts a method of blood centrifugation using the centrifuge of FIG. 45.

With reference to FIGS. 76-86, the centrifuge container 430 has a centrifuge cover 404 and tiered separation wheel or sequester device 405. The centrifuge cover 404 may be, for example, a disc with a top side 436 and a bottom side 435, with a centrifuge cover sidewall 437 extending away from the disc to a first end forming a ring or tube that is open or hollow at the first end. The centrifuge cover 404 further comprises a top end, a bottom end, an external or outer surface 437*a*, and/or an internal or inner surface 437*b*. The bottom end of the centrifuge cover 404 comprises an opening 437*c*, the centrifuge cover rim or edge connector 423 is adjacent to the opening 437*c* and/or the centrifuge cover rim or edge connector 423 surrounds the perimeter or the circumference of the opening 437*c*. The disc 436 is adjacent to the top end of the centrifuge cover 404. The centrifuge container 430 may have, for example, a height of approximately 29 mm to 35 mm, and more specifically 32 mm, from the first end 423 to the bottom side 435. Several holes exist, extending from the top surface 436 to the bottom surface 435, including a plurality of extraction holes 407 and at least one insertion hole 402. The plurality of extraction holes 407 may have an extraction barrier 443 occluding the plurality of extraction holes 407. Two of extraction barrier 443 are used to cover the two sets of the plurality of extraction holes 407, as shown in FIG. 86. Another barrier (not shown) may also be placed to occlude insertion hole 402. The extraction barrier 443 may be, for example, circular or ovular, fabricated from a plastic polymer material, and penetrable using a sharp object like, for example, a syringe.

With reference to FIGS. 77-86, 96-97, 102A-1021, the sequester device 405 comprises a base ring or flange 414, a rim 415, an inner container or central opening 420 and a plurality of concentric rings or tubes 416, 417, 418, 419 in a tiered formation a sloped formation and/or tapered formation extending from the outer ring 416 towards the inner ring 419. More specifically, the tops of the plurality of rings being tallest on the outer ring 416 and then decreasing in height as one progressed inwardly, with the shortest being the inner ring 419. The tiered formation, sloped formation, and/or tapered formation comprises the first ring 416 having the tallest height and the fourth ring 419 having the shortest height as shown in FIGS. 82, 97 and 102D-102G. The plurality of concentric rings 416, 417, 418, 419 having a first end, and a second end. The second end adjacent to a surface or a bottom surface 658, 660, 662, the first end adjacent to the top surface 633 of the container cover or centrifuge cover 625 or bottom surface of the container cover or centrifuge cover 625. The first end comprising a tapered end or a drafted end, the tapered end or drafted end being a 0.5% to 3% tapering, and/or a 0.5% to 1.5% tapering. Desirably, the tapering produces a draft angle between 0.5 degrees to 5 degrees to facilitate easy release of molds during manufacturing, and also helps facilitation of the blood product during centrifugation to climb or scale the walls easily and deposit in the plurality of channels, 440, 441, 442. Alternatively, in one embodiment, the sequester device 405 comprises a first ring 416, a second ring 417, a third ring 418, and a fourth ring 419, and the rings 416, 417, 418, 419 are aligned concentrically and/or are aligned coaxially. The base ring or flange 414 is planar and surrounds the outer circumference of the first ring 416 adjacent to a bottom end of the sequester device 405. The base ring or flange 414 extends outwardly from the first ring 416. The base ring or flange 414 comprises a first or top surface 444*a* and a second or bottom surface 444*b*. The base ring or base flange 414 has a rim 415, with the rim 415 having a diameter of, for example, approximately 68 mm, and an outer diameter or outer surface 415*b*. The rim 415 extends upwardly from the base flange 414 and/or from a first or top surface 444*a* of the base flange 414 and surrounds the perimeter or circumference of the base flange 414. The rim 415 is spaced apart from the outer ring 416 to form a rim channel or rim spacing 415*a*. At least a portion of the bottom end of the centrifuge cover 404, 625, 704 engages with the rim channel 415*a*. Accordingly, at least a portion of the rim or edge connector 423 at the bottom end of the centrifuge cover 404, 625, 704 engages with the rim channel 415*a*. At least a portion of the rim channel 415*a* is designed and configured to receive a portion of the bottom end and/or the rim or edge connector 423 of the centrifuge cover 404, 625, 704.

In another embodiment, the sequester device 405 comprises a central opening or inner container 420, a fourth ring 419, a third ring 418 and a second ring 417; the fourth ring 419, the third ring 418 and second ring 417 are spaced apart and aligned concentrically to create a first channel 440, and a second channel 441. The second ring 417 having a larger or taller height than the fourth ring 419. Each of the channels 440, 441 having a surface or a bottom surface 658, 660, 662 to hold blood products in a volume. At least a portion of the central opening or inner container 420 comprising a coating. The coating may comprise anticoagulants, preservatives, disinfectants or germicidal agents or pathogen reduction agents or pathogen inactivation agents, sterilants, antiseptics, clot activators, separator gels.

Figure 102A:
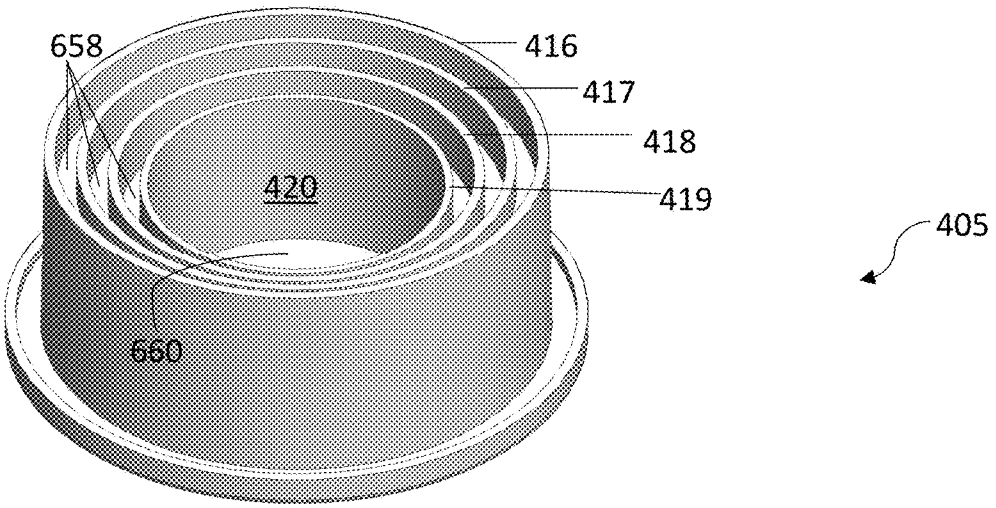
Figure 102B:
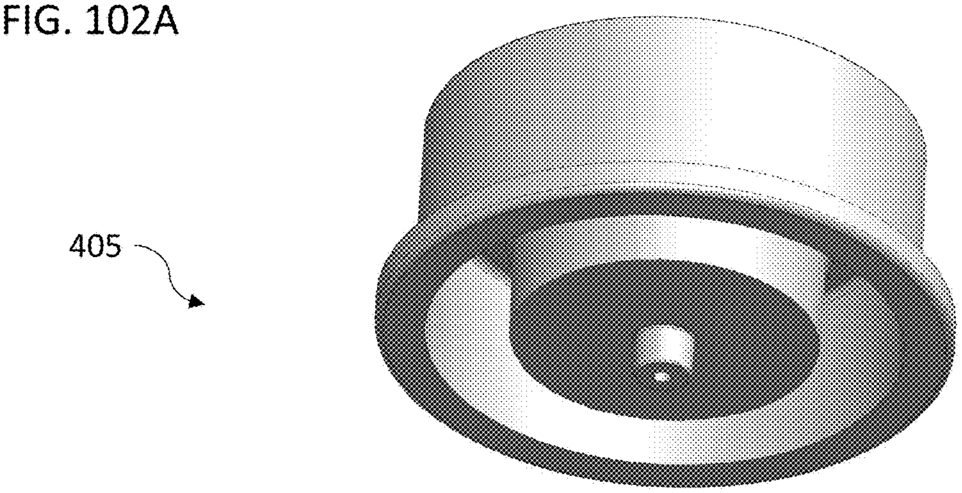
Figure 102C:
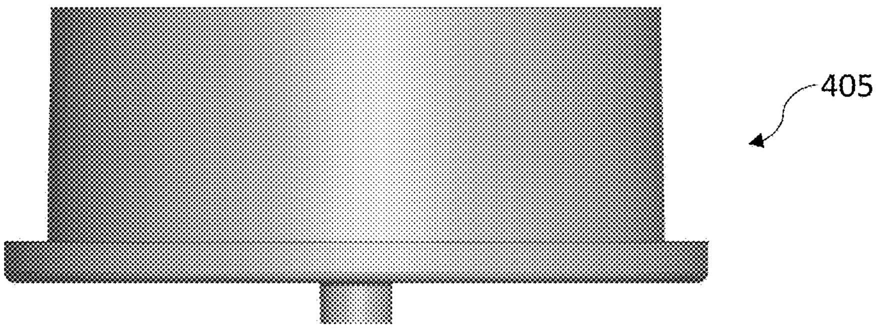
Figure 102D:
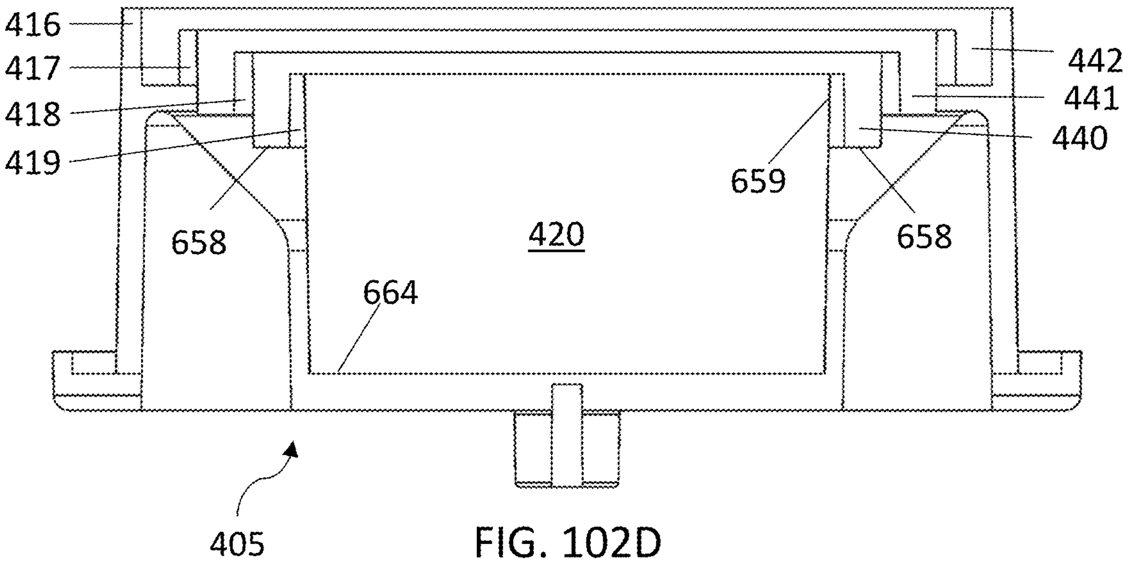
Figure 102E:
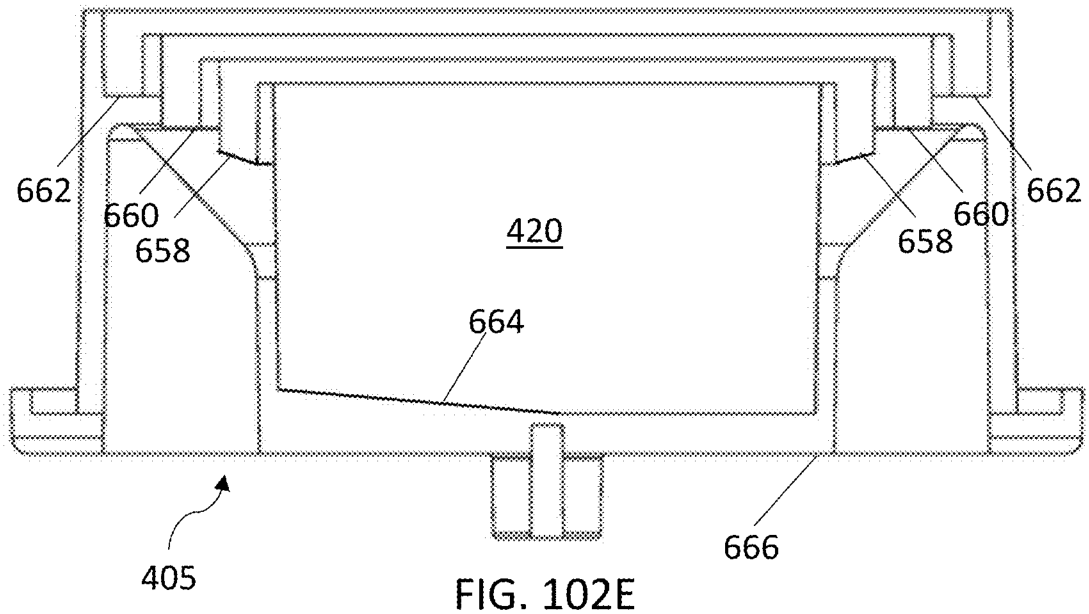
Figure 102F:
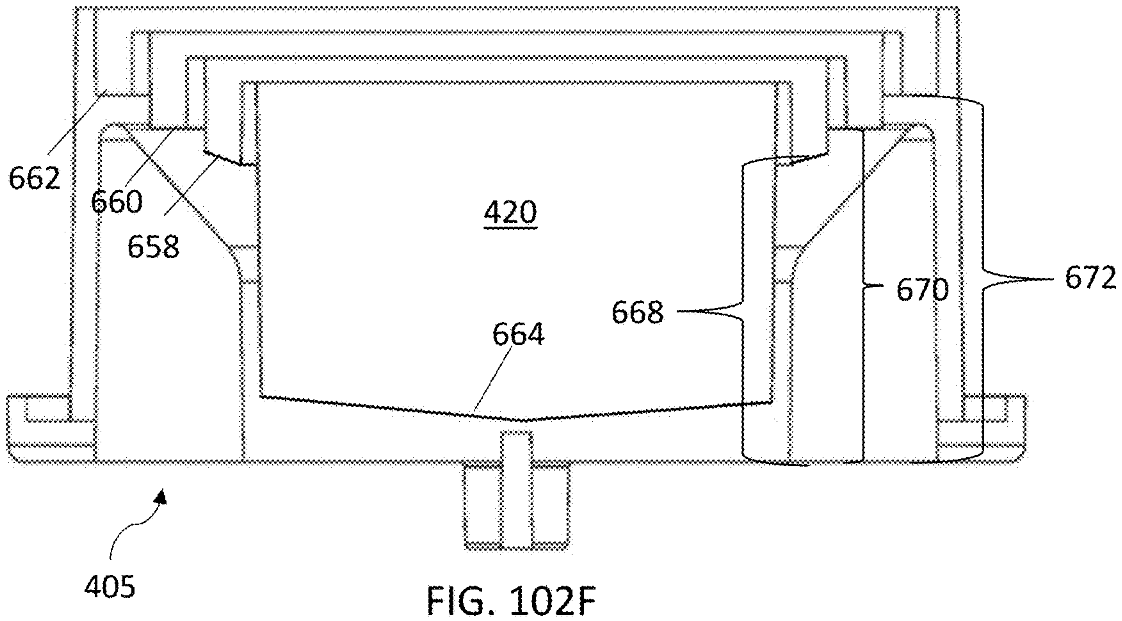
Figure 102G:
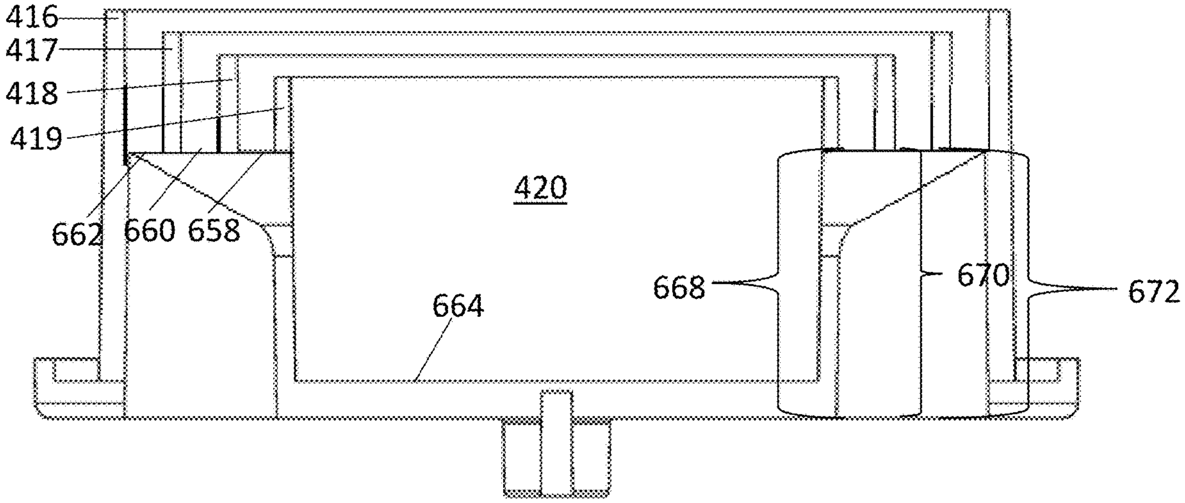
Figure 102H:
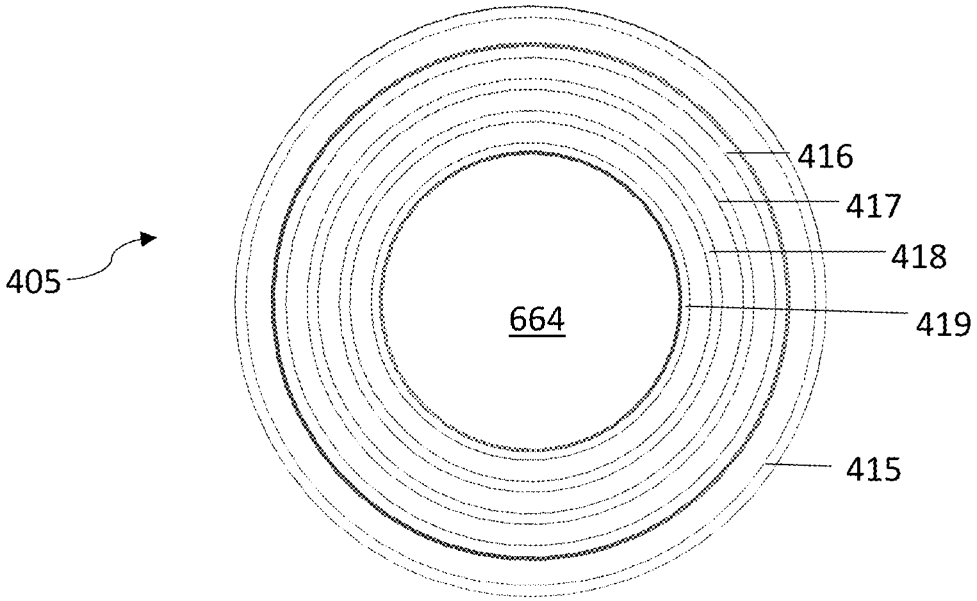
Figure 102I:
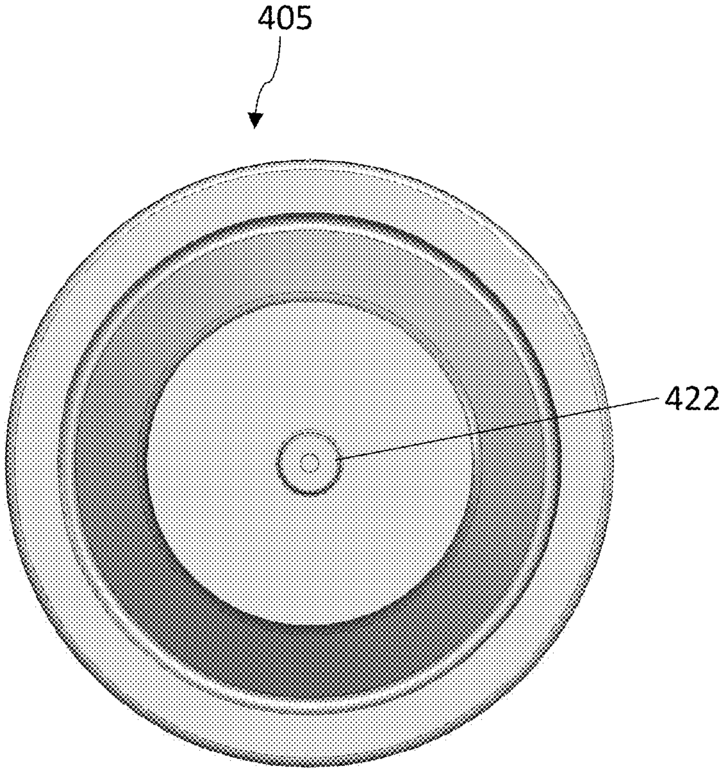

The first ring 416, the second ring 417, the third ring 418 are spaced apart from each other creating a first channel 440, a second channel 441, and a third channel 442. Each of the first channel 440, the second channel 441, and the third channel 442 comprising a bottom surface and/or connecting material 658, 660, 662. The bottom surface and/or connecting material 658, 660, 662 comprises a flat, planar surface or an angled and/or sloped surface. The angled or sloped surface includes an angle within the range of 1 degree to 10 degrees; or 1 degree to 5 degrees. The angle or sloping may be in a direction towards the central axis. The bottom surface or plurality of bottom surfaces 658,660,662 may be positioned at different heights 668,670, 672 from the bottom surface of the sequester wheel or device 405 resulting in a portion of the plurality of concentric rings 416, 417, 418, 419 having the same height as shown in FIG. 102F. Alternatively, the bottom surface or plurality of bottom surfaces 658,660,662 may be positioned at the same heights 668, 670, 672 from the bottom surface of the sequester wheel or device 405 resulting in a portion of the plurality of concentric rings 416, 417, 418, 419 having the different heights as shown in FIG. 102G.

Alternatively, the plurality of concentric rings 416, 417, 418, 419 each have connecting material 658,660, 662 forming a plurality of channels, with, for example, the third ring 418 and the fourth ring 419 forming a first channel 440, the second ring 417 and the third ring 418 forming a second channel 441, and the first ring 416 and the second ring 417 forming a third channel 442. The first channel 440, second channel 441, and the third channel 442 may, for example, be sized to have a volume of 1 ml to 2 ml, and more specifically a volume of 1.5 ml. The outer surface of the first ring 416 extends away from the top of the first ring towards a bottom where a sequester device base ring or base ring 414, extends approximately perpendicular from the first ring 416 in a concentric formation with the plurality of rings. At an outer circumference, the base ring or base flange 414 has a rim or connection edge 415, with the rim 415 having a diameter of, for example, approximately 68 mm. The fourth ring 419 has a top and a bottom, with the bottom area of the fourth ring 419 being enclosed and forming an inner bowl or inner container 420, having for example, a diameter of approximately 36 mm to 38 mm, and more specifically a diameter of 38 mm. The inner container 420 may have, for example, a volume of approximately 20 ml. The inner container 420 may comprise a cylindrical or circular wall 659 and a bottom surface 660. The bottom surface 660 may comprise a flat, planar surface (see FIG. 102D) and/or have a sloped or angled surface (see FIG. 102E-102F). The angled or sloped surface includes an angle within the range of 1 degree to 10 degrees; or 1 degree to 5 degrees. The angle or sloping may be in a direction towards the central axis. The angle or sloping may include a direction that is unidirectional (see FIG. 102E) or multi-directional or radial (e.g., where the sloping resembles a cone shape) (see FIG. 102F).

With reference to FIGS. 106, 107A-107B, 108A-108C, 109A-109B, 110A-110B, 111A-111E, the sequester device 706 comprises at least one concentric ring 419 that creates an inner container or central opening 420. The sequester device 706 may further a plurality of concentric rings 416, 417, 418, 419, which at least one of the plurality of concentric rings 416, 417, 418, 419 creates an inner container or central opening 420. The sequester device 706 further comprises a base ring 722, the base ring722 comprises a rim 415. The base ring 722 comprises a circular shape, a top surface 725 and a bottom surface 727. Other shapes may include regular polygons, such as a triangle, a square, a pentagon, a hexagon, a septagon, an octagon and/or any other combination thereof. Alternatively, other shapes may include symmetrical polygons. The rim 415 surrounds the circumference of the base ring 722 and extends upwardly from a top surface 725 of the base ring 722 to create a rim height. The at least one concentric ring 419 is concentric with the central axis 723 of the base ring 722. The rim 415 comprises an inner diameter 729, the inner diameter 729 is sized and configured to receive a portion of the container cover 704. More specifically, the inner diameter 729 is sized and configured to receive an offset rim 728 of the container cover 704. The motor connector or armature hub 422 extends longitudinally away from the bottom surface 727 of the base ring 722.

The inner container 420 of the at least one concentric ring 419 may be sized and configured to receive an eye dispenser mechanism 712, 716 and/or a filter 714. The eye dispenser mechanism 712 may comprise a pipette 716, a syringe, an eye dropper, and eye dropper with integral filter 720, a mechanical dispenser, and/or any dispensing mechanisms known in the art. For example, the filter 714 may comprise a blood serum filter, piston filter, a reagent filter and/or a pre-filter manufactured by POREX Filtration Group of Fairburn, GA. Alternatively, the filter 714 may comprise a HEMO-NATE blood filtration system manufactured by Utah Medical Products, Inc. of Midvale, UT and/or a standard cylindrical mesh with desired porosity or pore sizes (e.g. screen membranes). Such filters 714 removes small volumes of particulate debris to allow viable blood product to be extracted with ease. Accordingly, the pipette 716 and/or syringe may include a general-purpose transfer pipette or syringe for routine extraction of blood, blood components and/or any other biological fluids. The pipette 716 and/or syringe may hold different capacities or volumes (1 ml to 10 ml).

The at least one of the concentric rings 419 comprising a first end, and a second end. The second end adjacent to a surface or a bottom surface 658, the first end adjacent to the bottom surface 732 of the container cover 704. The first end comprising a tapered end or a drafted end, the tapered end or drafted end being a 0.5% to 3% tapering, and/or a 0.5% to 1.5% tapering. Desirably, the tapering produces a draft angle between 0.5 degrees to 5 degrees to facilitate easy release of molds during manufacturing, and also helps facilitation of the blood product during centrifugation to climb or scale the walls easily and deposit in the plurality of channels and/or cavity.

With continued reference to FIGS. 77-86, on a second side 445, the sequester device 405 has a base ring 414 and a motor connector or armature hub 422, extending from the underside of the inner container 420. The armature hub 422 may, for example, form an axis passing through the concentric center of the base ring 414, the first ring 416, the second ring 417, the third ring 418, and the fourth ring 419. There may be, for example, a channel between the base ring 414 and the underside of the inner container 420. The first ring 416, may be, for example, 24 mm to 28 mm, extending from the base ring to the top of the first ring 416, and more specifically 25 mm. The first ring 416 may have, for example, a diameter of 58 mm to 61 mm, and more specifically 61 mm. The second ring 417 may, for example, have a diameter of approximately 50 mm to 53 mm, and more specifically a diameter of 53 mm. The third ring 418 may, for example, have a diameter of approximately 43 mm to 46 mm, and more specifically a diameter of 46 mm.

With continued reference to FIGS. 77-86, the sequester device 405 has a slope, for example, of approximately between 5° and 45°, and more specifically a slope of approximately 20°. The height difference between each tier of the first ring 416, the second ring 417, the third ring 418, and the fourth ring 419, may be, for example, from 1.5 mm to 2 mm. The inner container 420 may have a height of, for example, approximately 20 mm from the bottom to the top of the fourth ring 419. The third ring 418 may be, for example, 2 mm above the fourth ring 419, and may have, for example, an approximate depth of 6 mm to the first channel 440 bottom. The second ring 417 may be, for example 2 mm above the third ring 418 and may have, for example, an approximate depth of 6 mm to the second channel 441 bottom. The first ring 416 may be, for example 2 mm above the second ring 418 and may have, for example, an approximate channel depth of 6 mm to the third channel 442 bottom.

The plurality of rings 416, 417, 418, 419 and/or the at least one concentric ring 419 comprises a shape. The shape includes a circle. The shape can further include regular polygons, such as a triangle, a square, a pentagon, a hexagon, a septagon, an octagon and/or any other combination thereof. Alternatively, other shapes may include symmetrical polygons. The shape of the plurality of rings 416, 417, 418, 419 may be the same or it may be different. The shape of each of the plurality of rings 416, 417, 418, 419 may be the same or it may be different.

With reference to FIGS. 74-78, the centrifuge cover 404 is connected with the sequester device 405 with outer rim 415 and the cover connector 423 engaged and/or sealed, creating a liquid impermeable connection, and forming the centrifuge container 430. The centrifuge cover may be, for example, cylindrical and have an axis between the center of sequester device 405 and a center of the centrifuge cover 404. A fourth channel 412 is created between the inner side of the sidewall 437 and the outer wall of the first ring 416, with the base ring 414 providing a channel bottom. The fourth channel 412 may have, for example, a volume of 10 ml to 11 ml and more specifically, a volume of 11 ml. Each of the first channel 440, the second channel 441, the third channel 442, and the fourth channel 412 may be aligned with one of the pluralities of extraction holes 407. The centrifuge container 430 may be, for example, connected to the rotational mechanism 330, with the motor armature 161 and the armature hub 422, connected having coaxial alignment and rotatable about the common axis 465. The common axis 165 may be, for example, the rotational axis of the armature 161. Clearance between the bottom of the base ring 414 and the base cover 102 may range from, 1 mm to 3 mm, and more specifically, approximately 2 mm. The protective cover 403 may be placed over centrifuge container 430, with activation tab 408 placed into activation slot 407 and into activation slider slot 156. There may be, for example, clearance between centrifuge container 430 and protective cover 403, with the clearance ranging from 1 mm to 3 mm, and more specifically, approximately 3 mm.

With reference to FIGS. 74-86 and 89, the method of use for the centrifuge 400 includes, removing the protective cover 470. Blood may then be introduced into the centrifuge container 471. Approximately, 30 ml of blood may be, for example, introduced into the centrifuge container 404 by a syringe, inserted through the insertion hole 402. The protective cover may then be replaced 472. Replacing protective cover 403 may include, inserting the activation tab 408 through activation slot 107 and into the activation slider slot 156. The protective cover may then be turned to activate the centrifuge 473. For example, as the protective cover 408 is turned, the conductive member 158 contacts the circuit members 159 and completed a circuit. A timer is triggered and the centrifuge container 430 may be, for example, rotated under the protective cover 403 by the motor 154 at, for example, approximately 10,000 rpm to 25,000 rpm, and more specifically at 20,000 rpm. The blood may separate into constituent components 475, with RBC flowing into the outer channel 476, PRP flowing into the tiered ring channels 477, and PPP may remain in the inner container 478. The blood may, for example, separates into constituent columns, with the RBC approximately in a column towards the sidewall 437 and above the fourth channel 412, the PRP approximately in a column above the first through third channels (e.g. the first channel 440, the second channel 441, and the third channel 442), and a PPP column approximately remaining within the inner container 420. A timer may send a stop signal to the motor 479 and the centrifuge container may stop rotation 480. As the timer opens the circuit and the centrifuge container 430 slows to a stop, the separated columns may, for example, fall or flow into their respective close-proximity channels, with the RBC column falling or flowing into the fourth channel 412, the PRP column falling or flowing into the first through third channels (e.g. the first channel 440, the second channel 441, and the third channel 442), and the PPP remaining in the inner container 420. The PRP may have, for example, a gradient of concentrations between the first channel 440 and the third channel 442.

With continued reference to FIGS. 74-86 and 89, the centrifuge container may stop rotation 480. The brake 401, may be, for example pressed, to make contact with the centrifuge container top side 436, using frictional contact to slow or stop the centrifuge container 430 from spinning. When the centrifuge container 430 stops, the protective cover 403 may be removed 481. The constituent components of blood may then be removed 482. The desired blood component (e.g. RBC, PRP, and PPP) may then be, for example, removed using a syringe (not shown) through one of the plurality of extraction holes 407, by piercing the extraction barrier 443, with a sharp object, such as, for example a syringe.

It is contemplated that the sequester wheel 405 of the centrifuge 400 may have, for example, one channel to five channels.

With reference to FIGS. 91-100, 106, 107A-107B, 108A-108C, 109A-109B and 113A-113B, another embodiment of a portable centrifuge 600,700, 738,744 is shown. The portable centrifuge 600,700,738,744 comprises a protective cover 601,702, a container cover 625,704,740,746 and a sequester wheel or sequester device 405,706, and a base 708,730,742. The base 708,730,742 comprises a rotational mechanism 110, 330, 650, a base plate 101, and a base cover 102. The portable centrifuge 600,700,738,744 may further comprise an eye dispensing mechanism, the eye dispensing mechanism includes a serum or plasma filter 714, a pipette or eye dropper 716, and/or an filtered eye dropper 718. The portable centrifuge 600,700,738,744 may further comprise a microfluidic mechanism.

The entire portable centrifuge 600,700,738,744 can be completely sterile, and single use. If the entire portable centrifuge is single use, the entire portable centrifuge is used once and then disposed appropriately. Alternatively, a portion of the entire portable centrifuge 600,700,738,744600, 700 can be sterile, and single use. If a portion of the portable centrifuge 600,700,738,744 is single use, a portion of the portable centrifuge 600,700 is used only once then discarded appropriately, and the remaining portion may be re-used again. In one embodiment, a portion of the portable centrifuge 600,700,738,744 comprises the sequester device 405, 706 and the container cover 625,704,740,746 being single use, and the protective cover 601,702 and the base re-useable. In another embodiment, a portion of the portable centrifuge 600,700,738,744 comprises the sequester device 405,706, the container cover 625,704, 740,746 and protective cover 601,702 being single use, and the base re-useable.

The base 708,730,742 of the centrifuge 600,700,738,744 comprises a rotational mechanism 650 disposed on a baseplate 101 which is enclosed within base cover 102 as shown in FIGS. 95-99 and 106, 107A-107B, 108A-108C, 109A-109B, 113A-113B. As rotational mechanisms 110 and 330 have already been described in detail herein, for the sake of brevity, rotational mechanism 650 will be described to include additional embodiment elements. The centrifuge 600,700 further has a protective cover 601,702 and container cover 625,704,738,744.

Figure 91:
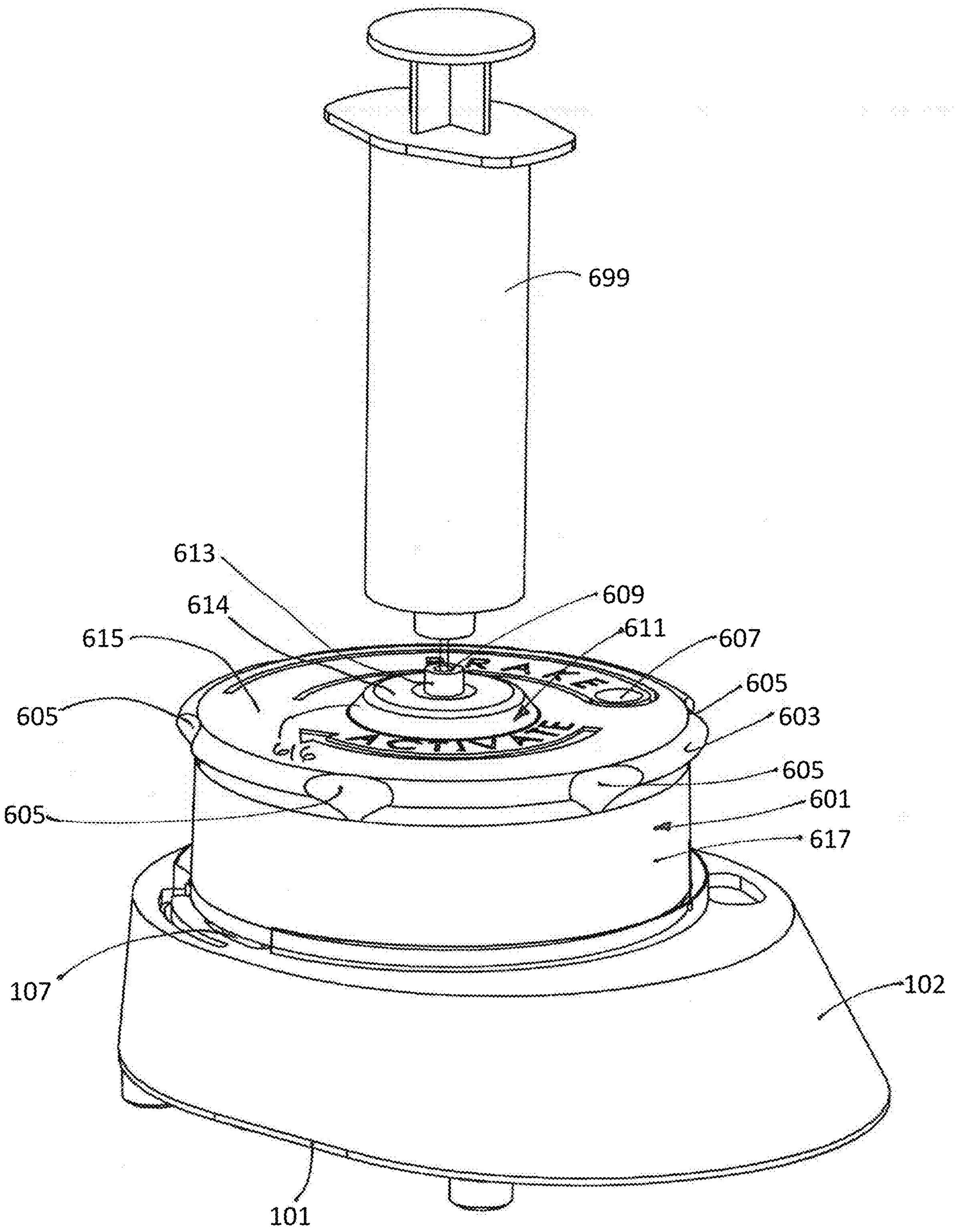
FIG. 91 is a top perspective view of an alternate embodiment of a centrifuge.
Figure 92:
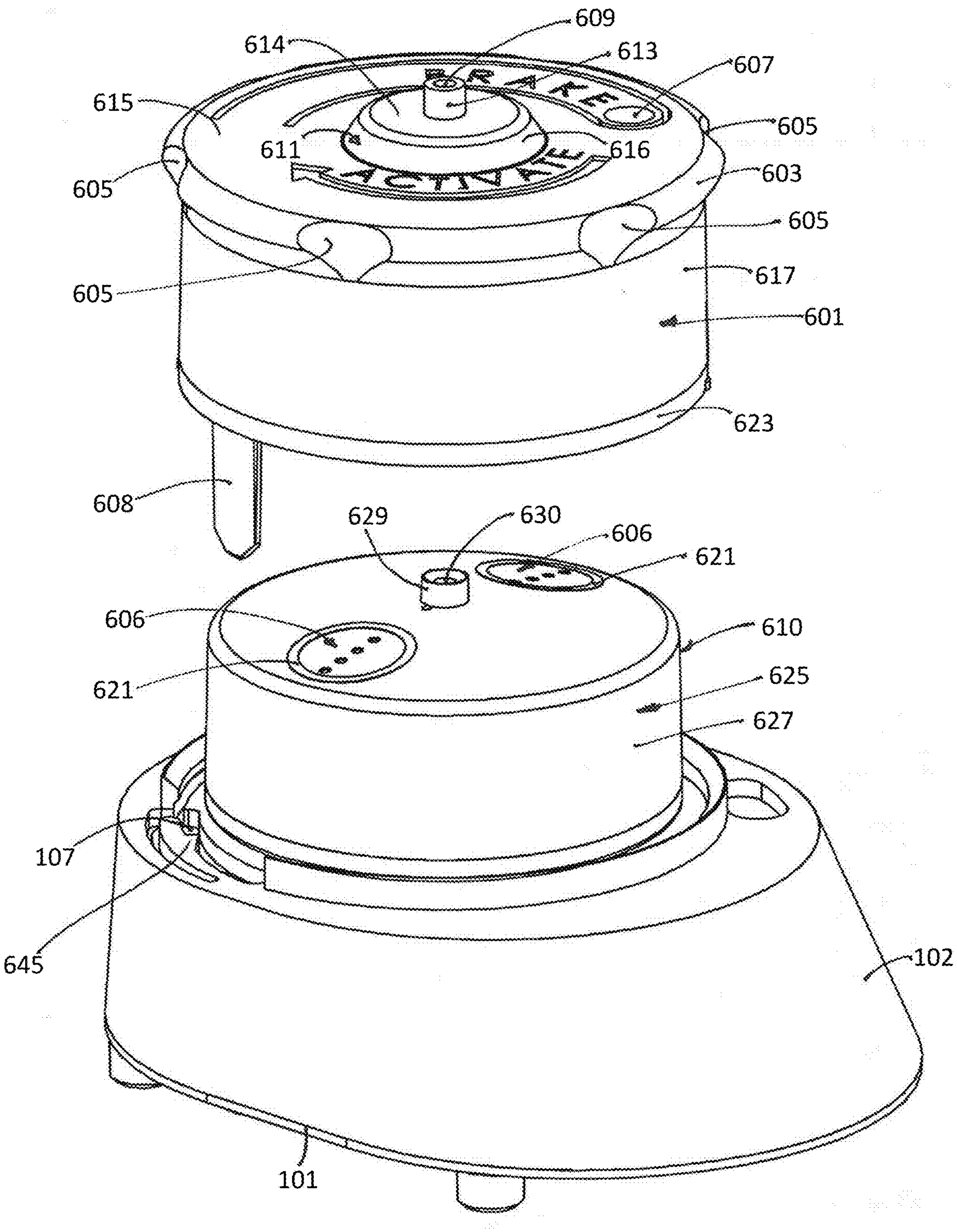
FIG. 92 is a top perspective view of the centrifuge of FIG. 91 with the protective cover removed.
Figure 106:
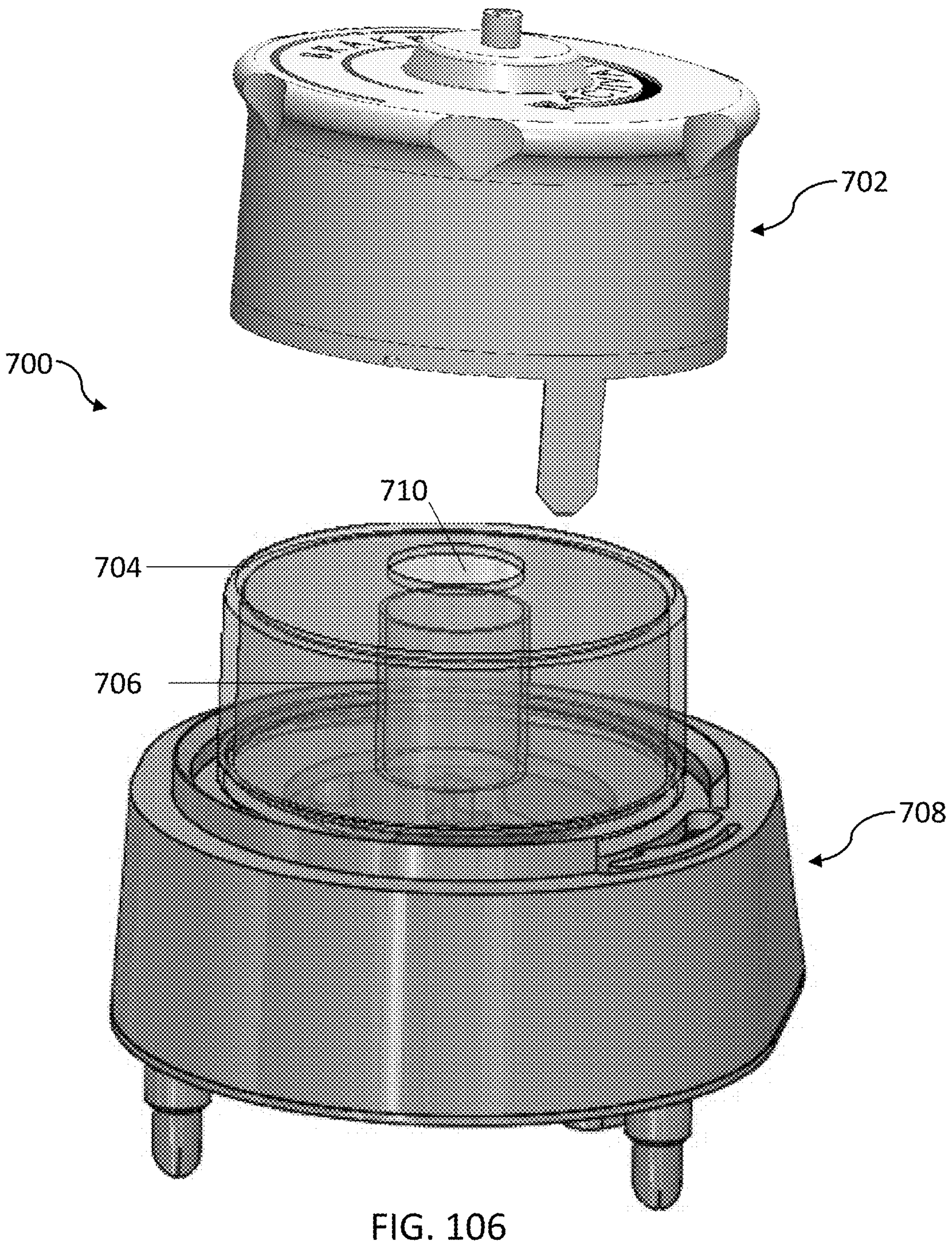
FIG. 106 depicts an alternate embodiment of a portable centrifuge device.
Figure 107A:
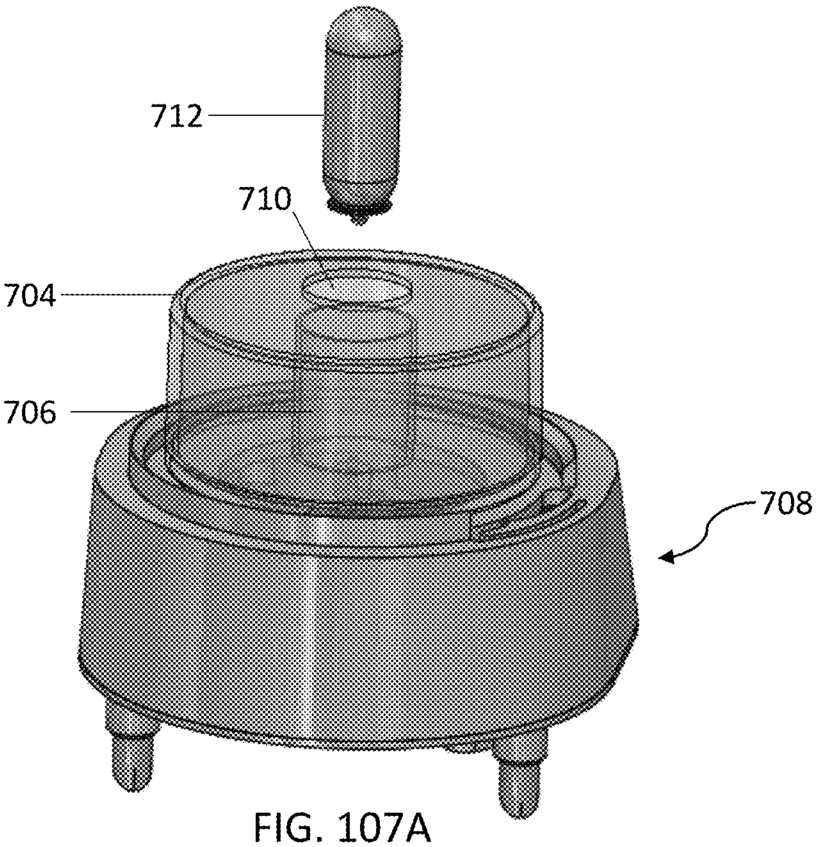
FIGS. 107A-107B depicts one embodiment for a method of extraction using a portable centrifuge device.
Figure 107B:
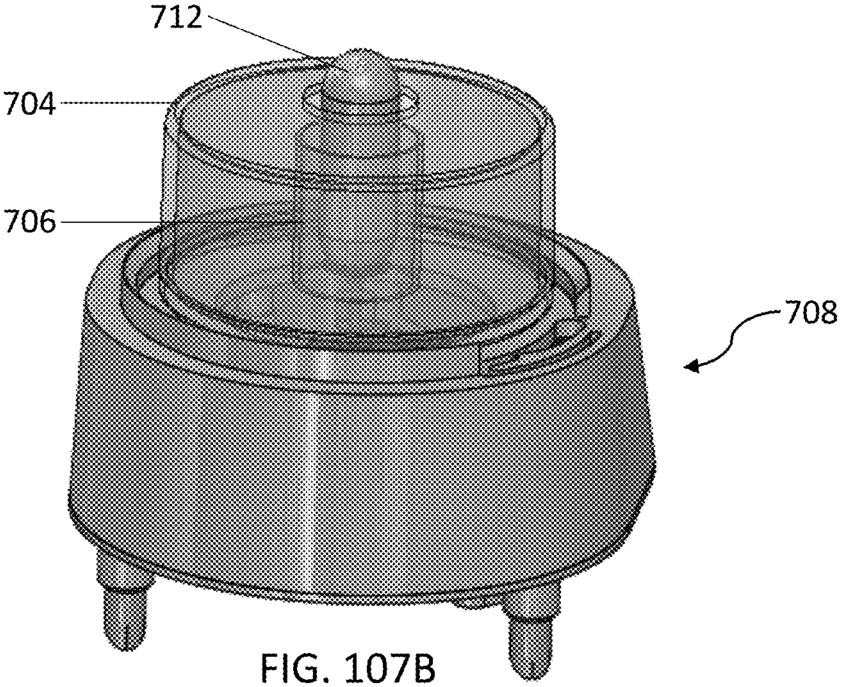
Figure 108A:
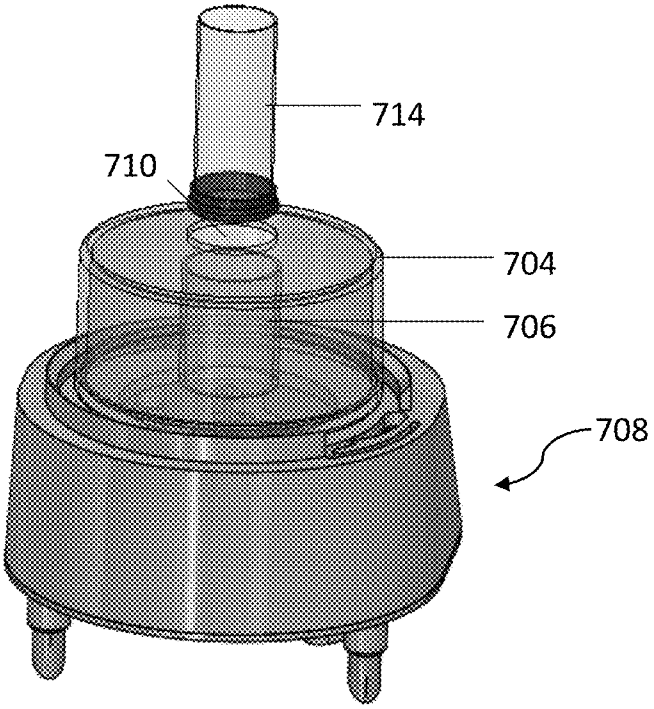
FIGS. 108A-108C depicts an alternate embodiment for a method of extraction using a portable centrifuge device.
Figure 108B:
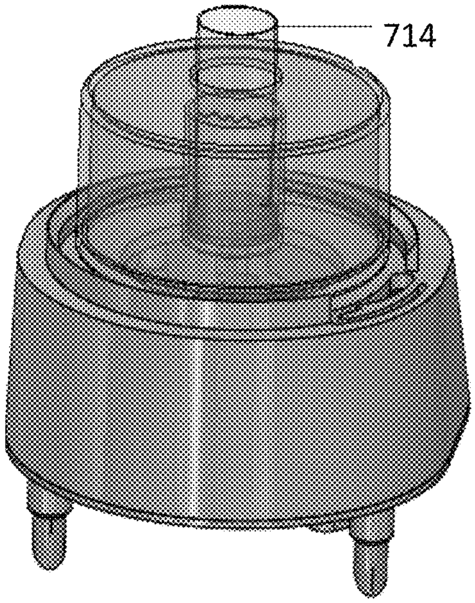
Figure 108C:
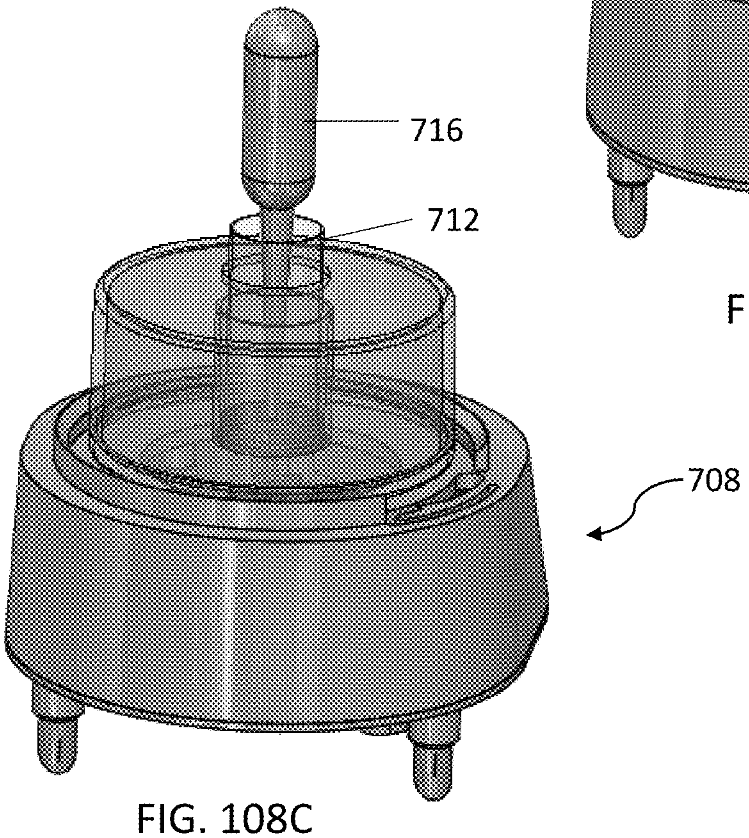
Figure 109A:
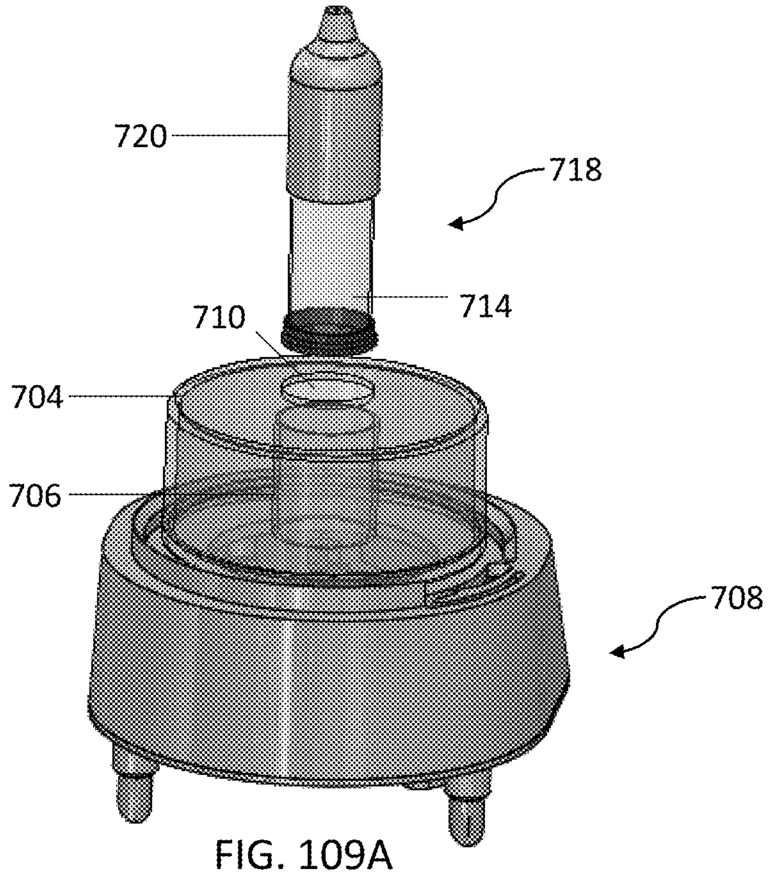
FIGS. 109A-109B depicts an alternate embodiment for a method of extraction using a portable centrifuge device.
Figure 109B:
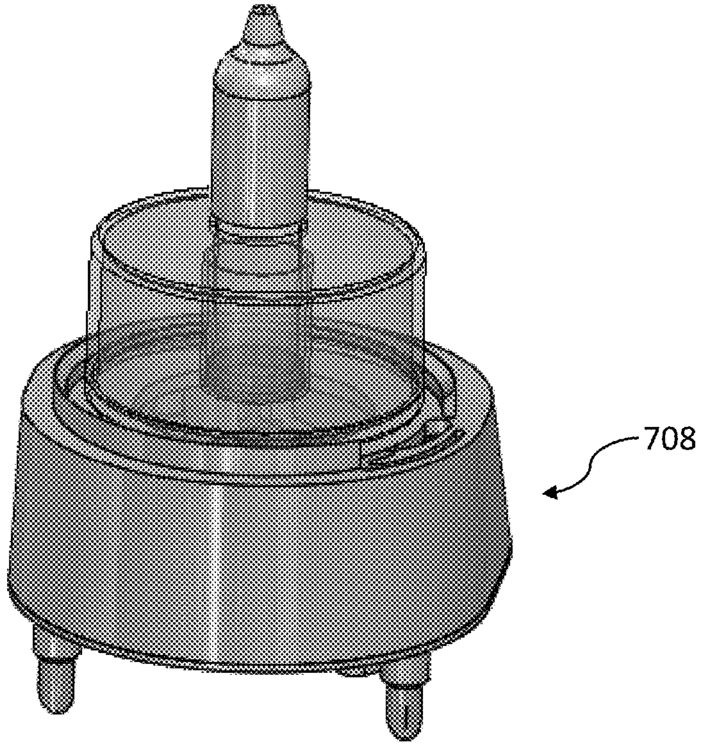
Figure 110A:
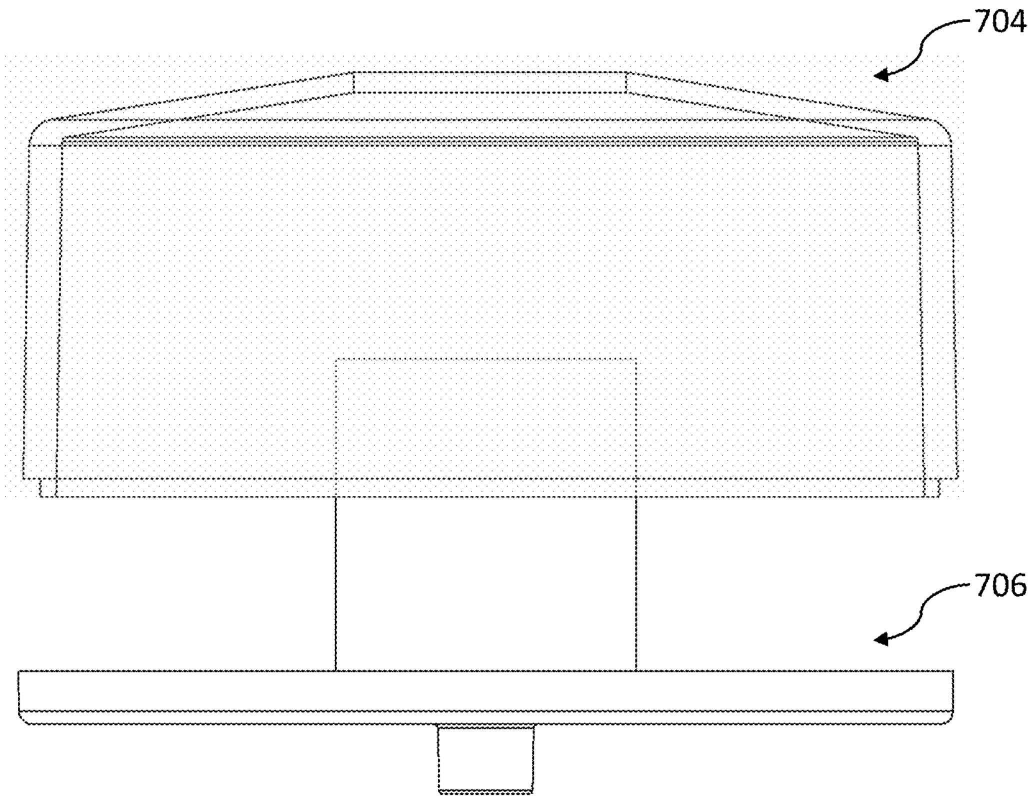
FIGS. 110A-110B depicts one embodiment of a sequester wheel and a container cover.
Figure 110B:
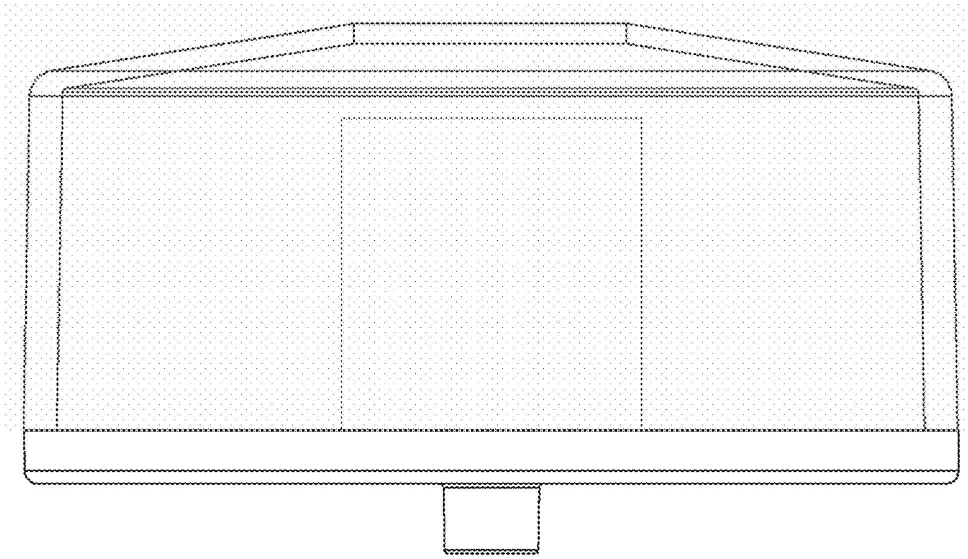
Figure 111A:
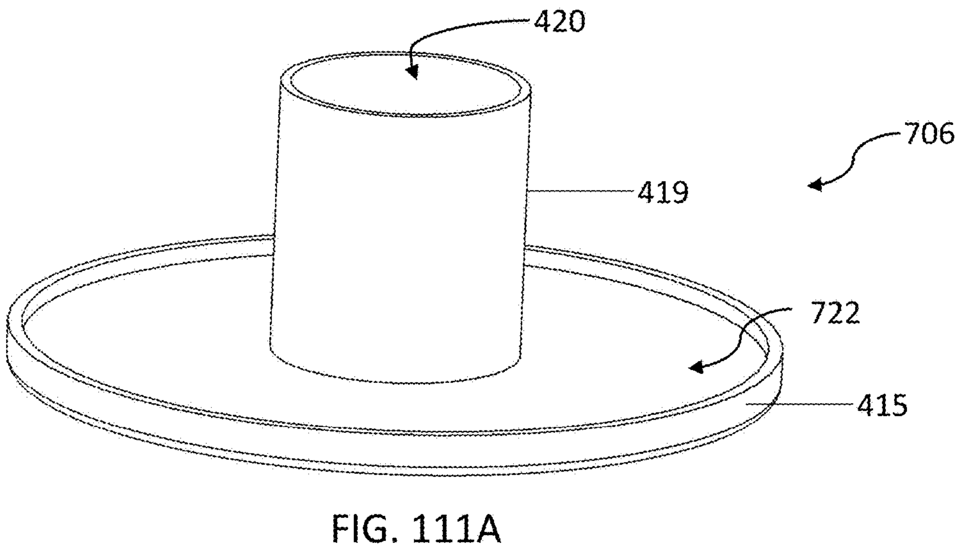
FIGS. 111A-111E depicts various plan views of an alternate embodiment of a sequester wheel or device.
Figure 111B:
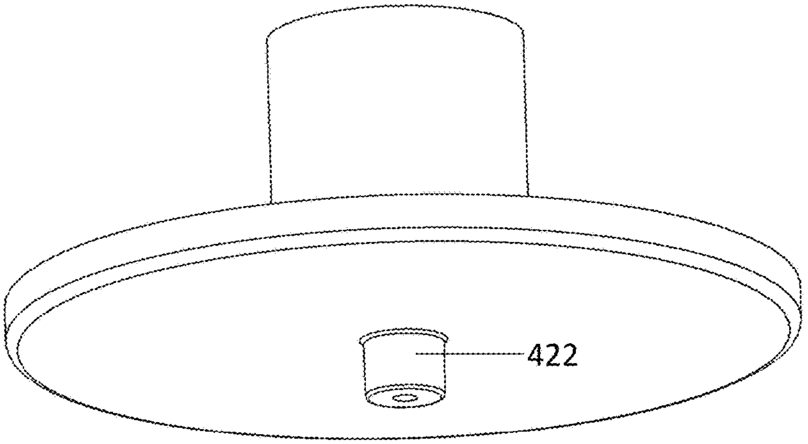
Figure 111C:
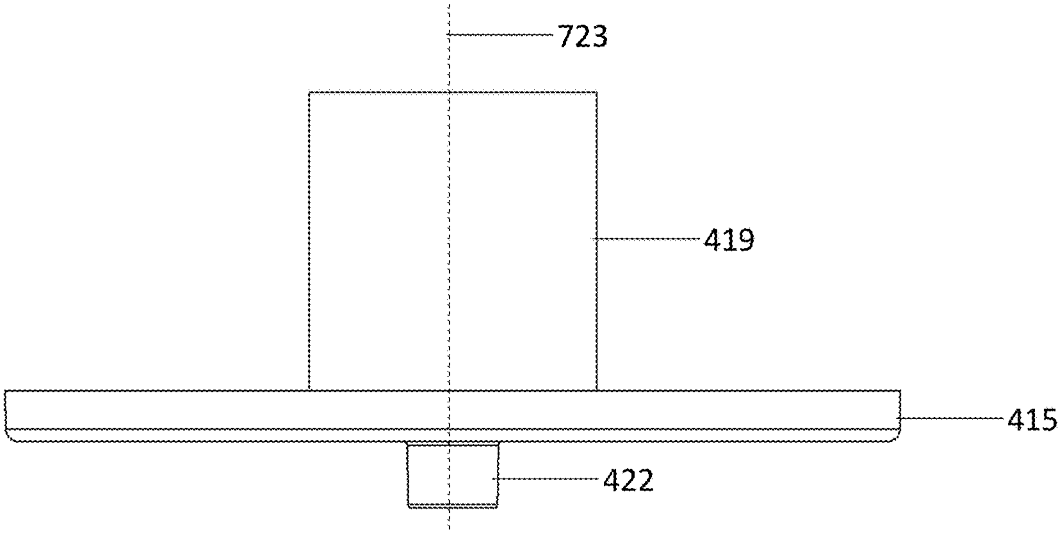
Figure 111D:
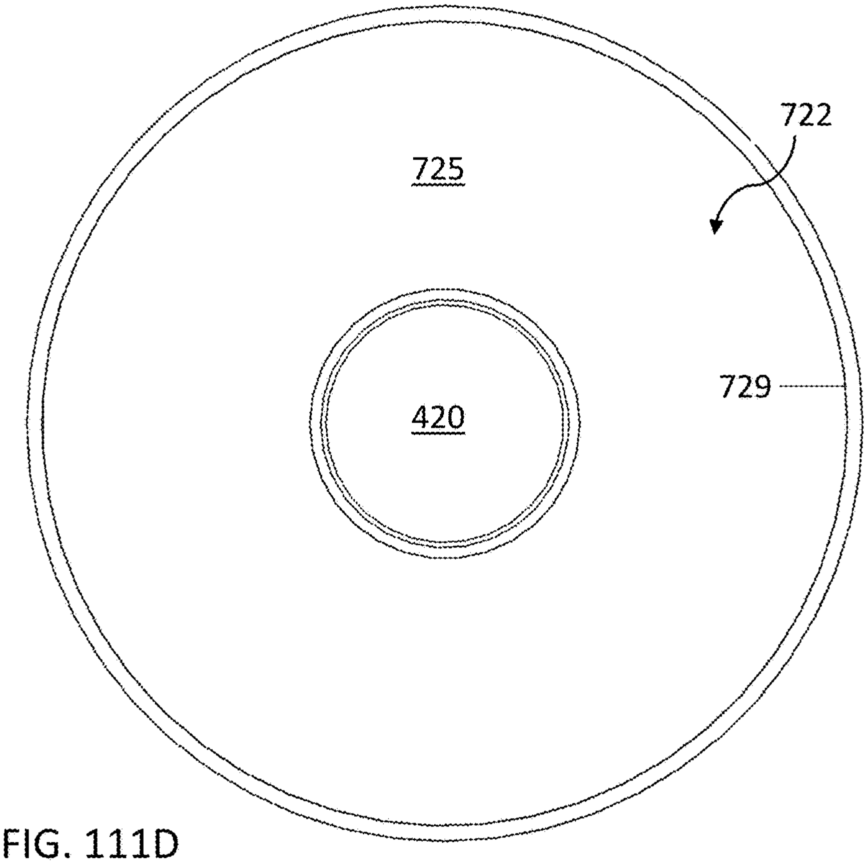
Figure 111E:
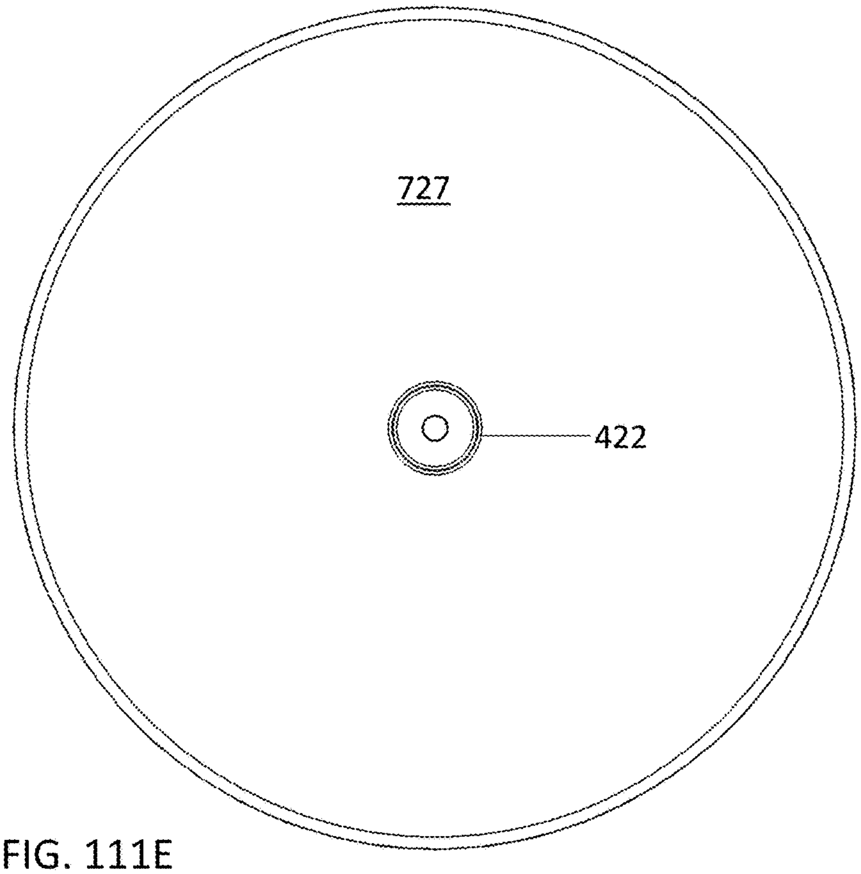
Figure 112A:
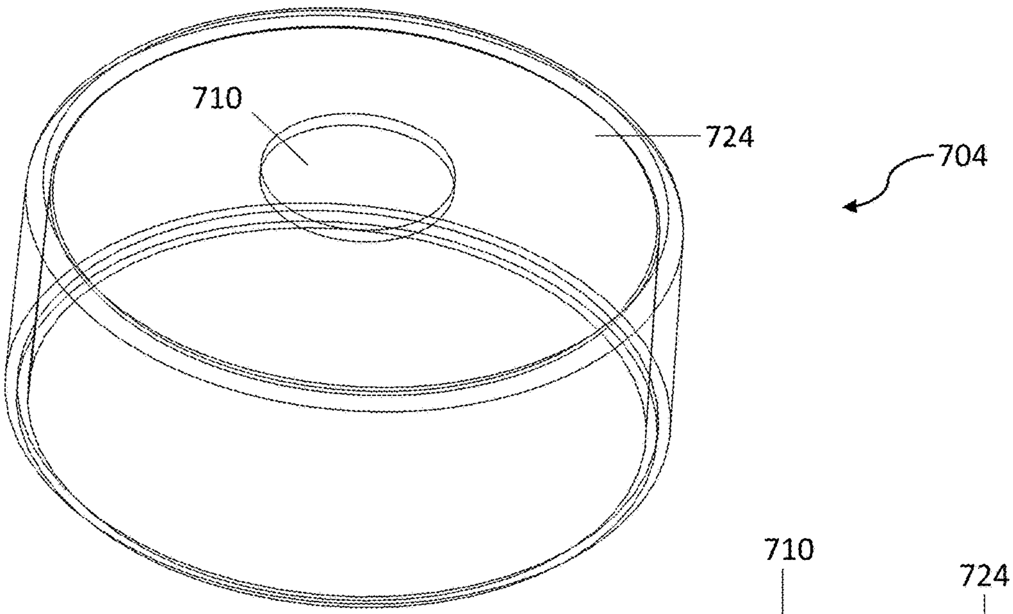
FIGS. 112A-112C depicts one embodiment of a container cover.
Figure 112B:
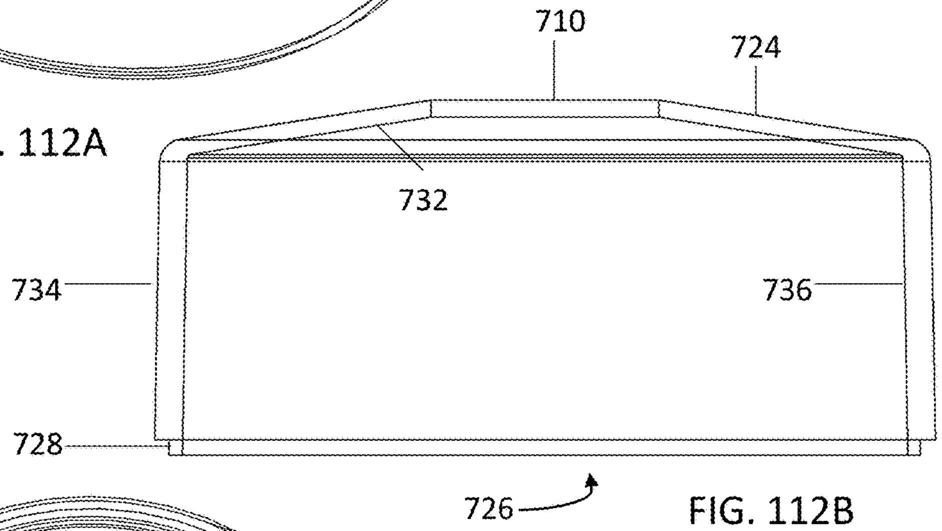
Figure 112C:
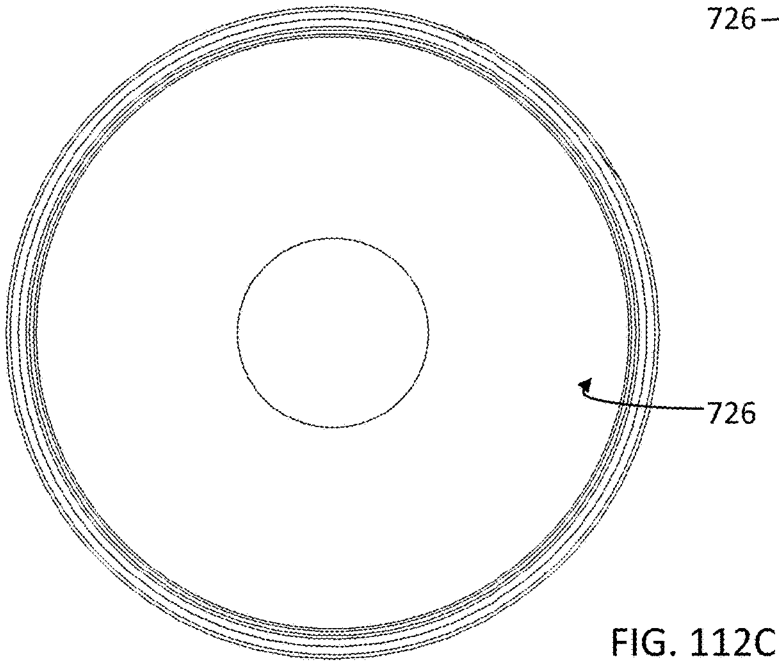

Referring to FIGS. 91-92 and 106, the protective cover 601,702 has a top surface 615 having an outer rim 603 with an external sidewall 617 extending in a direction away from the top surface 615. The top surface 615, may be, for example circular, with the outer rim 603 along the circumference of the top surface 615. In other embodiments, the top surface 615 may be, for example, conical. The external sidewall 617 may, for example, circumferentially extend in an approximately perpendicular direction from the top surface 615, and forming a cylinder. The outer rim 603 may be, for example, a curved section of the top surface connecting the top surface 615 to the sidewall 617 or a flared section of the external sidewall 617, connected to the top surface 615. The outer rim 603 may, for example, provide a plurality of finger holds 605 indented or recessed into the surface of the outer rim 603. There may be, for example, at least two finger holds 605.

FIGS. 91-94 and 106 further show the top surface 615 having a raised region or a seal support region 611 extending out from the top surface 615 and radially around an approximate center of the top surface 615. The raised region 611 is shown having a sloped side 616, extending out from the top surface 615, towards a top surface 614 of the raised region 611, and may, for example, form a conical structure. However, the raised region 611 may be any shape around the center of the top surface. Extending out from the raised region 611 is an insertion tube or port 613, having an opening or a hole 609 disposed on a top surface of the insertion tube or port 613. The insertion tube or port 613 and the raised region 611 may be, for example, approximately concentric with the top surface 615. The tube or port 613 extending from the raised region is shown as cylindrical, but may also be any shape. The hole 609 in the tube 613 may be, for example, sufficiently large and shaped to accommodate a syringe needle or cannula inserted into the hole 609, as shown in FIG. 91. A syringe 699 is shown with a cannula inserted into hole 609.

Figure 93:
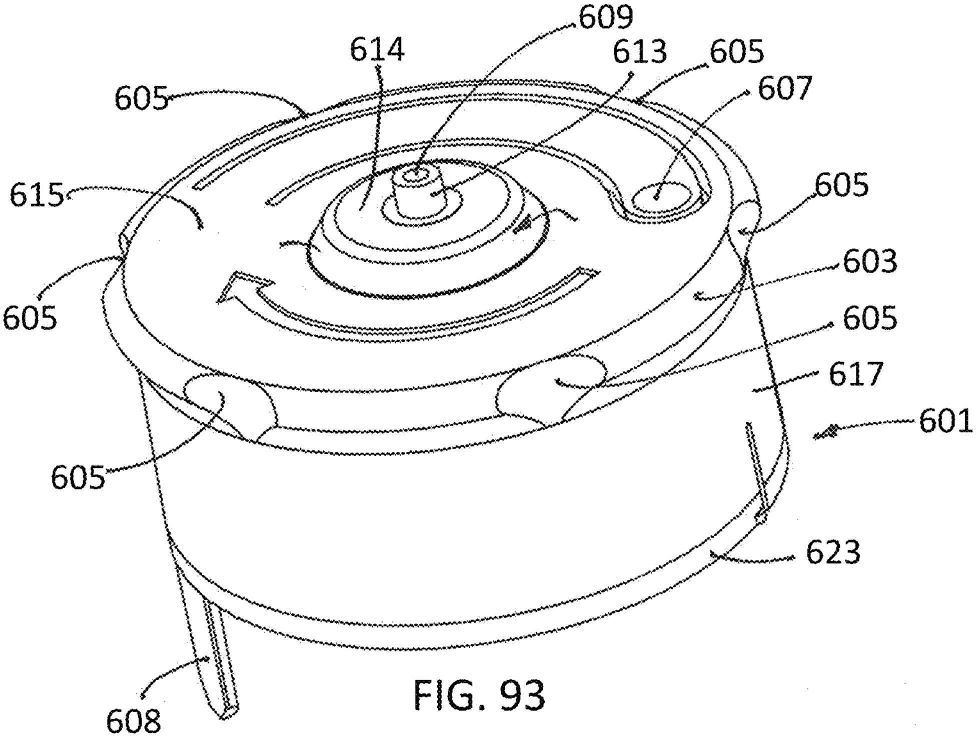
FIG. 93 is a top perspective view of the protective cover of the centrifuge of FIG. 91.
Figure 94:
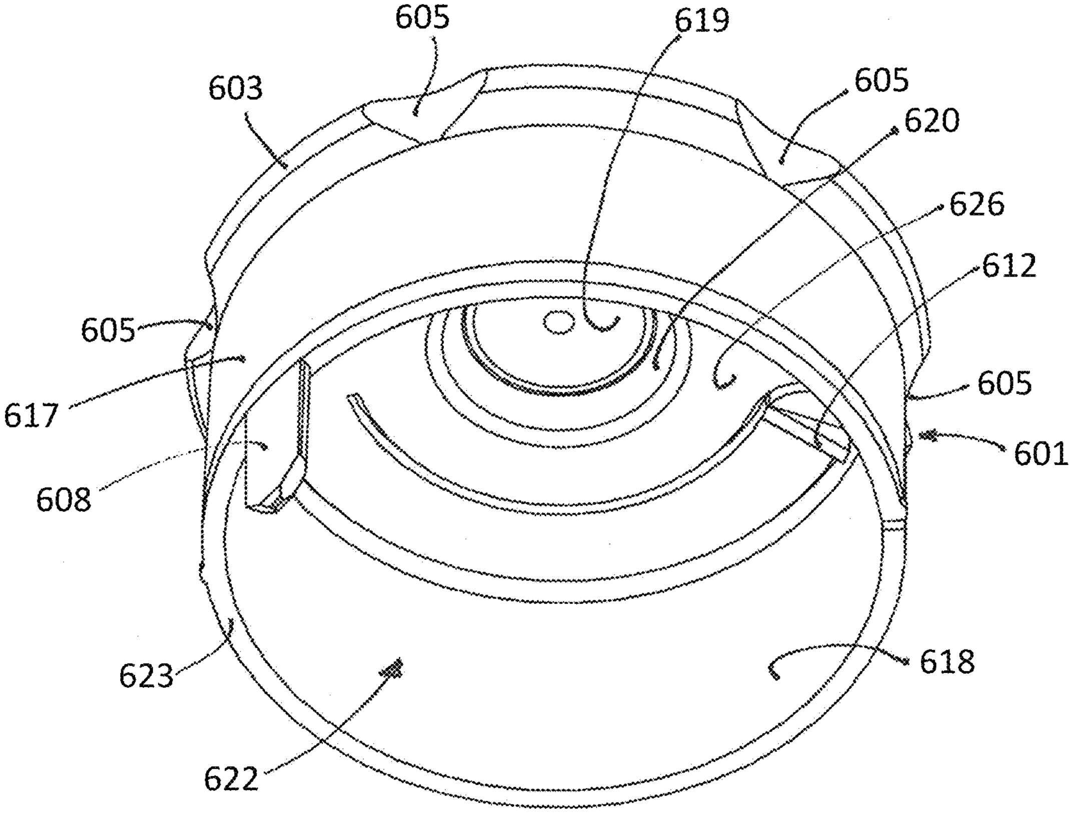
FIG. 94 is a bottom perspective view of the protective cover of FIG. 94.
Figure 95:
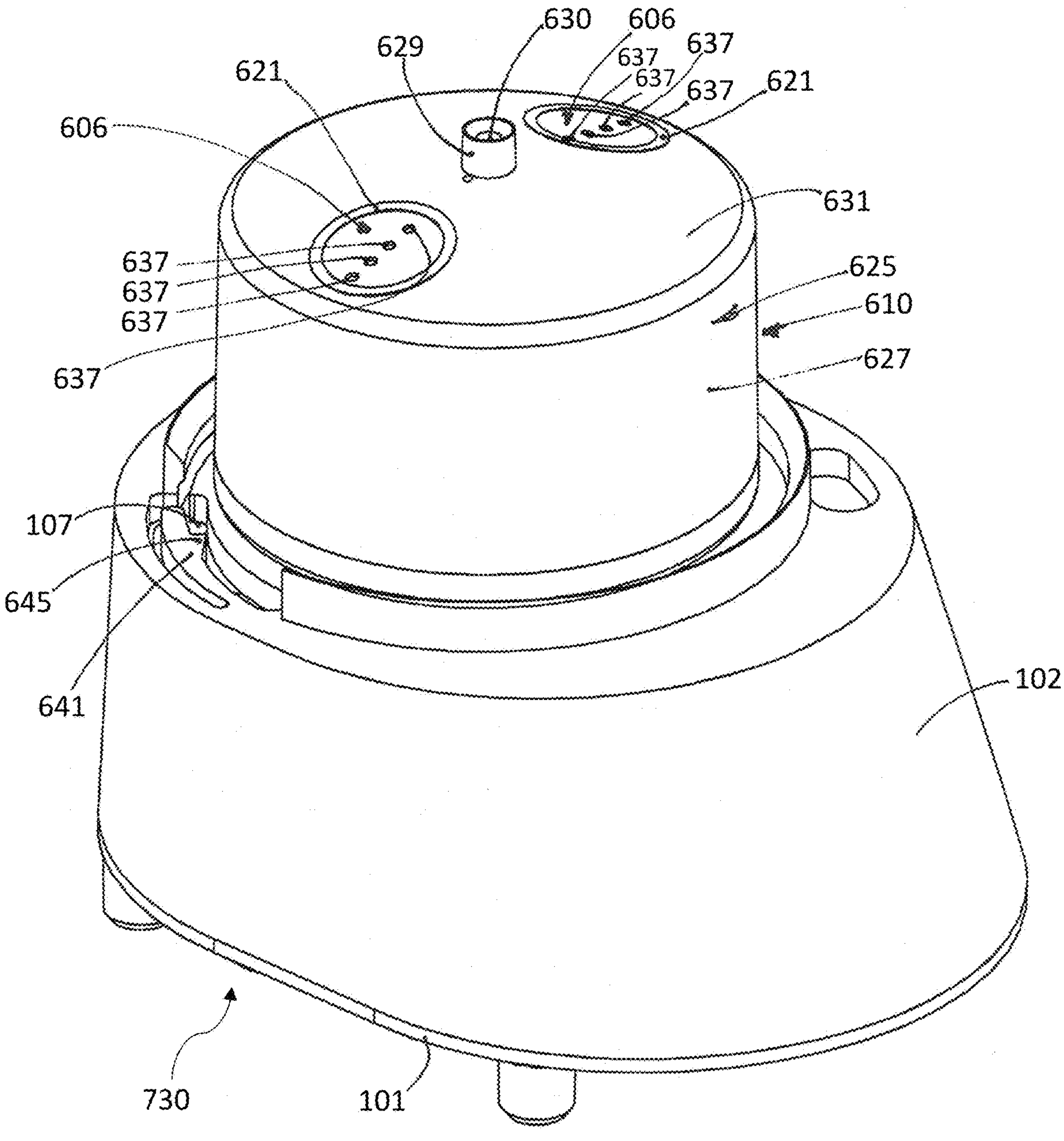
FIG. 95 is a top perspective view of the centrifuge container of the centrifuge of FIG. 91.

Referring to FIGS. 93-94 and 106, the external sidewall 617 extends from the top surface 615 to a bottom rim 623. The bottom rim 623 forms an opening 622 extending to a bottom side 626 of the top surface 615. The circumference of the opening 622 defines the internal sidewall 618. The bottom side 626 is opposite the top surface 615. A cavity 620 may be, for example, recessed into the bottom side 626 towards the top side 615, forming the raised region 611 extending from the top surface 615. The opening 609 extends through the bottom side 626. A seal or insertion barrier 619 may be, for example, positioned within the perimeter of the cavity 620 and separating the opening 609 from the interior of the protective cover 601. The insertion barrier 619 may be, for example, a circular or ovular membrane, fabricated from a plastic polymer material, and penetrable using a sharp object like, for example, the cannula of the syringe 699. The insertion barrier 619 may be, for example, approximately 0.8 mm to 1.2 mm thick, and more specifically, approximately 1 mm thick.

The protective cover 601,702 has an activation tab 608 extending from the bottom rim 623 as a freestanding member, configured (e.g. shaped and dimensioned) for insertion into the activation slot 107. The protective cover 601,702 is configured (e.g. shaped and dimensioned) to cover the centrifuge container 610 and/or the sequester wheel 405, 706, while providing clearance between an interior surface of the protective cover 626 and the centrifuge container 610 and/or the sequester wheel 405,706, and with the activation tab 608 inserted into the activation slot 107. The protective cover 601,702 further has a brake 607, which is similar to brake 401 and having already been described above, for the sake of brevity, will be described to note additional embodiment elements. The brake 607 may have, for example, a brake pad 612 extending from the bottom surface 626. The brake pad may be, for example, wedge shaped and positioned between the center of the bottom surface 626 and the sidewall 617, thickening in the direction of the sidewall 617. The protective cover 601,702 may, for example, be fabricated from a clear plastic polymer material or a material through which blood separation columns and/or plurality of rings may be visible.

In another embodiment, the protective cover 601,702 may comprise at least one light or a plurality of lights (not shown). The at least one light or the plurality of lights comprises a fluorescent lamp (CFL), an incandescent bulb, a halogen bulb, a light emitting diode (LED) bulb, an ultra-violet (UV) light, and/or any combination thereof. Each of the plurality of lights may be the same or they may be different. The at least one light or the plurality of lights coupled or positioned adjacent to the top surface 615, a bottom surface or bottom side 626, internal circumference sidewall 618 and the circumferential sidewall 617 of the protective cover 601,702.

In other embodiments, a syringe connector may be connected to the tube or port 613, such as, for example, a female Luer Lock adaptor for engagement with a male Luer Lock syringe. With a Luer Lock connector, a seal 619 may, for example, not be required. Also, during centrifugation, the syringe with the male Luer Lock connector may, for example, remain connected to the female Luer Lock connector.

The protective cover 601,702 may further comprise an insertion barrier 619. The insertion barrier is positioned between the opening 609 and the insertion opening 630. In embodiments where the insertion barrier 619 covers the cavity 620, a sealed space may, for example, exist between the protective cover 601,702 and the container cover 625, 704 when the protective cover 601,702 is engaged, with the activation tab 608 inserted into the activation slot 107. The insertion tube or port 613 of protective cover 601,702 may be, for example, aligned with the insertion tube or port 629 of the container cover 625,702.

Referring to FIG. 92, 95, 106, 110A-110B, 112A-112C and 113A-113B, the portable centrifuge 600,700,738,744 may further comprise a container cover 625,704,740,746. The container cover 625,704,740,746 may be disposed over a portion of a sequester device 405,706. The container cover 625,704,740,746 comprises a top surface 631,724, a bottom surface 633,732, an external circumferential sidewall 627, 734 that creates an opening or recess 632,726. The container cover 625,704 may further comprise an internal circumferential sidewall 628, 736 that extends below a bottom of the external circumferential sidewall 627,734 to create an offset rim 624. The container cover 625,704 may comprise a top surface 631,725 that is domed or conical. The container cover 625,704 may comprise a top surface 631,725 that is flat or planar. The container cover 625,704 comprises a circular cross-sectional shape and/or it has a cylindrical shape.

The conical shape of the top surface 631,724 may, for example, minimize the impact formation of an air pocket between the top of the sequester device 405,706 and the container cover 625,704. Such an air pocket may, for example, inhibit blood constituents from flowing out from the inner container 420 of the sequester ring 405,706, towards the channels (e.g. the first channel 440, the second channel 441, and the third channel 442). By having a conical top surface 631,724, an air pocket may, for example, form and be raised towards a region surrounding the insertion tube or port 629 and/or opening 710, with blood flow moving out from the central container 420 towards the channels (e.g. the first channel 440, the second channel 441, and the third channel 442) but below the air pocket.

The top surface 631,725 may further comprise an insertion tube or port 629 with an insertion opening 630 extending through the insertion tube 629 and into the interior of the centrifuge container 610. The insertion tube or port 629 may be centered and/or aligned over a longitudinal axis of the fourth ring 419 and/or disposed in the center. Alternatively, it may be offset from the longitudinal axis of the fourth 419 and/or offset from the center. The insertion tube or port 629 may be disposed between a one or more extraction regions 606; the insertion tube or port 629 may be disposed between the first extraction region and a second extraction region. At least a portion of the container cover 625,704 may comprise a coating. At least a portion of the internal circumferential sidewall 628,736 may comprise a coating. The coating may comprise anticoagulants, preservatives, disinfectants or germicidal agents or pathogen reduction agents or pathogen inactivation agents, sterilants, antiseptics, clot activators, separator gels.

The top surface 631,724 may comprise an opening 710. The opening 710 may be sized an configured to receive a serum or plasma filter 714, a pipette or eye dropper 716, and/or filtered eye dropper 718. The opening 710 may further comprise a lid (not shown) and/or a seal (not shown), the lid or seal may be fixed and/or removably connected. The opening 710 may extend through the top surface 631,724 through the bottom surface 633,732. The opening 710 may be centered on the top surface 631,724.

In another embodiment, the container cover or centrifuge cover 625,704 may comprise at least one light or a plurality of lights (not shown). The at least one light or the plurality of lights comprises a fluorescent lamp (CFL), an incandescent bulb, a halogen bulb, a light emitting diode (LED) bulb, an ultra-violet (UV) light, and/or any combination thereof. Each of the plurality of lights may be the same or they may be different. The at least one light or the plurality of lights coupled or positioned adjacent to the top surface 631,724, a bottom surface 633,732, an external circumferential sidewall 627,734 and/or an internal circumferential sidewall 628,736 of the container cover 625,704.

The top surface 631,724 comprise a circular shape with the insertion tube or port 629 approximately concentric or centered with the top surface 631,724. The top surface 631,724 and the insertion tube or port 629 are configured (e.g. shaped and dimensioned) for the protective cover 601,702 placement over the centrifugal container 610 and/or the sequester wheel 405,706 without inhibiting rotation of the centrifuge container 610 and/or the sequester wheel 405,706. The top surface 631,724 may further comprise one or more extraction regions 606, the one or more extraction regions 606 are spaced apart. The one or more extraction regions 606 may be spaced apart symmetrically or non-symmetrically around the circumference of the top surface 631,724. For example, the top surface 631,724 has a first extraction region and a second extraction region, the first extraction region and the second extraction region are spaced apart and/or diametrically opposed. The top surface 631,724 may, for example, have an external circumferential sidewall 627,734, with the sidewall 627,734 extending away from the top surface 631,724 and connected to an outer rim 415 of the sequester device 405, 706. The centrifuge cover 625,704 connected to the sequester device 405,706 may, for example, form a cylindrical structure. The sequester device 405,706 has already been described in detail, and for the sake of brevity, will not be further described.

The one or more extraction regions 606, the first extraction region and/or the second extraction region comprises one or more activity indicators 621. The top surface 631,734 may, for example, also include a plurality of extraction hole regions (e.g. multiple instances of the extraction region 606) surrounded by a plurality of activity indictors (e.g. multiple instances of the activity indicator 621). The one or more extraction regions 606, the first extraction region and/or the second extraction region may comprise a shape, the shape may include a circle, an oval, a regular polygon shape and/or any combination thereof. The activity indicator 621 is shown as a circular shaped ring surrounding the extraction region 606. The activity indicator 621 may comprise a visual indicator. The visual indicator may comprise a different colored material and/or at least one light (e.g., LED).

Alternatively, the one or more extraction regions 606, the first extraction region and/or the second extraction region may comprise a plurality of extraction holes 637. The plurality of extraction holes 637 and/or each of the plurality of extraction holes 637 may be spaced apart and disposed within the one or more extraction regions 606. The plurality of extraction holes 637 may be spaced apart and axially aligned. The plurality of extraction holes 637 may be spaced apart and offset. However, the activity indicator 621 may be, for example, shaped and colored to bring visual attention to the extraction region 606. During centrifugation, the centrifuge container 610 and/or the sequester wheel 405,706 spins, also spinning the activity indicator 621. The activity indicator 621 may, for example, provide a visual indication that the centrifuge is spinning and that the protective cover 601 should remain on until the centrifugation process is complete.

There may be more than two extraction regions 606. The multiple instances of extraction region 606, the extraction holes 637, and multiple instances of the activity indicator 621 may, for example, be positioned to minimize vibration and balance rotation of the centrifuge container. A plurality of extraction regions (e.g. multiple instances of extraction region 606) may be on the top surface 631 of the centrifuge cover 625 and, for example, radially approximately equally spaced and in approximately equal intervals on the top surface 631 to minimize vibration and to maintain balanced rotation of the centrifuge container 610.

The container cover 625,704 and/or the protective cover 601,702 comprises a material. The container cover 625,704 and/or the protective cover 601,702 may further comprise a coating. The material may be a polymer and/or a metal. The material may also include an opaque, clear, transparent, and/or translucent material. The material may further comprise a color. The colorant may be used to diffuse the luminescence of the at least one light and/or the plurality of lights. The coating may comprise anticoagulants, preservatives, disinfectants or germicidal agents or pathogen reduction agents or pathogen inactivation agents, sterilants, antiseptics, clot activators, separator gels. The pathogen reduction agents or germicidal agents may comprise alcohols, chlorine dioxide, chlorine mixtures, formaldehyde, glutaraldehyde, hydrogen peroxide, lodophor mixtures, peracetic acid, phenolic mixtures, quaternary ammonium mixtures, amotosalen or riboflavin, and/or any combination thereof. The pathogen reduction agents may be used alone and/or with combination of a UV light for enhanced pathogen reduction. The pathogens in whole blood or its blood components are inactivated by adding pathogen reducing agent and irradiating with UV light over a period of time, the period of time ranging from 5 to 90 minutes. This method reduces the infection levels of disease-causing agents by releasing active oxygen which damages the cell membrane of the pathogens and prevents replication of the carrier pathogens that may be found in whole blood or blood components for safer injection or transfusion. Pathogens may include viruses, bacteria, parasites, and/or white blood cells.

For example, in one embodiment, at least a portion of the container cover 625,704 and/or at least a portion of the protective cover 601,702 comprises a coating and at least one light. The coating includes germicidal agent, the germicidal agent is riboflavin. The at least one light includes a UV light, the UV light having a wavelength. The wavelength may comprise a range of 222 to 280 nanometers for proper activation of riboflavin to act as a germicidal agent. In another embodiment, the container cover 625,704 and/or the protective cover 601,702 comprises at least one light. The at least one light may be disposed onto a portion of the container cover 625,704 and/or the protective cover 601, 702, the at least one light may comprise a UV light, the UV light having a wavelength. The wavelength is a range of 250 to 400 nanometers to act as a germicidal agent alone and a coating may not be required.

Referring to FIGS. 96-97, 106, 110A-110B, and 112A-112C, centrifuge cover 625,704 is shown with the external circumferential sidewall 627,734 extending away from the top surface 631,724 to a centrifuge cover rim 624, 728. The rim 624,728 forms an opening 632,726 extending to the bottom side 633 of the top surface 631,724, with the rim 624,728 and an interior of the sidewall 628,736 surrounding the opening 632,726. The bottom surface 633,732 is opposite the top surface 631,724. The sequester device 405,706 is inserted into the opening 632,726, with rim 624,728 connected to rim 415, and forming the centrifuge container 610. The sequester device 405,706 and the centrifuge cover 625,704 may be, for example, connected so that the connection and/or coupling between rim 624,728 and rim 415 is sealed and liquid impermeable. The centrifuge cover 625, 704 is disposed onto the sequester device 405,706 to create a liquid impermeable seal. Accordingly, the opening or recess 632,726 is sized and configured to match or substantially match an outer diameter of the first ring 416 of the sequester wheel 405,706, the outer diameter of the base plate 722 and/or an inner surface of the rim 415 of the sequester wheel 405,706. Alternatively, a rubber seal may be disposed between the rim 624,728 of the centrifuge cover 625,704 and the rim 415 of the base ring to create a liquid impermeable seal.

Figure 97:
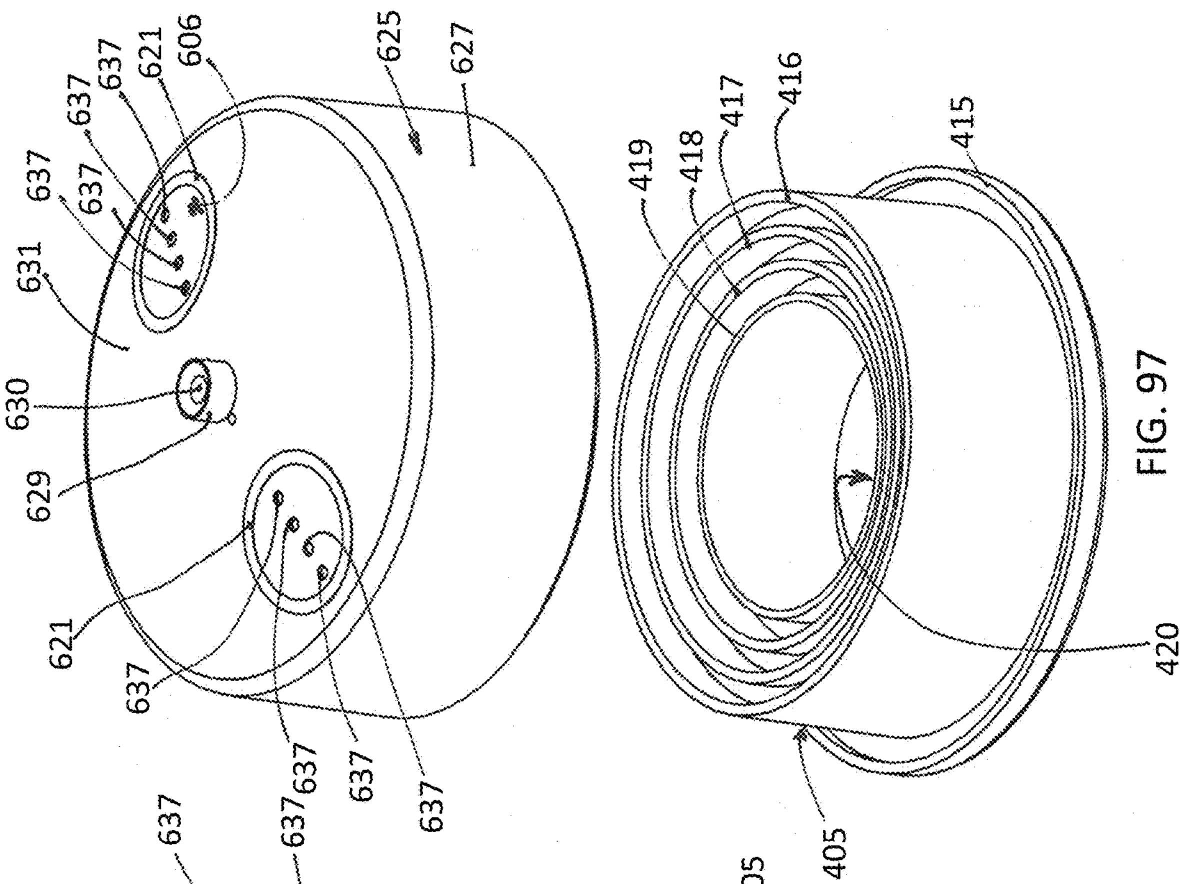
FIG. 97 is an exploded top perspective view of the centrifuge container of FIG. 96.
Figure 96:
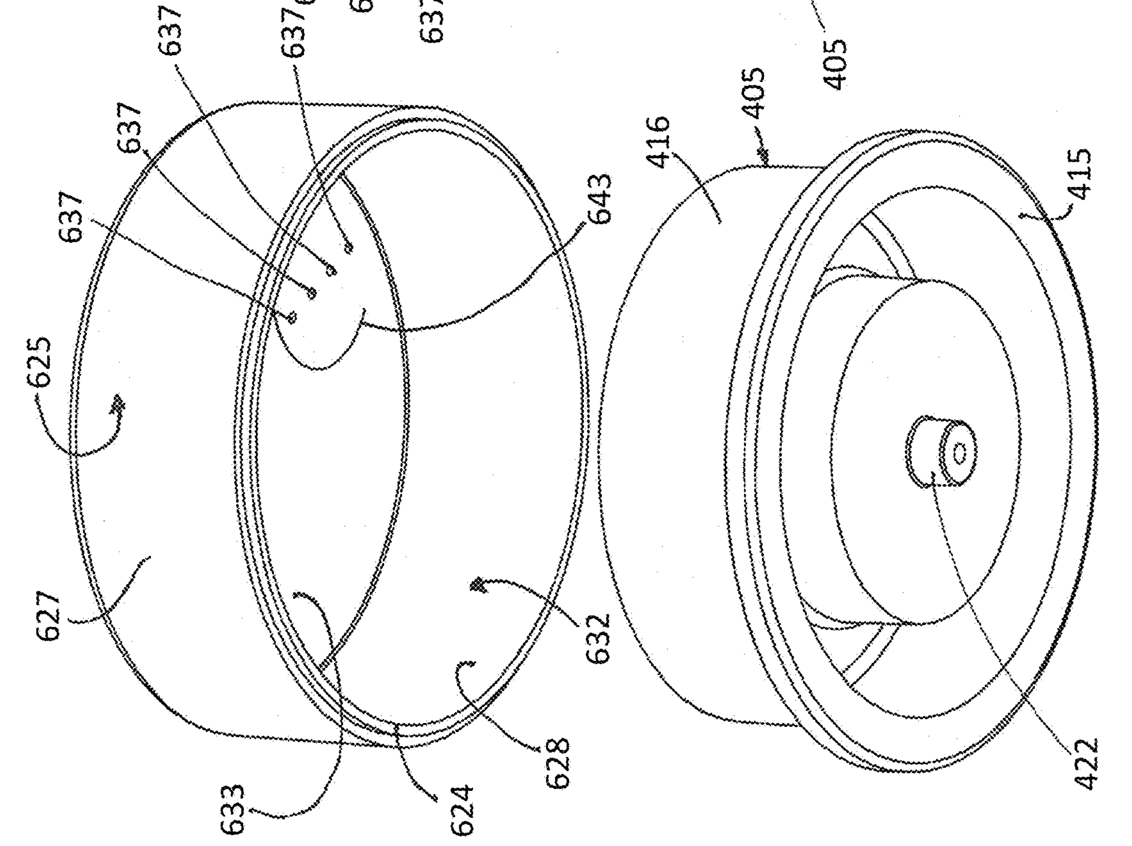
FIG. 96 is an exploded bottom perspective view of the centrifuge container of FIG. 96.
Figure 98:
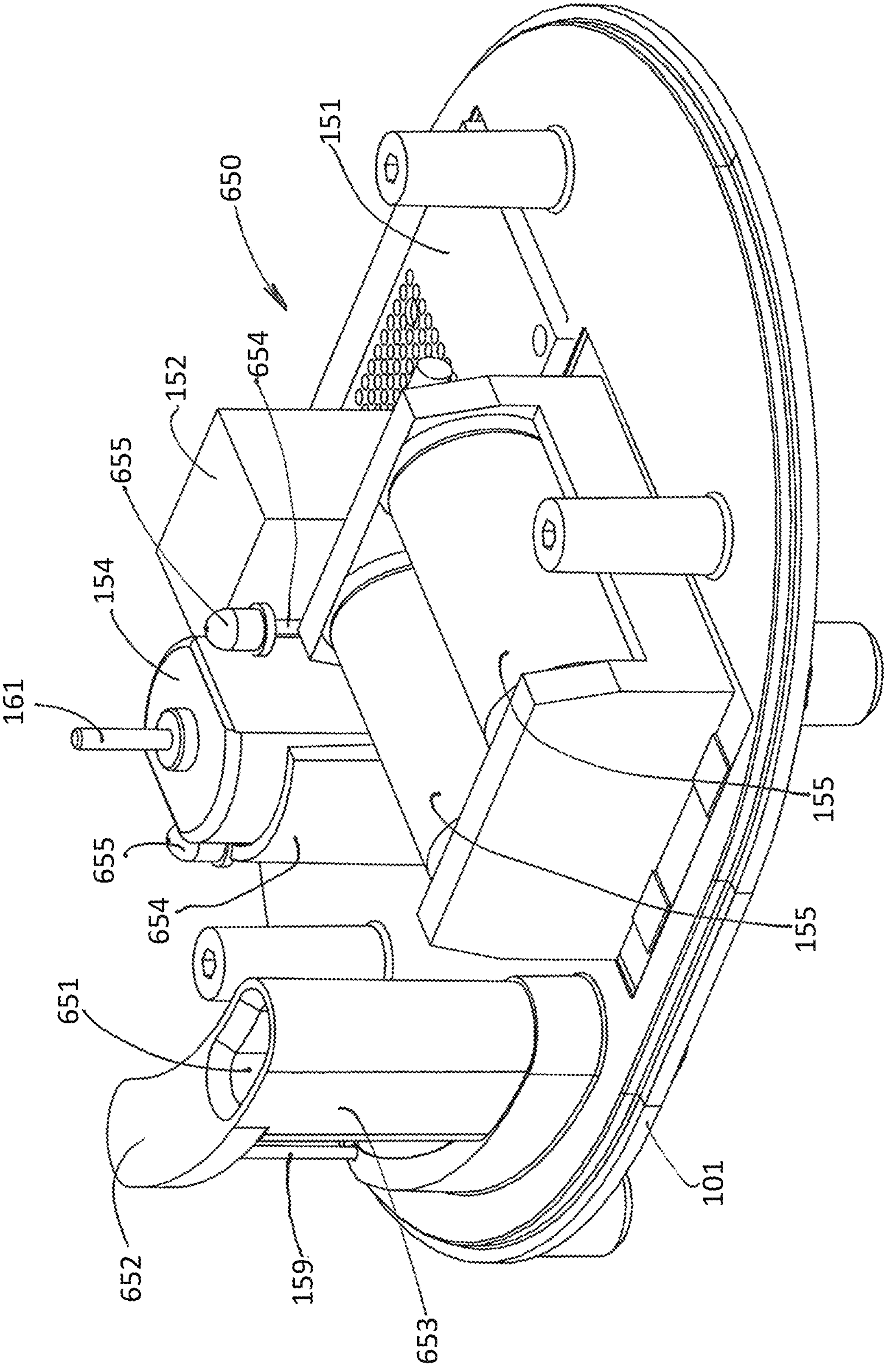
FIG. 98 is a top perspective view of the centrifuge motor of the centrifuge of FIG. 91.
Figure 99:
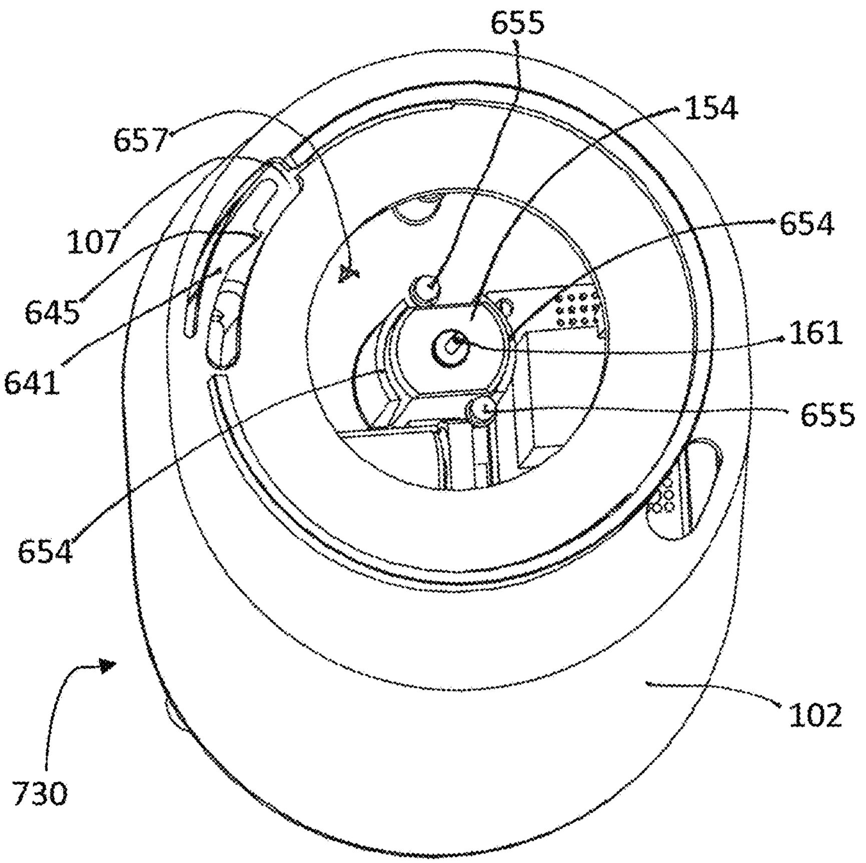
FIG. 99 is a top perspective view of the base cover and centrifuge motor of the centrifuge of FIG. 91.

Referring to FIGS. 96 and 97, the centrifuge cover 625,704 may comprise one or more extraction regions 606, a first extraction region and/or a second extraction region. The one or more extraction regions 606, a first extraction region and/or a second extraction region comprises a seal or an extraction barrier 643, The seal or extraction barrier 643 comprises a plurality of extraction holes 637. There may be, for example, two instances of the extraction region 606, with the extraction holes 637 of the two regions being approximately opposite each other and approximately forming a diametric line. Two instances of seal 643 are shown, with each instance of extraction region 606 having the seal 643 positioned under the extraction holes 637, and positioned on the bottom surface 633 of the centrifuge cover 625,704. The seal 643 may be, for example, a circular or ovular membrane, fabricated from a plastic polymer material, and penetrable using a sharp object like, for example, a syringe (e.g. the syringe 699). The insertion opening 630 extends through the bottom surface. The insertion opening 630 may be unsealed. However, in other embodiments, the insertion opening may be sealed using a circular or ovular membrane, fabricated from a plastic polymer material, and penetrable using a sharp object like, for example, a syringe (e.g. the syringe 699).

With reference to FIGS. 98-99, 106, 107A-107B, 108A-108C, 109A-109B, the portable centrifuge 600,700 comprises a base 708, 730, the base 708,730 may comprise a rotational mechanism 650. The rotational mechanism 650 includes an activation slider 653 having an activation slot 651, and an arm 652. The activation slot 651 may be, for example, positioned under the activation slot 107 and is configured (e.g. shaped and dimensioned) to engage with the activation tab 608. The activation slot 651 is shown as at least one recess into which the activation tab 608 is insertable. By inserting activation tab 608 into activation slot 651 and rotating the protective cover 601, the activation slider 653 may be, for example, moved to make contact with the circuit member 159 and complete a circuit to activate the centrifuge.

The portable centrifuge 600,700 comprises a base 708, 730, the base 708,730 may comprise a motor 154. The motor 154 may be held in position or secured by a motor support wall 654. The support wall 654 may, for example, extend away from the baseplate 101 in an approximately perpendicular direction. The motor 154 is shown on the baseplate with the armature 161 extending out from the motor 154. The motor 154 may be, for example, positioned between two opposing sections of the support wall 654, such that the motor 154 is supported on two opposing sides.

In one embodiment, the base 708,730 of the portable centrifuge 600 may comprise at least one light or a plurality of lights 655. A light 655 may be, for example, positioned near or adjacent to the motor 154. Light 655 may be a single light source or a plurality of light sources. The light 655 may comprise a compact fluorescent lamp (CFL), an incandescent bulb, a halogen bulb, a light emitting diode (LED) bulb and/or an ultra-violet (UV) light. The light may be used as a visual indicator to inform the user of a started or completed centrifugation cycle, used to illuminate or provide a back light to the separated blood products for easier constituent selection and extraction. The UV light may also be used as a chemical free, highly effective disinfectant against harmful microorganisms. UV light includes a specific range of wavelengths within the UV-A, UV-B, or UV-C range that are categorized as germicidal-meaning they are capable of inactivating microorganisms, such as bacteria, viruses and protozoa (see FIGS. 105A-105B). In one embodiment, the wavelength comprises a range of 100 to 450 nanometers; the wavelength comprises 100 to 300 nanometers; the wavelength comprises 200 to 300 nanometers and specifically, the range may comprise 222 to 280 nanometers, the range may comprise 250 to 280 nanometers, the range may comprise 315 to 400 nanometers.

Alternatively, the wavelength comprises 264 nanometers. When bacteria, viruses and protozoa are exposed to the germicidal wavelengths of UV light, they are rendered incapable of reproducing and infecting. However, other light bulbs or similar light sources may be used. The light 655 may be connected to the motor support wall 654 and if there is a plurality of lights, the lights may be on opposite sides of the motor 154. In alternate embodiments, the light 655 may be positioned on a stand or a support extending out from the baseplate 101.

Accordingly, the base 708,730 may comprise a first light and a second light. The first light is different than the second light. The first and/or second light may comprise different color lights, different wavelengths, different bulb watts or different bulb sizes or diameters, different bulb types, different bulb types, different bulb intensities. For example, the first light being a violet colored LED bulb for a first visual indicator for activating the centrifugation process, the second light being a while colored LED bulb for a second visual indicator when the centrifugation cycle is complete. Another example includes a first light being an LED bulb type and the second light being a UV bulb type. Alternatively, the base 708,730 may comprise a first light, a second light and a third light. Each of the first, second and third lights are different from each other.

In another embodiment, the protective cover 601,704 and/or the container cover 625,702 may comprise at least one light 655. The at least one light 655 may be disposed onto an internal circumference sidewall 618 of the protective cover 601, 704 and/or the external sidewall 627,734 of the container cover or activation cover 103, 625, 702. The at least one light 655 may be disposed onto the top surface of the protective cover 601, 704 and/or the container cover 103, 625,702. Alternatively, the protective cover 601,704 and/or the container cover 103, 625 may comprise a first light and a second light. The first light is different than the second light. The first and/or second light may comprise different color lights, different wavelengths, different bulb watts or different bulb sizes or diameters, different bulb types, different bulb types, different bulb intensities. For example, the first light being a violet colored LED bulb for a first visual indicator for activating the centrifugation process, the second light being a while colored LED bulb for a second visual indicator when the centrifugation cycle is complete. Another example includes a first light being an LED bulb type and the second light being a UV bulb type. Alternatively, the protective cover 601,704 and/or the container cover 103, 625,702 may comprise a first light, a second light and a third light. Each of the first, second and third lights are different from each other.

In still further embodiments, the base 708,730 may comprise a base cover 102. The base cover 102 may have supports to secure the light 655. The light 655 may be, for example, positioned to shine light through the base cover opening 657. The armature 161 may be, for example, engaged with the armature hub 422 of the sequester device 405, and positioning the light 655 close to the motor 154 provides for light transmission into the centrifuge container 610. The centrifuge cover 625,702 and the sequester device 405,706 may, for example, be fabricated from a clear polymer plastic material or a material through which blood separation columns may be visible and through which emissions from the light 655 may be visible. The light 655 may, for example, be connected to a timer on the circuit board 151 which activates the light 655 when the centrifugation process is complete. The light 655 may display as continuously (e.g., "always on") and/or it may be flashing, which flashing delivers quick bursts of light over a period of time.

Continuing with FIGS. 98-99, 106, 107A-107B, 108A-108C, 109A-109B, the light 655 may comprise different colors for different functions. The colors include different color frequencies provided for different centrifugation applications. For blood separation, a white light may, for example, be used to more easily see and identify the blood concentration spectrum in the various channels (e.g. the first channel 440, the second channel 441, and the third channel 442). For example, a red or blue light may be more suitable for other applications. In still other centrifugation applications lighting may be used to identify tracer materials in the blood such as, for example, a black-light (lighting devices emitting ultraviolet frequencies) used to identify a phosphorous tracer.

Figure 100:
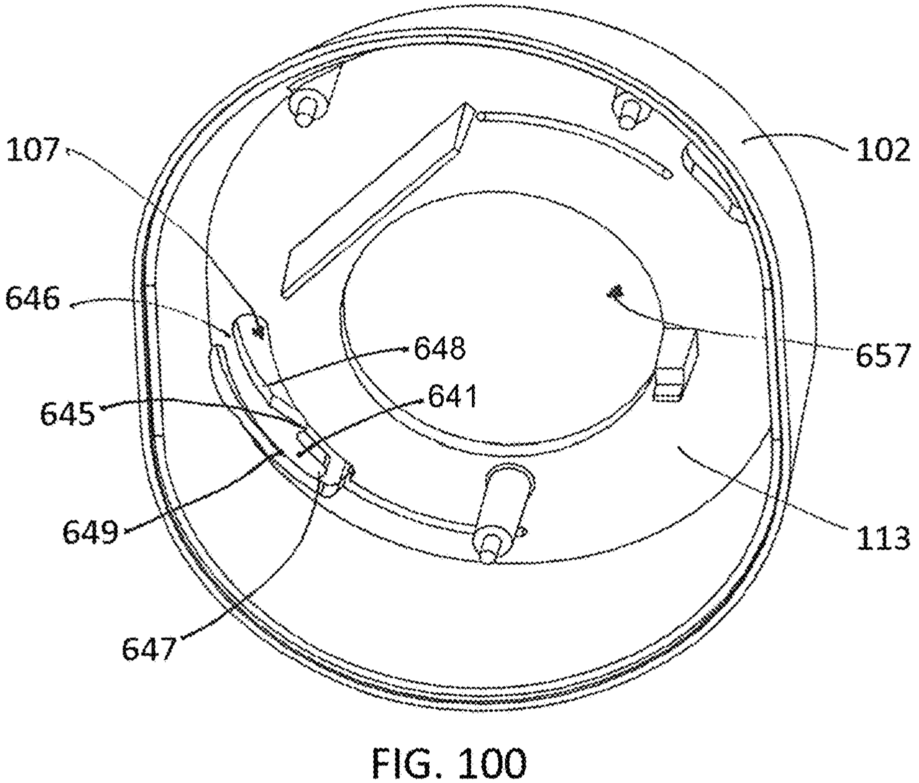
FIG. 100 is a bottom perspective view of the base cover of the centrifuge of FIG. 91.
Figure 101:
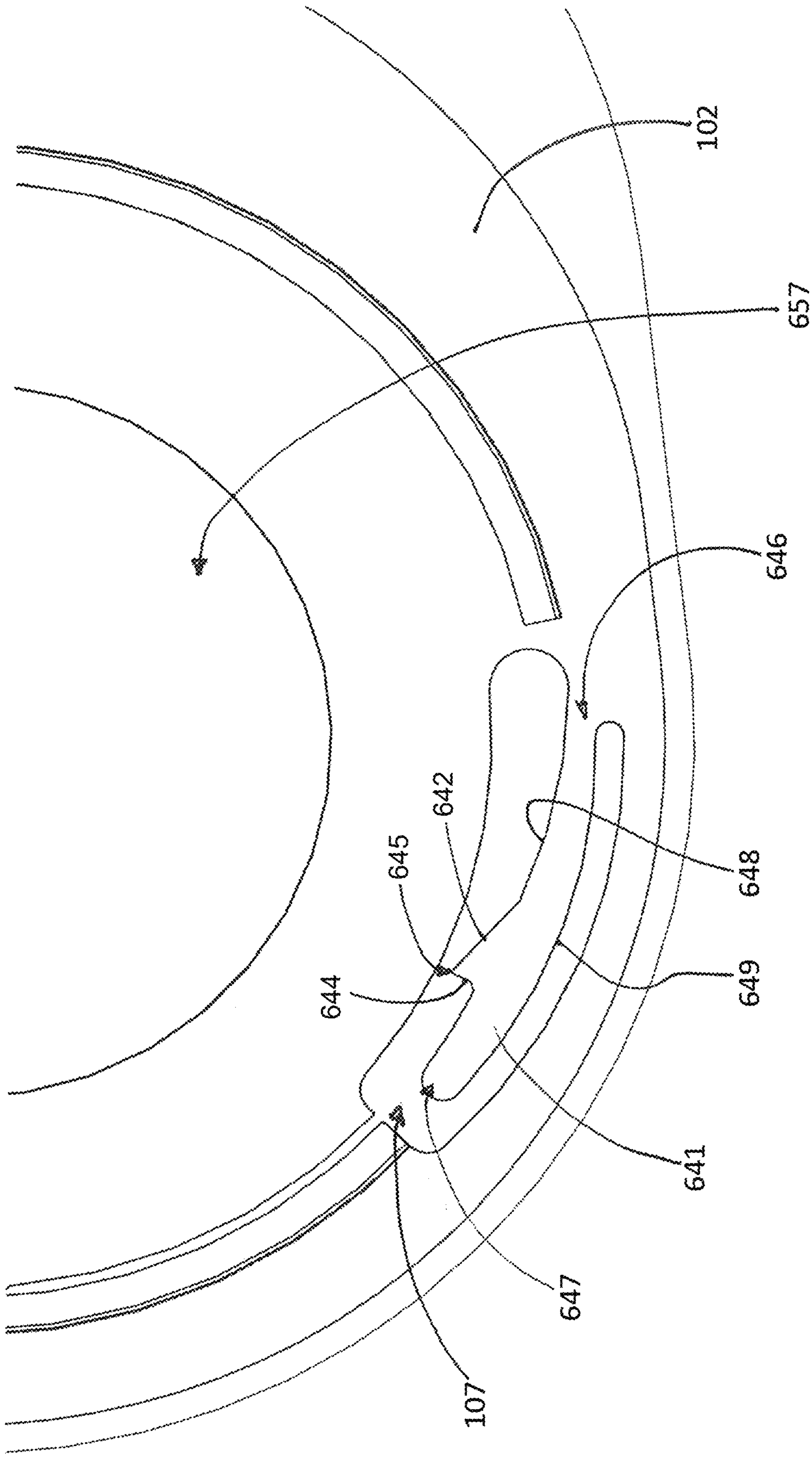
FIG. 101 is a top perspective view of the activation slot of the centrifuge of FIG. 91.

With reference to FIGS. 100 and 101, the activation slot 107 is an elongated opening through the base cover 102 configured (e.g. shaped and dimensioned) to admit the activation tab 608. The activation slot 107 has an arm 641 within the activation slot 107 extending from a first end 646 connected to the base cover 102, towards a free second end 647. The arm 641 has a lock 645 shown as a triangular protrusion from the arm 641. A first side 648 of the arm 641 may have, for example, a sloped section 642 followed by a ledge 644 towards arm 641, forming the lock 645. The ledge 644 may be, for example, curved or approximately perpendicular extending from the first side 648 to meet the sloped section 642. The activation tab 608 may be, for example, moved within the activation slot 107 sliding along arm 641. However, once the activation tab passes the lock 645, the activation tab 608 may continue moving in the original direction to towards the free second end 647, but be prevented from moving back past the lock 645 towards the first end 646. By moving the activation tab 608 along the first side 648 of arm 641, the arm 641 and the lock 645 are bent away from the activation tab 608 as the activation tab 608 moves along the sloped section 642. Once the activation tab 608 has passed the ledge 644, the arm 641 snaps back or unbends, positioning the lock 645 behind activation tab 608 and returning arm 641 to an approximate original position.

The portable centrifuge 600,700 may comprise a base 708,730, the base comprises a lock 654. The lock 654 may, for example, prevent the centrifuge 600 from being reactivated while the centrifuge container 610 is still spinning. The centrifugation process is timed, and reactivation may cause delays or may damage blood cells through repeated centrifugation.

With reference to FIGS. 91-99, 106, 107A-107B, 108A-108C, 109A-109B, the rotational mechanism 650 and baseplate 101 are covered by the base cover 102. The armature 161 may be approximately centered within the base cover opening 657 for engagement with the armature hub 422 of the centrifuge container 610. The centrifuge container 610 and/or the sequester wheel 405,706 may be, rotatably engaged with the armature 161, with the centrifuge container 610 and/or the sequester wheel 405,706 positioned over the motor 154 and concentric with a rotational axis of the motor armature 161. The protective cover 601,702 may be, for example, positioned over the centrifuge container 610 and/or the sequester wheel 405,706, with the activation tab 608 inserted into the activation slot 107 and into the activation slider slot 651. The insertion barrier 619 may be, for example, positioned above the insertion tube 629 and covering the opening 609 of insertion tube 613.

The portable centrifuge 600,700 may comprise a base 708,730, the base 708,730 comprises a brake 607. The brake 607 may be, for example, engaged to stop rotation of centrifuge container 610 and/or the sequester wheel 405,706 after the rotational mechanism 650 has been turned off. The brake comprises a brake pad 612. The brake pad 612 wedge shape may be, for example, configured (e.g. shaped and dimensioned) to match the conical slope of the top surface 631. Depressing the brake button 607 may, for example, push brake pad 612 against the top surface 631, frictionally slowing the centrifugal container. The brake 607 is movable from a first position to a second position, the first position comprising the brake pad 612 having no contact with the sequester device, and a second position comprising the brake pad 612 contacting or engaging the sequester device to slow the revolutions per minute (RPM) to a complete stop via friction.

With reference to FIGS. 91-99, a method of use for a portable centrifuge 600, 700 may include extracting blood from a patient using a syringe (e.g. the syringe 600), inserting the syringe cannula into the opening 609 of the insertion tube 613 and piercing the seal 619 to insert the cannula into the opening 630 of tube 629, and depressing the plunger to introduce blood into a portion of the centrifuge container 610 and/or a portion of the sequester wheel 405, 706. Furthermore, the centrifuge 600 may be in close proximity to the patient and may remain within a sterile environment. Grasping at least two finger holds 605, rotating the protective cover, moving the activation tab positioned within the activation slot past the lock 645, connecting the activation slider 653 with the circuit members 159, completing the circuit, activating a timer, activating the motor 154, and spinning the centrifuge container 610. Observing the activity indicator 621 to confirm that the centrifuge container 610 is spinning. Reaching a threshold time, the light 655 is activated and power is stopped to the motor 154. Depressing the brake 607 to frictionally slow and stop the spin of the centrifuge container 610.

Observing the activity indicators 621 to determine if the centrifuge container 610 has stopped. Removing the protective cover 601. Observing the desired blood composition. Inserting a syringe cannula into a desired extraction hole 637. Pulling a syringe plunger to remove a desired blood constituent through the cannula and into the syringe. Removing the syringe.

For centrifuges 100, 400, 500, and 600, the positioning of extraction holes (e.g. 121, 407, and 637) and extraction barriers (e.g. 443 and 643) may be to, for example, minimize vibrations and help balance centrifuge container rotation. In addition, activity indicator 621 may be applied to centrifuges 100, 400, 500, and 600 around the extraction holes (e.g. 121, 407, and 637) to form an extraction region.

Referring to FIGS. 1, 2, 36, 37, and 44, another alternate embodiment of centrifuge 500 is shown. As centrifuges 100, 300, and 400 have been described in detail, above, for the sake of brevity, similar components will not be further described herein. The centrifuge 500 has the centrifuge motor or rotational mechanism 330 on the baseplate 101 and enclosed in the base cover 102. The centrifuge 500 further has the protective cover 103 and a centrifuge container 530, with the centrifuge cover 104 and a baseplate 506. The baseplate 506 may be, for example, of similar structure to the baseplate 106, however baseplate 506 has a solid top surface 536. The baseplate 506 has the base motor connector 120 and the protrusion 126 and may be, for example, circular or cylindrical.

Figure 44:
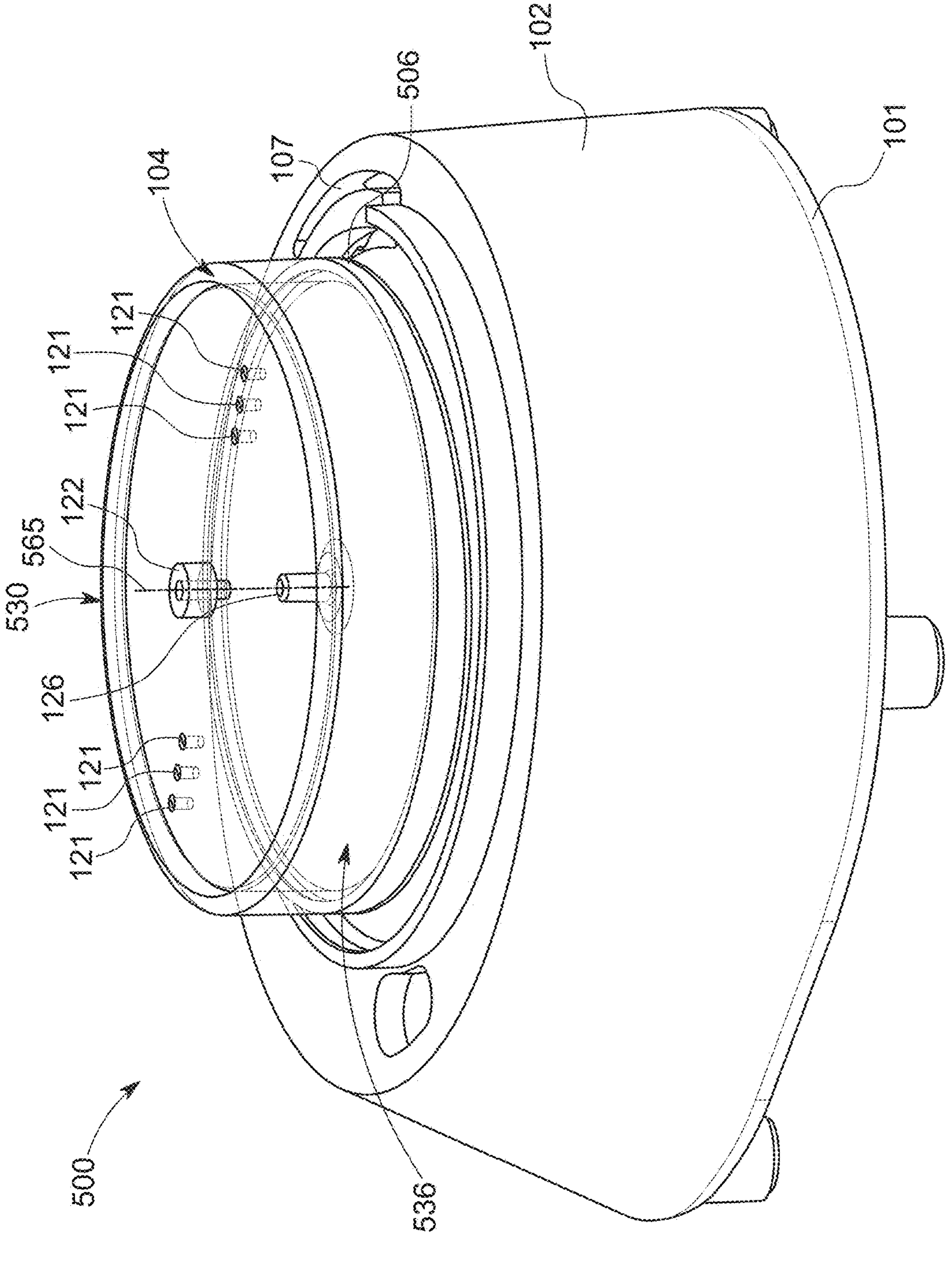
FIG. 44 is a top perspective view of an alternate embodiment of a centrifuge.

With continued reference to FIG. 44 the centrifuge cover 104 may be, for example, placed onto the baseplate 106 and sealed creating a liquid impermeable connection. A thixotropic separation gel and an anti-coagulant may be introduced to the centrifuge container 530, for example, prior to being sealed, forming a thin layer on the baseplate top surface 536 or along the interior surface of the sidewall 137. Polymer barriers may be used to, for example, seal openings in the centrifuge cover 104 (e.g. the plurality of extraction holes 121 and the at least one insertion hole 122). In another aspect of the centrifuge 500, the centrifuge container 530 may be sealed and empty, with the separation gel and anti-coagulant added through the insertion hole 122 to the centrifuge container 530 just prior to introducing the blood sample.

Figure 16:
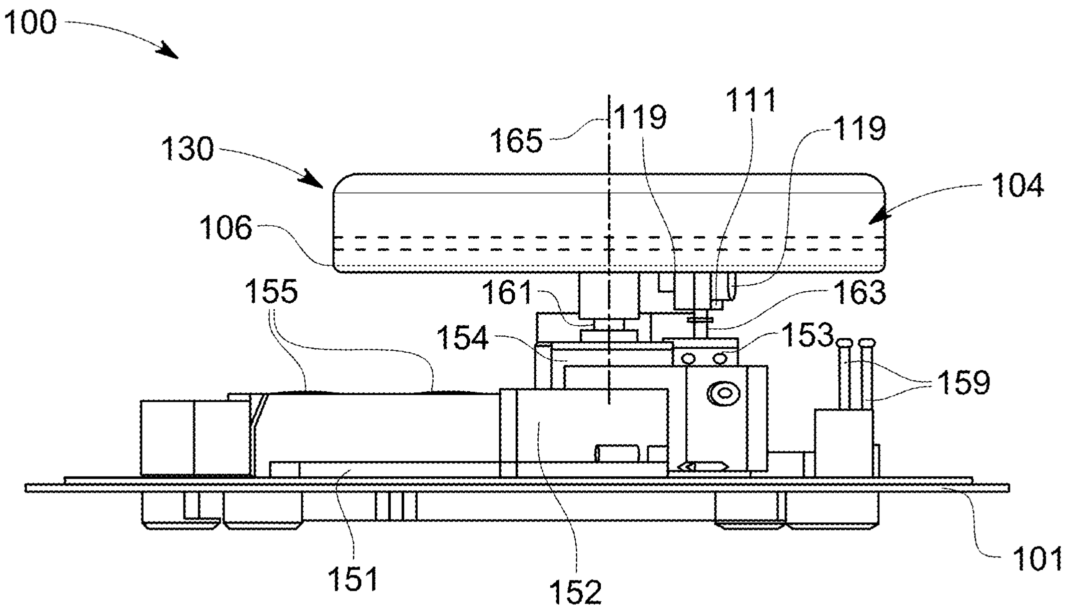
FIG. 16 is a right side view of the centrifuge of FIG. 1 without an activation cover and base cover.
Figure 17:
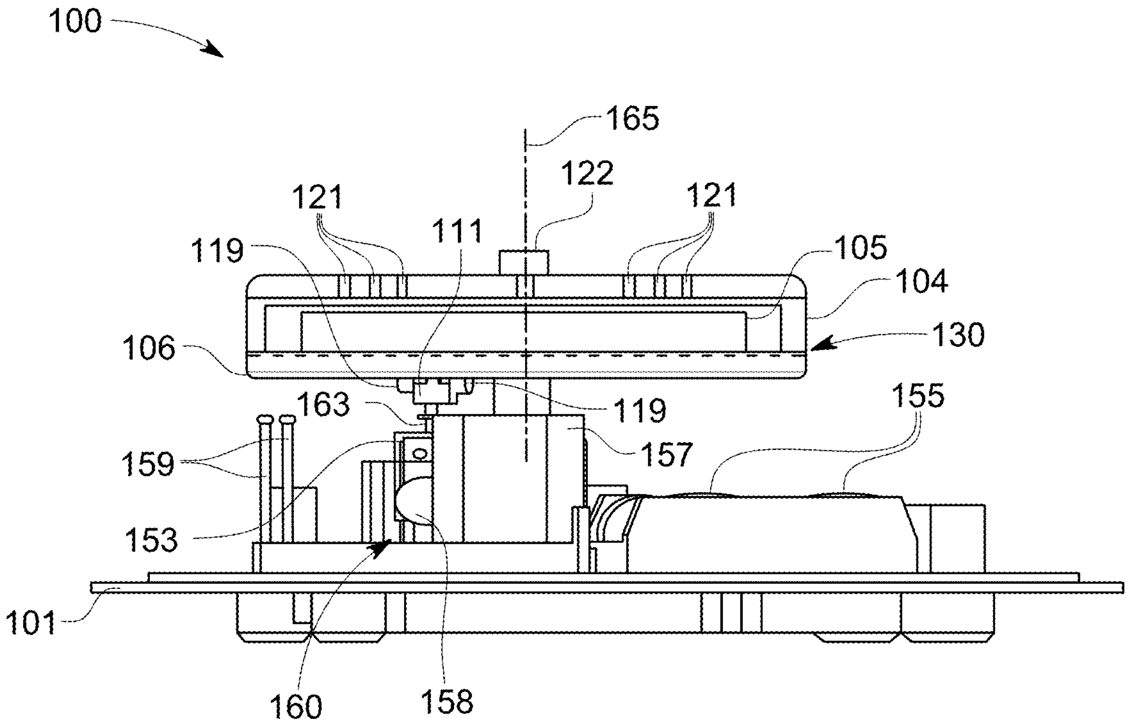
FIG. 17 is a left side view cut-away of the centrifuge of FIG. 1 without the activation cover and base cover.
Figure 18:
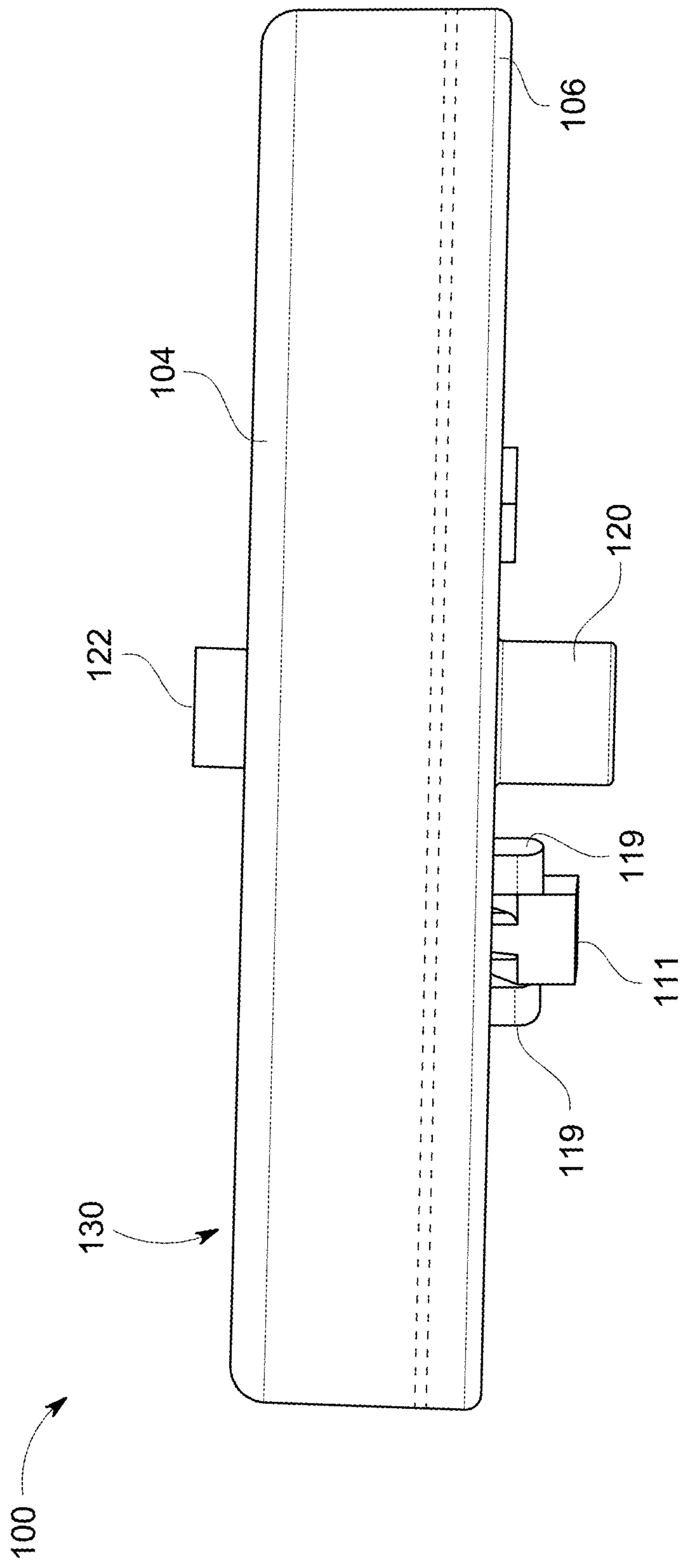
FIG. 18 is a side view of a centrifuge container of the centrifuge of FIG. 1.
Figure 19:
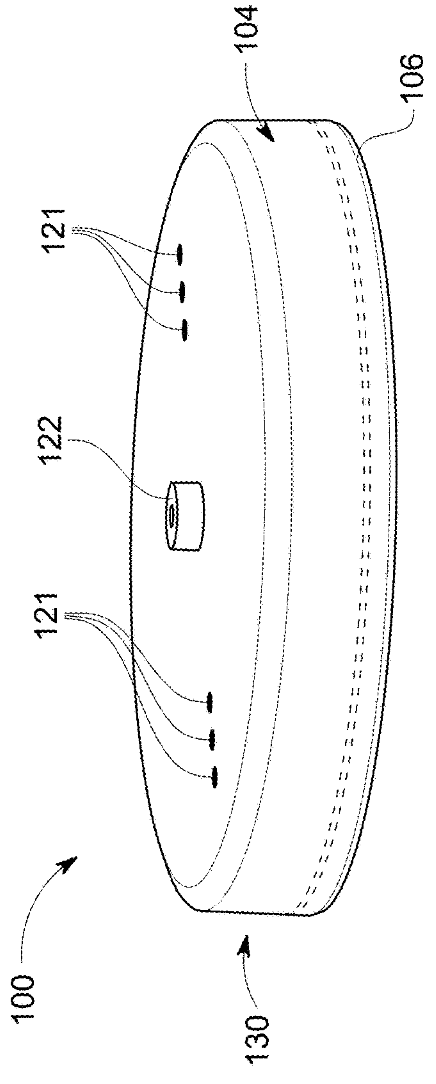
FIG. 19 is a top perspective view of the centrifuge container of FIG. 18.
Figure 20:
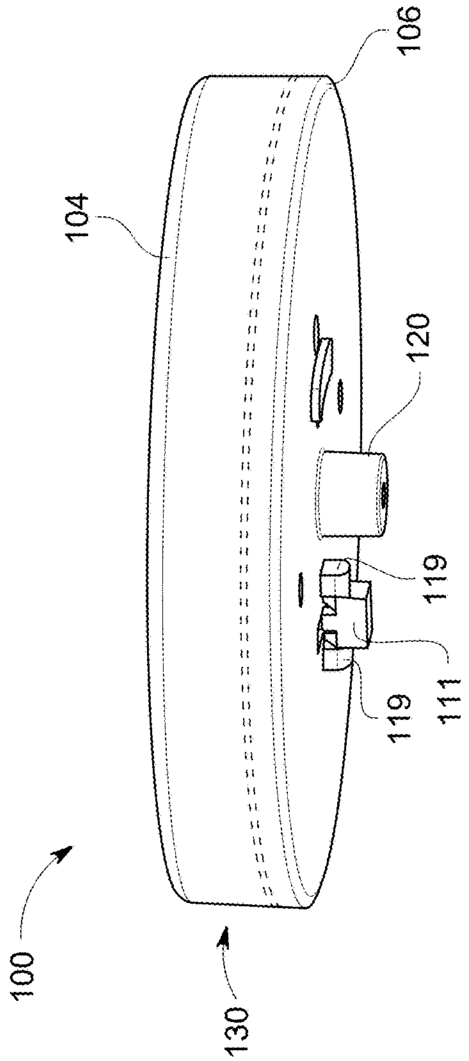
FIG. 20 is a bottom perspective view of the centrifuge container of FIG. 18
Figure 21:
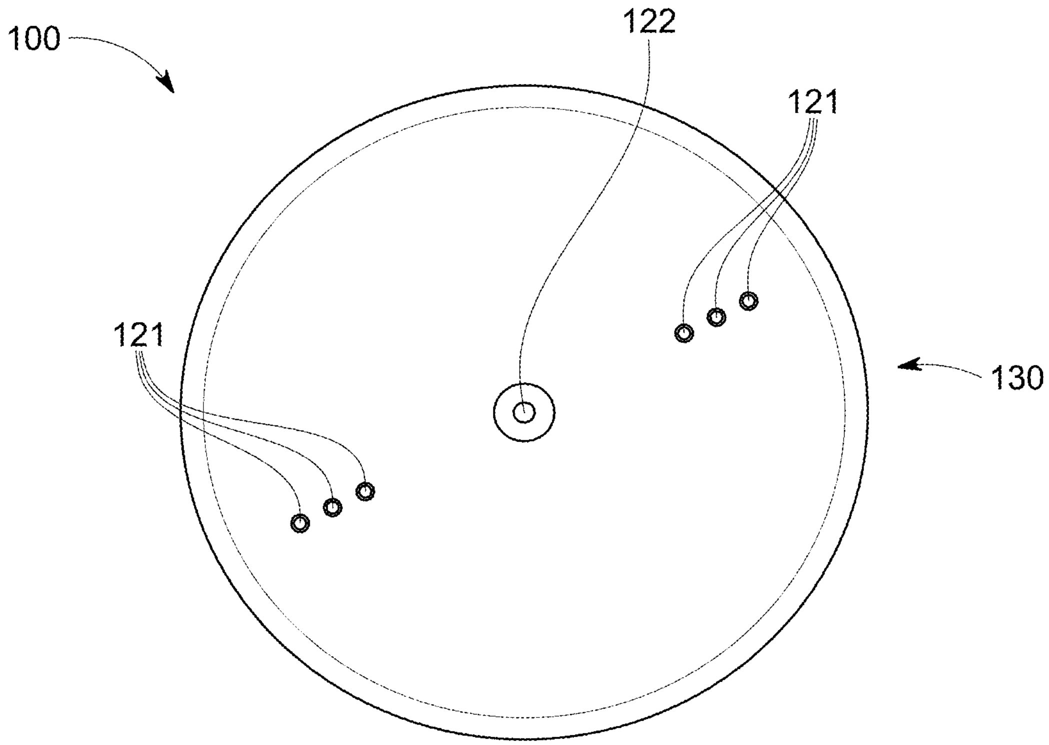
FIG. 21 is top view of the centrifuge container of FIG. 18.
Figure 22:
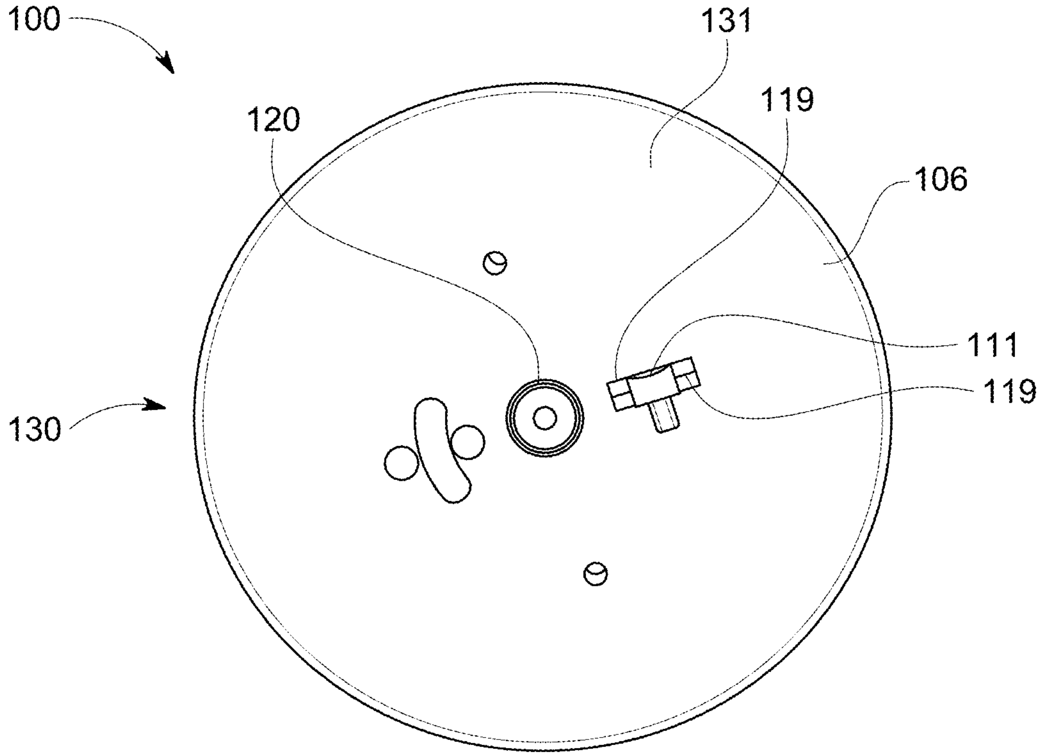
FIG. 22 is a bottom view of the centrifuge container of FIG. 18.
Figure 23:
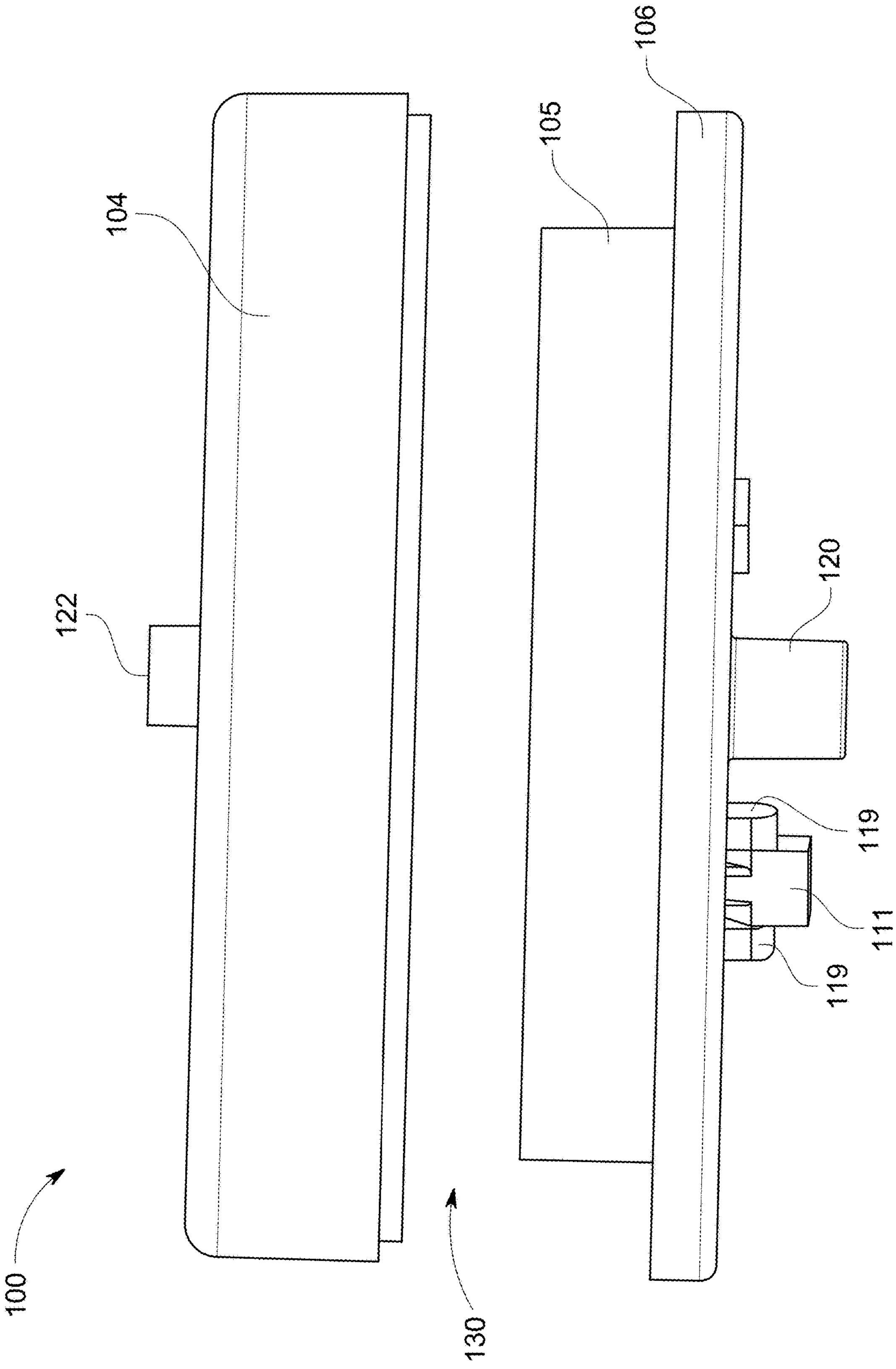
FIG. 23 is a side view of the centrifuge container of FIG. 18 with the centrifuge cover removed.
Figure 24:
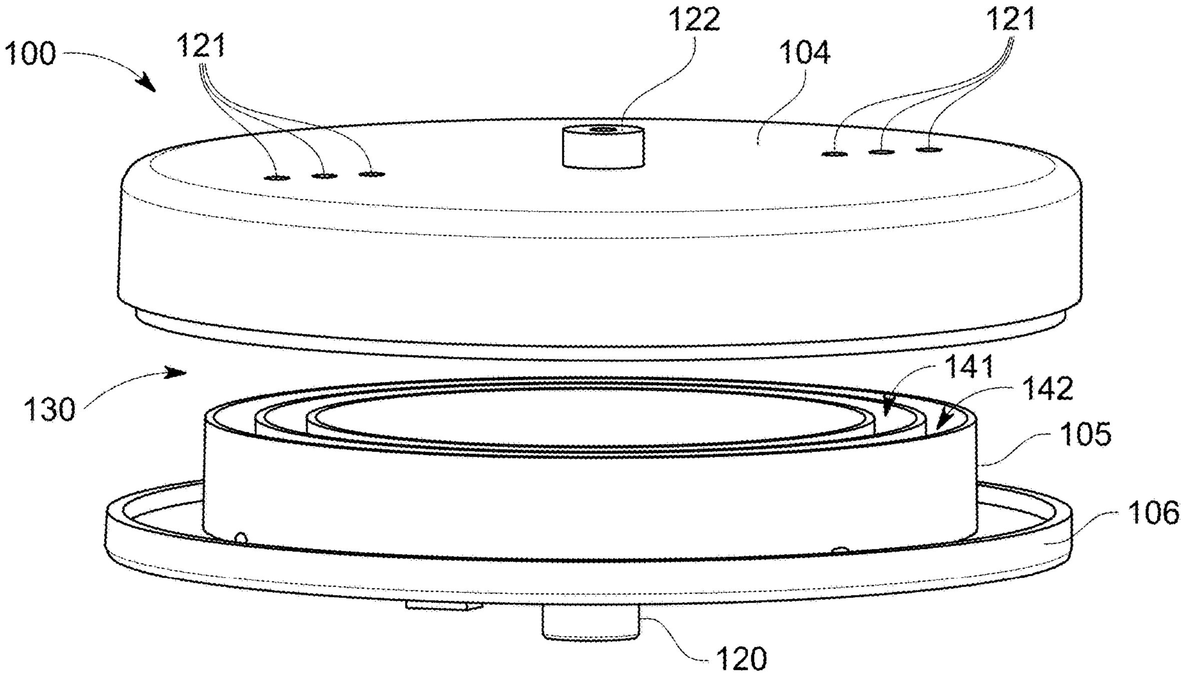
FIG. 24 is a side perspective view of the centrifuge container of FIG. 18.
Figure 25:
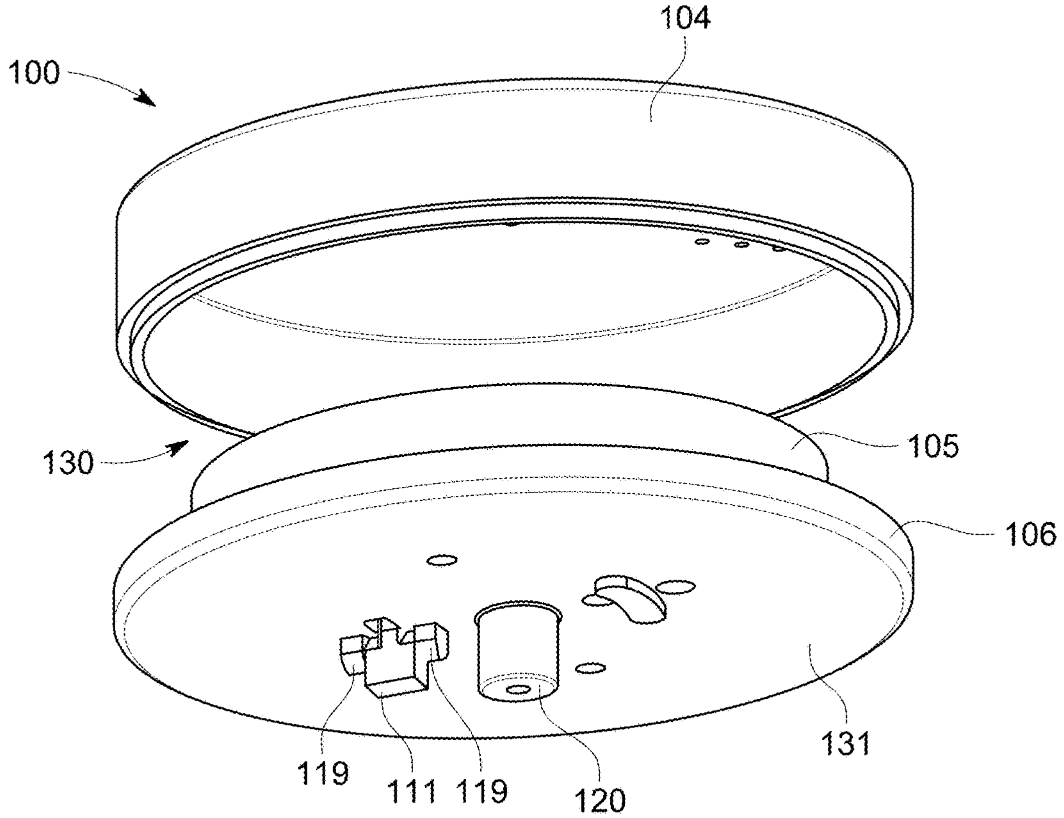
FIG. 25 a bottom perspective view of the centrifuge container of FIG. 18.
Figure 27:
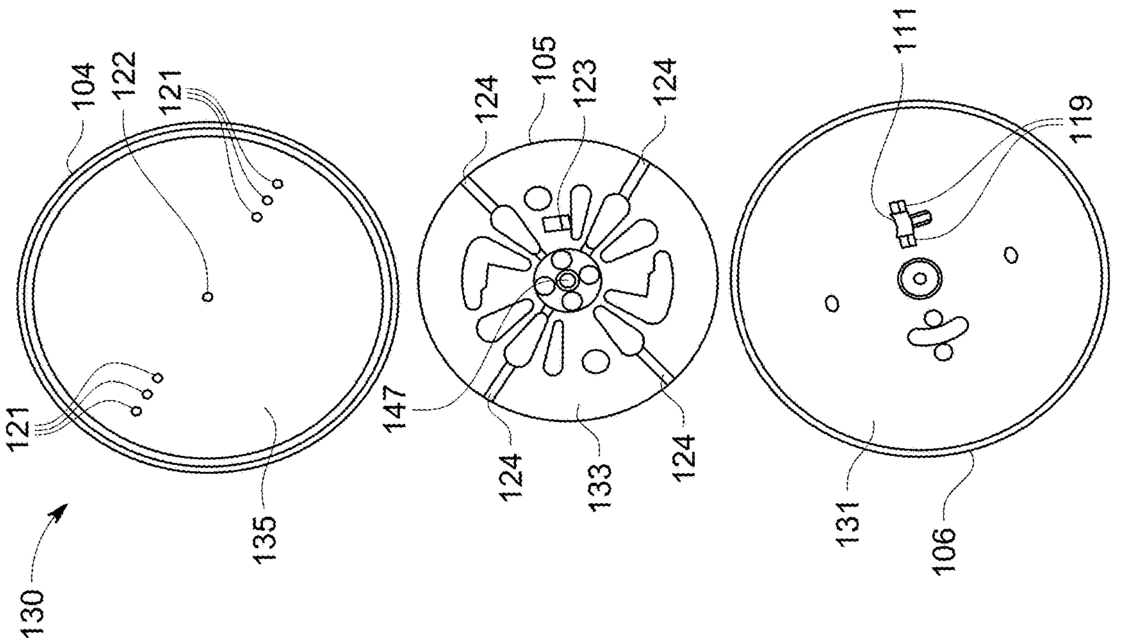
FIG. 27 is a bottom exploded view of the centrifuge cover, the sequester wheel, and the centrifuge base plate of FIG. 18.
Figure 26:
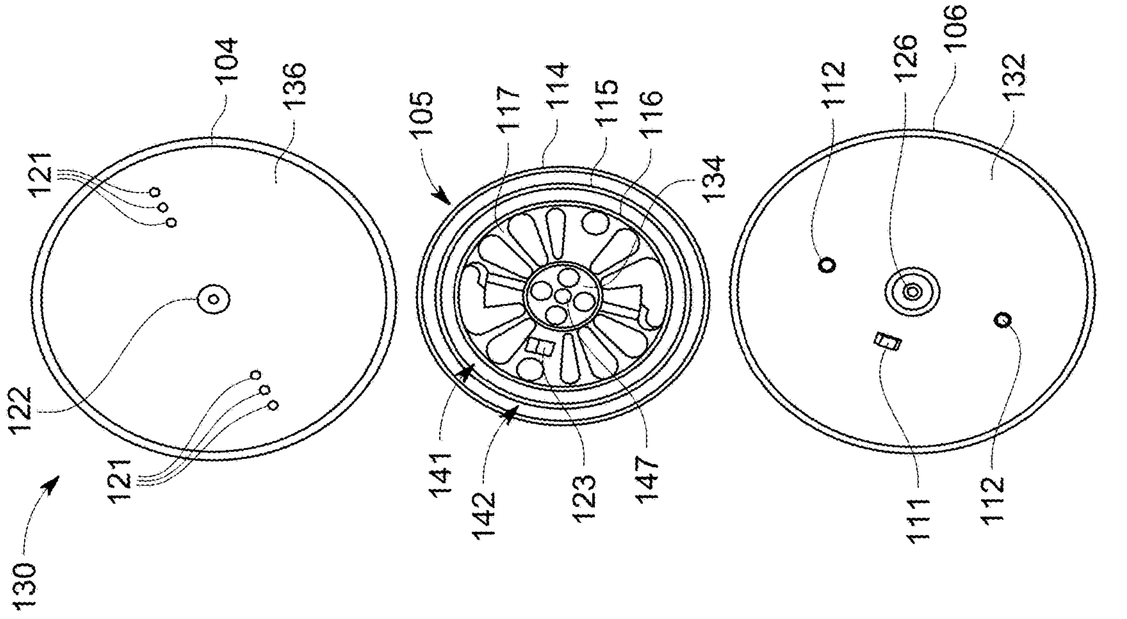
FIG. 26 is a top exploded view of a centrifuge cover, a sequester wheel, and a centrifuge base plate of the centrifuge container of FIG. 18.
Figure 28:
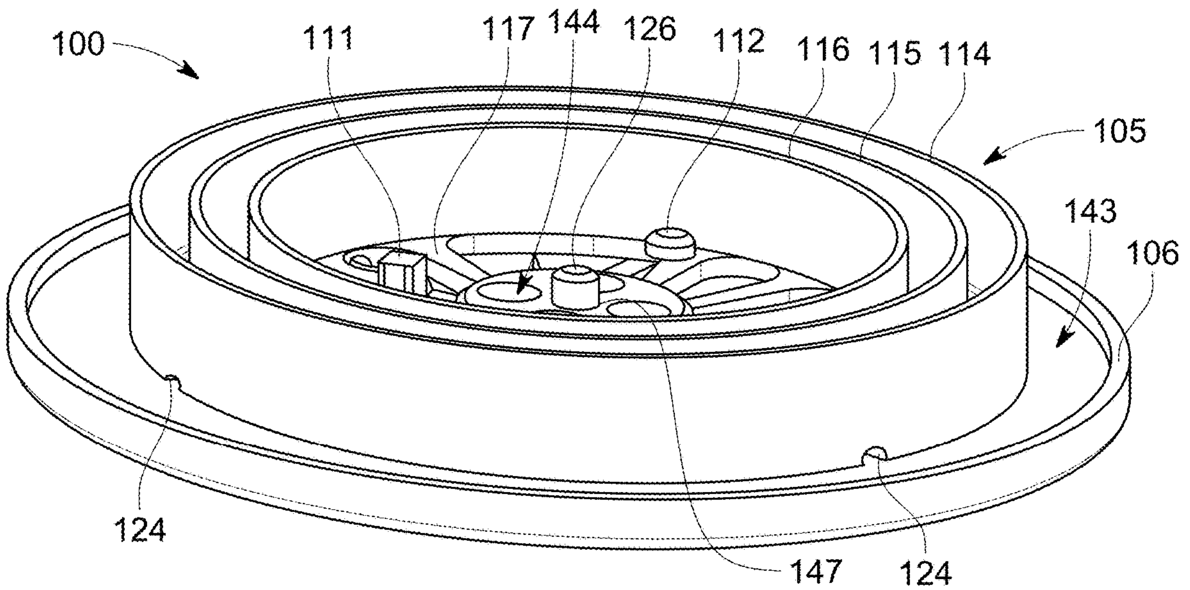
FIG. 28 is a top perspective view of the sequester wheel and the centrifuge base plate of FIG. 26.
Figure 29:
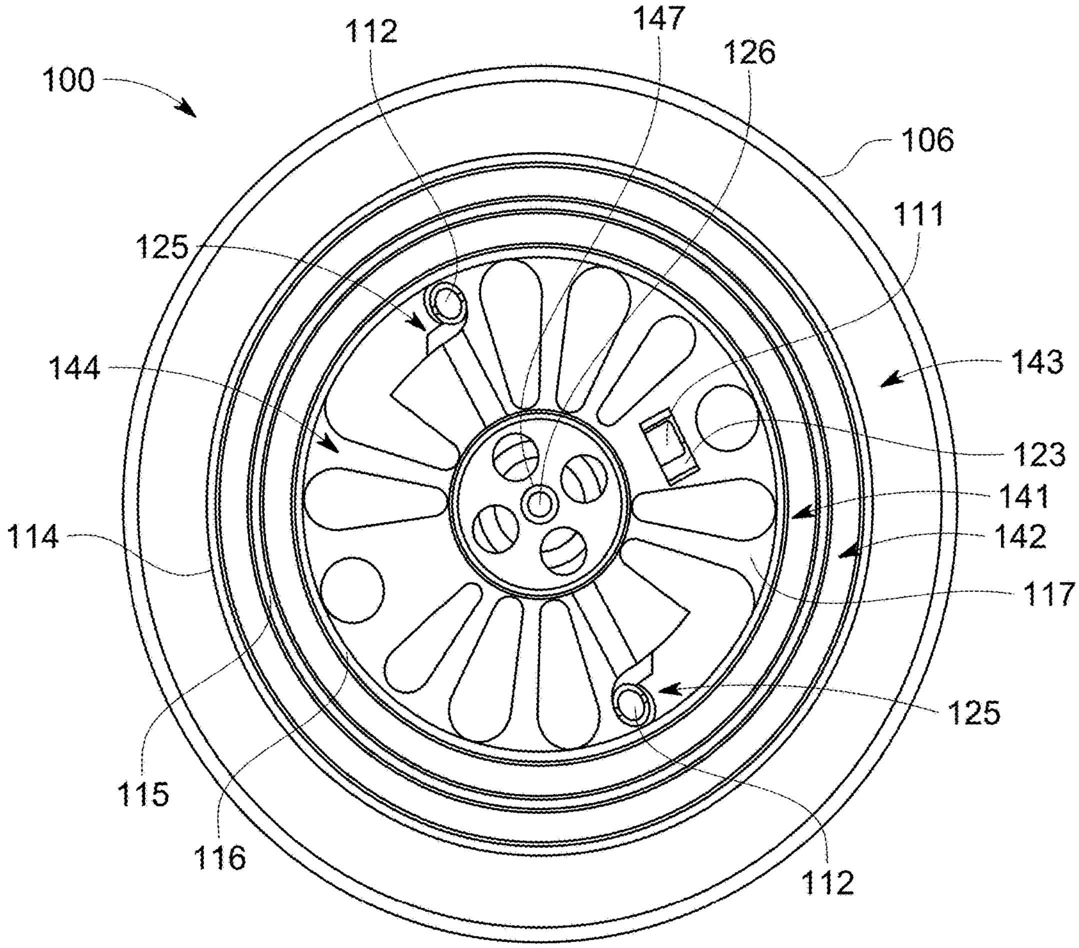
FIG. 29 is a top view of the sequester wheel and the centrifuge base plate of FIG. 26.
Figure 30:
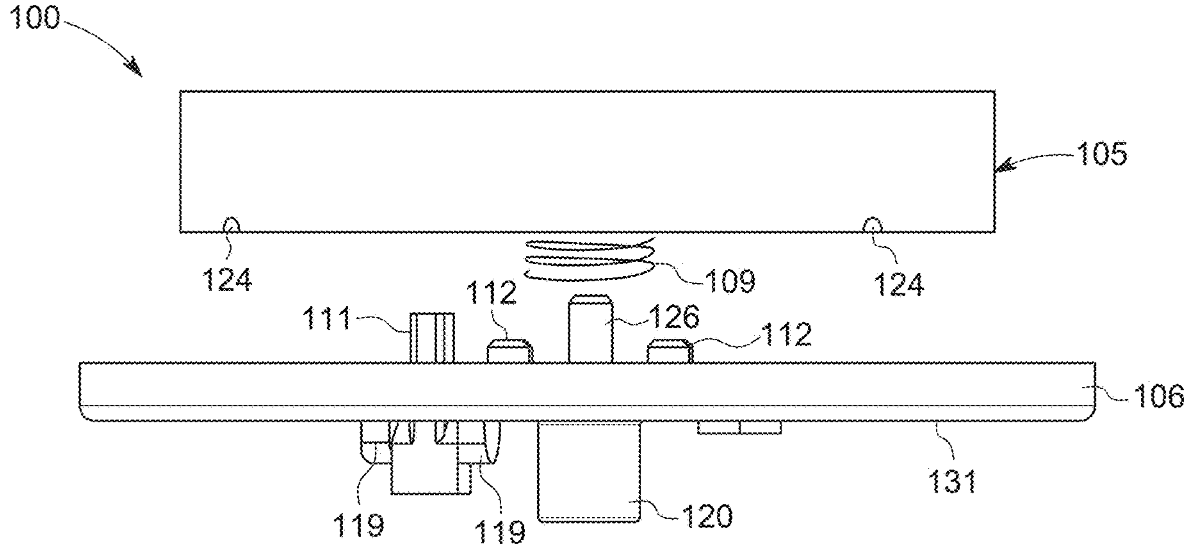
FIG. 30 is an exploded side view of the sequester wheel and the centrifuge base plate of FIG. 26.
Figure 31:
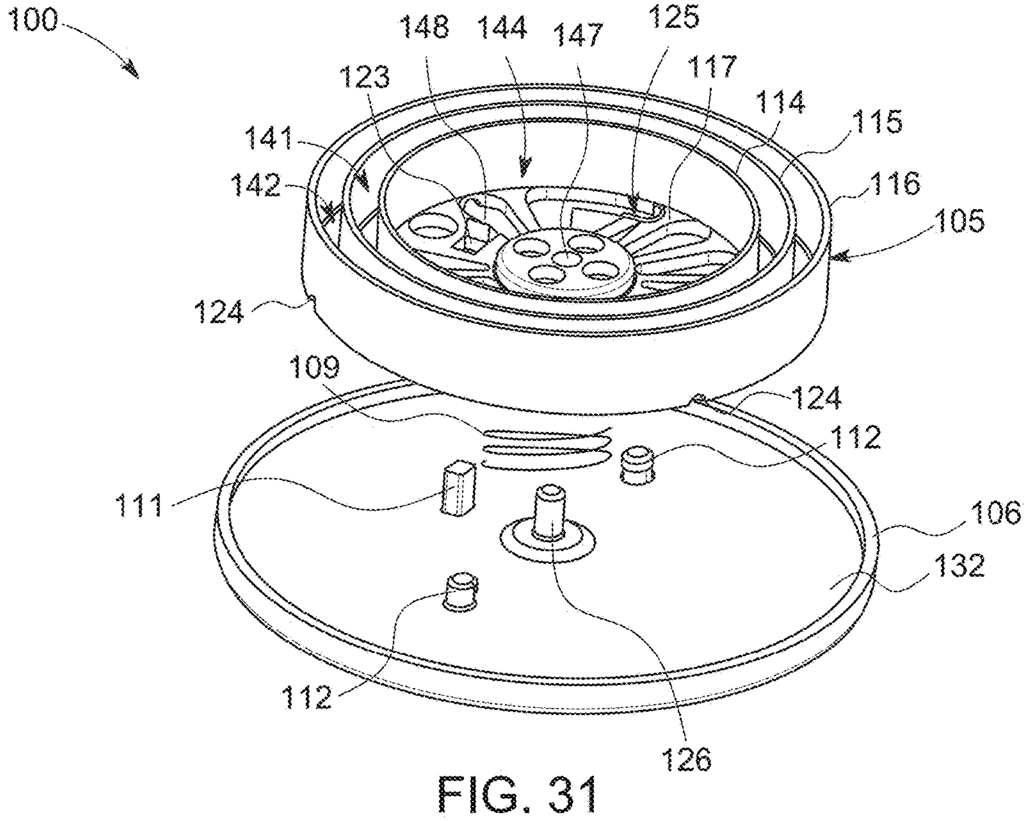
FIG. 31 is an exploded top perspective view of the sequester wheel and the centrifuge base plate of FIG. 26.
Figure 32:
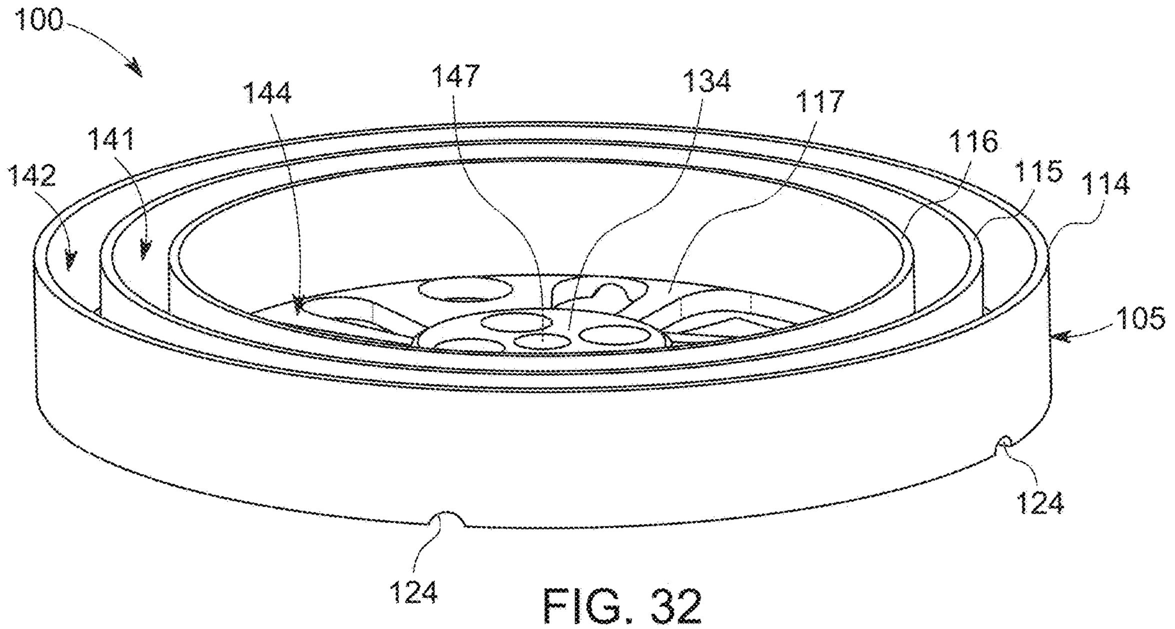
FIG. 32 is a top perspective view of the sequester wheel of the centrifuge of FIG. 1.
Figure 33:
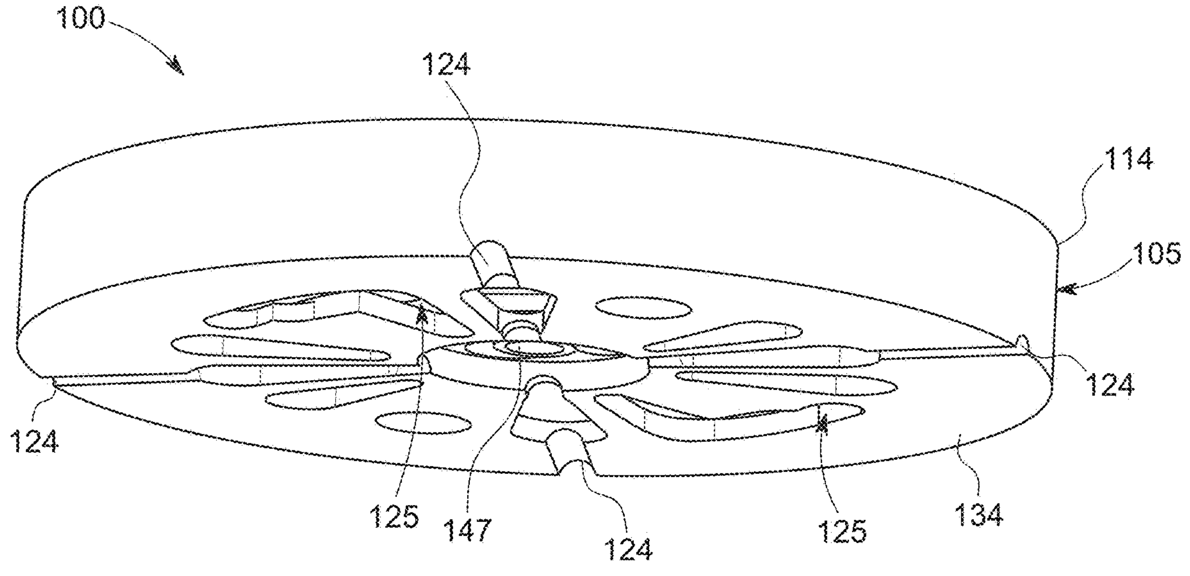
FIG. 33 is a bottom perspective view of the sequester wheel of the centrifuge of FIG. 1.
Figure 34:
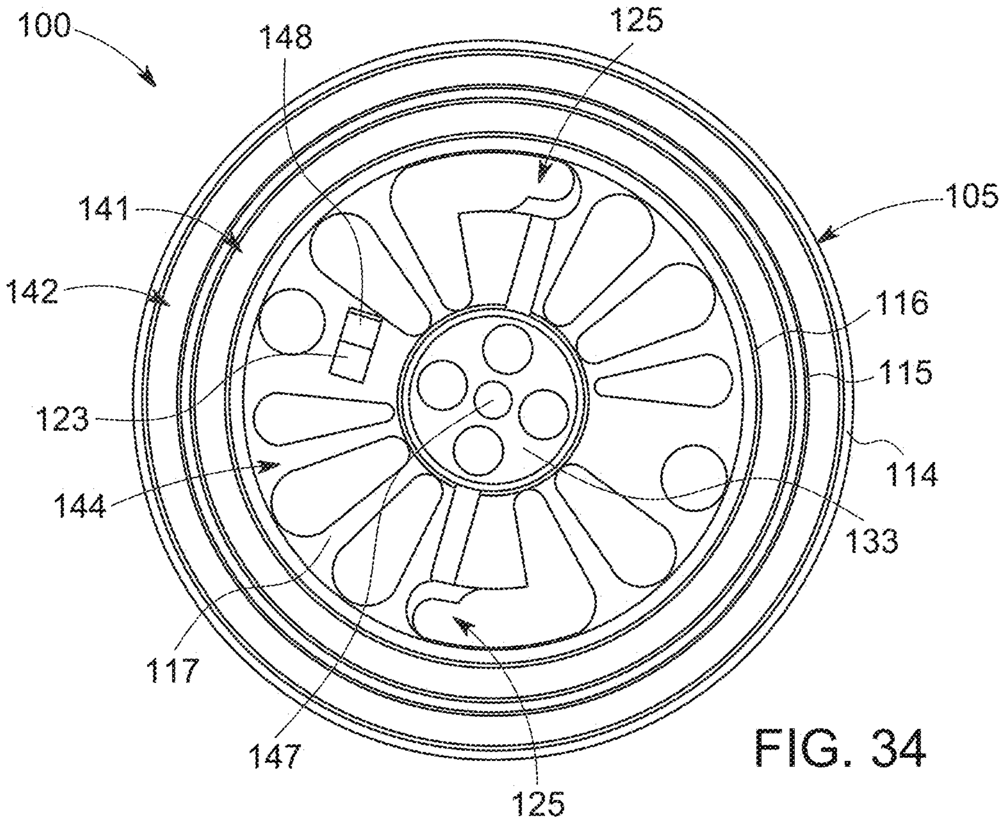
FIG. 34 is a top view of the sequester wheel of the centrifuge of FIG. 1.
Figure 35:
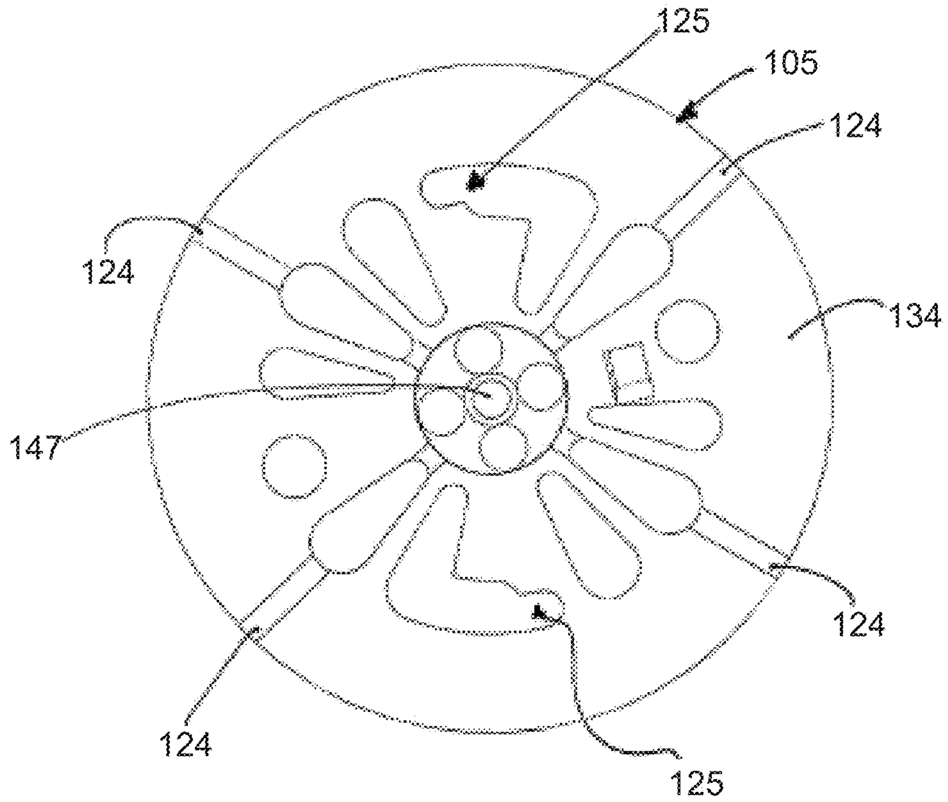
FIG. 35 is a bottom view of the sequester wheel of the centrifuge of FIG. 1.
Figure 36:
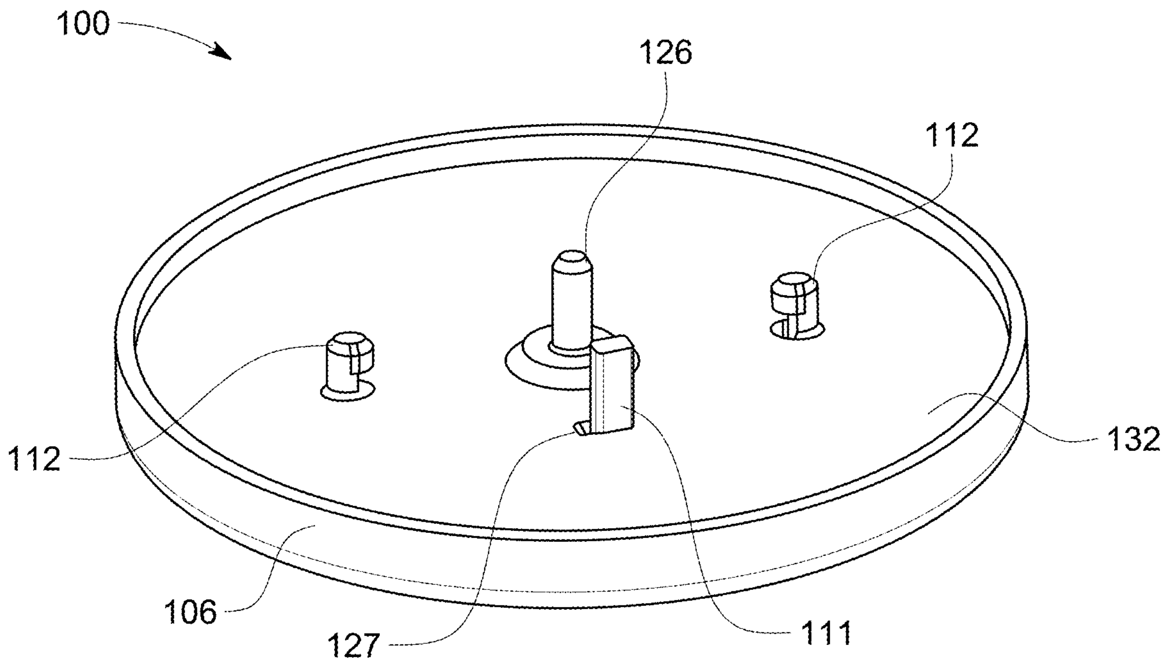
FIG. 36 is a top perspective view of the centrifuge base plate of the centrifuge of FIG. 1.
Figure 37:
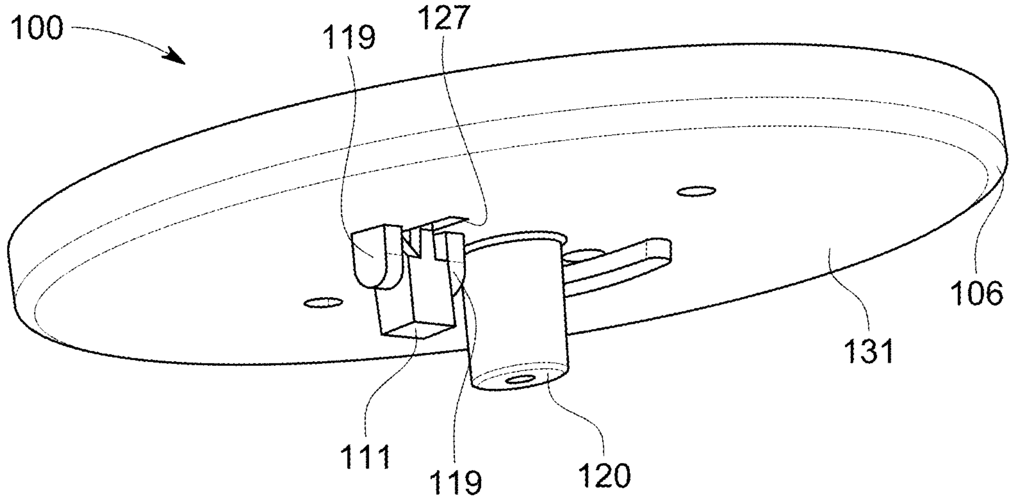
FIG. 37 is a bottom perspective view of the centrifuge base plate of the centrifuge of FIG. 1.
Figure 38:
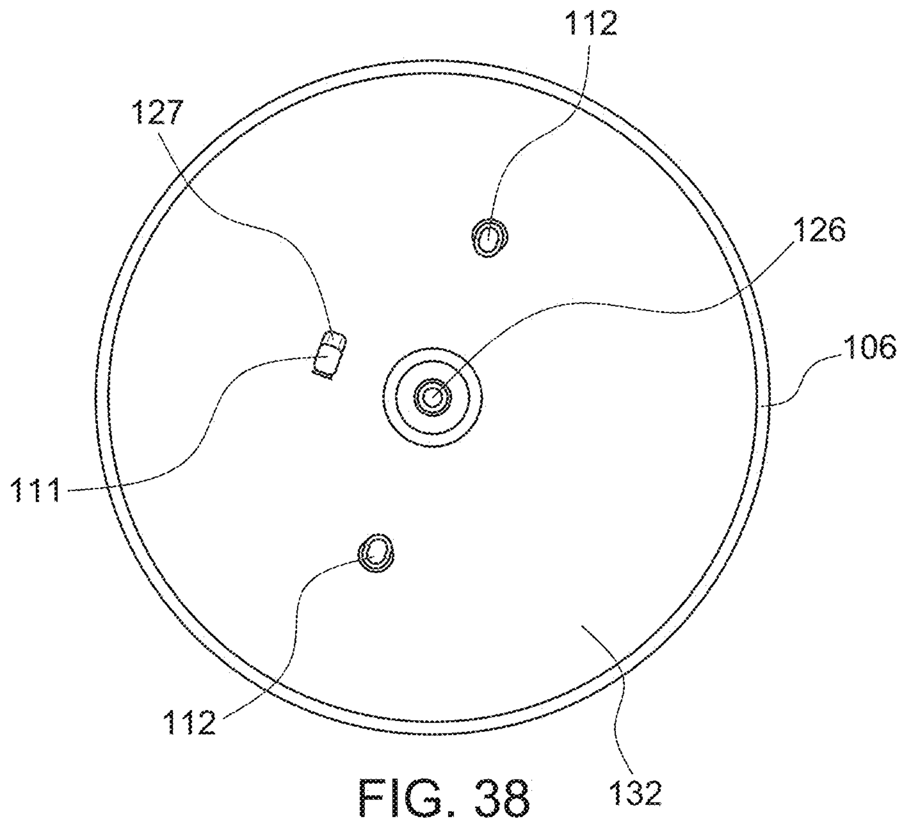
FIG. 38 is a top view of the centrifuge base plate of the centrifuge of FIG. 1.
Figure 39:
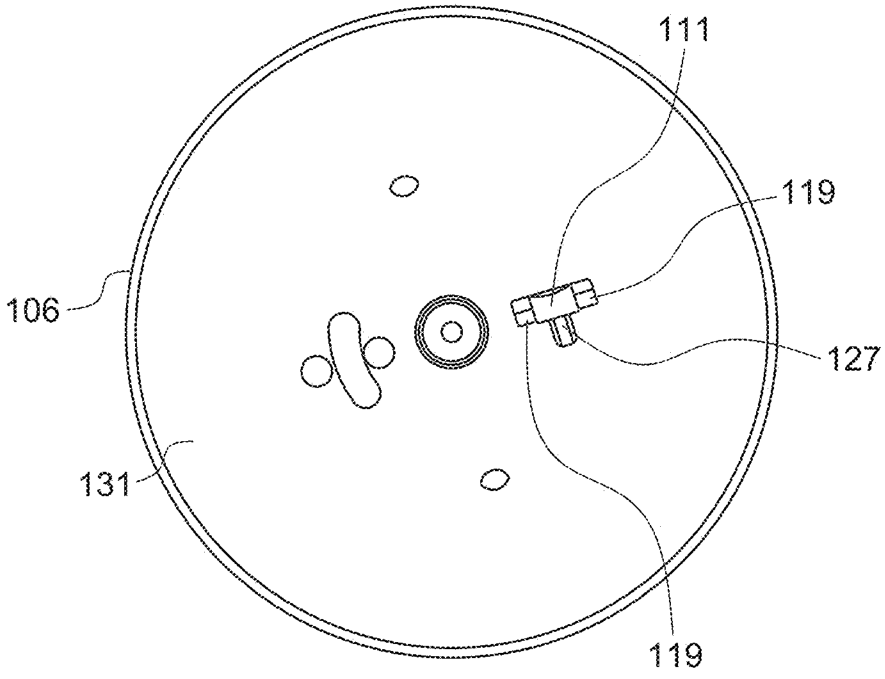
FIG. 39 is a bottom view of the centrifuge base plate of the centrifuge of FIG. 1.
Figure 40:
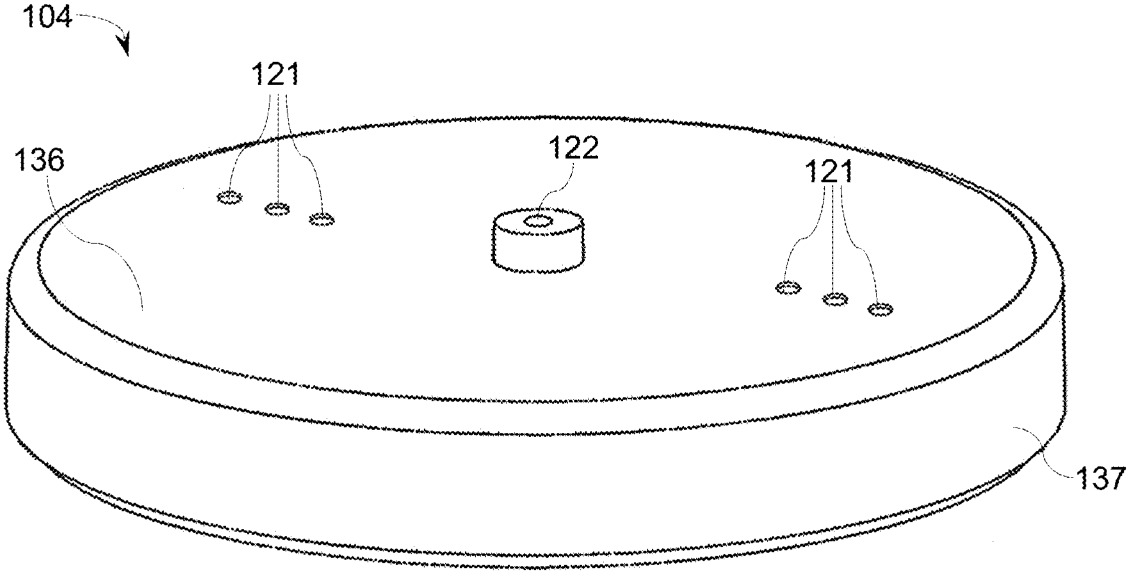
FIG. 40 is a side perspective view of the centrifuge cover of the centrifuge of FIG. 1.
Figure 41:
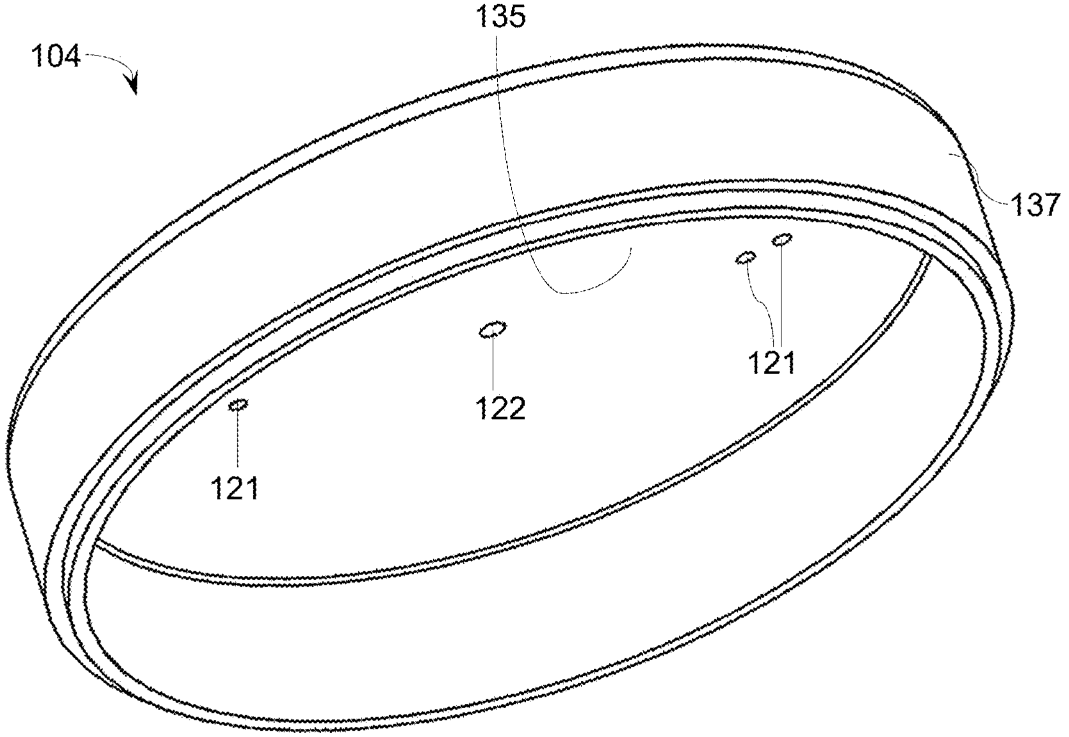
FIG. 41 is a bottom perspective view of the centrifuge cover of the centrifuge of FIG. 1.
Figure 42:
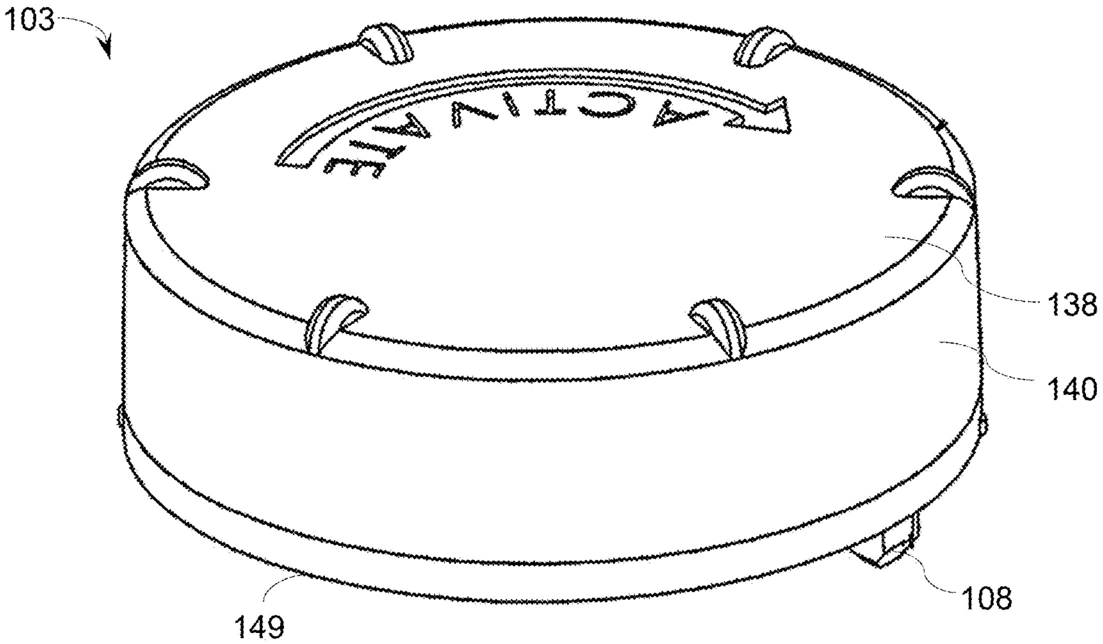
FIG. 42 is a top perspective view of the protective cover of the centrifuge of FIG. 1.
Figure 43:
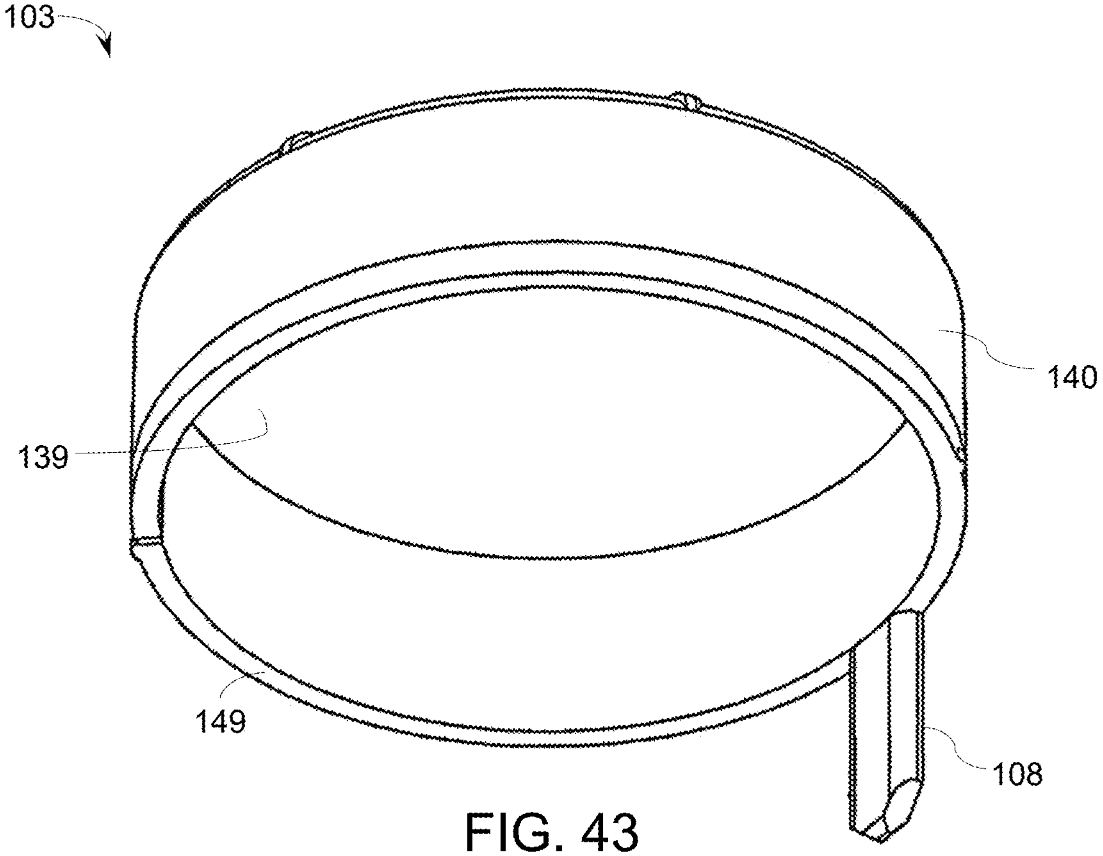
FIG. 43 is a bottom perspective view of the protective cover of the centrifuge of FIG. 1.
Figure 64A:
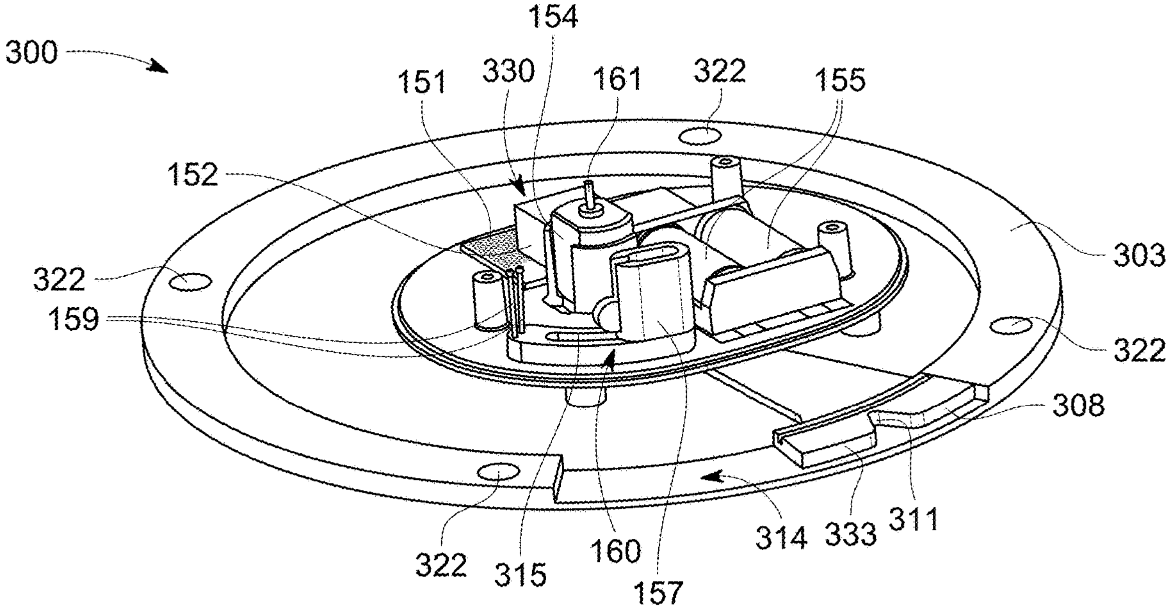
FIG. 64A is a top perspective view of the rotational mechanism of the centrifuge of FIG. 45.
Figure 64B:
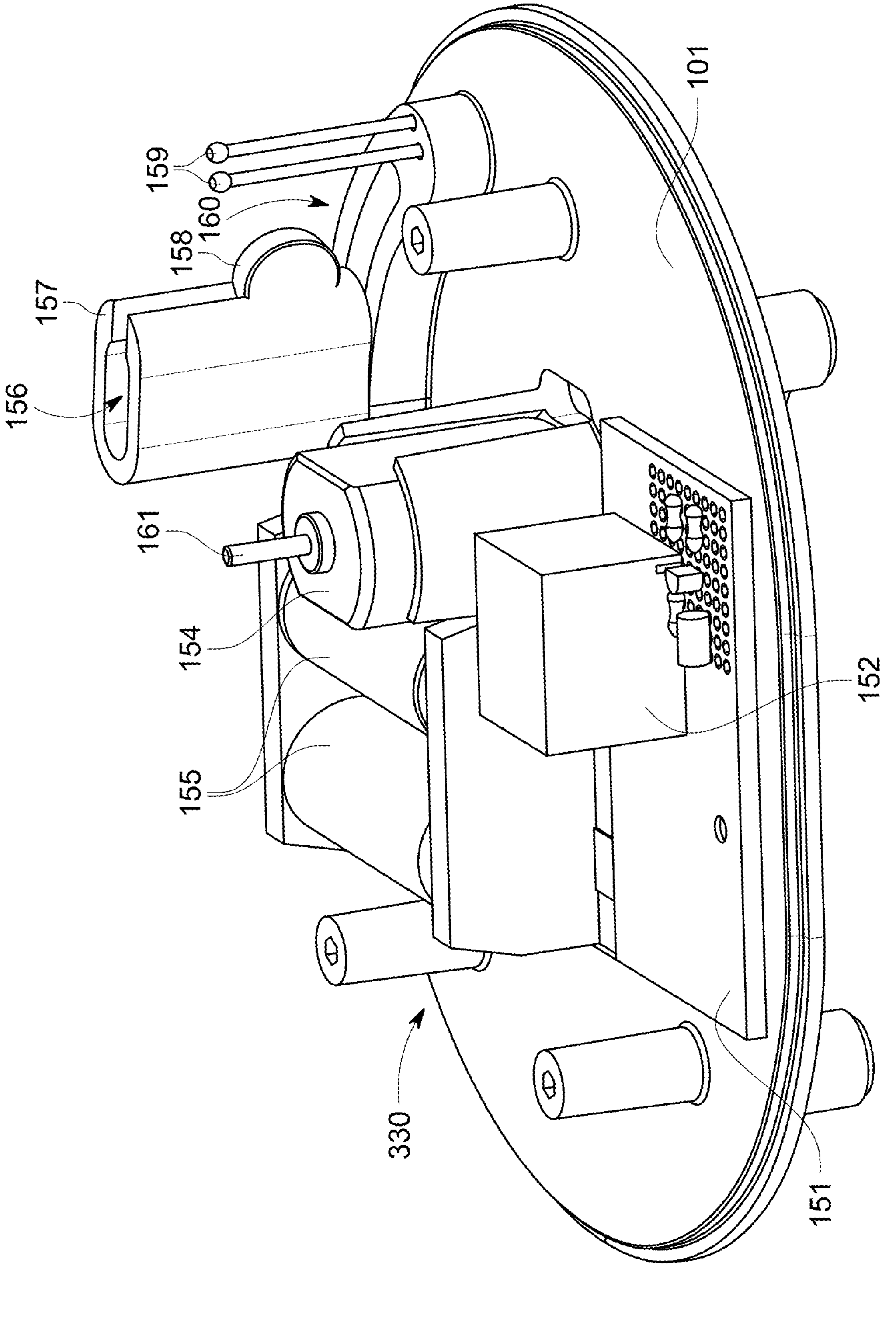
FIG. 64B is a top perspective view of the rotational mechanism of the centrifuge of FIG. 45.
Figure 65:
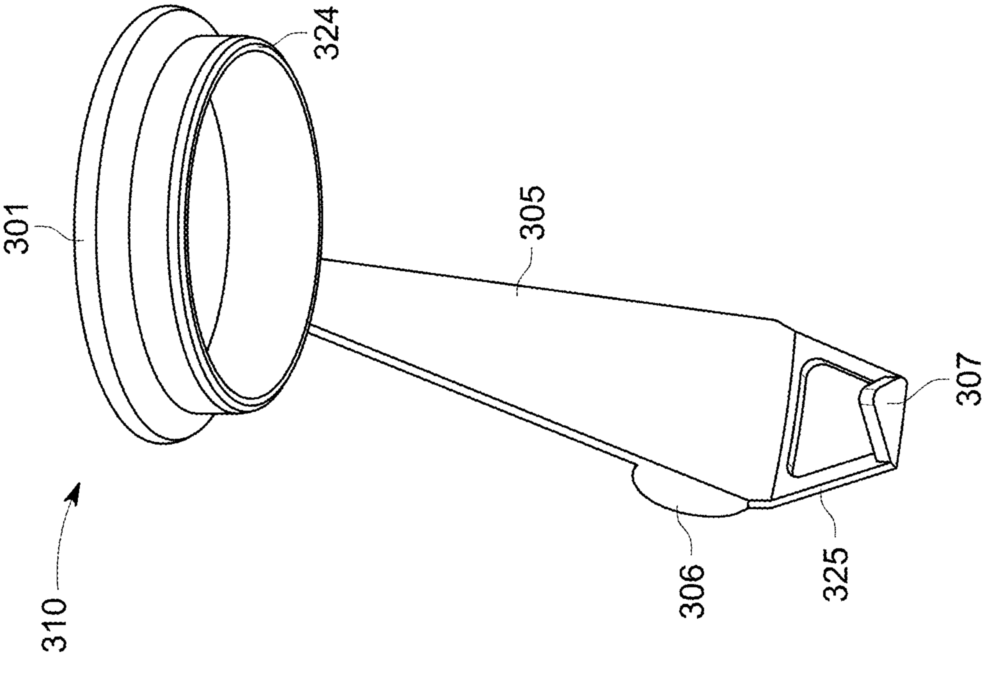
FIG. 65 is a bottom perspective view of the cap assembly of the centrifuge of FIG. 45.
Figure 66:
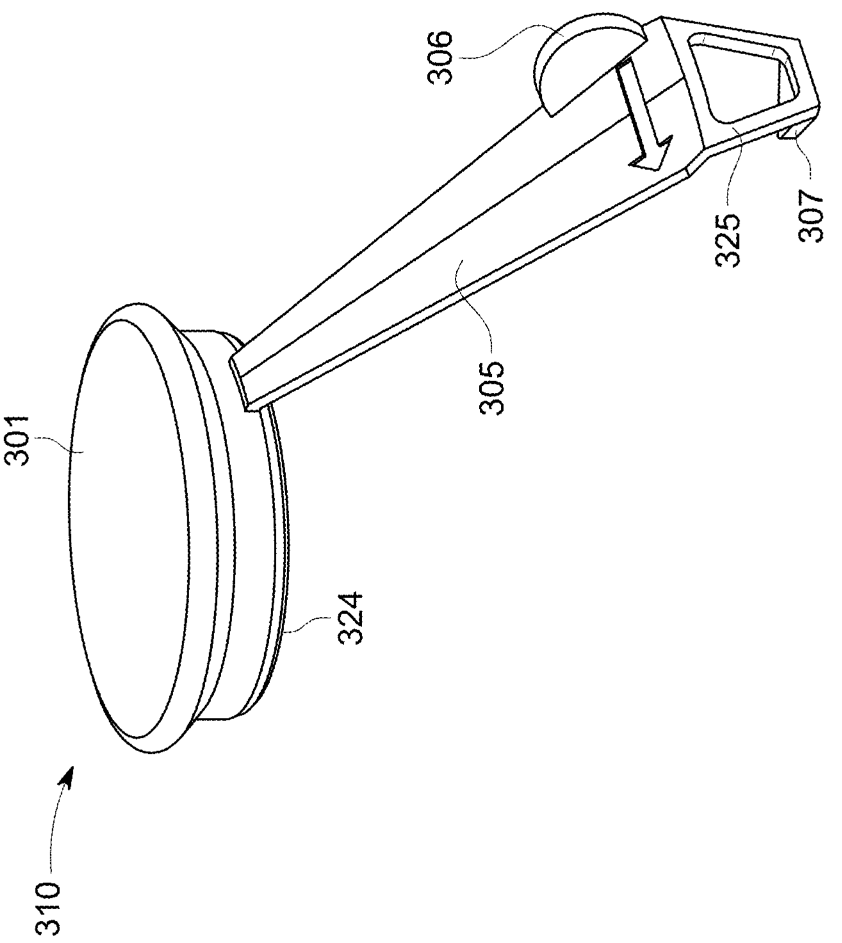
FIG. 66 is a top perspective view of the cap assembly of the centrifuge of FIG. 45.
Figure 67:
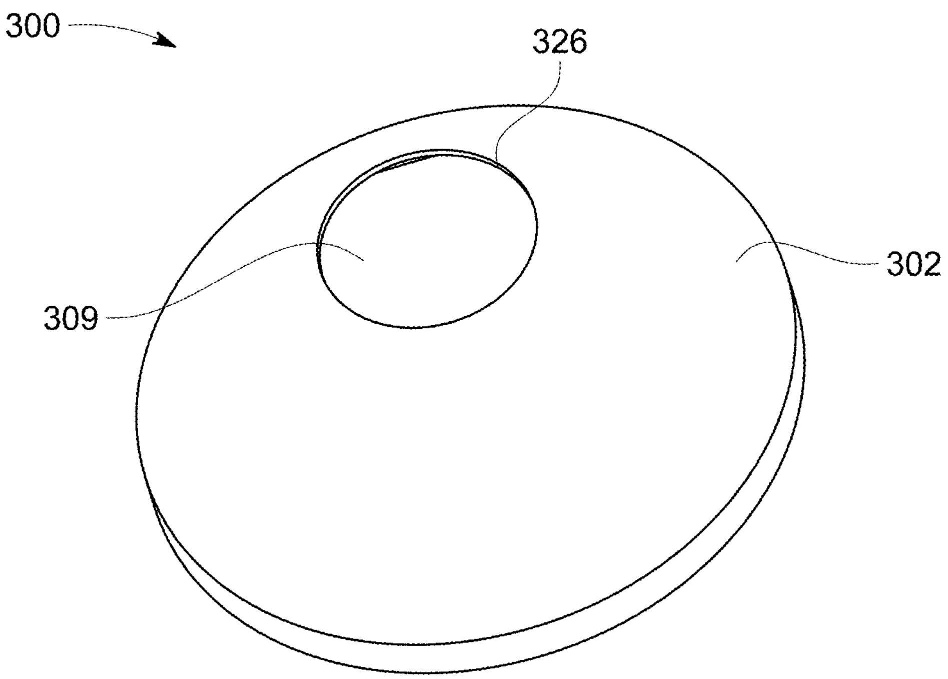
FIG. 67 is a top perspective view of the protective cover of the centrifuge of FIG. 45.
Figure 68:
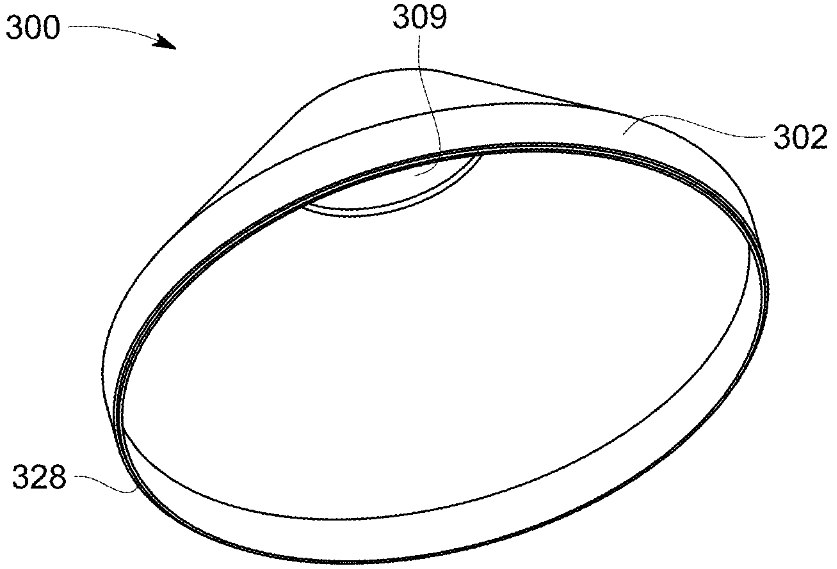
FIG. 68 is a bottom view of the protective cover of the centrifuge of FIG. 45.
Figure 69:
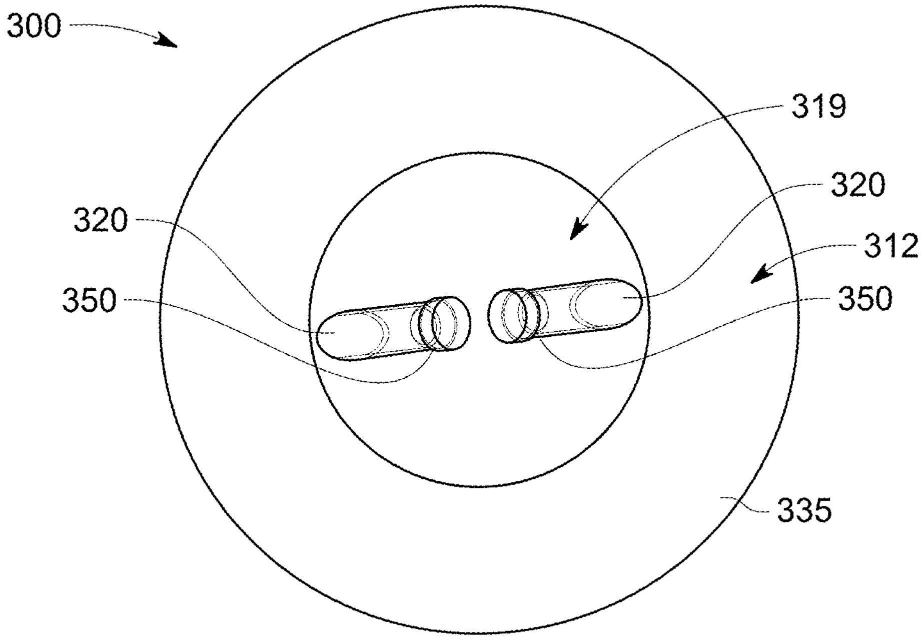
FIG. 69 is a top view of the test-tube armature of the centrifuge of FIG. 45.
Figure 70:
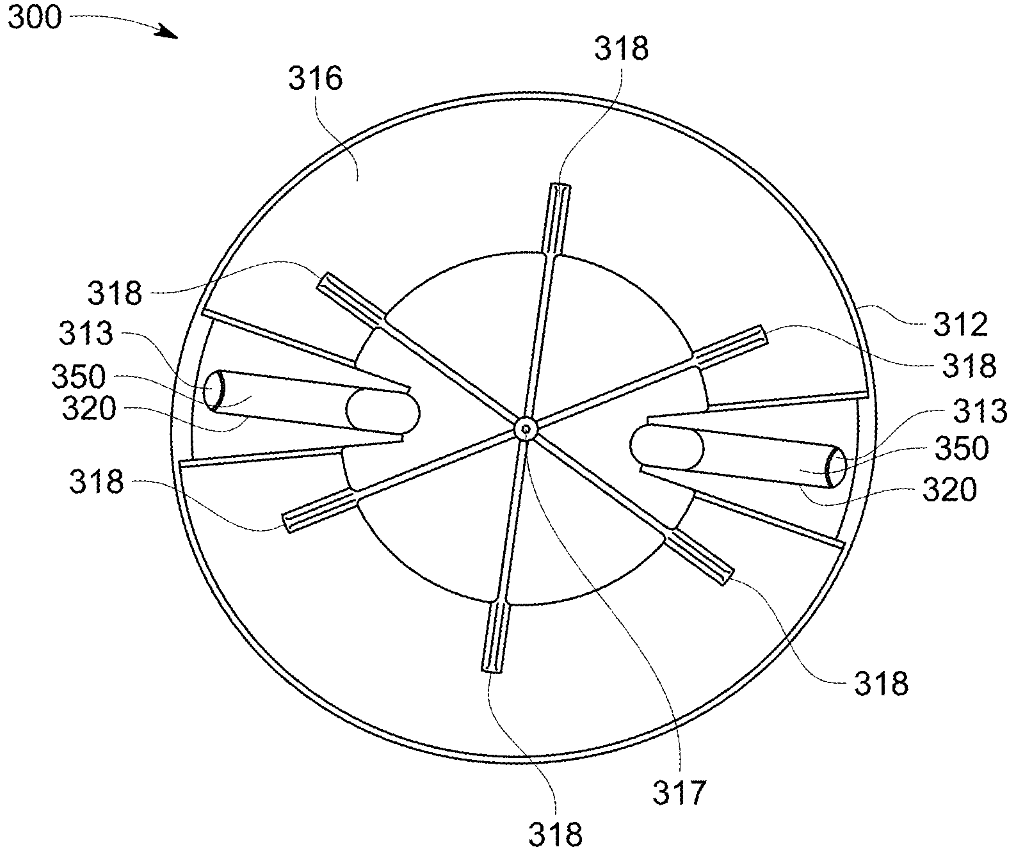
FIG. 70 is bottom view of the test-tube armature of the centrifuge of FIG. 45
Figure 71:
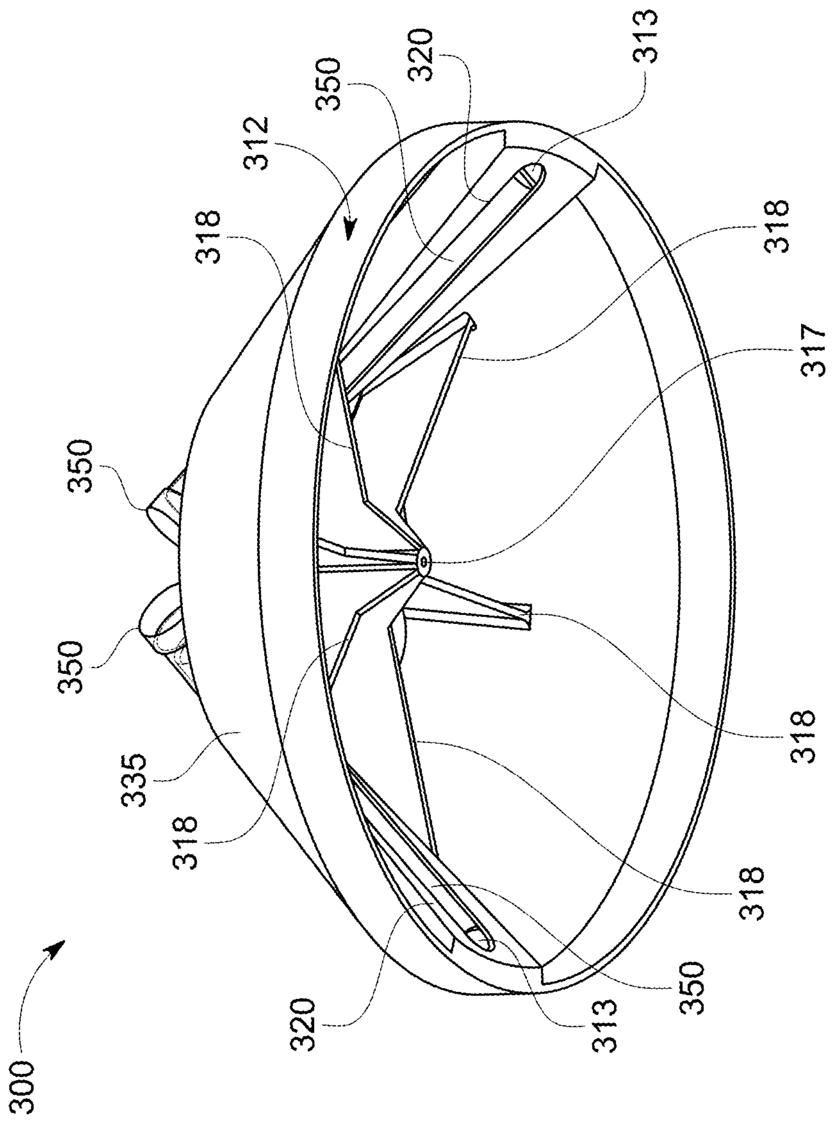
FIG. 71 is a bottom perspective view of the test-tube armature of the centrifuge of FIG. 45.
Figure 72:
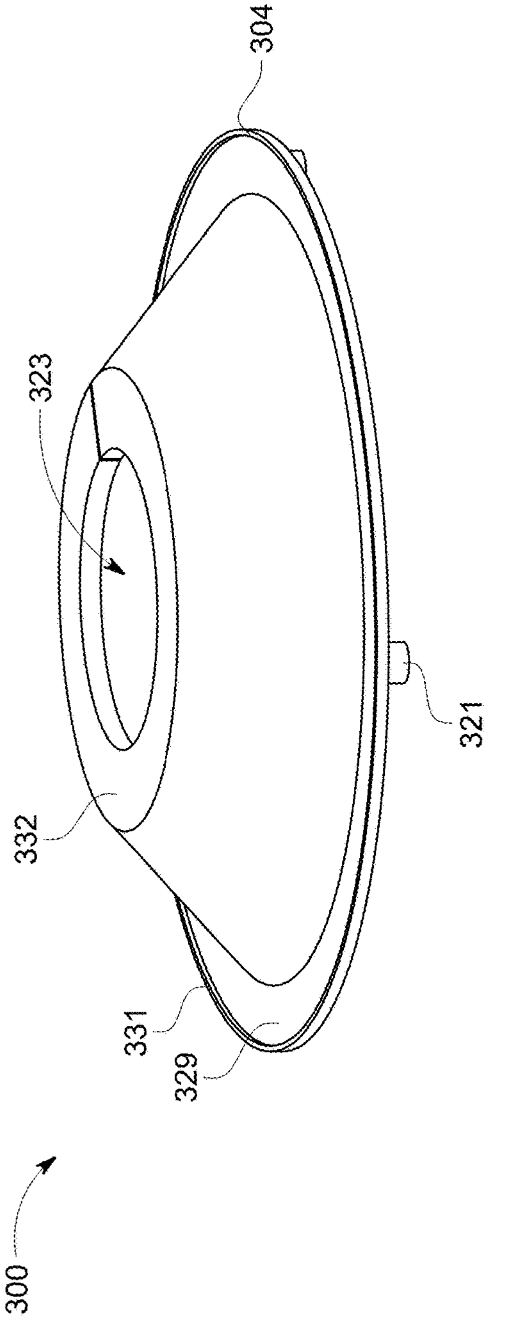
FIG. 72 is a top perspective view of the base frame cover of the centrifuge of FIG. 45.
Figure 73:
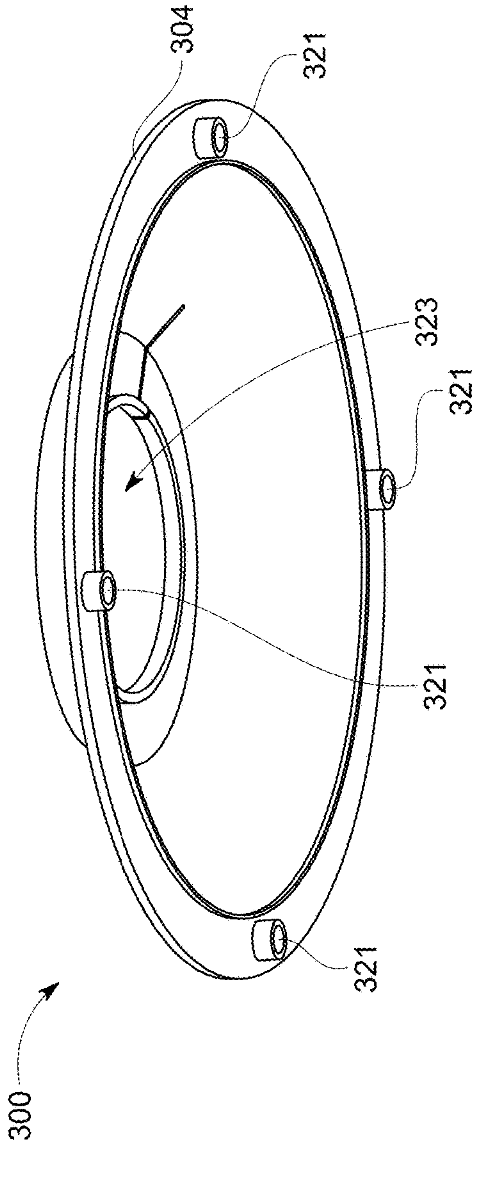
FIG. 73 is a bottom perspective view of the base frame cover of the centrifuge of FIG. 45.

Referring to FIGS. 16, 44, and 64B, centrifuge container 530 may be, for example, connected to the motor 154, with the motor armature 161, the base motor connector 120, the baseplate 506, and the protrusion 126 connected for coaxial alignment and rotation about a common axis 565. The protective cover 103 may be placed over the centrifuge container 530, with the activation tab 108 inserted through the activation slot 107 and into the activation slider slot 156. While the axle 126 is shown, there may be aspects of the centrifuge 500 that do not have the axle 126.

With reference to FIGS. 1, 2, 14, 44, 64B, and 88, a method of use for centrifuge 500 may include removing the protective cover 570 and introducing blood into the centrifuge container 571. Blood may be introduced into the centrifuge container 530 through, for example, the insertion hole 122 into the centrifuge container 530, using for example, a syringe (not shown). Replacing the protective cover 103, the activation tab 108 is inserted through the activation slot 107 and into the activation slider slot 156. The protective cover may be turned to activate the centrifuge 573 and the centrifuge container may rotate 574. The blood may interact with the thixotropic gel and the anti-coagulant 575 and may separate into constituent components 576. Turning the protective cap 103, causes the activation tab 108 to move the sliding switch 157 so that the conductive member 158 contacts the circuit members 159 and creates a closed circuit. The electric motor 154 spins the centrifuge container 530. The separation gel may, for example, interact with the RBCs, creating a barrier for RBCs, while the anti-coagulant may, for example, inhibit PRP and PPP from coagulating. A timer may send a stop signal to the motor 577 and the centrifuge container may stop rotation 578. The timer on the circuit board 151 opens the circuit after a threshold time is reached, and the rotation of the centrifuge container 530 continues, slowing to a stop. The protective cover 103 may be removed 579. The use of a separation gel and an anti-coagulant creates distinguishable separation of the blood constituents (e.g., RBC, PRP, and PPP). PRP is generally in a gradient of concentrations between a PPP constituent volume and the PRP constituent volume, allowing extraction of a desired PRP concentration. The blood constituent components may be removed 580. The RBC, PRP, and/or PPP may then, for example, be removed using the plurality of extraction holes 121 by inserting a sharp object, such as, for example, a syringe (not shown).

In other aspects of the centrifuges 300, 400, 500, the rotational mechanism 110 may be used instead of rotational mechanism 330. If rotational mechanism 110 is used with centrifuges 300, 400, and 500, the solenoid 153 and thus solenoid armature 163 may be used to provide braking by triggering and extending the solenoid armature 163 to make contact with the rotor 312 or centrifuge container 430 or 330.

Figure 74:
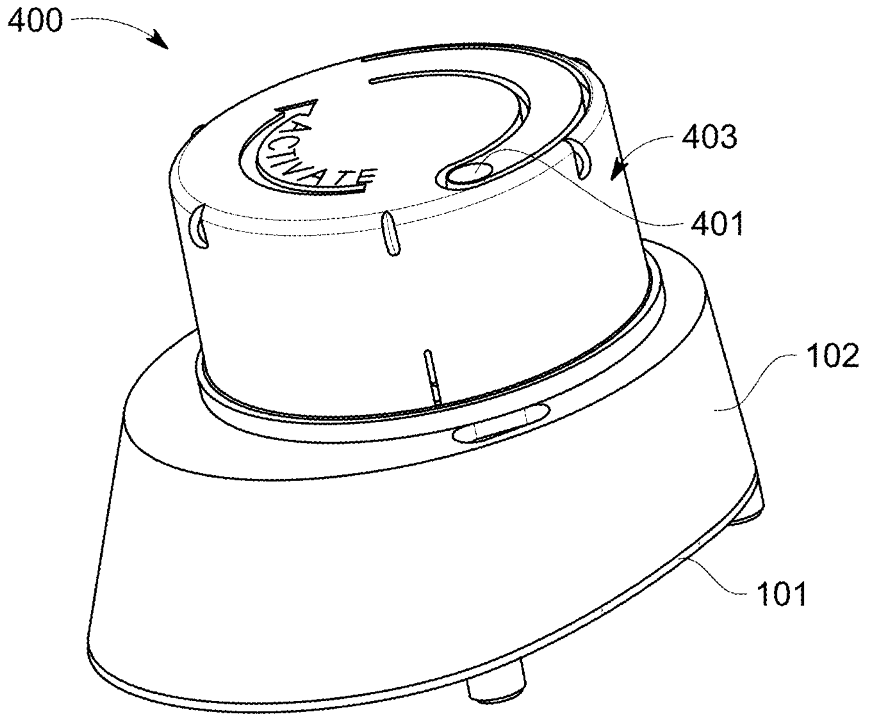
FIG. 74 is a top perspective view of an alternate embodiment of a centrifuge.
Figure 75:
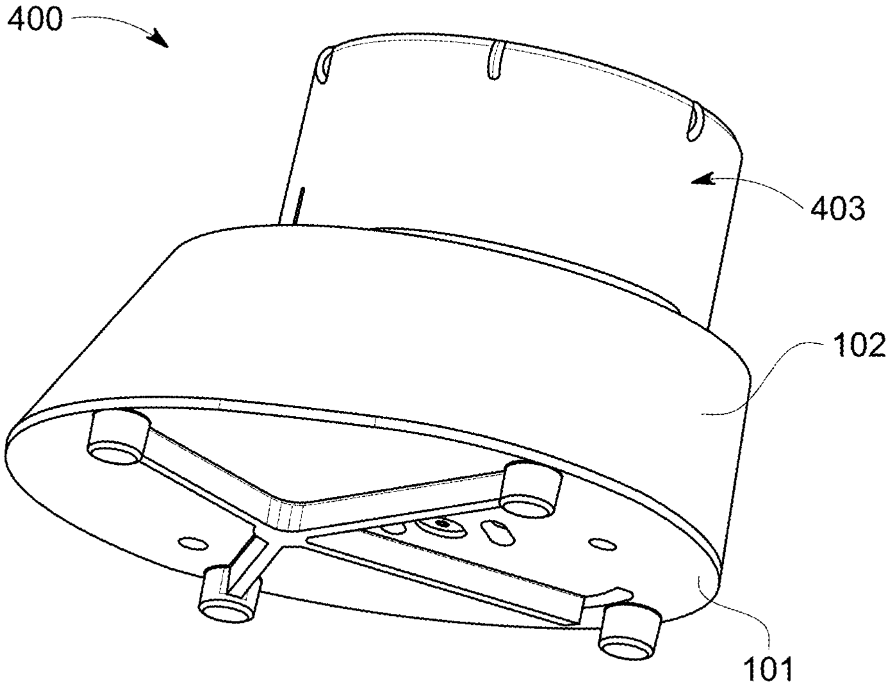
FIG. 75 is a bottom perspective view of the centrifuge of FIG. 74.
Figure 77:
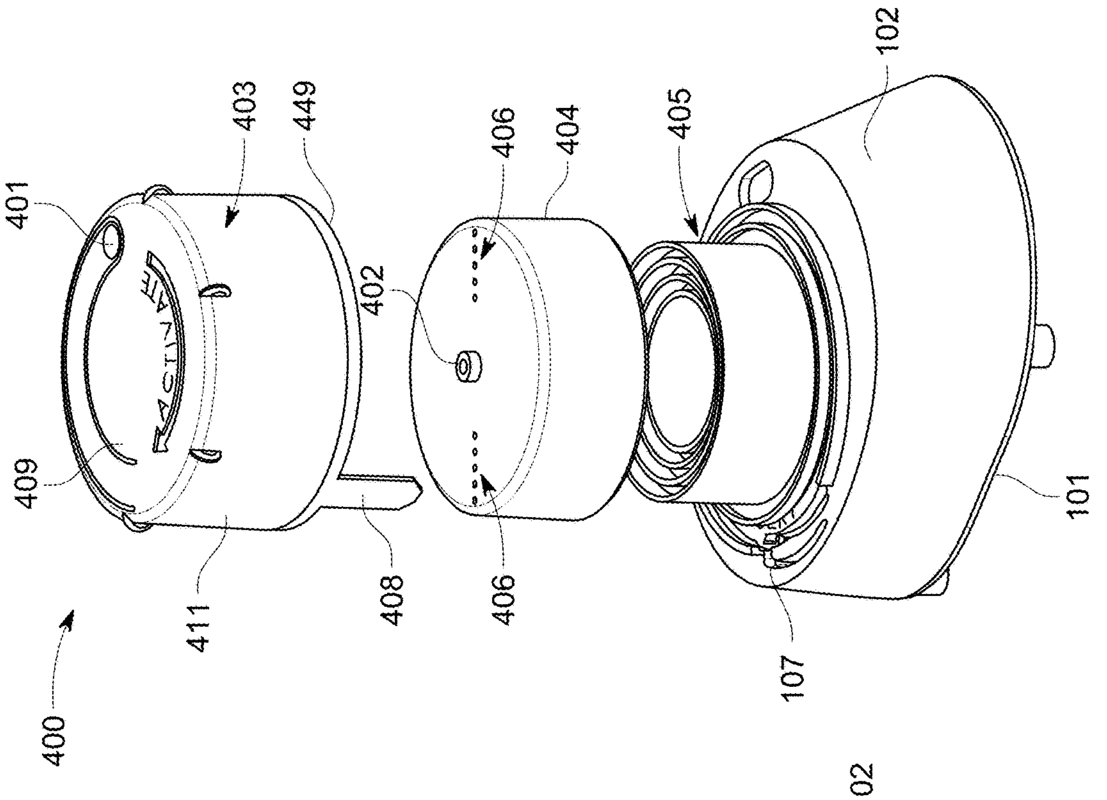
FIG. 77 is a top perspective view of the centrifuge of FIG. 74 with a protective cover and centrifuge cover removed.
Figure 76:
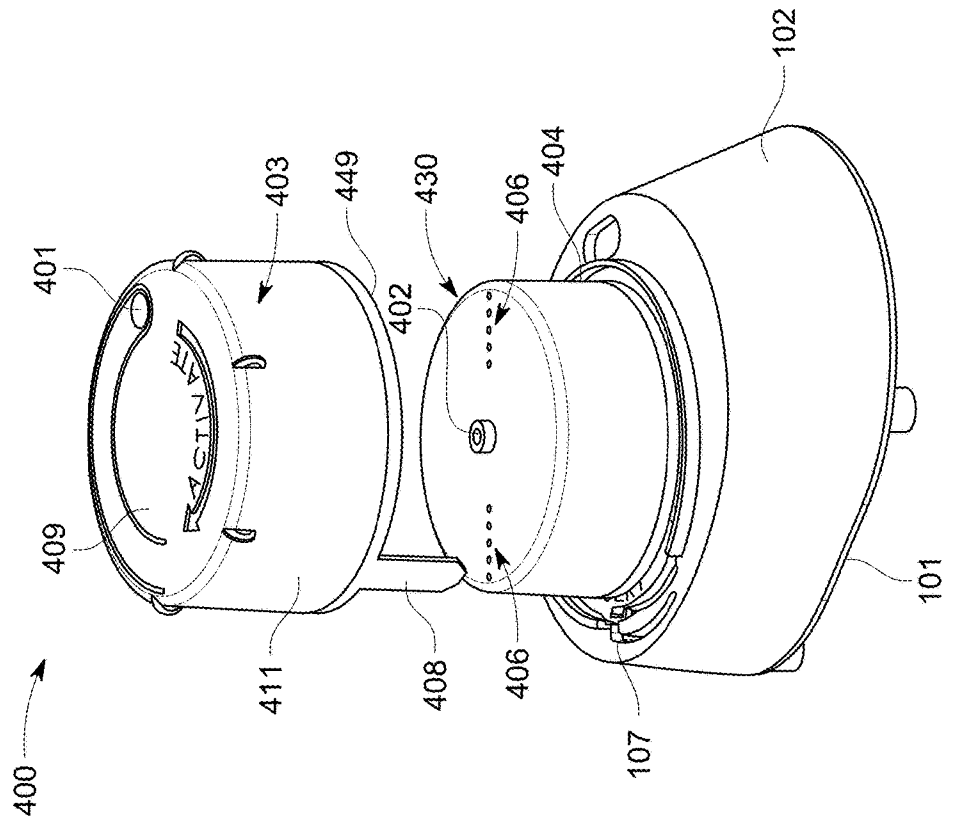
FIG. 76 is a top perspective view of the centrifuge of FIG. 74 with a protective cover removed.
Figure 78:
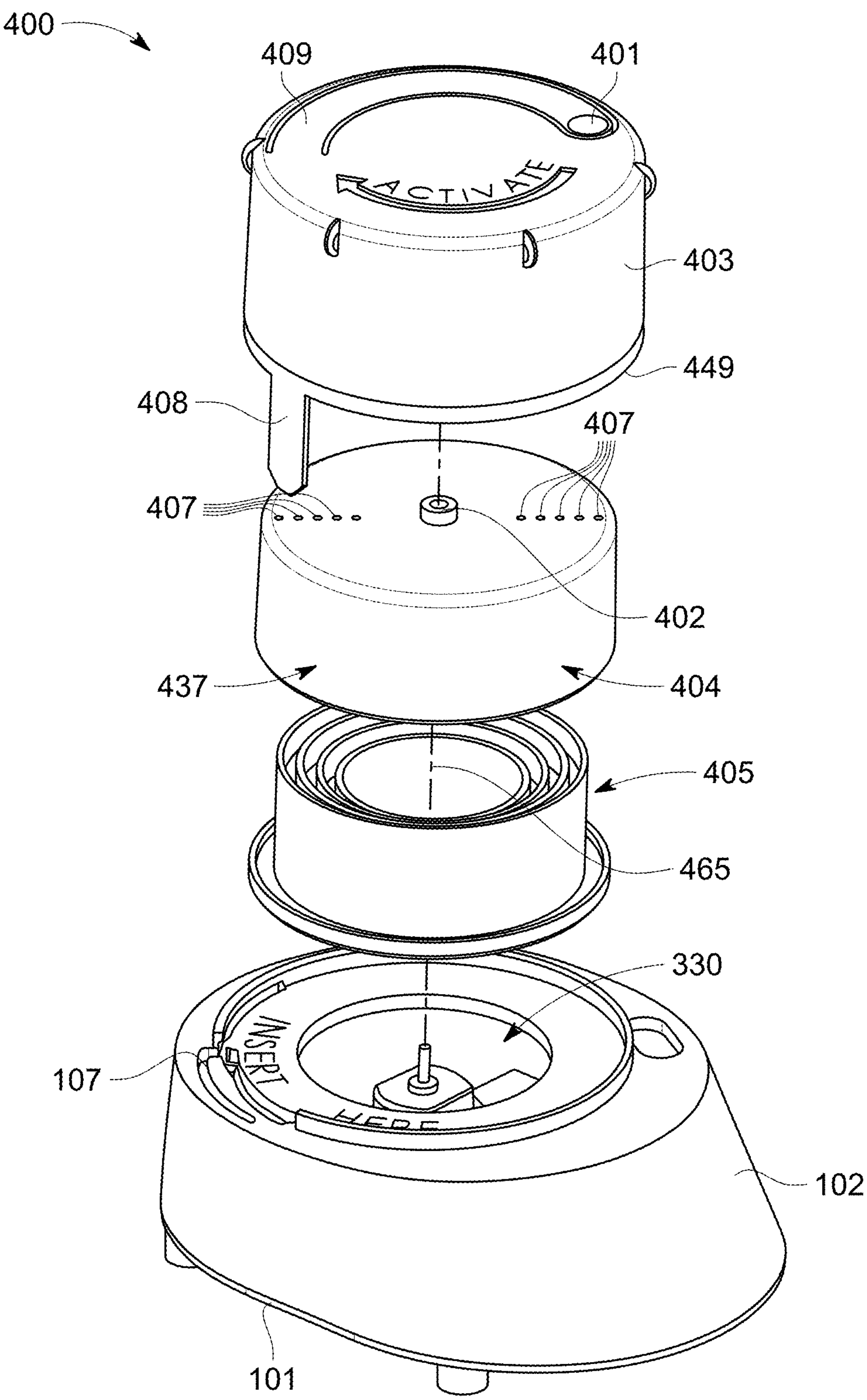
FIG. 78 is an exploded top perspective view of the centrifuge of FIG. 74.
Figure 80:
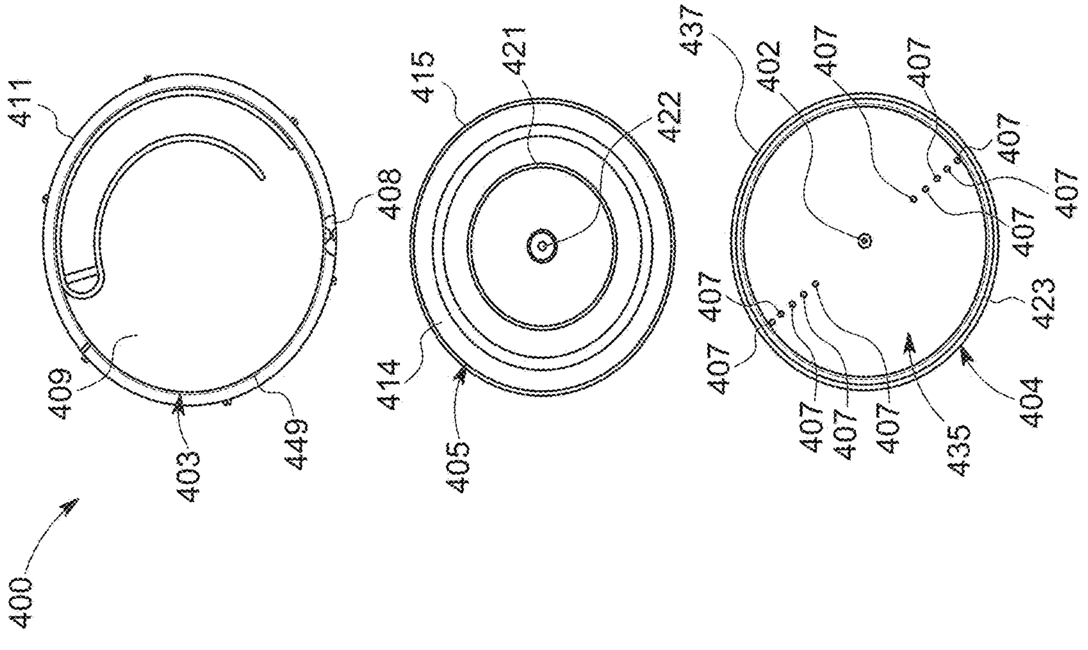
FIG. 80 is a bottom view of the protective cover, the centrifuge cover, and the tiered separation wheel of the centrifuge of FIG. 74.
Figure 79:
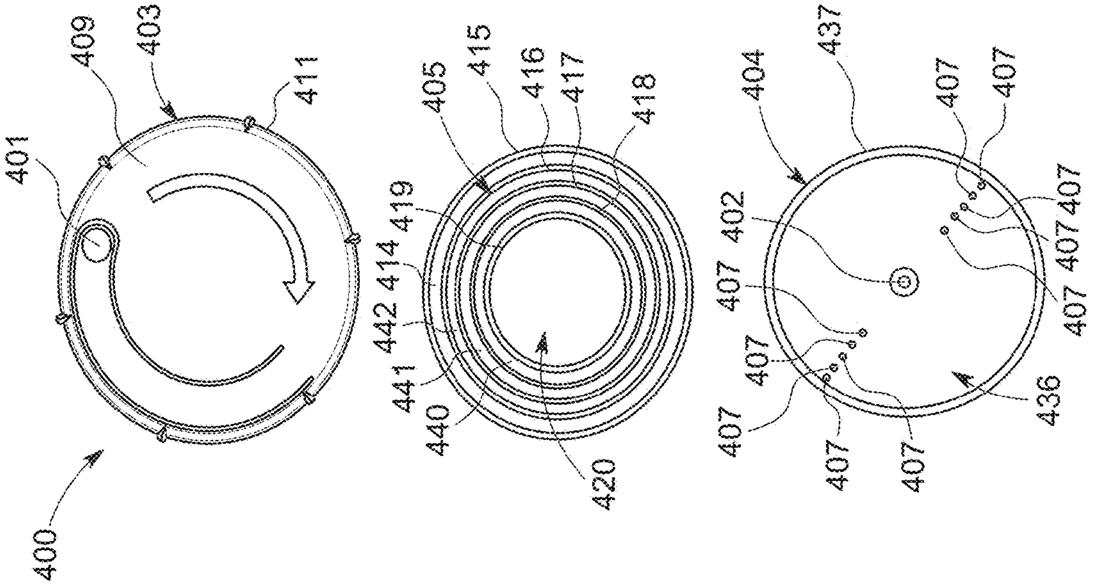
FIG. 79 is a top view of the protective cover, the centrifuge cover, and the tiered separation wheel of FIG. 78.
Figure 81:
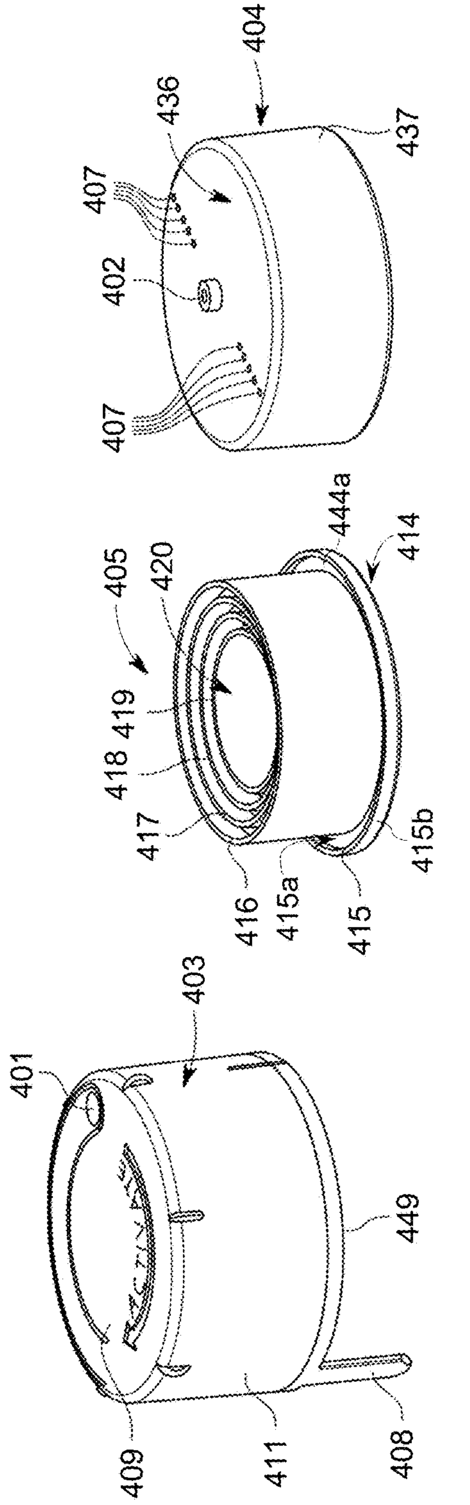
FIG. 81 is a top perspective view of the protective cover, the centrifuge cover, and the tiered separation wheel of the centrifuge of FIG. 74.
Figure 82:
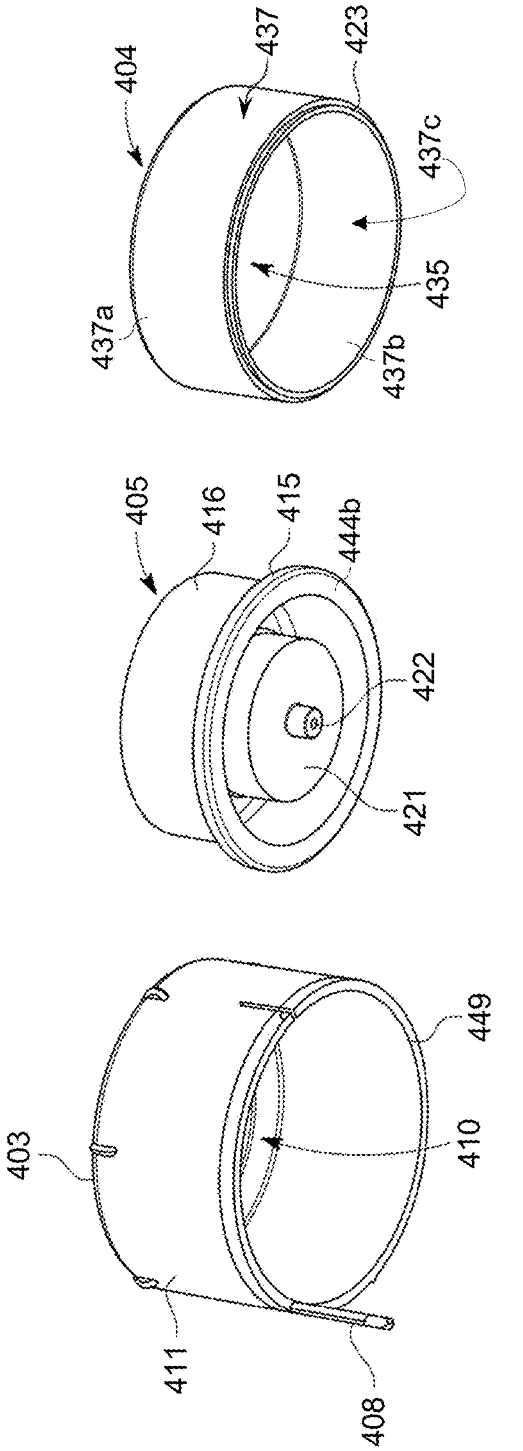
FIG. 82 is a bottom perspective view of the protective cover, the centrifuge cover, and the tiered separation wheel of the centrifuge of FIG. 74.
Figure 83:
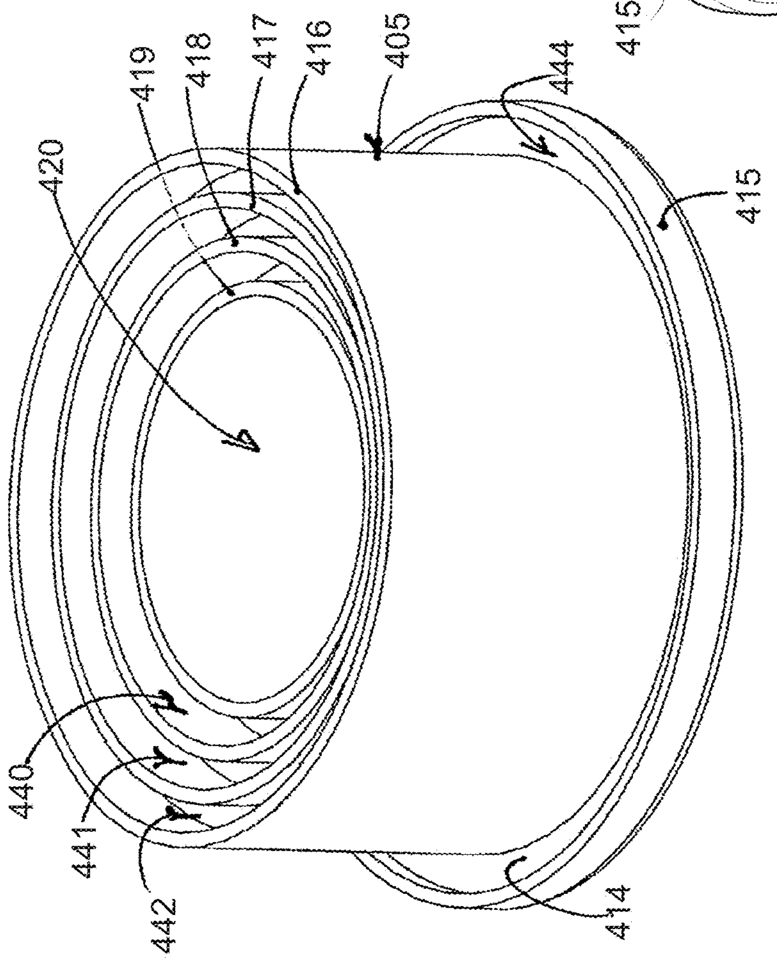
FIG. 83 is a top perspective view of the tiered separation wheel of the centrifuge of FIG. 74.
Figure 84:
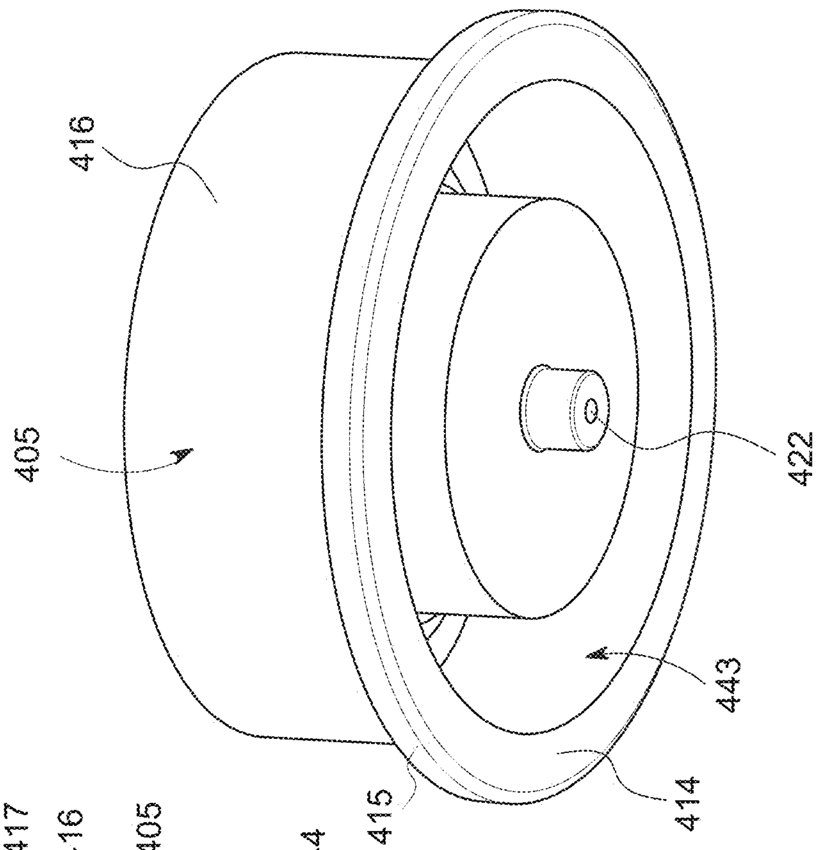
FIG. 84 is a bottom perspective view of the tiered separation wheel of the centrifuge of FIG. 74.
Figure 85:
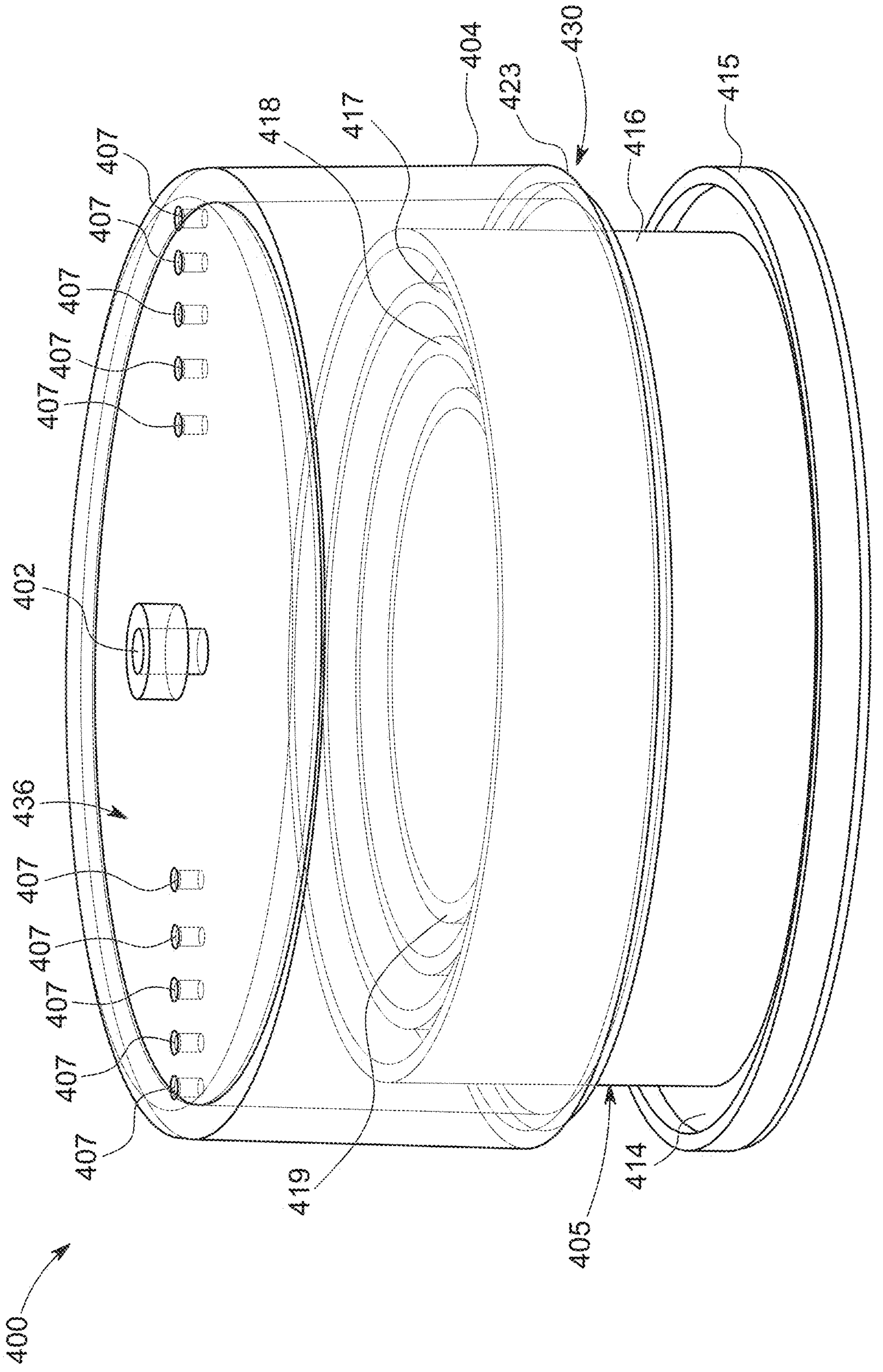
FIG. 85 is a cut-away side perspective view of the centrifuge container of the centrifuge of FIG. 74.

The protective cover 103 for the centrifuges 100, 400, and 500 is shown as clockwise twistable in FIGS. 1 and 74, however the specific configuration of the internal components of the rotational mechanisms (e.g., 110 and 330) may be changed to provide for counter-clockwise activation. Furthermore, one skilled in the art would understand that other activation methods that close a circuit may be used in place of activation by twisting the protective cover 103.

With reference to FIGS. 75-82, the brake 401 is shown and described as part of the protective cover 403 and centrifuge 400. However, the centrifuges 100 and 500 may have, for example, the protective cover 103 with brake 401. Furthermore, protective cover 403 may be, for example, sized and dimensioned for use with centrifuges 100 and 500.

With reference to FIG. 86, the extraction barrier 443 is shown covering the plurality of extraction holes 407 of the centrifuge 400. The extraction barriers 443 are shown as being on the bottom side 435 of centrifuge cover 404. In other aspects, the extraction barriers 443 may, for example, be positioned on the top side 436 of centrifuge cover. In other aspects, centrifuge 100 and centrifuge 500 may have, for example, the extraction barrier 443 on the centrifuge cover 104, with the extraction barrier 443 on either the top side 136 or the bottom side 135. For still other aspects of centrifuges 100, 400, and 500, the extraction barrier 443 may be a single barrier covering the plurality of extraction holes 121, 407 and the insertion hole 402, 122 or the extraction barrier 443 may be a plurality of individual barriers for each of the plurality of extraction holes 121, 407 and insertion holes 402, 122.

With reference to FIGS. 1-86, the centrifuges (e.g., 100, 300, 400, 500) may be, for example sealed and sterilized prior to use, and may be delivered in a sealed container or packaging. The centrifuges (e.g., 100, 300, 400, 500) are also sized to be portable. The centrifuges (e.g., 100, 300, 400, 500) are self-powered, having an internal power supply (e.g., at least one battery 155) that does not have external cords or cables or require an external power supply (i.e. an electrical outlet or a generator). The combination of being sealed, sterilized, and portable with at least one internal battery, provides centrifuges (e.g., 100, 300, 400, 500) that may be opened in a sterile environment and made available for use in the sterile environment (e.g., a surgical operating room). This obviates the need for leaving the sterile environment to obtain blood separation. The centrifuges (e.g., 100, 300, 400, 500) may, for example, also be single use devices, disposable or recyclable after each use and minimizing blood handling or exposure. Further, the centrifuges (e.g., 100, 300, 400, 500) may be part of a sealed and sterilized kit including, for example, a syringe and/or hypodermic needle for insertion and extraction of the blood, bone marrow, or tissue.

Microfluidic Portable Centrifuge

Hemostatic disorders are both complex and costly in relation to both their treatment and subsequent management. There is an ever-increasing drive to improve the diagnosis and prevention of hemostatic disorders because traditional diagnostic methods contain various disadvantages. Various tests and devices have been developed over many decades to assess blood clotting and platelet function in-vitro, including assays for bleeding time, activated clotting time (ACT), activated partial thromboplastin time (aPTT), thromboelastography and platelet aggregometry.

While these traditional tests provide useful information regarding coagulation status or platelet function, they are limited in terms of their ability to predict thrombotic or bleeding risk in clinical settings at least in part because they fail to incorporate many of the key contributors to hemostasis control that exist in-vivo. For example, a major limitation of these assays is that they require extraction of large or exact volumes of blood by venipuncture and measure clotting behavior under static (no flow) or irrelevant flow conditions, and thus, they fail to incorporate the effects of hemodynamic forces (pressure, flow and shear stress) and related cellular interactions that are known to significantly impact whole blood thrombosis in the living vasculature. Notably, flow acceleration and deceleration (fluid shear gradients) have been shown to initiate platelet aggregation during arterial thrombosis in-vivo and clotting in extracorporeal devices usually occurs at sites of sudden flow disturbances, stagnation points and stenosed sections of tubing. However, none of the routinely used hemostasis assays incorporate these physiological conditions in their assessment of blood coagulation, as well as require expert/experienced personnel to perform the process and interpret the results.

As a result, point-of-care (POC) or similarly named nearly-patient-testing (NPT) is playing more of an important role in hemostasis diagnostic settings. A need remains to create or manufacture a detection method and apparatus for POC and/or NPT clotting time determination. The detection method and apparatus may comprise smaller and/or unmeasured whole blood samples, in the microliter scale, for rapid determination of clot-time while the whole blood is being centrifuged into its constituent components. Furthermore, such a detection method and apparatus can be used to determine the relative clotting/coagulation potential at the time of use, prophylactic actions could be taken to adjust the patients' medical treatment(s) to improve their healing potential. This can also be used as a relative research tool because doctors usually do not know how active the platelets are and if they have this knowledge, they could adjust other surgical interventions knowing how viable the platelets were at the time of use.

In one embodiment, the portable centrifuge comprises a microfluidic mechanism for POC, NPT or real-time monitoring of hemostasis that permits rapid determination of clotting time for whole blood as its perfused through at least one fluid channel (hereinafter the "microfluidic centrifuge). In another embodiment, the portable centrifuge comprises a microfluidic mechanism for POC, NPT or real-time monitoring of hemostasis that permits rapid determination of clotting time for whole blood as its perfused through at least one fluid channel (hereinafter the "microfluidic centrifuge) and/or perform centrifugation of whole blood into its constituent components. The microfluidic centrifuge may further comprise a plurality of fluid channels that mimics local physiologic relevant changes in hemodynamic flow conditions experienced in living stenosed arterioles.

Microfluidic mechanisms offer several benefits over conventional detection methods. Microfluidic mechanisms exploit the physical and chemical properties of liquids and gases at a microscale, and allow the analysis and use of less volume of samples, chemicals and reagents reducing the global fees for analysis. Many microfluidic mechanisms can be executed at the same time due to their compact size, while shortening the time of experiment. They also offer an excellent data quality and substantial parameter control which allows process automation while preserving its performance. The microfluidic chip allows the user to generate multi-step analysis requiring low level of expertise and a lot of functionalities.

In another embodiment, the microfluidic centrifuge (or portable centrifuge with microfluidic mechanism) could determine coagulation by whole blood flowing into the at least one fluid channel via capillary action or flow pressure. Upon entry of the whole blood into the at least one channel would yield a relative clotting potential based on time and differential pressure induced by the portable centrifuge. The relative clotting/coagulation potential would be measured and/or calibrated against laboratory settings to initially determine its accuracy.

Figure 113A:
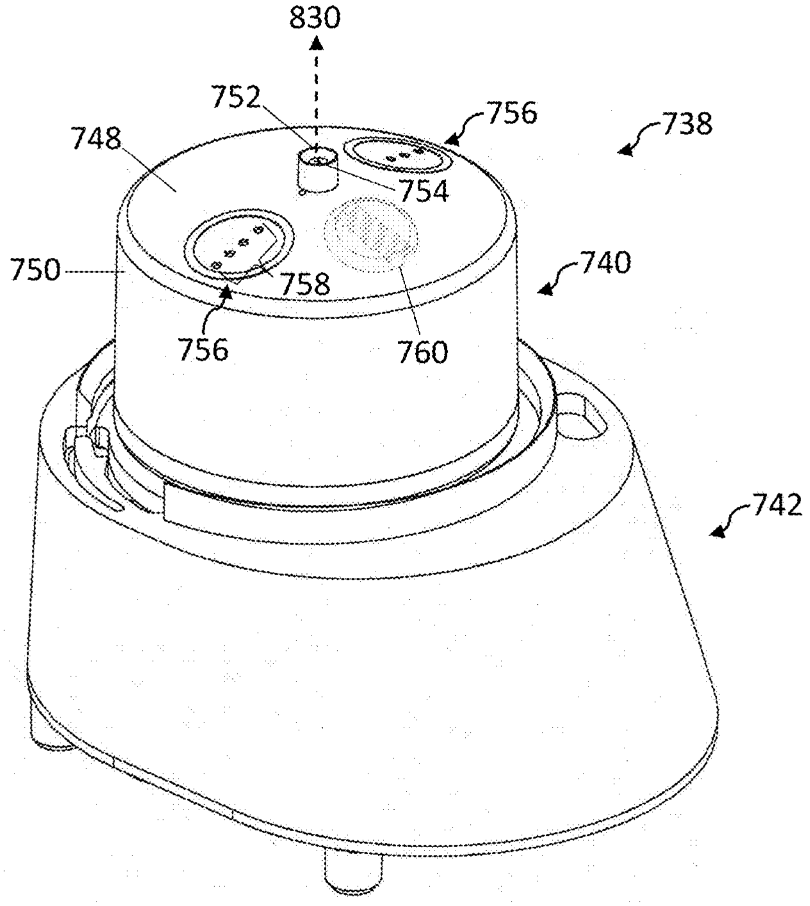
FIGS. 113A-113B depicts isometric views of one embodiment of a protective centrifuge with a microfluidic mechanism.
Figure 113B:
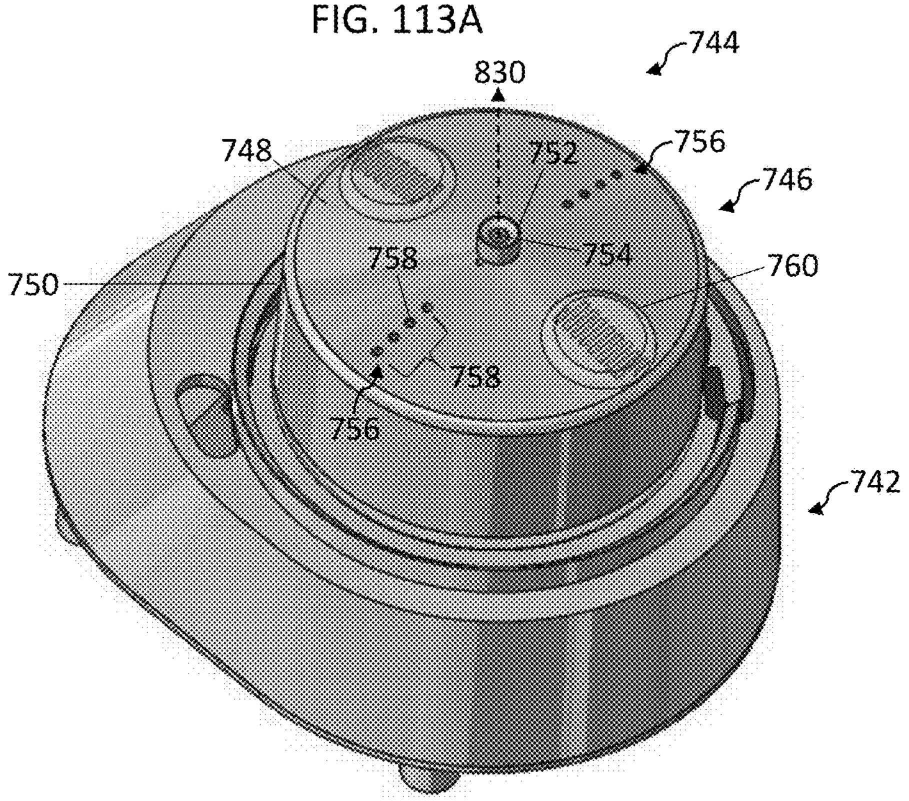
Figure 114A:
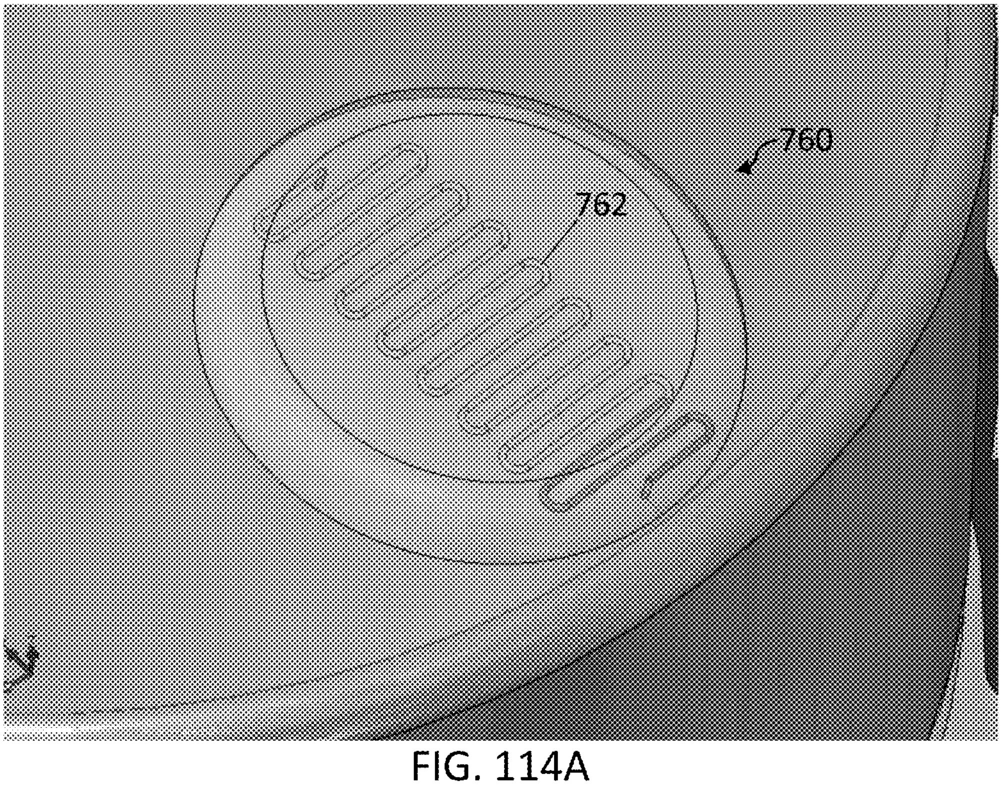
FIGS. 114A-114D depicts an isometric and front view of one embodiment of a microfluidic mechanism.
Figure 114B:
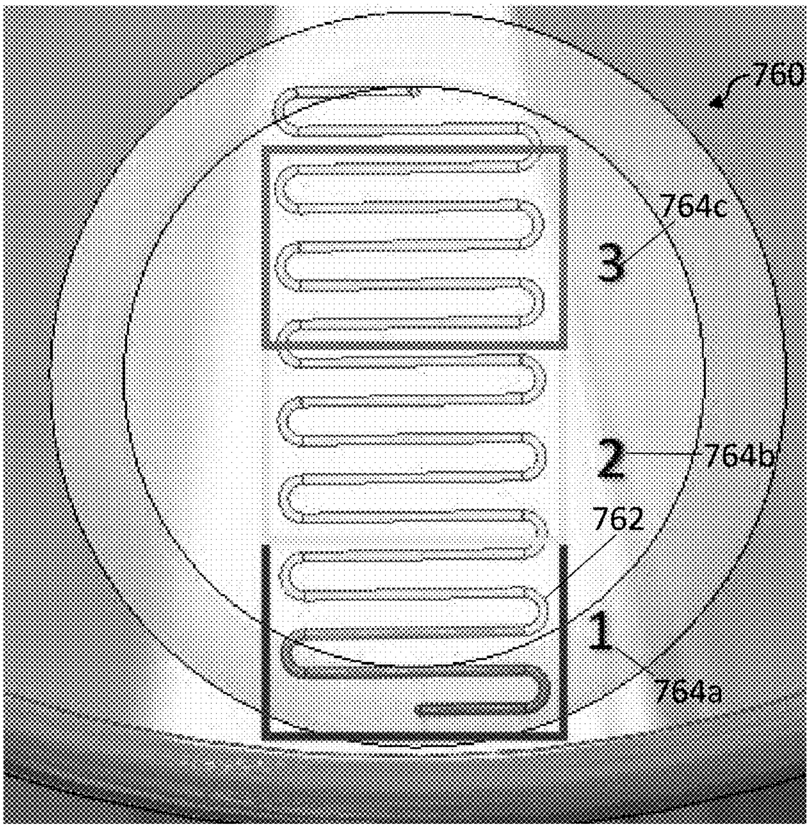
Figure 114C:
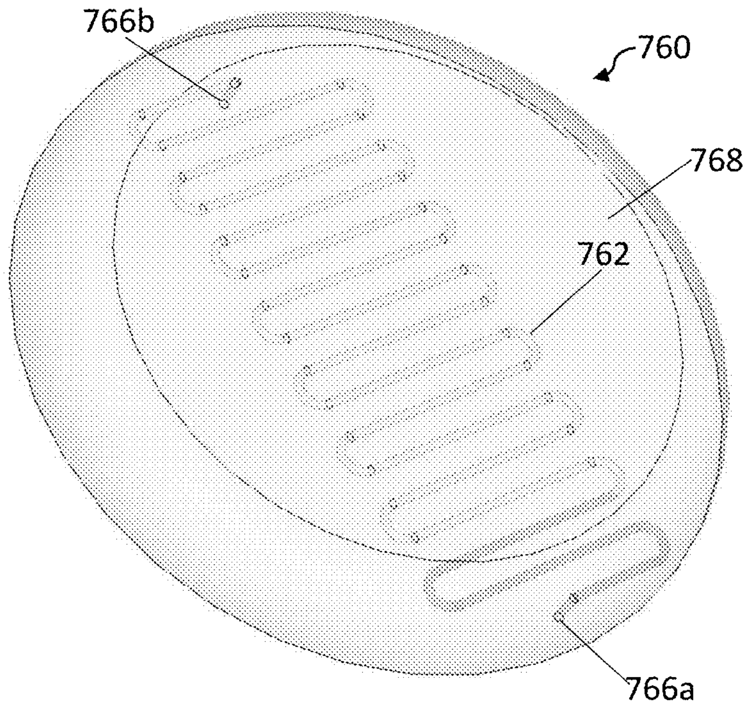
Figure 114D:
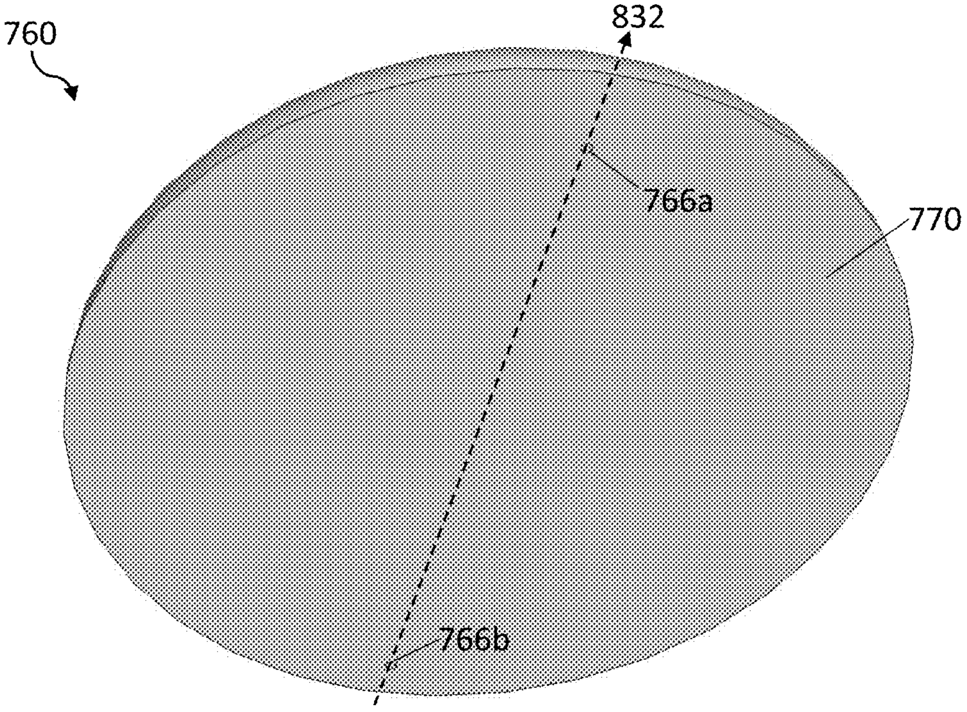

With reference to FIGS. 113A-113B, another embodiment of a portable centrifuge 738,744 is shown. The portable centrifuge 738,744 comprises a protective cover (not shown), a container cover 740,746 and a sequester wheel or sequester device (not shown), and a base 742. The base 742 comprises a rotational mechanism (not shown), a base plate (not shown), and a base cover (not shown). The protective cover, the container cover, the sequester device, the base, rotational mechanism, base plate, base cover, and the protective cover has already been described in detail in the above paragraphs, and for the sake of brevity, will not be further described, unless new features are identified below. The portable centrifuge 738,744 may further comprise at least one coagulation module 760 with a microfluidic mechanism 762.

In another embodiment, the portable centrifuge 738, 744 comprises a plurality of coagulation modules 760 (for spinning balance) to determine coagulation or clot-time as shown in FIG. 113B. The plurality of coagulation modules 760 disposed onto the container cover with at least one of the blood communication ports 766*a*, 766*b* to the outer radius of the sequester wheel. Alternatively, the at least one blood communication port 766*a*, 766*b* may be proximate to the central axis 830 of the sequester wheel. Because the pressure increases from the central axis 830 of the sequester wheel to the outside radius or perimeter of the sequester wheel, the differential pressure would push, force, direct and/or drive the initial blood or fluid portion through inlet 766*a* and then through the micro-fluidic chamber 762 of at least one of the plurality of coagulation modules 760 resulting in a first fluid transport direction away or outwards from the central axis 830 to the outer perimeter of the sequester wheel or portable centrifuge. Instead of using capillary action in most technologies, the blood and/or fluid is pushed, directed or forced via differential pressure through the microfluidic chamber 762 resulting in a second fluid or blood transport direction inward towards the central axis 830. At some point during this flow, the blood or fluid would clot or coagulate in the microfluidic chamber 762 to provide a relative coagulation potential. The centrifugal force becomes less inwardly providing an extended blood or fluid path and increased accuracy as the blood starts to thicken. Ultimately, the first fluid transport direction is different or opposite of the second fluid transport direction. Also, clotting indicators 764*a*, 764*b*, 754*c* could be established for acceptable results.

The entire portable centrifuge 738,744 can be completely sterile, and single use. If the entire portable centrifuge is single use, the entire portable centrifuge is used once and then disposed appropriately. Alternatively, a portion of the entire portable centrifuge, 738,744 can be sterile, and single use. If a portion of the portable centrifuge 738,744 is single use, a portion of the portable centrifuge 738,744 is used only once then discarded appropriately, and the remaining portion may be re-used again. In one embodiment, a portion of the portable centrifuge 738,744 comprises the sequester device and the container cover 740,746 being single use, and the protective cover and the base re-useable. In another embodiment, a portion of the portable centrifuge 738,744 comprises the sequester device 405,706, the container cover 740,746 and protective cover being single use, and the base re-useable.

Referring to FIGS. 113A-113B and 114A-114D, the portable centrifuge 738,744 may further comprise a container cover 740,746. The container cover 740,746 may be disposed over a portion of a sequester device. The container cover 740,746 comprises a top surface 748, a bottom surface (not shown), an external circumferential sidewall 750 that creates an opening or recess (not shown). The container cover 740,746 may further comprise an internal circumferential sidewall (not shown). The container cover 740,746 may comprise a top surface 748 that is flat or planar, domed or conical. The container cover 740,746 comprises a circular cross-sectional shape and/or it has a cylindrical shape.

The top surface 748 may comprise a circular shape with the insertion tube or port 752 with an opening 754 approximately concentric or centered with the top surface 748. The top surface 748 and the insertion tube or port 752 are configured (e.g., shaped and dimensioned) to receive the protective cover without inhibiting rotation of the sequester device and/or the sequester wheel. The top surface 748 may further comprise one or more extraction regions 756, the one or more extraction regions 756 are spaced apart. The one or more extraction regions 756 may be spaced apart symmetrically or non-symmetrically around the circumference of the top surface 748. For example, the top surface 748 has a first extraction region and a second extraction region, the first extraction region and the second extraction region are spaced apart and/or diametrically opposed. The top surface 748 may, for example, have an external circumferential sidewall 750, with the sidewall 750 extending away from the top surface 748 or extending downward and connected or contacting an outer rim of the sequester device.

The one or more extraction regions 756, the first extraction region and/or the second extraction region may further comprise one or more activity indicators (not shown). The top surface 748 may also include a plurality of extraction hole regions (e.g., multiple instances of the extraction region 756) surrounded by a plurality of activity indictors (e.g., multiple instances of the activity indicators). The one or more extraction regions 756, the first extraction region and/or the second extraction region may comprise a shape, the shape may include a circle, an oval, a regular polygon shape and/or any combination thereof.

Alternatively, the one or more extraction regions 756, the first extraction region and/or the second extraction region may comprise a plurality of extraction holes 758. The plurality of extraction holes 758 and/or each of the plurality of extraction holes 758 may be spaced apart and disposed within the one or more extraction regions 756. Alternatively, the plurality of extraction holes 758 may be spaced apart and disposed onto the top surface 748 of the container cover 740. The plurality of extraction holes 758 may be spaced apart and axially aligned. The plurality of extraction holes 758 may be spaced apart and offset. Alternatively, each of the plurality of extraction holes 758 may be spaced apart and axially aligned, and/or each of the plurality of extraction holes 758 may be spaced apart and offset. However, the activity indicator may be, for example, shaped and colored to bring visual attention to the extraction region 756 and/or may be positioned adjacent to the extraction region 756 and/or the plurality of extraction holes 758. During centrifugation, the container cover 740 and/or the sequester wheel spins, also spinning the activity indicator. The activity indicator may, for example, provide a visual indication that the centrifuge is spinning and that the protective cover should remain on until the centrifugation process is complete.

The container cover 740,746 may further comprise one or more coagulation modules 760. The container cover 740,746 includes a top surface 748 and a bottom surface (not shown). The top surface 748 may further comprise one or more coagulation modules 760. The one or more coagulation modules 760 are spaced apart. The one or more coagulation modules 760 may be spaced apart symmetrically or non-symmetrically around the circumference of the top surface 748. For example, the top surface 748 has a first coagulation module and a second coagulation module, the first coagulation module and the second coagulation module are spaced apart and/or diametrically opposed. The one or more coagulation modules 760, the first coagulation module and/or the second coagulation modules 760 are disposed above and/or below the top surface 748 of the container cover 740, 746. At least a portion of the one or more coagulation modules 760, at least a portion of the first coagulation module and/or at least a portion of the second coagulation modules 760 are disposed above and below the top surface 748 of the container cover 740, 746. The one or more coagulation modules 760, the first coagulation module and/or the second coagulation modules 760 comprises at least one surface that is even and/or flush with the top surface 748 of the container cover 740, 746. At least a portion of the one or more coagulation modules 760, at least portion of the first coagulation module and/or at least a portion of the second coagulation modules 760 comprises at least one surface that extends above the top surface 748 of the container cover 740,746.

The one or more coagulation modules 760 comprise at least one microfluidic mechanism 762 and/or microfluidic chamber and/or one or more blood communication ports 766*a*, 766*b*. The coagulation modules 760 may further comprise at least one clotting potential region or clotting indicator 764*a*, 764*b*, 764*c*. The at least one microfluidic mechanism or microfluidic chamber 762 comprises a volume, shape and a configuration that would allow a fluid and/or whole blood into the at least one microfluidic mechanism or chamber 762 by capillary action and/or by flow induced by the differential pressure of the centrifuge. The one or more blood communication ports 766*a*, 766*b* may comprise an inlet 766*a* and an outlet 766*b*. In one embodiment, the one or more coagulation modules 760 may comprise a clotting potential action or a clotting driving force. Clotting potential, the clotting potential action and/or the clotting driving force of the one or more coagulation modules 760 may be provided by capillary action or differential pressure action. The capillary action may typically involve laminar flow, which the clotting potential is based the diffusion rate of the media. Clotting potential or clotting driving force based on flow induced by centrifugal forces is governed by a pressure differential caused by rotating the portable centrifuge at defined speeds resulting in centrifugal forces that are at different points within the portable centrifuge, including at a radii (point A) radii or different distances than at radii (point B) within the sequester wheel or device and/or container cover 740, 746. Thus, blood clotting time or a blood clotting potential can be measured by monitoring the change in viscosity of the fluid or blood over time.

Upon entry of the whole blood through one or more blood communication ports 766*a*, 766*b* into the at least one microfluidic mechanism or chamber 762 would yield a relative clotting potential based on time and differential pressure induced by the portable centrifuge. The relative clotting/coagulation potential would be measured and/or calibrated against laboratory settings to initially determine its accuracy. The relative clotting potential may be correlated to the at least one clotting region or clotting indicator 764*a*, 764*b*, 764*c* for easy visual determination of clot time. The at least one clotting region or clotting indicator 764*a*, 764*b*, 764*c* may comprise at least one indicator descriptor. The clotting time may be measured using at least one indicator descriptor, the at least one indicator descriptor may include a relative time, a clotting description, a color, and/or any combination thereof.

For example, the clotting descriptors may include numbers or words that describe a relative time. Using "1" may be perceived as high clotting potential that occurred at a lowest amount of time than expected or compared to clinical clotting times, "2" may be perceived as normal clotting potential that occurred at a normal expected time or a normal clinical clotting time, and/or "3" may be perceived at low clotting potential that occurred at a longer clotting time than expected or compared to clinical clotting times. Alternatively, region 1 may use the word "high clot time," region 2, may be "average or normal clot time," and region 3 may be "low clot time."

The coagulation module 760 comprises a top surface 768, a bottom surface 770, and at least one microfluidic mechanism or chamber 762. The at least one microfluidic mechanism or chamber 762 disposed between the top surface 768 and the bottom surface 770. The at least one microfluidic mechanism or fluid chamber 762 is planar or substantially planar (meaning 0.25 to 10 degrees from planar). The at least one microfluidic mechanism or microfluid chamber 762 is parallel to the top surface 768 of the container cover. The bottom surface 770 comprises at least one blood communication port 766*a*, 766*b*. Alternatively, the bottom surface 770 comprises a first blood communication port 766*a* and a second blood communication port 766*b*. Accordingly, the bottom surface 770 comprises an inlet 766*a* and an outlet 766*b*. The first blood communication port 766*b* or outlet 766*b* is proximate to the center or central axis or longitudinal axis 830 of the centrifuge and the second blood communication port 766*a* or the inlet 766*a* is proximate to the outer channel or outer perimeter 750 of the container cover 740, 746 and/or the sequester wheel. The first blood communication port 766*b* and/or outlet 766*b* is in fluid communication with the at least one microfluidic chamber 762 allowing exit of blood or fluid. The second blood communication port 766*a* and/or the inlet 766*a* is in fluid communication with the at least one microfluidic chamber 762 allowing the entry of blood or fluid. The first blood communication port 766*a* is spaced apart from the second blood communication port 766*b*. The first blood communication port or outlet 766*b* is axially aligned 832 with the second blood communication port or inlet 766*a*. Alternatively, the first blood communication port or outlet 766*b* is not axially aligned 832 with the second blood communication port or inlet 766*a*.

The coagulation module 760, the top surface 768 and the bottom surface 770 comprises a material. The coagulation module 760, the top surface 768 and the bottom surface 770 may further comprise a coating. The material may be a glass/ceramic, polymer and/or a metal. The polymer materials may comprise polydimethylsiloxane (PDMS), polymethylmethacrylate (PMMA), polystyrene (PS), polycarbonate (PC), polyethylene terephthalate (PET), polytetrafluoroethylene ethylene (PTFE) and other materials known in the art for fabricating microfluidic channels or chambers 762.

The material may also include an opaque, clear, transparent, and/or translucent material. The material may further comprise a color. The colorant may be used to diffuse the luminescence of the at least one light and/or the plurality of lights. The top surface material of the coagulation module 670 may be the same as the bottom surface material of the coagulation module 770. The top surface material of the coagulation module 670 may be different as the bottom surface material of the coagulation module 770. The top surface 768 of the coagulation module 760 may comprise magnification.

The coating may comprise anticoagulants, preservatives, disinfectants or germicidal agents or pathogen reduction agents or pathogen inactivation agents, sterilants, antiseptics, clot activators, separator gels. The pathogen reduction agents or germicidal agents may comprise alcohols, chlorine dioxide, chlorine mixtures, formaldehyde, glutaraldehyde, hydrogen peroxide, lodophor mixtures, peracetic acid, phenolic mixtures, quaternary ammonium mixtures, amotosalen or riboflavin, and/or any combination thereof. The pathogen reduction agents may be used alone and/or with combination of a UV light for enhanced pathogen reduction. The pathogens in whole blood or its blood components are inactivated by adding pathogen reducing agent and irradiating with UV light over a period of time, the period of time ranging from 5 to 90 minutes. This method reduces the infection levels of disease-causing agents by releasing active oxygen which damages the cell membrane of the pathogens and prevents replication of the carrier pathogens that may be found in whole blood or blood components for safer injection or transfusion. Pathogens may include viruses, bacteria, parasites, and/or white blood cells.

Figure 115A:
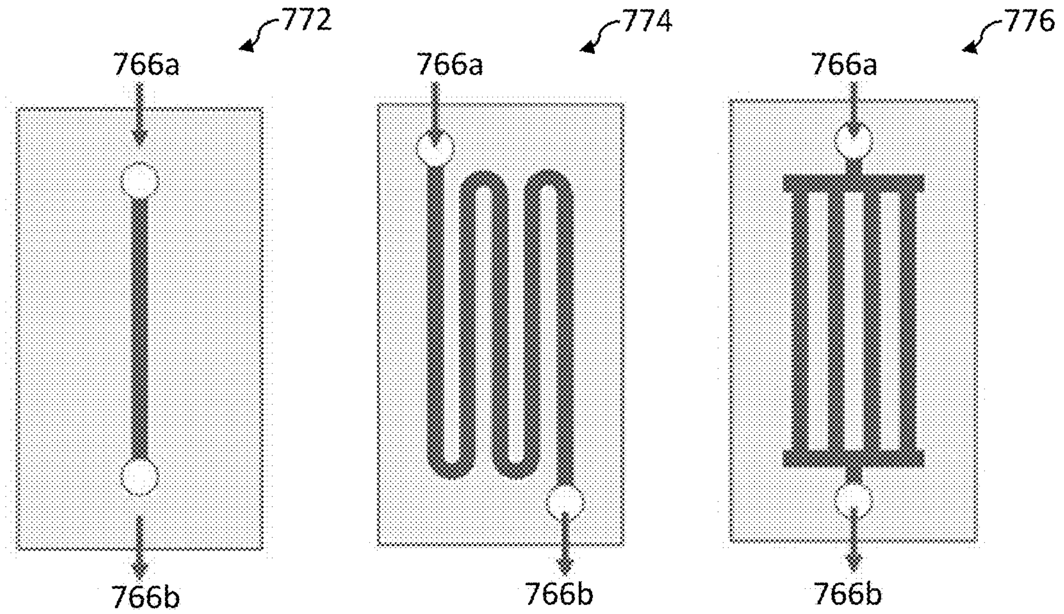
FIGS. 115A-115B depicts different configurations of microfluidic mechanisms.
Figure 115B:
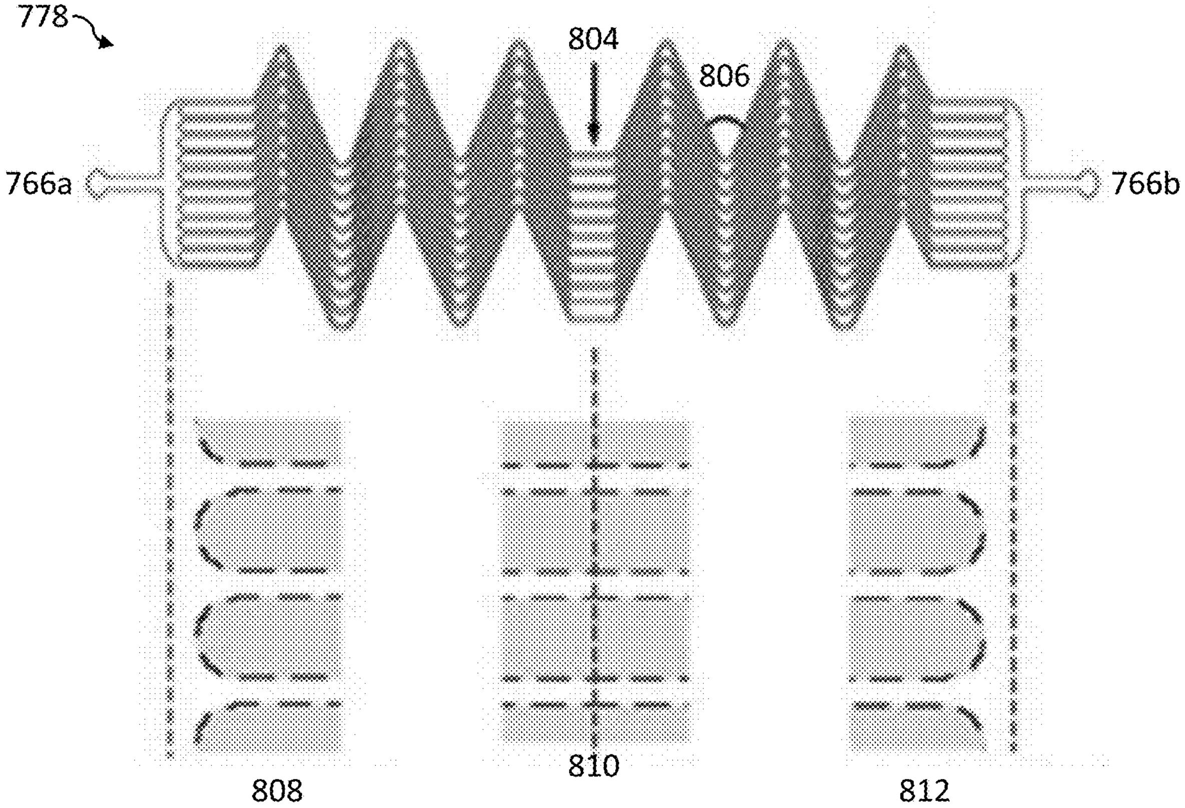

Referring to FIGS. 115A-115B, the at least one microfluidic mechanism 762 comprises different configuration designs. The different configuration designs include a single channel 772, a single serpentine channel 774, a multi-channel 776, a multi-serpentine channel 778, and/or any combination thereof. The single-channel 772 includes only one straight channel or chamber with an inlet 766*a* and an outlet 766*b* for the transport or mobilization of blood. The serpentine channel 774 (or curved channel or undulating channel or sinusoidal channel) is accordingly designed by folding up a single microchannel into a serpentine (curved) configuration to increase the effective volume for mobilization of fluid or blood through the inlet 766*a* and/or the outlet 766*b*. The multi-channel 776 a plurality of microchannels or chambers that are spaced apart and parallel to the adjacent plurality of microchannels or chambers arranged to share one inlet 766*a* and one outlet 766*b*. The multi-serpentine channel 778 includes a plurality of microchannels or chambers that are arranged into a straight and/or serpentine or curved shape at an angle 806 with each of the plurality of microchannels or chambers are spaced apart and in parallel with the adjacent plurality of microchannels or chambers. The serpentine configuration may further comprise a rectangular-serpentine, a U-serpentine, a V-serpentine and/or any combination thereof. The single serpentine 774 and/or the multi-serpentine channel 778 may mimic, match or substantially match stenosed arterioles (arterioles narrowed due to atherosclerotic plaque formation) to create sudden fluid changes throughout the clotting time. The changes may include acceleration (pre-stenosis) 808, followed by a region of uniform shear (stenosed region) 810 that includes a straight chamber section 804, and then by a region with a sudden deceleration (post-stenosis) 812, when whole blood or fluid is perfused through the microfluidic chamber. Such mimicking, matching or substantially matching to a network of small vessels (e.g., arterioles) allows the microchannels to maximize the surface area exposed to flowing blood to increase the likelihood of clot formation. The plurality of microchannels or chambers may comprise a range of 1 to 20 channels or chambers; the plurality of channels or chambers may comprise 2 to 15 channels; the plurality of channels or chambers may comprise 2 to 12 channels or chambers; the plurality of channels or chambers may comprise 2 to 6 channels or chambers.

Referring to FIGS. 116A-116B, the at least one microfluidic mechanism or microfluidic chamber 780 comprises a channel length (Lc) 818, a channel width 816, a channel height, 814, a channel or chamber shape or cross-sectional shape 784, an inlet 766*a* and an outlet 766*b*. The at least one microfluidic mechanism 780 may further comprise at least one of a wavelength 820, amplitude (A) 822, a frequency (F), a first radius (R1), a second radius (R2), and inlet length 824 and an outlet length 826. The at least one microfluidic mechanism 780 may further comprise one or more straight channel portions or members 824, 826. The one or more straight channel portions or members may be in alignment with or parallel to the axis 782 of at least one microfluidic mechanism 780 and/or the one or more straight channel portions or members may be oblique and/or perpendicular to the axis 782 of at least one microfluidic mechanism 780. The one or more straight channel portions may comprise an inlet 824 and an outlet 826. The different channel configurations include a single channel 772, a single serpentine channel 774, a multi-channel 776, a multi-serpentine channel 778, and/or any combination thereof as shown in FIGS. 115A-115B.

The channel cross-sectional shape 784 may comprise a rectangular or circular shape as described in FIG. 116B. The shape may comprise a regular or irregular polygon. The amplitude 822 and frequency (F) may be the same or uniform along the channel length 818 of the at least one microchannel 780. Alternatively, the amplitude 822 and the frequency (F) may be non-uniform along the channel length 818 of the at least one microchannel 780. The channel cross-sectional shape 784 may include a height 814 and/or a width or diameter 816.

Figure 117A:
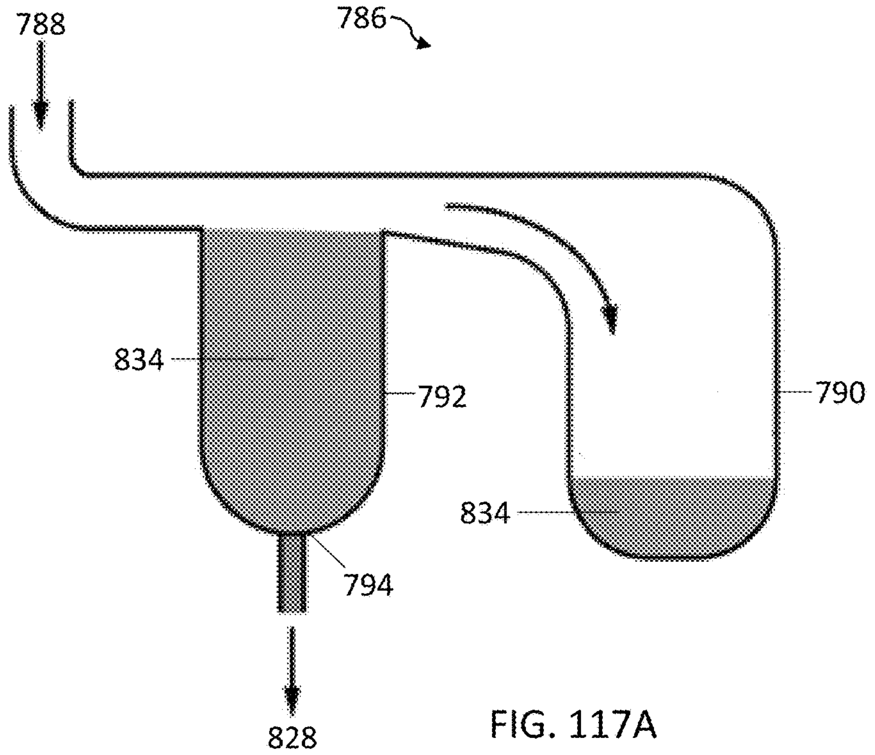

Referring to FIG. 117A, the at least one microfluidic mechanism 780 further comprises one or more metering mechanisms 786. The one or more metering mechanisms 786 would help monitor input volumes of blood to obtain quantitatively reproduceable results. The one or more metering mechanisms 786 may comprise an inlet 788, a metering outlet 828, a metering chamber 792 and a waste chamber 790. The metering inlet 788 of the one or more metering mechanisms 789 may be in communication with the inlet 766*a* to allow the blood or fluid 834 to enter the metering chamber 792 with a defined volume, and an overflow or excess of the blood or fluid 834 enters or goes into a waste chamber 790. Alternatively, the metering inlet 788 may be the same as the inlet 766*a* of the microfluidic mechanism. The metered blood or fluid 834 enters the at least one microfluidic mechanism 780 via the metering outlet 828. The metering outlet 828 may further include fluid communication with the inlet 766*a* of the microfluidic mechanism. The one or more metering mechanisms 786 and/or metering chambers 792 may further comprise at least one valve 794. The at least one valve 794 may be disposed at the radially outer end of the metering chamber 792 and/or adjacent to the metering outlet 828 to allow for further fluidic processing of the metered blood. The at least one valve 794 may include a hydrophobic, capillary siphon, and centrifuge-pneumatic valves. The metering accuracy is mainly affected by the variation of the cavity size within the fabrication tolerances and the wicking effects at liquid interfaces due to capillary forces, centrifugal forces and/or differential pressures. The at least one valve 794 may be counteracted or activated by the relative capillary forces, centrifugal forces or differential pressures—e.g., the at least one valve 794 can automatically open with the pressure or force has been met or been exceeded, and the at least one valve 794 returns or closes when it's below the opening pressure or force.

Figure 117B:
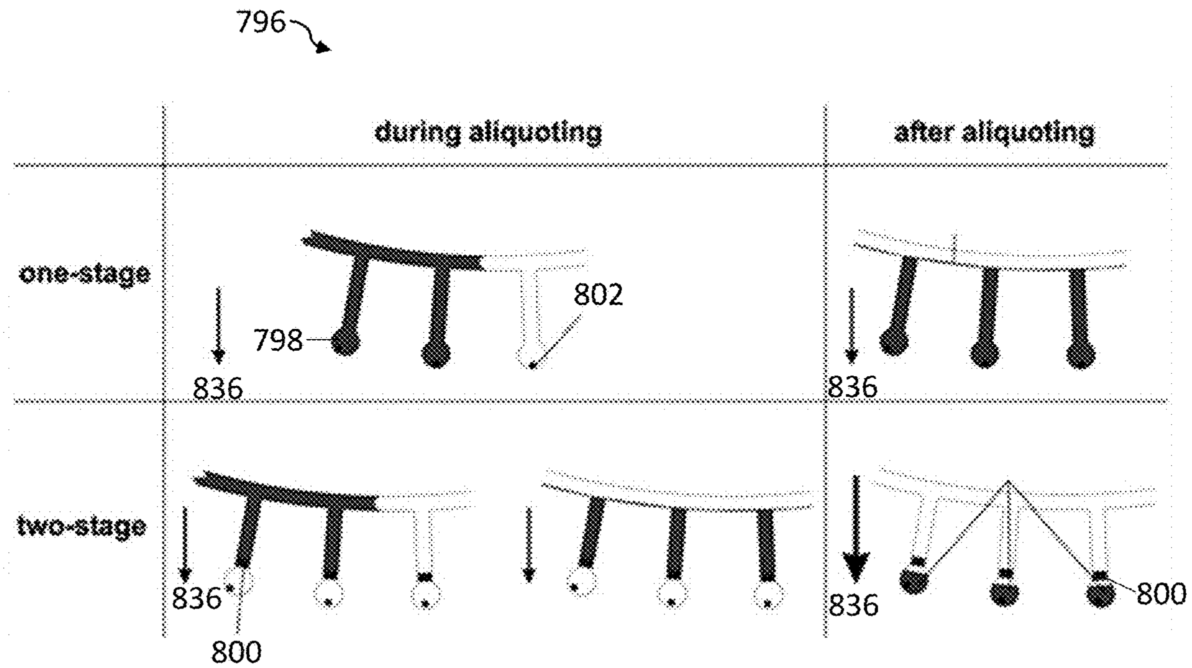
Figure 118:
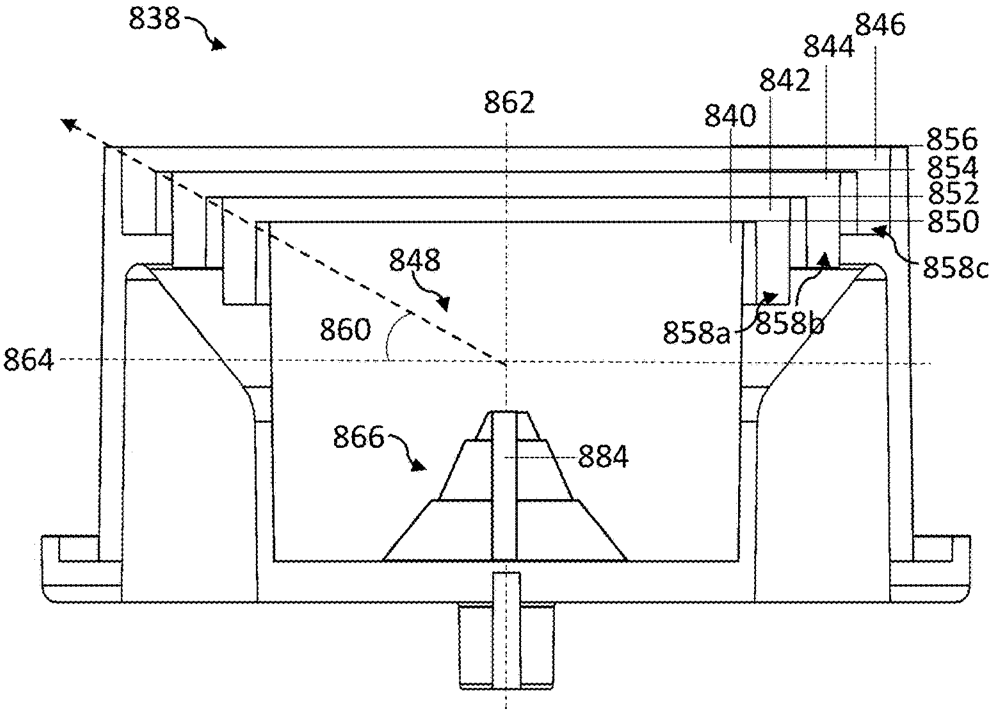

Referring to FIG. 117B, the at least one microfluidic mechanism 780 further comprises one or more aliquoting mechanisms 796. The one or more aliquoting mechanisms 796 comprises one or more receiving chambers 798. The one or more receiving chambers 798 may further comprise at least one or more valves 800 and/or at least one reagent 802. In single-stage aliquoting, fluid volumes are metered directly into the one or more receiving chambers 800 with or without at least one reagent 802 for the purposes of isolating and/or retaining a portion of the fluid for future analyzing or to perform multiple parallel assays. Two-stage aliquoting allows the fluid to be first metered and split into sub-volumes, then forwarded to the one or more receiving chambers 800. The two-stage is desirable when independent metering is required, cross contamination is an issue, or when further fluidic processing of the individual aliquots is required. Two-stage aliquoting combines the parallel metering of one-step aliquoting with normally closed valves at the radial outer side of each metering finger. After metering, the single aliquots can pass the valve and be used for further fluidic processing. The basic principle of the aliquoting processing allows the fluid to be introduced via centrifugation of the portable centrifuge via capillary flow, centrifugal flow, and/or differential pressure flow 836 into the one or more aliquoting mechanisms 796. The one or more aliquoting mechanisms 796 are sloping or substantially sloping. The centrifugal flow, capillary flow and/or differential pressures flow 836 directs a portion of the fluid through the one or more valves 800 into separate one or more receiving chambers 798.

In one embodiment, the at least one microfluidic mechanism 780 further comprises one or more valves (not shown). The one or more valves may be integrated or removably attached. The one or more valves may be normally closed. The burst or opening of a normally closed passive valve is triggered by a centrifugal pressure, capillary forces, and/or the instability of a liquid/gas interface (hydrophobic barrier or a burstable seal). The valve may be movable from a first position to a second position, the first position comprises a "closed" position prevent fluid flow or blood flow, and the second position is the "open" position to allow fluid flow or blood flow. To pass or open the one or more valves, the forces or pressure has to exceed the counter pressure exhibited by the one or more valves. The one or more valves may be disposed at the inlet and/or the outlet. The one or more valves may be disposed between the inlet and the outlet, and/or the one or more valves may be disposed anywhere along the length of the at least microfluidic mechanism 780.

The coagulation modules 760 may be manufactured by standard methods known in the art. Such methods may include photolithography, soft lithography, thermoforming, casting, injection molding, embossing, and imprinting techniques, wet and dry etching methods, laser-based micromachining techniques, 3D printing and/or any combination thereof. In addition, other methods may be contemplated, such as solid wax and inkjet printing.

Stem Cell Isolation

The portable centrifuge 896, 934 may be used and/or adapted to isolate different types of stem cells and/or cell types from mesenchymal stem cells (MSC), mononuclear cells (MNCs) and/or stromal vascular fraction (SVF) from different types of tissues for on-site or same day therapeutic and/or regenerative treatment purposes. MSCs or stromal cells can be isolated from different tissues, which include adipose tissue, tendons, periodontal ligament, synovial membranes, trabecular bone, bone marrow, embryonic tissue, the nervous system, skin, periosteum, muscle, peripheral blood, and/or any combination thereof. Accordingly, MNCs can be isolated from tissues, including bone marrow, umbilical cord, peripheral blood, and/or spleen. Furthermore, SVF is a heterogenous mixture of cells isolated by enzymatic or non-enzymatic dissociation of the lipoaspirate obtained from liposuction of excess adipose tissue that contains a large population of adipose derived stem cells (ADSCs), and other types of cells (e.g., endothelial cells, erythrocytes, fibroblasts, lymphocytes, monocytes, pericytes, etc.).

In another embodiment, the portable centrifuge 896, 934 can isolate peripheral blood mononuclear cells (PBMCs) from peripheral blood and/or isolate stem cells from PBMCs. PBMCs are blood cells with round nuclei that encompass a heterogeneous cell population comprising various amounts of lymphocytes (T cells, B cells, and NK cells), dendritic cells, and monocytes. These cells are critical components of the innate and adaptive immune system which defends the body against viral, bacterial, and parasitic infection and destroys tumor cells and foreign substances. PBMCs can be isolated by density gradient centrifugation, as different components of the blood have different densities and can be separated accordingly allowing the portable centrifuge to operate at a constant rotational speed for set time based on the organelles sedimentation rate. Further processing known in the art may be used with the portable centrifuge and/or other techniques to facilitate isolation of stem cells, MSC's from the isolated MNCs.

In another embodiment, the portable centrifuge 896, 934 can isolate SVF from adipose tissue using enzymatic and/or non-enzymatic techniques and/or isolate stem cells from SVF. As described herein, SVF cells are obtained through liposuction and contain multiple cell types, including adipose-derived stem cells (ADSCs) with potential tissue regenerative activity. Upon isolation and processing, the adipose-derived SVF cells can differentiate into different tissue types, support neovascularization, replace cells and repair injured issue. Further processing known in the art may be used with the portable centrifuge and/or other techniques to facilitate isolation of stem cells, other cell types, and/or MSC's from the SVF.

In another embodiment, the portable centrifuge 896, 934 can isolate mononuclear cells (MNCs) and mesenchymal stem cells (MSCs) from bone marrow and/or stem cells from MNCs or MSCs. BM-MSC isolation procedures may use density centrifugation with a density medium to separate the mononuclear cell (MNC) fraction from the other marrow constituents (i.e., red blood cells, plasma, lipids). This MNC fraction contains an enriched population of T-cells, B-cells, monocytes, hemopoetic stem cells (HSCs), endothelial progenitor cells and MSCs. The BM-MSCs are further isolated via plating onto tissue culture flasks. BM-MSCs are an attractive therapeutic tool due to their potential to be differentiated into a variety of cell types and their immunosuppressive properties. Their application is being explored in cell transplantation, regenerative therapy, correcting genetic disorders, diseases, and tissue engineering. Further processing known in the art may be used with the portable centrifuge and/or other techniques to facilitate isolation of stem cells and/or other cell types.

In one embodiment, the portable centrifuge 896, 934 comprises: a protective cover (not shown), a container cover 898, 940, a sequester wheel or sequester device 838, 900 and a base 904. The base 904 comprises a rotational mechanism (not shown). The base 904 may further comprise a base plate (not shown), and a base cover (not shown). The portable centrifuge 896, 934 may further comprise at least one or more of: a disaggregating mechanism 866, 868, 870, 872, disaggregating elements 874*a*, 874*b*, 876, 878, 880, an agitation mechanism (not shown), an incubator 940, 942, 944, 952, a filtration ring 902, one or more blister modules 906*a*, 906*b*, at least one reagent 938 and/or any combination thereof. The protective cover, the container cover 898, 940, the sequester device 838, 900, the base 904, rotational mechanism, base plate, the base cover and/or many other features have already been described in detail in the above paragraphs, and for the sake of brevity, those features will not be further described, unless new features are identified below.

In one embodiment, the portable centrifuge 896, 934 comprises a container cover 898, 940. The container cover 898, 940 may further comprise at least one blister module 906*a*, 906*b*. The container cover 898, 940 may be disposed over a portion of a sequester device 838, 900. The container cover 898, 940 comprises a top surface 901, a bottom surface (not shown), an external circumferential sidewall 903 that creates an opening or recess. The container cover 898, 940 may further comprise an internal circumferential sidewall (not shown). The container cover 898, 940 may comprise a top surface 901 that comprises a flat or planar, domed or conical shape. The container cover 898, 940 comprises a circular cross-sectional shape and/or it has a cylindrical shape. The top surface 904 and the insertion tube or port 910 are configured (e.g., shaped and dimensioned) to receive the protective cover without inhibiting rotation of the sequester device and/or the sequester wheel.

Figure 121A:
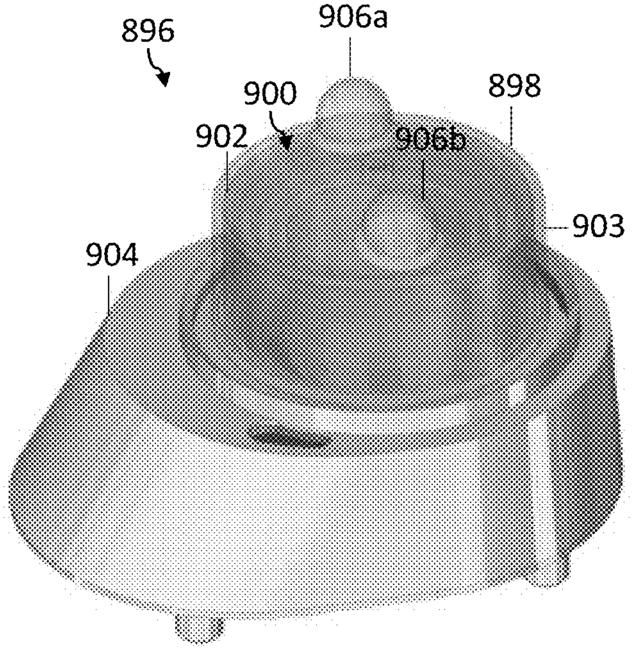
Figure 123:
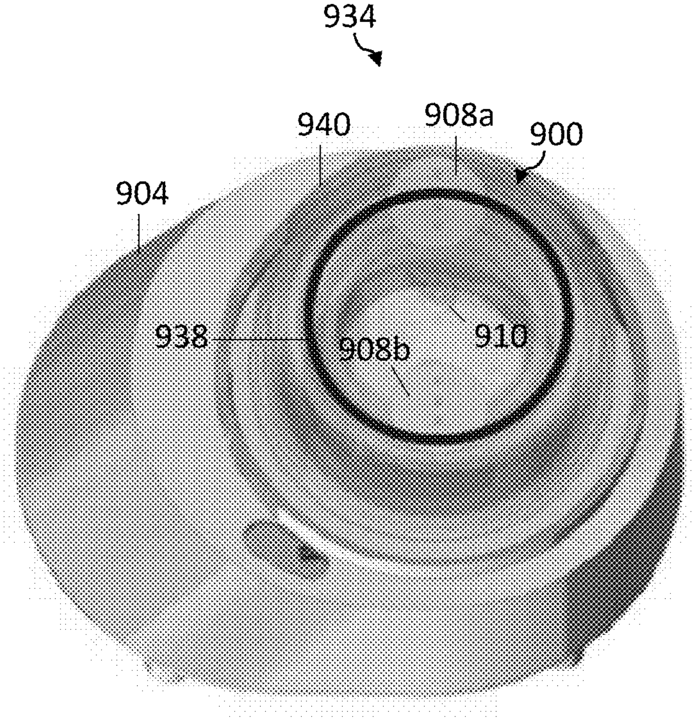

With reference to FIG. 121A and 123, the top surface 901 of the container cover 898, 940 may comprise an insertion tube or port 910 with an opening approximately concentric or centered with the top surface 901. The top surface 901 of the container cover 898, 940 may further comprise one or more extraction regions 908*a*, 908*b* that may be spaced apart symmetrically or non-symmetrically around the circumference of the top surface 901. For example, the top surface 901 has a first extraction region 908*a* and a second extraction region 908*b*, the first extraction region 908*a* and the second extraction region 908*b* are spaced apart and/or diametrically opposed. The one or more extraction regions 908*a*, 908*b*, the first extraction region 908*a* and/or the second extraction region 908*b* may comprise a plurality of extraction holes 905. The plurality of extraction holes 905 and/or each of the plurality of extraction holes 905 may be spaced apart and disposed within the one or more extraction regions 908*a*, 908*b*. One or more of the extraction holes 905 may be aligned with the at least one channel 928, 930, 932, a first channel 928, a second channel 930 and/or a third channel 932.

Figure 121B:
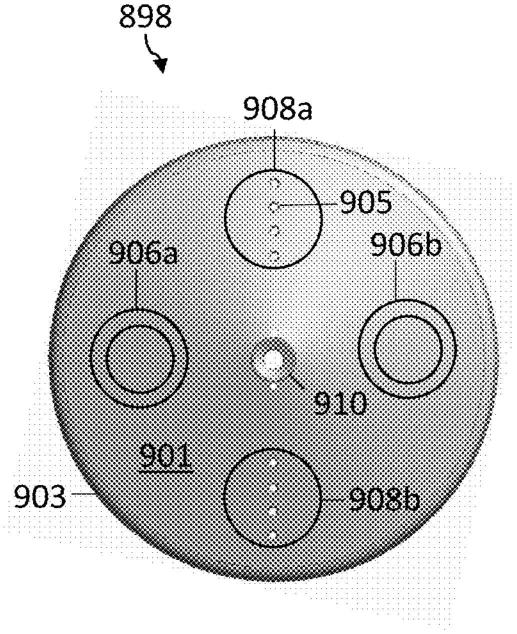
Figure 121C:
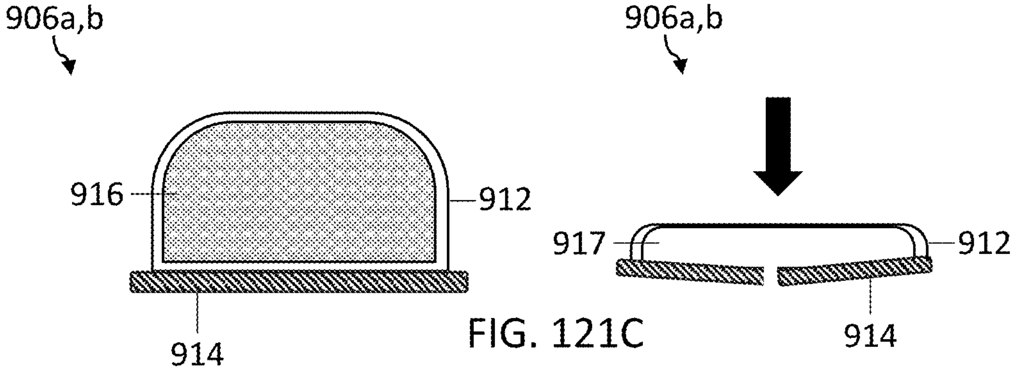

The container cover 898, 940 may further comprise one or more blister modules 908*a*, 908*b* as shown in FIG. 121A-121C. The at least one blister module 908*a*, 908*b* and/or one or more blister modules 908*a*, 908*b* may be used to dispense any necessary reagents 916 while the portable centrifuge is in operation and/or while it is not in operation to protect the sterility of the tissue samples. The at least one blister module 908*a*, 908*b* comprises a packaging and/or container 912 that includes a chamber, cavity or pocket 917 used to encapsulate the at least one reagent 916. The chamber, pocket, cavity 917 is disposed onto a frangible base or breakable base 914. Alternatively, the chamber, pocket or cavity 917 is coupled onto a frangible seal or breakable seal 914. The chamber, pocket or cavity 917 includes at least one reagent 916. The one or more blister modules 906*a*, 906*b* may be removably connected onto the container cover 898, 940. When the one or more blister modules 906*a*, 906*b* are emptied, they may be replaced with filled blister modules 906*a*, 906*n*. Alternatively, the one or more blister modules 906*a*, 906*b* may be integrated and/or fixed onto the container cover 898, 940.

The chamber 917 and/or container 912 is movable from a first position that is uncompressed with the chamber 917 filled with the at least one reagent 916 to a second position that is compressed breaking the frangible base 914 and/or and the at least one reagent 916 is in fluid communication with an opening (not shown) disposed onto the centrifuge container cover 898, 940 to dispense the at least one reagent 916 into the sequester device 838, 900. The at least one opening disposed on the centrifuge container cover 898, 940 comprises a seal (not shown), the seal should self-seal after being in fluid communication with the at least one reagent 916 and/or the at least one reagent forces or pushes the seal to open to allow the at least one reagent 916 to be dispensed into the sequester device 838, 900.

Compressing the chamber 917 and the container 912 filled with the at least one reagent 916 should comprise sufficient pressure to overcome the seal to allow the at least one reagent 916 to be in fluid communication with the opening and the sequester device 838, 900. Alternatively, the at least one blister module 906*a*, 906*b* is movable from a undispensed position with the at least one blister module 906*a*, 906*b* filled with at least one reagent 916, and a dispensed position with the blister module 906*a*, 906*b* unfilled or empty after the at least one blister module 906*a*, 906*b* is compressed or depressed. The blister container 912 may comprise a material known in the art for dispensing a liquid or a solid. The blister module 906*a*, 906*b* and/or container 912 may comprise and/or be filled with at least one or more reagents 916.

The at least one reagent 916 may comprise solids and/or liquids. The liquids may include any pharmaceutical, chemical, solution, reagents and/or any combination thereof. The one or more reagents 916 may include saline; phosphate buffered saline (PBS); digestion enzyme, erythrolysis buffer, thixotropic gels, anticoagulants, density gradient media, buffer, dilution media and/or any combination thereof. The digestion enzyme comprises collagenase Type I-IV, dipase, trypase and/or any combination thereof. The density gradient media comprises FICOLL-PAQUE, PANCOLL, PERCOLL, LYMPHOPREP, a polyester thixotropic gel, separation gel, and/or any combination thereof. Anticoagulants comprises sodium citrate, sodium heparin, and ACD-A.

With reference to FIG. 118, 121A, 122B-122E and 123, the portable centrifuge 896, 934 may comprise a sequester device 838, 900. The sequester device 838, 900 comprising a longitudinal or central axis 862 and an axial or horizontal axis 864. The sequester device 838, 900 being disposed onto the base, the sequester device 838, 900 including a first concentric ring 840, 918 including a first height 850 and first diameter and a second concentric ring 842, 920 including a second height 852 and a second diameter, the first concentric ring 840, 918 forms a central container 848, 926, the second concentric ring 842, 920 is spaced apart from the first concentric ring 840, 918 to form at least one channel 858*a*, 858*b*, 858*c*, 928, 930, 932, the second height 852 of the second concentric ring 842, 920 is larger than the first height 850 of the first concentric ring 840, 918, the second diameter of the second concentric ring 842, 920 is larger than the first diameter of the first concentric ring 840, 918.

In another embodiment, the sequester device 838, 900 comprises a first concentric ring 840, 918 including a first height 850 and first diameter, a second concentric ring 842, 920 including a second height 852 and a second diameter, and a third concentric ring 844, 922 having a third height 854 and a third diameter. The first concentric ring 840, 918 forms the central container 848, 926. The third diameter is larger than the second diameter and the second diameter is larger than the first diameter; each of the concentric rings 840, 842, 844, 918, 920, 922 are tiered 860. Each of the first, second and third concentric rings 840, 842, 844, 918, 920, 922 are spaced apart from each other, the spacing forming a plurality of channels 858*a*, 858*b*, 858*c*, 928, 930, 932. Tiering 860 may comprise a 15 degree to 60 degree angle; it may comprise a 15 degree to 45 degree angle; or a 15 degree to 30 degree angle; or a 30 degree to 45 degree angle. In another embodiment, the sequester device 838, 900 comprises a first concentric ring 840, 918 including a first height 850 and first diameter, a second concentric ring 842, 920 including a second height 852 and a second diameter. The first concentric ring 840, 918 forms the central container 848, 926. The second diameter is larger than the first diameter; each of the concentric rings 840, 842 are tiered 860. In another embodiment, the sequester device 838, 940 comprises a first concentric ring 840, 918, a second concentric ring 842, 920, a third concentric ring 844, 922, and a fourth concentric ring 846, 924. The fourth concentric ring 846, 924 is larger than the third concentric ring 844, 922, the third concentric ring 844, 922 is larger than the second concentric ring 842, 920, and the second concentric ring 842, 920 is larger than the first concentric ring 840, 918. Each of the first, second, third and fourth concentric rings 840, 842, 844, 846, 918, 920, 922, 924 are concentric to each other, and they are tiered 860. The fourth concentric ring 846, 924 includes a fourth diameter and a fourth height 856.

Figure 122A:
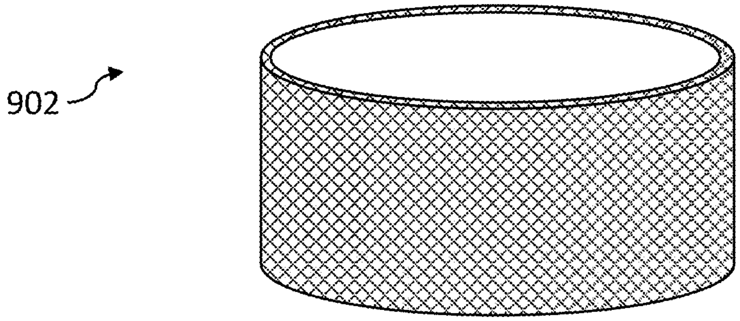
Figure 122B:
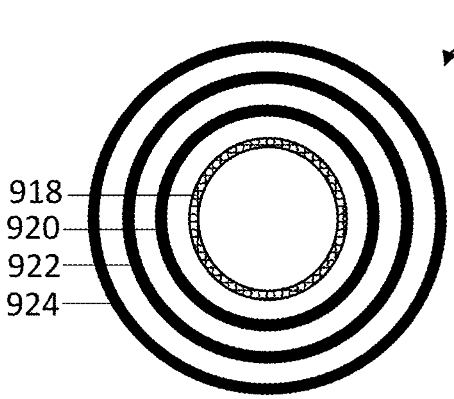
Figure 122C:
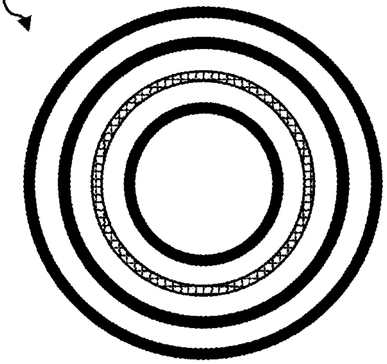
Figure 122D:
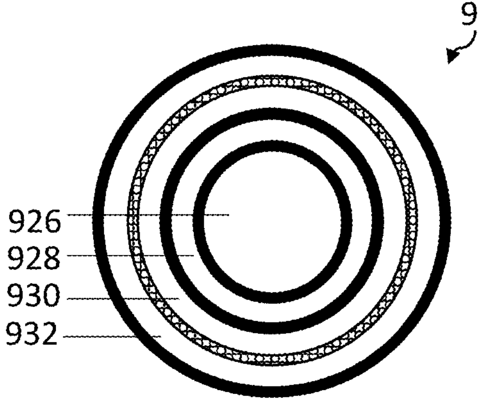
Figure 122E:
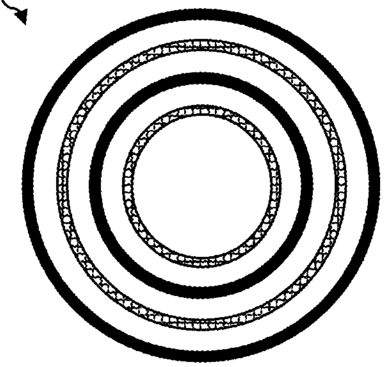

In another embodiment, at least one or more of the first 840, 918 the second 842, 920 third concentric ring 844, 922 and/or fourth concentric ring 846, 924 may comprise one or more filtration rings 902 as shown in FIGS. 121A and 122A-122E. The one or more filtration rings 902 may be integral to the sequester device 838, 900 and/or removably connected. The one or more filtration rings 902 may comprise a filter mesh size, the filter mesh size includes a 40 micrometer to 100 micrometer filter; a 40 micrometer to 90 micrometer filter; a 60 micrometer to 80 micrometer filter; a 70 micrometer to 80 micrometer filter. In an exemplary embodiment, the one or more filtration rings 902 comprises a 70 micrometer filter. The one or more filtration rings 902 having a cylindrical shape, a height and a diameter. The height of the one or more filtration rings 902 may be larger than the height of the first, second and/or third concentric ring 840, 842, 844, 918, 920, 922. Alternatively, the sequester device 838, 900 may comprise a plurality filtration rings 902 as shown in FIG. 122E. Each of the plurality of filtration rings 902 comprises a filtration mesh size, each of the filtration mesh sizes may be the same or they may be different. In another embodiment, the first concentric ring 840, 918 and the second concentric ring 842, 920 comprises a filtration ring 902. In another embodiment, the first concentric ring 840, 918 and the third concentric ring 844, 922 comprises a filtration ring 902. In another embodiment, the second concentric ring 842, 920 and the third concentric ring 844, 922 comprises a filtration ring 902.

In another embodiment, the spacing and/or channels 858*a*, 858*b*, 858*c*, 928, 930, 932 disposed between at least one of the first 840, 918, second 842, 920 and/or third concentric rings 844, 922 may comprise one or more reagents 938 as shown in FIG. 123. Alternatively, the central container 848, 926 formed from the first concentric ring 840, 918 comprises at least one or more reagents 938. The one or more reagents include the density gradient media, anticoagulant, buffer, diluting medium and/or any combination thereof. The one or more reagents 938 may be integral (e.g., pre-laced) to the sequester device 838, 900 prior to the fluid and/or whole blood being dispensed into the sequester device 838, 900. Accordingly, the one or more reagents 938 may be subsequently added or introduced into the sequester device 838, 900 after the fluid and/or the blood is dispensed into the sequester device 838, 900. The one or more reagents 838, 900 may be layered under the whole blood/fluid and/or bone marrow prior to activating the portable centrifuge 896, 934. The one or more reagents 938 may be layered over the whole blood or fluid without mixing the two layers prior to activating the portable centrifuge 896, 934. The one or more density gradient media comprises FICOLL-PAQUE (manufactured by GE Healthcare Pharmacia/Cytiva in Waukesa, WI), PANCOLL (manufactured by PAN-Biotech GmbH in Aldenbach, Germany), LYMPHOPREP and OPTIPREP (manufactured by StemCell Technologies, Inc. in Vancouver, British Columbia, Canada), PBMC-SPIN or PBMC24+ SPIN (manufactured by PluriSelect in El Cajon, CA), polyester thixotropic separation gel, and/or any combination thereof. Anticoagulants comprises sodium citrate, sodium heparin, and ACD-A. The buffer comprises phosphate buffered saline (PBS) or saline.

With reference to FIGS. 118, 119A-119C and FIGS. 120A-120C, the portable centrifuge 896, 934 may further comprise a disaggregation mechanism 866 and/or disaggregation elements 874*a*, 874*b*, 876, 878, 880. Disaggregating includes emulsifying, grinding, mincing and/or chopping lipoaspirate into smaller pieces to facilitate digestion via the enzyme. In one embodiment, the disaggregation mechanism 866 may comprise at least one central element. The one or more central elements may be fixed and/or static relative to the direction of rotation of the portable centrifuge 896, 934. Alternatively, the one or more central elements may be rotating or spinning in an opposite direction relative to the direction of rotation of the portable centrifuge 896, 934. The disaggregating mechanism 866 and/or the one or more central elements may be disposed within the sequester device 838, 900. The disaggregating mechanism 866 and/or one or more central elements may be disposed in the center of the sequester device 838, 900. The disaggregating mechanism 866 and/or one or more central elements may be disposed in the center of the sequester device 838, 900 within the central container. The disaggregating mechanism 866 and/or one or more central elements may be integral with the sequester device 838, 900 and/or removable connected to the sequester device 838, 900.

Figure 119A:
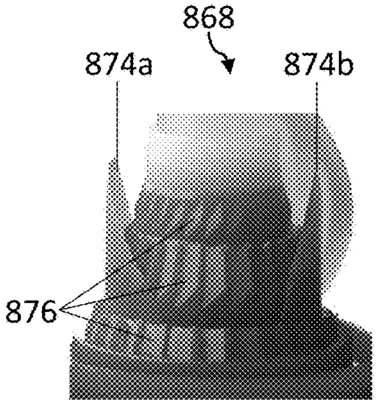

The central element comprises a shape, the shape is a straight cylinder or a frustum shaped cylinder. The one or more central elements may comprise a plurality of cylinders stacked on top of each other as shown in FIG. 119A, with each of the plurality of cylinders having a different diameter. The one or more central elements may be hollow or solid. The one or more central elements and/or each of the one or more central elements further comprises a central opening 884. The central opening 884 may be sized and configured to receive a portion of a central rod 882. Furthermore, the disaggregating mechanism 866 and/or the one or more central elements may further comprise at least one external surface or external diameter. At least a portion of the external surface and/or the outer diameter or external diameter comprises one or more disaggregating features or elements 874*a*, 874*b*, 876, 878, 880. The one or more disaggregating features 874*a*, 874*b*, 876, 878, 880 may be the same or different on each of the outer diameters of the one or more central elements and/or the disaggregating mechanism 866. Also, the one or more disaggregating features 874*a*, 874*b*, 876, 878, 880 may be the same or different on each of the plurality of cylinders of the one or more central elements.

The disaggregating features 874*a*, 874*b*, 876, 878, 880 may comprise at least one cutting disc 874*a*, 874*b*, and/or a plurality of teeth or facets 876, 878, 880 that extend obliquely from the outer diameter of the central element and/or extend away from the outer diameter or external surface of the central element and/or disaggregating mechanism 866. The disaggregating features 874*a*, 874*b*, 876, 878, 880 may further comprise sharp edges that extend along a length of the central element and/or the disaggregating mechanism 866. The disaggregating features 874*a*, 874*b*, 876, 878, 880 may further comprise sharp edges that extend along at least a portion of the central element and/or disaggregating mechanism 866.

Figure 119B:
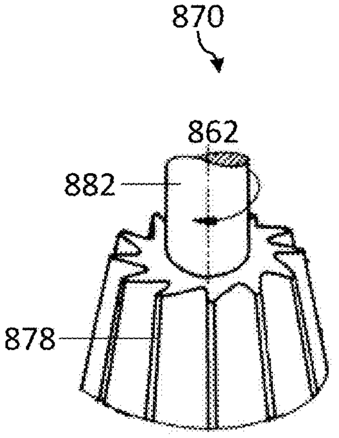
Figure 119C:
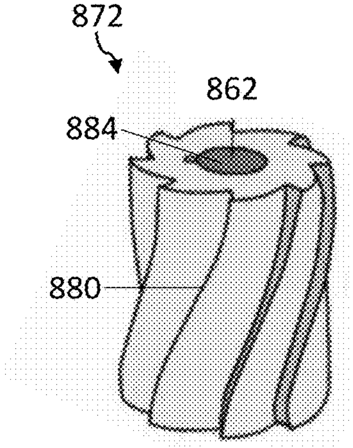
Figure 120A:
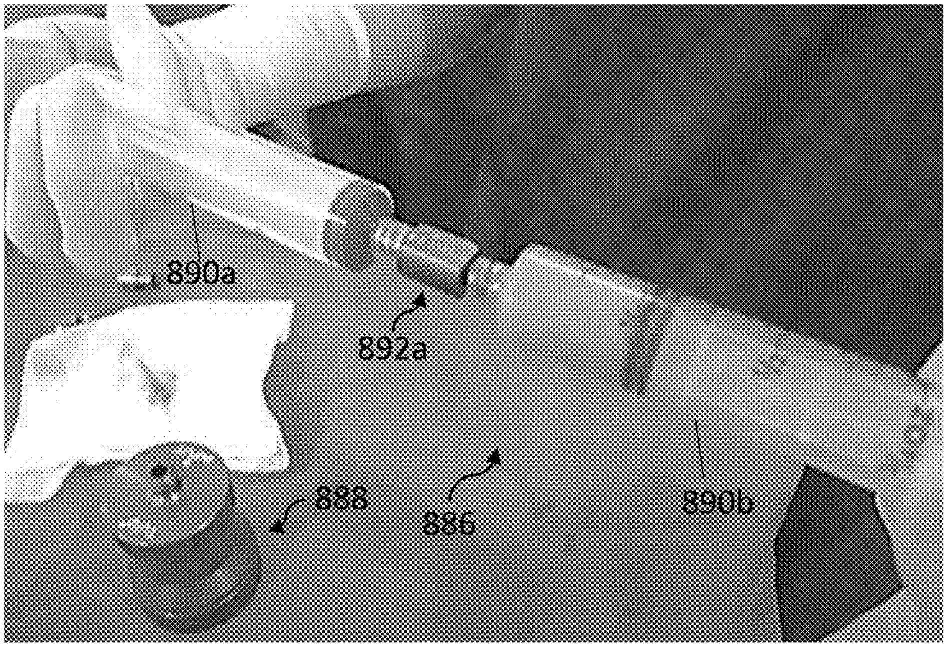
Figure 120B:
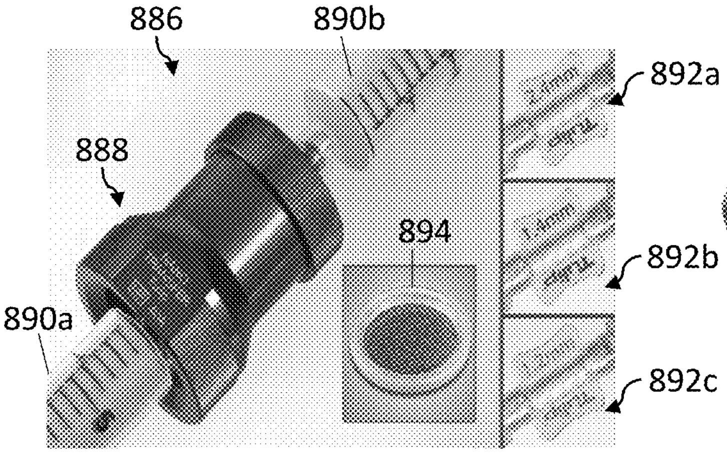
Figure 120C:
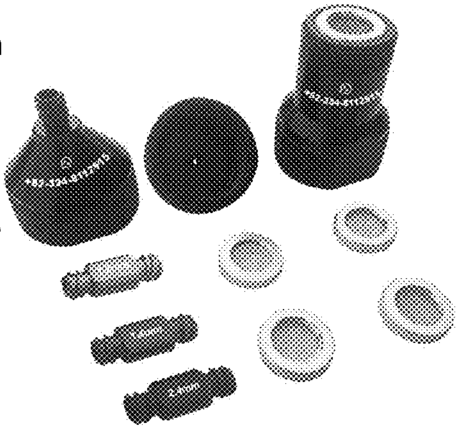

The sharp edges may be straight or in a non-straight pattern as shown in FIG. 119B-119C. The non-straight pattern may be spiral, helical, or undulated. In one embodiment, a plurality of disaggregating features 874*a*, 874*b*, 876, 878, 880 may be disposed onto the external surface or external diameter of the central element and/or disaggregating mechanism 866 in repeated rows. The repeated rows may be parallel and aligned to the adjacent repeated row. The repeated rows may be parallel and offset to the adjacent repeated rows. In one embodiment, a spacing may be positioned between a first repeated row and a second repeated row. Alternatively, no spacing may exist between the first repeated row and a second repeated row.

In another embodiment, at least a portion of the at least one of the concentric rings 840, 842, 844, 846, 918, 920, 922, 924 comprises disaggregating features disposed 874*a*, 874*b*, 876, 878, 880. The disaggregating features 874*a*, 874*b*, 876, 878, 880 onto at least a portion of at least one of a top surface, an inner diameter and/or an outer diameter of at least one of the concentric rings 840, 842, 844, 846, 918, 920, 922, 924 within the sequester device (not shown) 838, 900. The disaggregating features 874*a*, 874*b*, 876, 878, 880 may comprise at least one cutting disc 874*a*, 874*b*, and/or a plurality of teeth or facets 876, 878, 8880 that extend obliquely from the inner diameter and/or outer diameter of the central element and/or extend away from the at least one of a top surface, the inner diameter, the outer diameter of the concentric rings. The disaggregating features 874*a*, 874*b*, 876, 878, 880 may comprise sharp edges that extend away and/or extend obliquely from the at least one of the top surface, the inner diameter and/or outer diameter. The sharp edges may be straight or in a non-straight pattern as shown in FIG. 119B-119C. The non-straight pattern may be spiral, helical and/or undulated. In one embodiment, a plurality of disaggregating features 874*a*, 874*b*, 876, 878, 880 may be disposed onto the at least a portion of the at least one of the concentric rings 840, 842, 844, 846, 918, 920, 922, 924 in repeated rows. The repeated rows may be parallel and aligned to the adjacent repeated row. The repeated rows may be parallel and offset to the adjacent repeated rows. In one embodiment, a spacing may be positioned between a first repeated row, a second repeated row and/or between each of the plurality of repeated rows. Alternatively, no spacing may exist between the first repeated row, a second repeated row and/or each of the plurality of repeated rows.

The disaggregation mechanism 866 may comprise a nanofat emulsifier 886 to grind, mince, cut, emulsify the lipoaspirate. The nanofat emulsifier 886 may be integrated within portable centrifuge 896, 934 and/or a modular mechanism that can be removably connected. Alternatively, it can be a separate nano-fat emulsifier provided as part of a kit, such as the Autologous Cellular Matrix Device (ACM) manufactured by Tulip Medical Systems, San Diego, CA for Healean Medical, Newport Beach, CA or the Tulip GEMS by Tulip Medical Systems, San Diego, CA. The lipoaspirate may be transferred to one or more luered syringes 890*a*, 890*b* to engage in standard protocol for one or more emulsification of adipose tissue by shifting of fat between two luered syringes 890*a*, 890*b* connected to each other by a transfer connector 888, mini transfer connectors 892*a*, 892*b*, 892*c* and/or filtration cartridges 894. The mini transfer connectors 892*a*, 892*b*, 892*c* includes sizes of a 1.2 mm, a 1.4 mm and/or a 2.4 mm. The lipoaspirate is manually transferred between the two syringes 890*a*, 890*b* through the first transfer connector 888 at least 30 times. Then manually transferred between the two syringes through a second transfer connector 892*a*, 892*b*, 892*c* at least 30 times. The second transfer connector may comprise a smaller filtration mesh than the first transfer connector.

The disaggregation mechanism 866 may comprise a nanofat emulsifier 886 that may be coupled to the portable centrifuge 896, 934. The nanofat emulsifier may further include a luer port connector. The luer port connector may be disposed onto the luer port and/or insertion hole of the container cover 898, 940 of the portable centrifuge 896, 934. The luer port connector allows the transfer connector 888 and/or the mini transfer connectors 892*a*, 892*b*, 892*c* to be coupled together to dispense and/or inject the lipoaspirate through the transfer connectors 888, 892*a*, 892*b*, 892*c* into the luer port and/or insertion hole to fill the central container 848, 926 with the emulsified lipoaspirate.

The portable centrifuge 896, 934 may further comprise an agitation mechanism (not shown). The agitation mechanism may facilitate the washing step and/or the digestion step once the enzyme is introduced. The agitation mechanism may provide at least one action, which includes shaking, vortexing, sonication, vibration and/or any combination thereof. The agitation mechanism may allow for a set frequency and a set time. The agitation mechanism may be integral with the portable centrifuge or a separate mechanism. The agitation mechanism may be disposed within the base. Alternatively, the washing step and/or the digestion step may be further completed by the rotational mechanism at a set speed (rpm) and/or a set time.

The portable centrifuge 896, 934 may further comprise one or more incubators and/or heaters 940, 942, 944, 952. The one or more incubator or heaters 940, 942, 944, 952 may comprise electrical heaters 944, hydroponic heaters, radiator heaters, oil-based heaters, chemical heaters 940, 942 and/or any combination thereof. Electrical heaters may comprise a light bulb (e.g., incandescent, fluorescent or halogen) (not shown), a 5 W ceramic resistor (not shown), electrical heating elements (coils or wires or plates) 944 and/or any combination thereof. The chemical heater may comprise magnesium and/or magnesium-iron, air-activated heater (zinc with activated carbon and other solvents), and/or hydrogen-free ration heater (HRH). The magnesium-iron heater activates with an exothermic reaction as soon as it comes in contact with water. The water dissolves the sodium chloride into an electrolyte solution causing magnesium and iron to function as an anode and cathode, respectively. The incubator and/or heater 940, 942, 944, 952 may further comprise thermometer. In another embodiment, the incubator and/or heater 940, 942, 944, 952 may further comprise at least one or more of a thermometer, a heater control dial, and a temperature display. The incubator and/or heater 940, 942, 944, 952 may be disposed within the base. Accordingly, the incubator and/or heater 940, 942, 944, 952 may be disposed on the top of the base, the incubator and/or heater 940, 942, 944, 952 between the base 904 and the sequester device 838, 900. Alternatively, the incubator and/or heater 940, 942, 944, 952 may be disposed within the container cover 898, 940 and/or the protective cover. The incubator and/or heater 940, 942, 944, 952 may be disposed onto at least one surface of the container cover 898, 940 and/or the protective cover. The incubator and/or heater 940, 942, 944, 952 may be disposed on top of the sequester device 838, 900, which is between the sequester device 838 and the container cover 898, 940.

In another embodiment, the one or more incubator and/or heaters 940, 942, 944, 952 may comprise one or more pads (not shown) that attaches and/or surrounds at least a portion the perimeter and/or at least a portion of the outside diameter of the sequester device 838, 900 as shown as FIGS. 124A-124D. The one or more pads may be activated simultaneously and/or activated individually. The one or more pads may further comprise an electric cord 946. The electric cord 946 may comprise a USB cord, a standard 120 V cord, and/or a 220V cord. Alternatively, the electric cord 946 may obtain electricity from the rechargeable batteries (not shown) of the portable centrifuge 896, 934. The one or more pads may comprise an electrical or chemical heater.

Figure 124A:
Figure 124B:
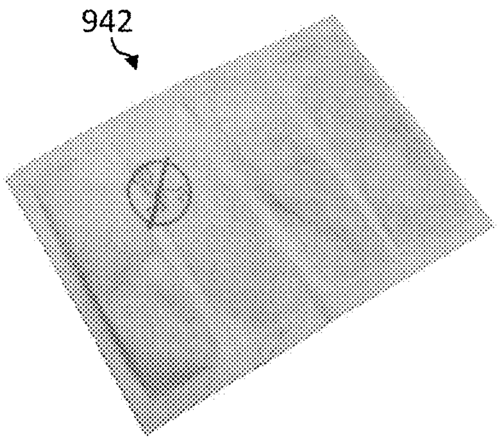
Figure 124C:
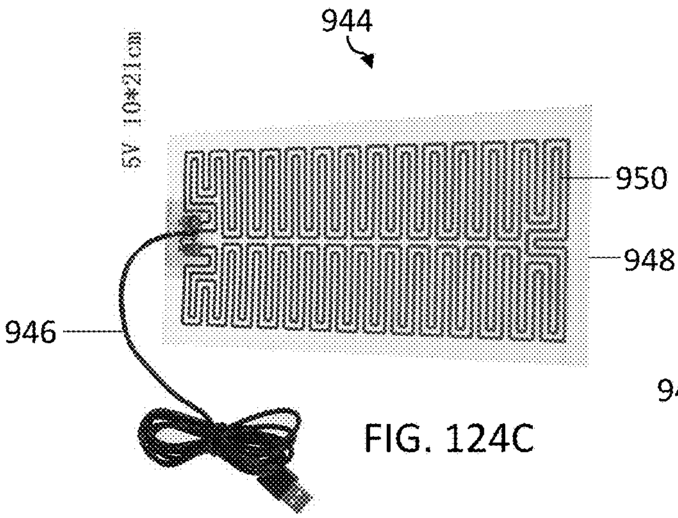
Figure 124D:
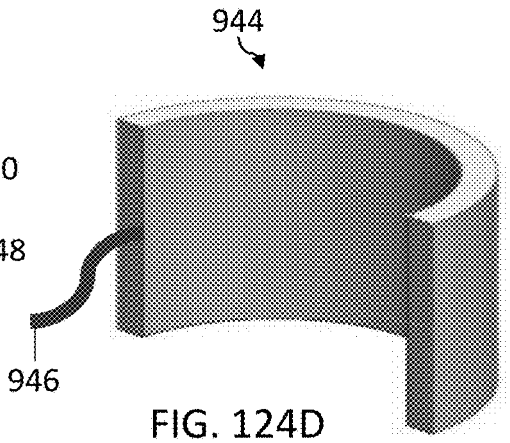
Figure 124E:
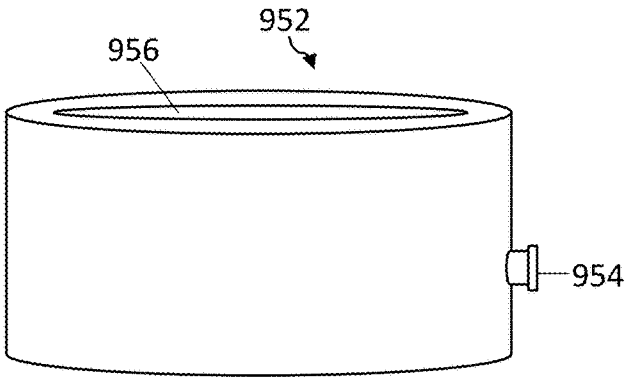

In another embodiment, the incubator and/or heater 940, 942, 944, 952 may further comprise one or more sleeves 952 that surrounds the perimeter and/or outside diameter of the sequester device 838, 900 as shown in FIGS. 124E. The incubator and/or heater sleeve 952 comprises a hollow cylinder shape and/or semi-cylinder shape, which includes an opening 956 that matches or substantially matches the outer diameter of the sequester device 838, 900. The one or more incubator and/or heater sleeves 952 may include one or more chambers (not shown), each of the one or more chambers comprising an electrical or chemical heater. The one or more chambers of the one or more incubator and/or heater sleeve 952 may be connected and/or coupled to each other or they are separate. Additionally, the incubator and/or heater may further comprise one or more inlet ports 954. The inlet port 954 may comprise a luer port. The inlet port 954 may be used to introduce a fluid, water and/or air to activate the chemical heater. The one or more incubator and/or heater sleeves 952 may further comprise an electrical cord 946.

The portable centrifuge may further comprise modular filters. The modular filters may be disposed and/or coupled onto the central luer port on the container cover, a syringe, a pipette, and/or any combination thereof. The modular filters may comprise cannulas or needles with filters, cell strainers (e.g., FALCON cell strainer from Corning Inc. in Corning, NY), pipette tips with filters (e.g., FLOWMI cell strainer tips from Bel-Art-SP Scienceware in Wayne, NJ), syringe filters (e.g., TITAN, TARGET or CHOICE syringe filters from ThermoFisher Scientific in Waltham, MA). The modular filter may comprise a filter size, the filter size includes a 40 micrometer to 100 micrometer filter; a 40 micrometer to 90 micrometer filter; a 60 micrometer to 80 micrometer filter; a 70 micrometer to 80 micrometer filter. In an exemplary embodiment, the modular filter comprises a 70 micrometer filter.

Methods

In one embodiment, a method of separating blood into blood components comprises the steps of: removing a protective cover from a portable centrifuge, the protective cover having an activation tab, the portable centrifuge comprising a rotational mechanism, an activation switch, and a timer; injecting whole blood through an injection tube disposed onto a container cover into a central container within the portable centrifuge; activating the portable centrifuge by replacing the protective cover over the container cover and the activation tab of the protective cover contacting the activation switch to trigger rotation of the rotation mechanism and the timer; separating the blood into constituent components into a plurality of channels; removing the protective cover after the rotation ceases; and extracting the blood constituent components through the container cover.

In an alternate embodiment, a method of separating blood into blood components comprises the steps of: injecting whole blood through an injection tube disposed onto a container cover and/or a protective cover into a central container of the sequester wheel; disposing a protective cover over a portion of the sequester wheel to activate the rotation mechanism and the timer; separating the blood into constituent components into a plurality of channels; removing the protective cover after the rotation ceases; and extracting the blood constituent components from one or more extraction regions through the container cover.

In an alternate embodiment, a method of separating blood into blood components for treatment of ocular disorders comprises the steps of: injecting whole blood through an injection tube disposed onto a container cover and/or a protective cover into a central container of a sequester wheel; disposing a protective cover over a portion of the sequester wheel to activate the rotation mechanism and the timer; separating the blood into constituent components into the central container and at least one channel; removing the protective cover after the rotation ceases; inserting a serum filter through the opening of the container cover to filter the blood constituent component deposited within the central container and extracting the blood constituent components through the opening of the container cover for ocular application. Extracting may include a pipette, eye dropper, a syringe, and/or any mechanical or non-mechanical eye dispensing mechanisms known in the art.

In an alternate embodiment, a method of separating blood into blood components for treatment of ocular disorders comprises the steps of: injecting whole blood through an injection tube disposed onto a container cover and/or a protective cover into a central container of a sequester wheel; disposing a protective cover over a portion of the sequester wheel to activate the rotation mechanism and the timer; separating the blood into constituent components into the central container and at least one channel; removing the protective cover after the rotation ceases; inserting a eye dispenser comprising an integral serum filter through the opening of the container cover to filter and extract the blood constituent component deposited within the central container and removing the eye dispenser mechanism comprising an integral serum filter through the opening of the container cover for ocular application.

In an alternate embodiment, a method of separating blood into blood components and reducing pathogens comprises the steps of: injecting whole blood through an injection tube disposed onto a container cover and/or a protective cover into a central container of a sequester wheel; activating the portable centrifuge by positioning the protective cover over the container cover to activate the rotation of the rotation mechanism, the timer and the UV light; separating the blood into constituent components into a plurality of channels; disinfecting the blood constituent components during rotation by using the irradiation of the UV light; removing the protective cover after the rotation ceases; and extracting the disinfected blood constituent components through at least one of the extraction regions on the container cover.

In another embodiment, a method of separating blood into blood components and reducing pathogens comprises the steps of: injecting whole blood through an injection tube disposed onto a container cover and/or protective cover into a central container within the portable centrifuge; activating the portable centrifuge by positioning the protective cover over the container cover to activate the rotation of the rotation mechanism, the timer and a UV light; separating the blood into constituent components into a plurality of channels and the central container; disinfecting the constituent components during rotation using the irradiation of the UV light to activate a pathogen reduction coating deposited on at least one surface of the central container and a plurality of channels; removing the protective cover after the rotation ceases; and extracting the disinfected blood constituent components through at least one of the extraction regions on the container cover.

In another embodiment, a method of separating blood into blood components and reducing pathogens for treatment of ocular disorders comprises the steps of: injecting whole blood through an injection tube disposed onto a container cover and/or protective cover into a central container within the portable centrifuge; activating the portable centrifuge by positioning the protective cover over the container cover to activate the rotation of the rotation mechanism, the timer and a UV light; separating the blood into constituent components into the central container; disinfecting the constituent components during rotation using the irradiation of the UV light to activate a pathogen reduction coating deposited on at least one surface of the central container; removing the protective cover after the rotation ceases; inserting a serum filter through the opening of the container cover to filter the blood constituent component deposited within the central container; and extracting the disinfected and filtered blood constituent components through the container cover.

In another embodiment, a method of separating blood into blood components and reducing pathogens for treatment of ocular disorders comprises the steps of: injecting whole blood through an injection tube disposed onto a container cover and/or protective cover into a central container within the portable centrifuge; activating the portable centrifuge by positioning the protective cover over the container cover to activate the rotation of the rotation mechanism, the timer and a UV light; separating the blood into constituent components into the central container; disinfecting the constituent components during rotation using the irradiation of the UV light to activate a pathogen reduction coating deposited on at least one surface of the central container; removing the protective cover after the rotation ceases; and inserting an eye dispensing mechanism with an integral filter through the opening of the container cover to filter and extract the disinfected and filtered blood constituent component deposited within the central container.

In another embodiment, a method of separating blood into blood components and reducing pathogens for treatment of ocular disorders comprises the steps of: injecting whole blood through an injection tube disposed onto a container cover and/or protective cover into a central container within the portable centrifuge; activating the portable centrifuge by positioning the protective cover over the container cover to activate the rotation of the rotation mechanism, the timer and a UV light; separating the blood into constituent components into the central container; disinfecting the constituent components during rotation using the irradiation of the UV light to activate a pathogen reduction coating deposited on at least one surface of the central container; removing the protective cover after the rotation ceases; inserting a serum filter through the opening of the container cover to filter the blood constituent component deposited within the central container; and extracting the disinfected and filtered blood constituent components through the container cover.

In another embodiment, a method of calculating a specific volume of PRP/RBCs prior to separation of blood into blood components comprises the steps of: acquiring hematocrit (HCT) from a patient (i.e., HCT measures the volume of packed red blood cells (RBC) relative to the whole blood); selecting a total volume of blood to inject into the portable centrifuge; calculating PRP/RBC volume by multiplying the total volume of blood with HCT and calculating plasma volume by subtracting the total volume of blood from the PRP/RBC volume; removing a protective cover from a portable centrifuge, the protective cover having an activation tab, the portable centrifuge comprising a rotational mechanism, an activation switch, and a timer; injecting the selected total volume of whole blood through an injection tube disposed onto a container cover into a central container within the portable centrifuge; activating the portable centrifuge by replacing the protective cover over the container cover and the activation tab of the protective cover contacting the activation switch to trigger rotation of the rotation mechanism and the timer; separating the whole blood into constituent components into a plurality of channels; removing the protective cover after the rotation ceases; and extracting the calculated blood constituent components through the container cover. Using HCT to calculate the necessary volume of blood to be drawn from a patient would help the practitioner understand the resulting volume of PRP/RBCs that will used for injection or transfusion, and can help the practitioner modify the drawn blood to reach the resulting volume of PRP/RBC's needed. The total volume of blood may comprise 100 cc to 1000 cc; or 200 cc to 400 cc. For example, a patient having a 45% HCT and 200 cc of whole blood drawn yields 90 cc (0.45×200 cc) of PRP/RBC and 110 cc (200 cc minus 90 cc) of Plasma. Hematocrit may be acquired by standard procedures known in the art, including fingerstick, heelstick, venipuncture and/or any combination thereof.

In another embodiment, a method of calculating total whole blood volume to yield specific volume of PRP/RBCs prior to separation of blood into blood components comprises the steps of: acquiring hematocrit (HCT) from a patient (i.e., HCT measures the volume of packed red blood cells (RBC) relative to the whole blood); selecting a desired volume of PRP/RBC that will yield after centrifugation using the portable centrifuge; calculating total whole blood volume by dividing the desired volume of PRP/RBC by the HCT and calculating plasma volume by subtracting the calculated total whole blood volume minus the desired volume of PRP/RBC; drawing the calculated total whole blood volume; removing a protective cover from a portable centrifuge, the protective cover having an activation tab, the portable centrifuge comprising a rotational mechanism, an activation switch, and a timer; injecting the calculated total volume of whole blood through an injection tube disposed onto a container cover into a central container within the portable centrifuge; activating the portable centrifuge by replacing the protective cover over the container cover and the activation tab of the protective cover contacting the activation switch to trigger rotation of the rotation mechanism and the timer; separating the calculated whole blood volume into constituent components into a plurality of channels; removing the protective cover after the rotation ceases; and extracting the calculated blood constituent components through the container cover, calculated blood constituent components comprise the desired volume of PRP/RBCs and calculated plasma. Using HCT to calculate the whole blood to be drawn from a patient would help the practitioner understand the desired volume of PRP/RBCs that will used for injection or transfusion, and can help the practitioner modify the drawn blood volume to prevent waste or unnecessary multiple blood drawings to reach the desired volume of PRP/RBC's needed. The total volume of blood may comprise 100 cc to 1000 cc or 200 cc to 400 cc. For example, a patient having a 55% HCT and selecting a desired 90 cc of PRP/RBCs yields 164 cc (90 cc divided by 0.55) of total whole blood volume and 74 cc (164 cc minus 90 cc) of Plasma.

In another embodiment, a method of acquiring blood clotting time comprises the steps of: injecting whole blood through an injection tube disposed onto a container cover into a central container of the sequester wheel; disposing a protective cover over a portion of the sequester wheel to activate the rotation mechanism and the timer; separating the blood into constituent components into a plurality of channels and propelling a portion of the blood to enter a first blood communication port of a coagulation module; transporting blood through the at least one microchannel via centrifugal forces and/or a pressure differential to evaluate for clot time; removing the protective cover after the rotation ceases; analyzing clot time from the coagulation module; and extracting the blood constituent components from one or more extraction regions through the container cover.

In another embodiment, a method of acquiring blood clotting time comprises the steps of: injecting whole blood through an injection tube disposed onto a container cover into a central container of the sequester wheel; disposing a protective cover over a portion of the sequester wheel to activate the rotation mechanism and the timer; propelling a portion of the blood to enter a first blood communication port of a coagulation module; removing the protective cover after the rotation ceases; transporting blood through the at least one microchannel to evaluate for clot time using capillary action; and analyzing clot time from the coagulation module.

Figure 125A:
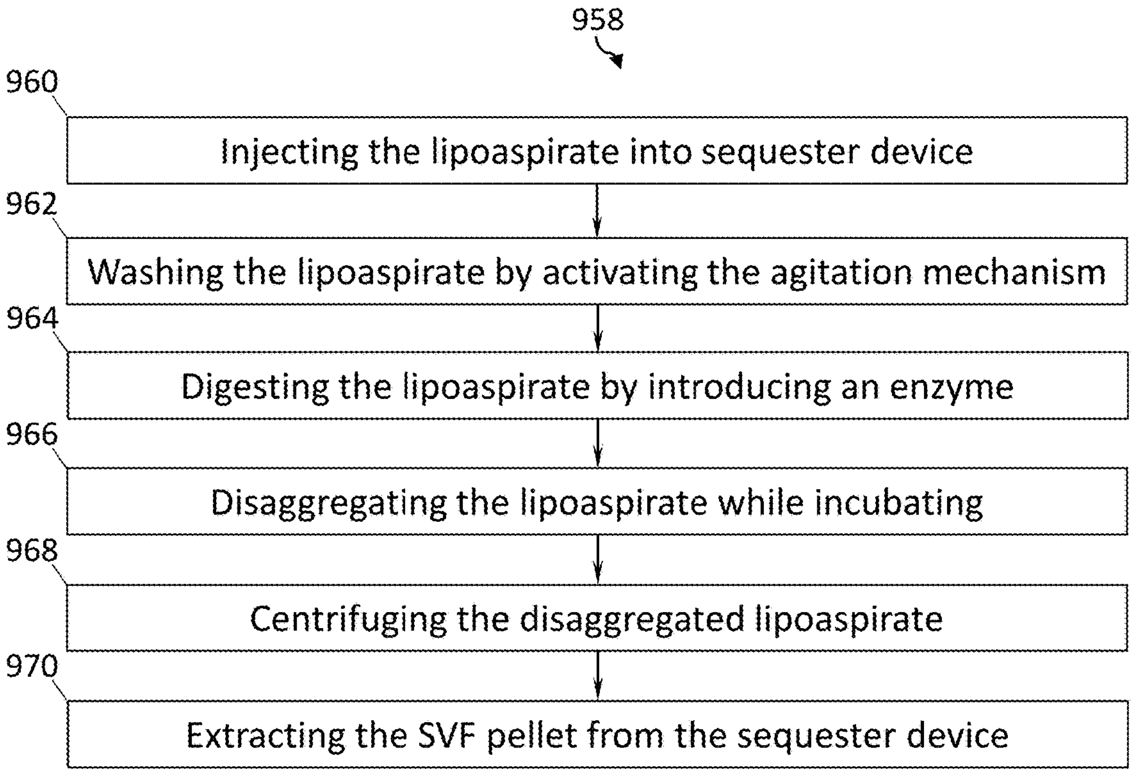

In another embodiment, FIG. 125A discloses a method of isolating SVF from adipose tissue using enzymatic techniques to acquire stem cells or other cell types 958 that comprises the steps of: injecting the lipoaspirate into the sequester device of the portable centrifuge 960; washing the lipoaspirate by activating the agitation mechanism for a set time and set frequency 962; digesting the lipoaspirate by introducing an enzyme 964; disaggregating the digesting lipoaspirate and activating incubator for a set time and set temperature 966; and centrifugating the digested lipoaspirate for a set speed (rpm) and a set time 968. The method of isolating SVF from adipose tissue may further comprise the steps of extracting the SVF pellet from the centrifuged lipoaspirate that separated into its distinct channels within the sequester device 970. The method of isolating SVF from adipose issue may further comprise the steps of: lysing the centrifuged lipoaspirate to remove red blood cells by introducing a erythrocyte lysis buffer and activating the incubator for a set time and set temperature; centrifuging the lysed SVF for a set speed (rpm) and set time; and extracting the lysed SVF pellet. Introducing the enzyme may comprise at least one of the enzymes collagenase, trypsin, and/or dispase. Furthermore, introducing the enzyme may include syringe injection through central port and/or liquid blister pack and/or blister module dispensing. Activating the agitation mechanism includes at least one of: oscillating, shaking, spinning/rotating (e.g., centrifugation), vortexing, sonication, vibration and/or any combination thereof. Disaggregating includes grinding, mincing and/or chopping lipoaspirate into smaller pieces to facilitate digestion using a disaggregation mechanism and/or disaggregation features. Centrifugation may occur at set times greater than 1 minute; set times of at least 1 minute; and/or set times of 1 minute to 10 minutes. Centrifugation speed comprises 1000 rpms or greater; speed of at least 1000 rpm; speed ranging from 1000 rpm to 10,000 rpm.

Figure 125B:
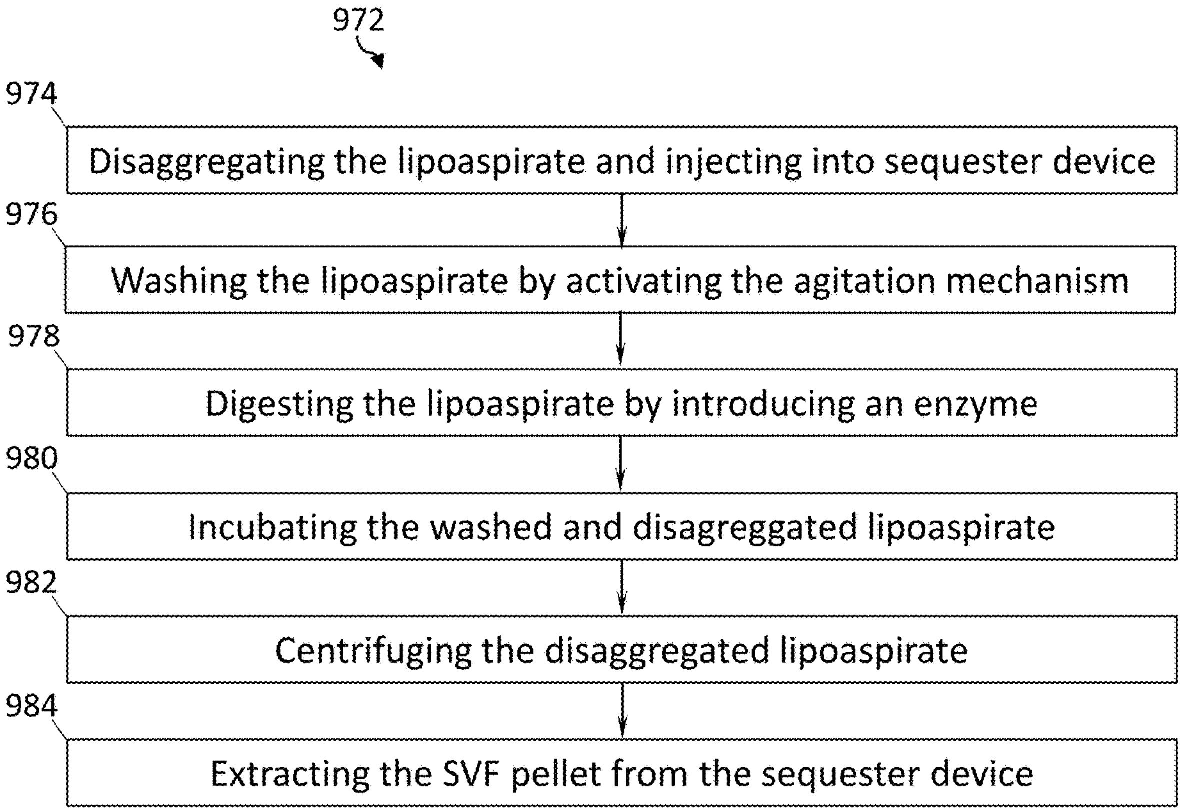

In another embodiment, FIG. 125B discloses a method of isolating SVF from adipose tissue using enzymatic techniques to further isolate stem cells or other cell types 972 that comprises the steps of: disaggregating the lipoaspirate and injecting into the sequester device of the portable centrifuge 974; washing the lipoaspirate by activating the agitation mechanism for a set time and set frequency 976; digesting the lipoaspirate by introducing an enzyme 978; incubating the washed and disaggregated lipoaspirate for a set time and set temperature 980; and centrifugating the incubated lipoaspirate for a set speed (rpm) and a set time 982. The method of isolating SVF from adipose tissue may further comprise the steps of extracting the SVF pellet from the centrifuged lipoaspirate that separated into its distinct channels within the sequester device 984. The method of isolating SVF from adipose issue may further comprise the steps of: lysing the centrifuged lipoaspirate to remove red blood cells by introducing a erythrocyte lysis buffer and activating the incubator for a set time and set temperature; centrifuging the lysed SVF for a set speed (rpm) and set time; and extracting the lysed SVF pellet. Introducing the enzyme may comprise at least one of the enzymes collagenase, trypsin, and/or dispase. Furthermore, introducing the enzyme may include syringe injection through central port and/or liquid blister pack and/or blister module dispensing. Activating the agitation mechanism includes at least one of: oscillating, shaking, spinning/rotating (e.g., centrifugation), vortexing, sonication, vibration and/or any combination thereof. Disaggregating includes grinding, mincing and/or chopping lipoaspirate into smaller pieces to facilitate digestion via a disaggregating mechanism disposed within the sequester device and/or disaggregating features disposed onto at least one surface of the concentric rings. Centrifugation may occur at set times greater than 1 minute; set times of at least 1 minute; and/or set times of 1 minute to 10 minutes. Centrifugation speed comprises 1000 rpms or greater; speed of at least 1000 rpm; speed ranging from 1000 rpm to 10,000 rpm.

Figure 126A:
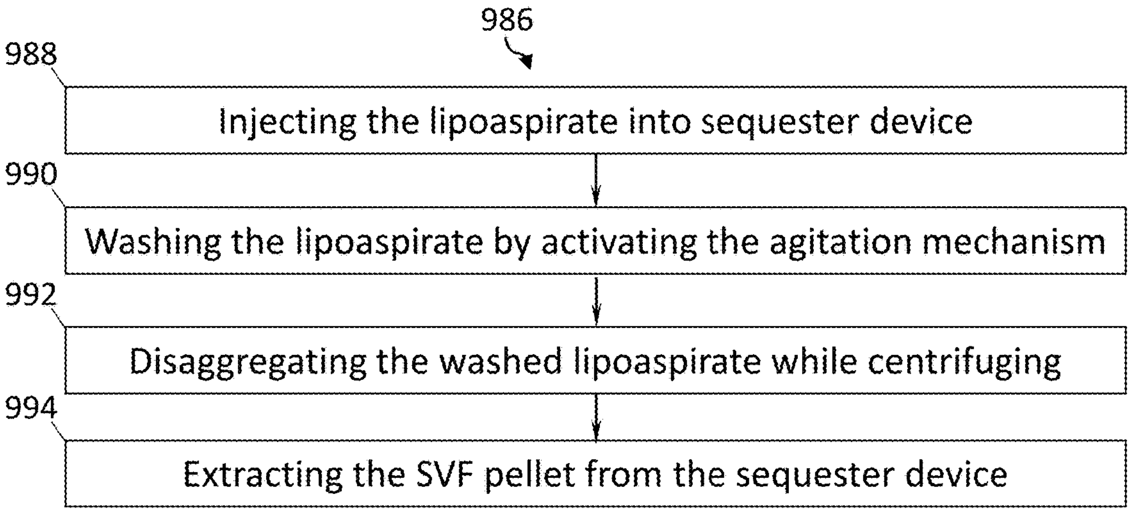

In another embodiment, FIG. 126A discloses a method of isolating SVF from adipose tissue using non-enzymatic techniques to acquire stem cells or other cell types 986 that comprises the steps of: injecting the lipoaspirate into the sequester device 986; washing the lipoaspirate by activating the agitation mechanism 990; disaggregating the washed lipoaspirate while centrifuging at a set time and speed 992; extracting the SVF pellet from sequester device 994. Activating the agitation mechanism includes at least one of: oscillating, shaking, spinning/rotating (e.g., centrifugation), vortexing, sonication, vibration and/or any combination thereof. Disaggregating includes grinding, mincing and/or chopping lipoaspirate into smaller pieces to facilitate digestion via a disaggregating mechanism disposed within the sequester device and/or disaggregation features disposed onto at least one surface of one or more of the concentric rings of the sequester device. Centrifugation may occur at set times greater than 1 minute; set times of at least 1 minute;

and/or set times of 1 minute to 10 minutes. Centrifugation speed comprises 1000 rpms or greater; speed of at least 1000 rpm; speed ranging from 1000 rpm to 10,000 rpm. The method of isolating SVF from adipose issue may further comprise the steps of: lysing the centrifuged lipoaspirate to remove red blood cells by introducing a erythrocyte lysis buffer and activating the incubator for a set time and set temperature; centrifuging the lysed SVF for a set speed (rpm) and set time prior to extracting the SVF pellet.

Figure 126B:
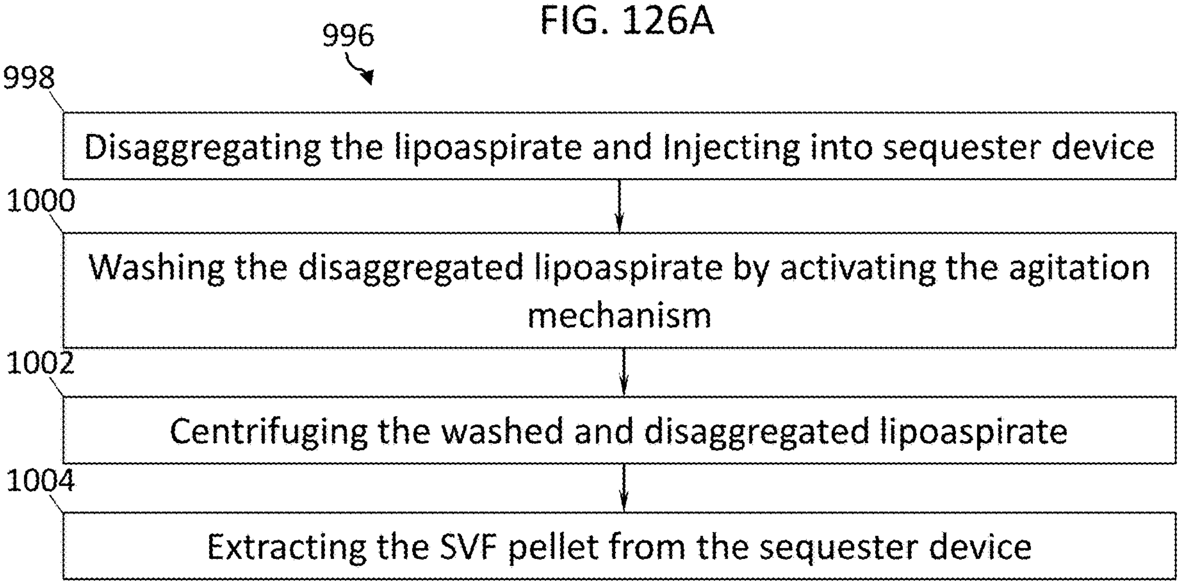

In another embodiment, FIG. 126B discloses a method of isolating SVF from adipose tissue using non-enzymatic techniques to acquire stem cells or other cell types 996 that comprises the steps of: disaggregating the lipoaspirate and injecting the lipoaspirate into the sequester device 998; washing the lipoaspirate by activating the agitation mechanism 1000; centrifuging the disaggregated and washed lipoaspirate at a set time and speed 1002; extracting the SVF pellet from sequester device 1004. Activating the agitation mechanism includes at least one of: oscillating, shaking, spinning/rotating (e.g., centrifugation), vortexing, sonication, vibration and/or any combination thereof. Disaggregating includes grinding, mincing and/or chopping lipoaspirate into smaller pieces to facilitate digestion via an disaggregating mechanism disposed within the sequester device and/or disaggregating features disposed onto at least one surface of one or more of the concentric rings. Centrifugation may occur at set times greater than 1 minute; set times of at least 1 minute; and/or set times of 1 minute to 10 minutes. Centrifugation speed comprises 1000 rpms or greater; speed of at least 1000 rpm; speed ranging from 1000 rpm to 10,000 rpm. The method of isolating SVF from adipose issue may further comprise the steps of: lysing the centrifuged lipoaspirate to remove red blood cells by introducing a erythrocyte lysis buffer and activating the incubator for a set time and set temperature; centrifuging the lysed SVF for a set speed (rpm) and set time prior to extracting the SVF pellet.

Figure 126C:
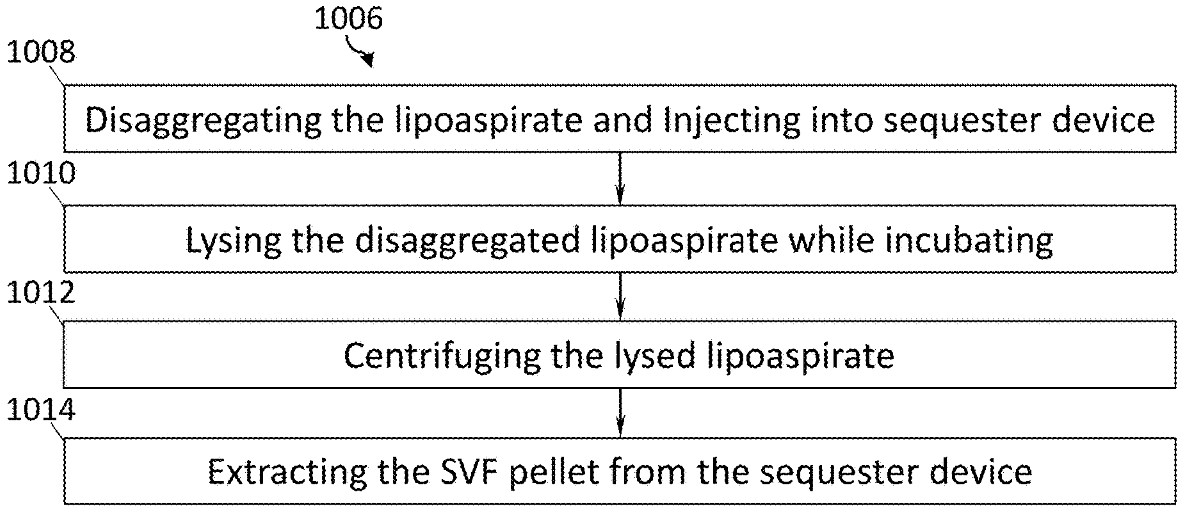

In another embodiment, FIG. 126C discloses a method of isolating SVF from adipose tissue using non-ezymatic techniques to acquire stem cells or other cell types 1006 that comprises the steps of: injecting lipoaspirate into sequester device 1006; lysing the lipoaspirate while incubating 1008; centrifuging the lysed aspirate at a set time and set speed 1012; extracting the SVF pellet from sequester device 1014. The method of isolating SVF from adipose tissue may further comprise disaggregating the lipoaspirate prior to injecting the lipoaspirate and/or desegregating the lipoaspirate while injecting the lipoaspirate. Alternatively, the method of isolating SVF from adipose tissue may further comprise disaggregating the lipoaspirate during centrifugation. Activating the agitation mechanism includes at least one of: oscillating, shaking, spinning/rotating (e.g., centrifugation), vortexing, sonication, vibration and/or any combination thereof. Disaggregating includes grinding, mincing and/or chopping lipoaspirate into smaller pieces to facilitate digestion via an disaggregating mechanism disposed within the sequester device and/or disaggregation features disposed onto at least one surface of one or more of the concentric rings. Centrifugation may occur at set times greater than 1 minute; set times of at least 1 minute; and/or set times of 1 minute to 10 minutes. Centrifugation speed comprises 1000 rpms or greater; speed of at least 1000 rpm; speed ranging from 1000 rpm to 10,000 rpm.

Figure 127A:
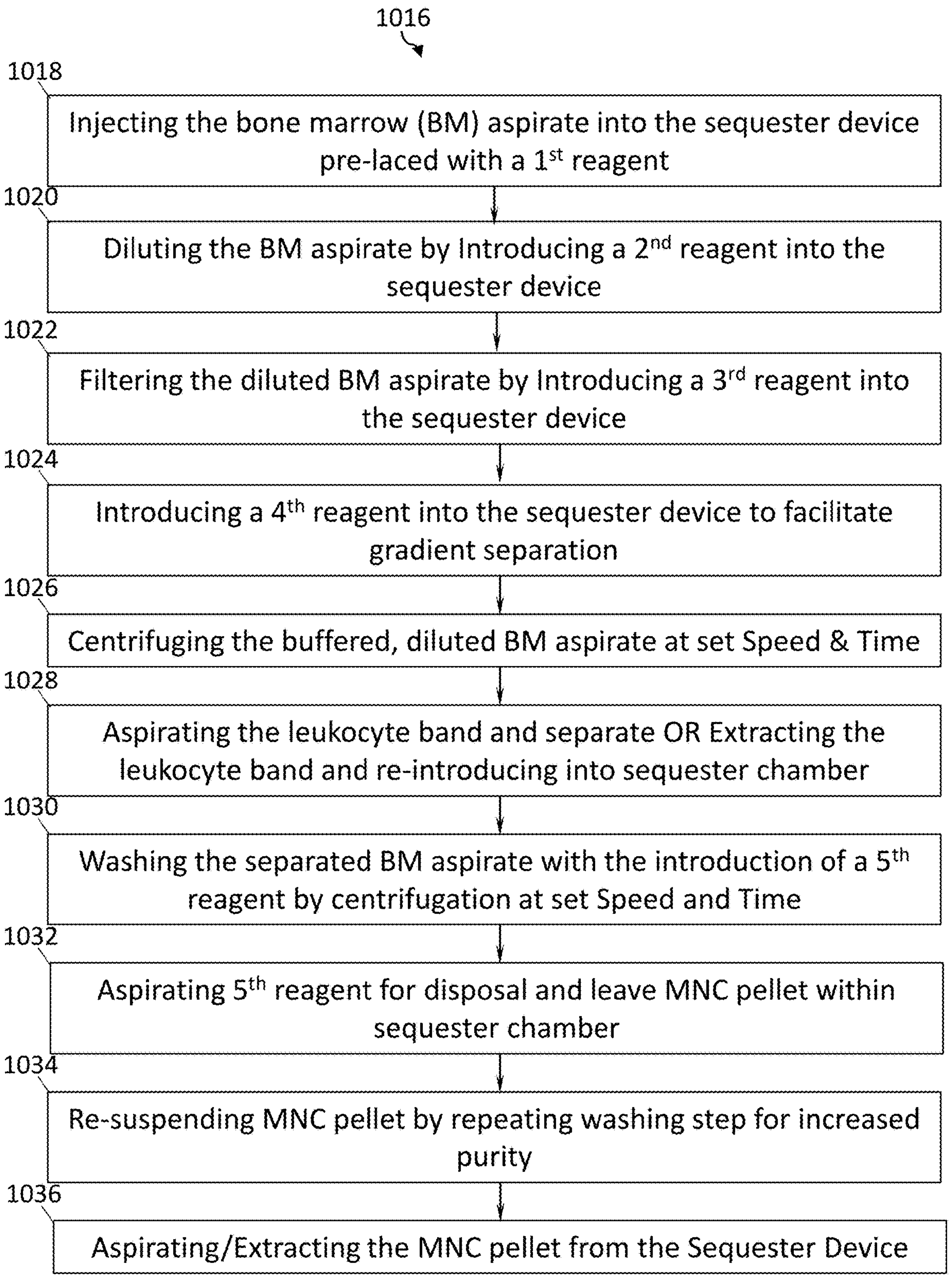

In another embodiment, FIG. 127A discloses a method of isolating MNCs from bone marrow (BM-MNCs) 1016 that comprises the steps of: injecting the bone marrow (BM) aspirate into the sequester device that is pre-laced with a first reagent 1018; diluting the BM aspirate by introducing a 2nd reagent 1020; filtering the diluted BM aspirate by introducing a 3rd reagent 1022; introducing a 4th reagent to facilitate gradient separation 1024; centrifuging the buffered, diluted BM aspirate at a set time and speed 1026; aspirating/extracting the leukocyte band and transfer to a 2nd sequester chamber OR aspirating/extracting the leukocyte band and re-introduce into same sequester device 1028; washing the separated BM aspirate and/or MNCs with the introduction of a 5th reagent by centrifugation at a set speed and time 1030;

aspirating/extracting the 5th reagent for disposal leaving the MNC pellet 1032; re-suspending the MNC pellet to repeat washing step for increased purity 1034; aspirating/extracting the MNC pellet from the sequester device 1036. Introduction of the reagents may comprise dispensing via syringe though central luer port disposed on the container cover and/or dispensing via one or more blister modules by compressing the blister. The reagents may comprise digestion enzyme, buffers, thixotropic gels, anticoagulants, density gradient media, dilution media and/or any combination thereof. Centrifugation speed may comprise 200 g to 600 g; 200 g to 400 g; 300 g to 400 g. The centrifugation time may comprise 10 minutes to 40 minutes. The first, second and any other subsequent centrifugation cycles may comprise the same or different set times and speed. Filtration step comprises filtering with a filtering ring, the at least one of the first, second, third concentric rings, and/or fourth concentric ring comprises a filtration ring.

Figure 127B:
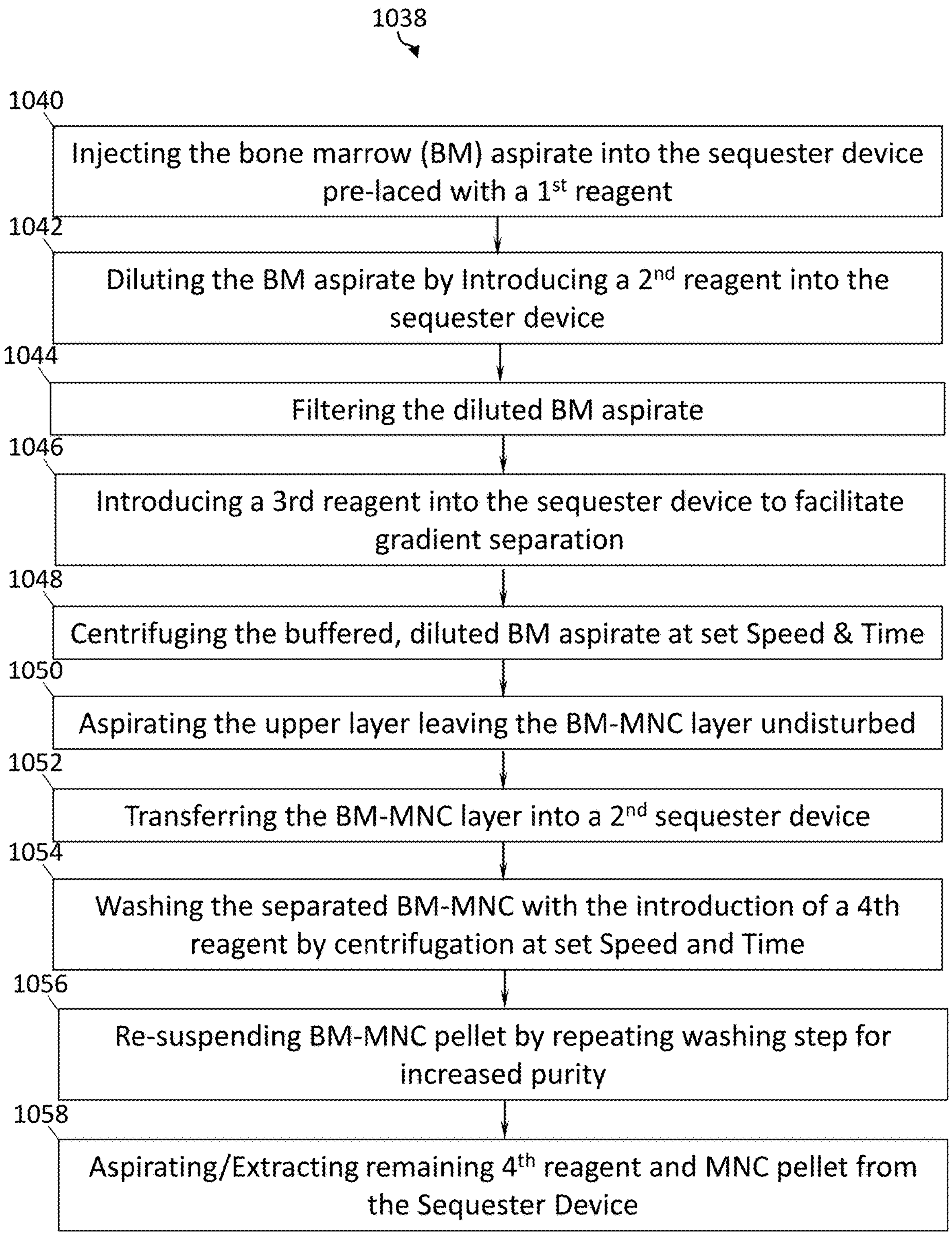
Figure 128A:
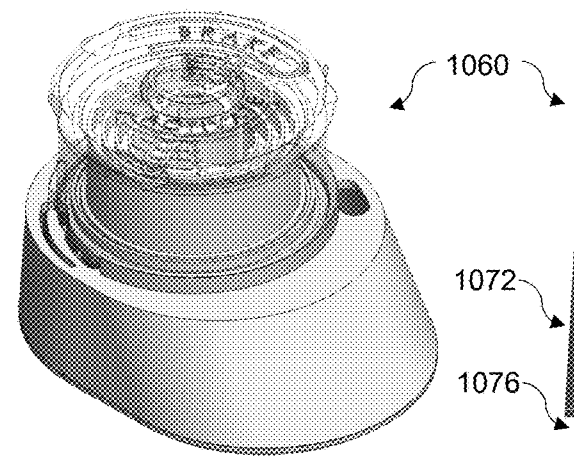
Figure 128B:
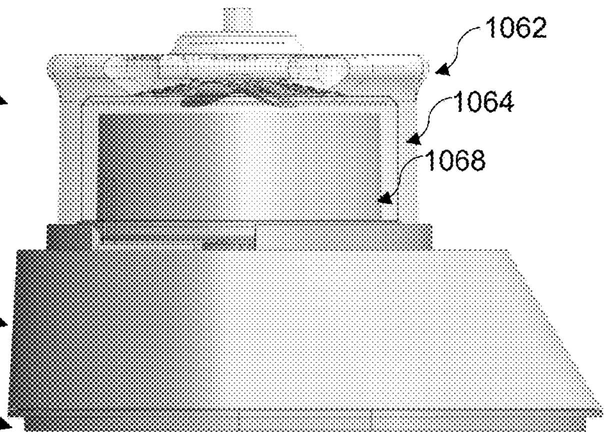
Figure 128C:
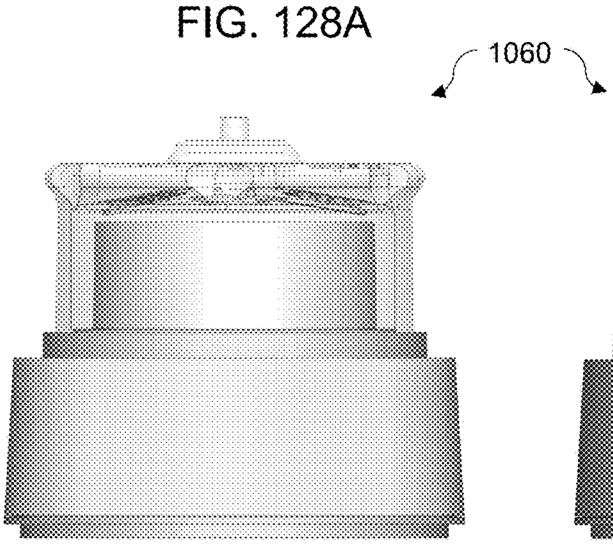
Figure 128D:
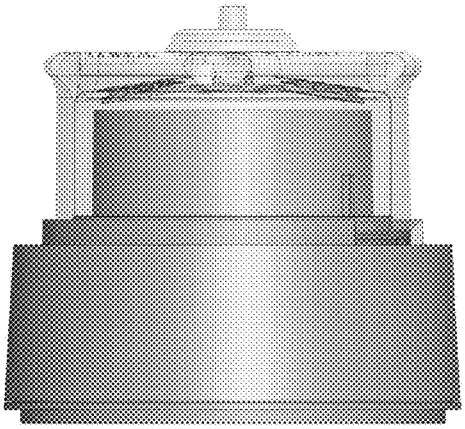
Figure 128E:
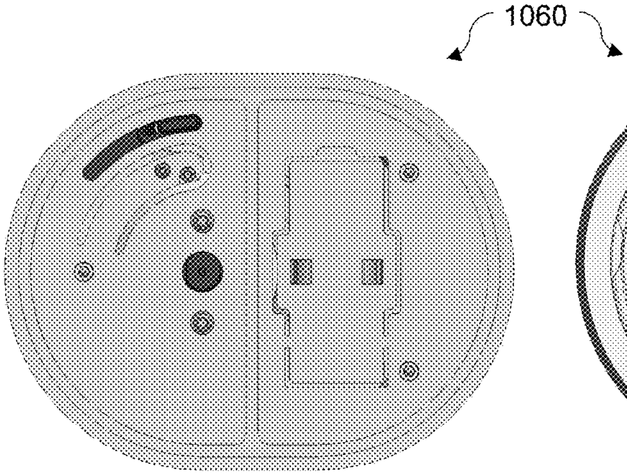
Figure 128F:
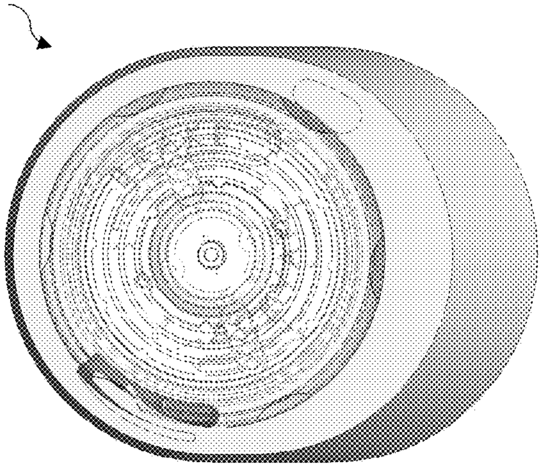
Figure 129A:
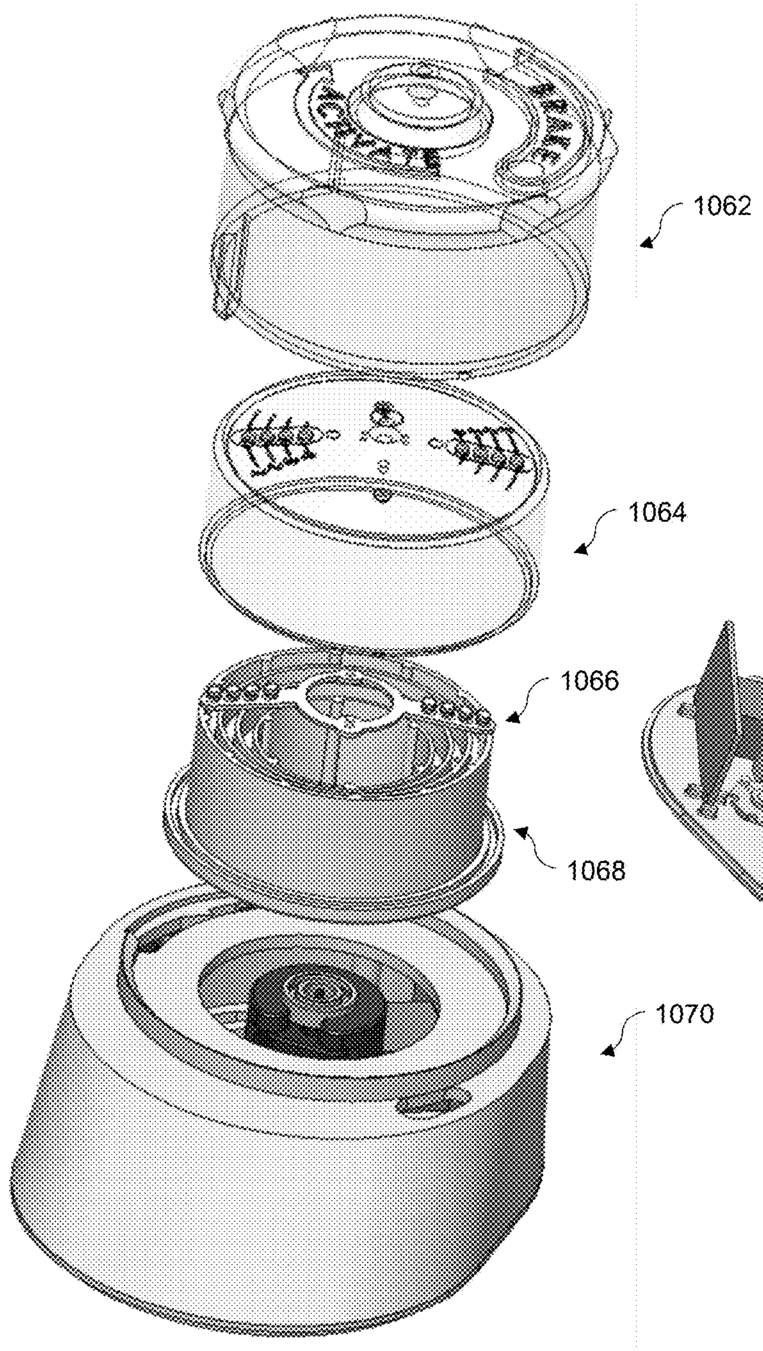
Figure 129B:
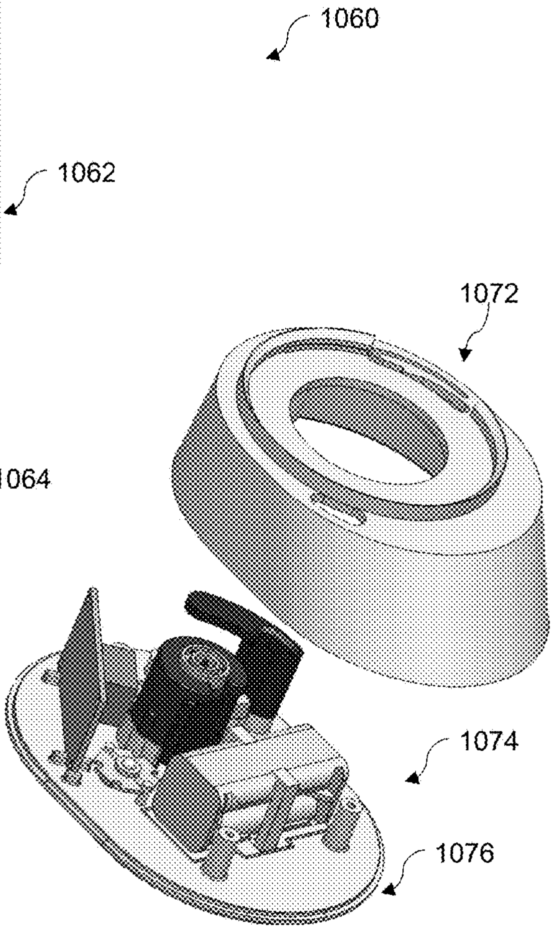
Figure 130A:
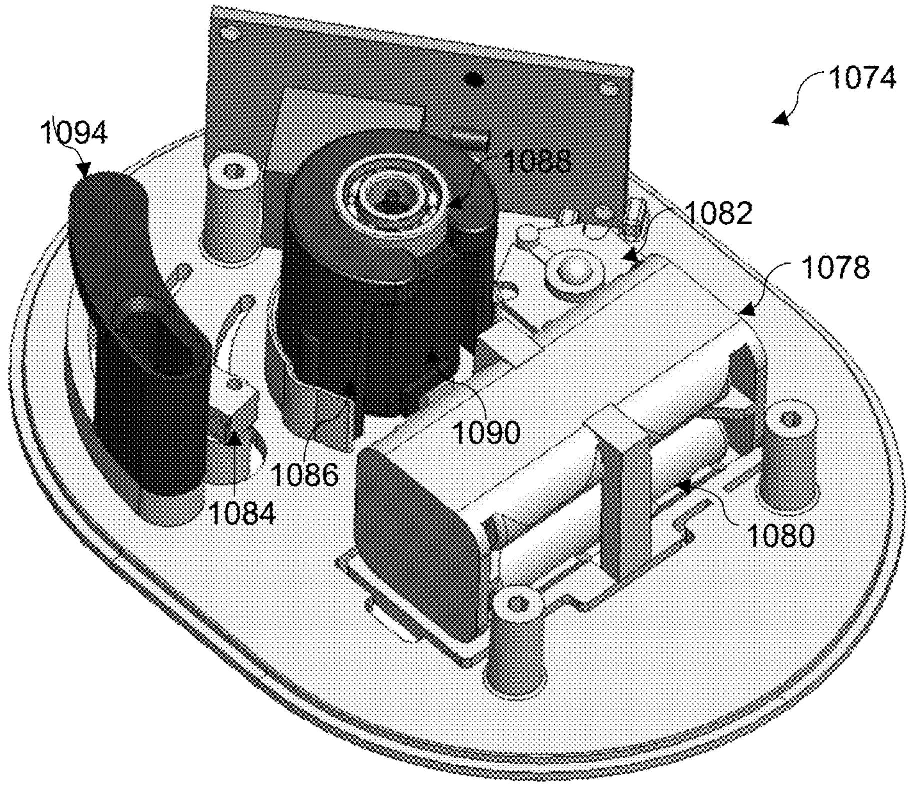
Figure 130B:
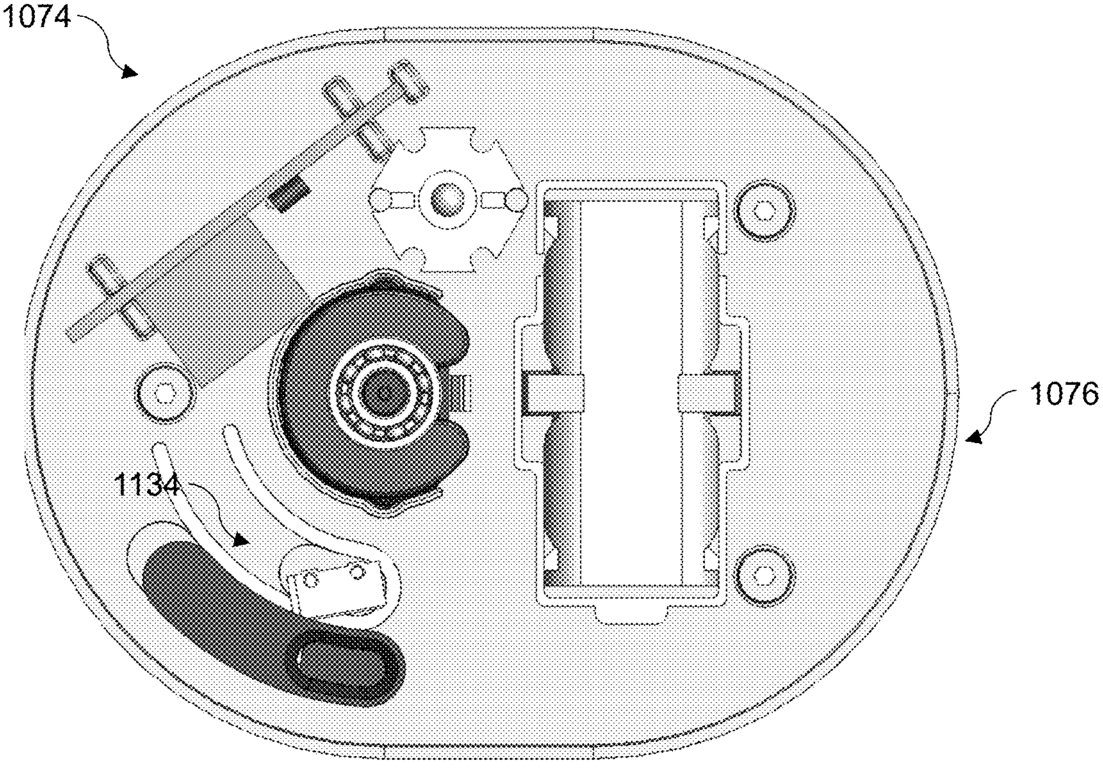
Figure 130C:
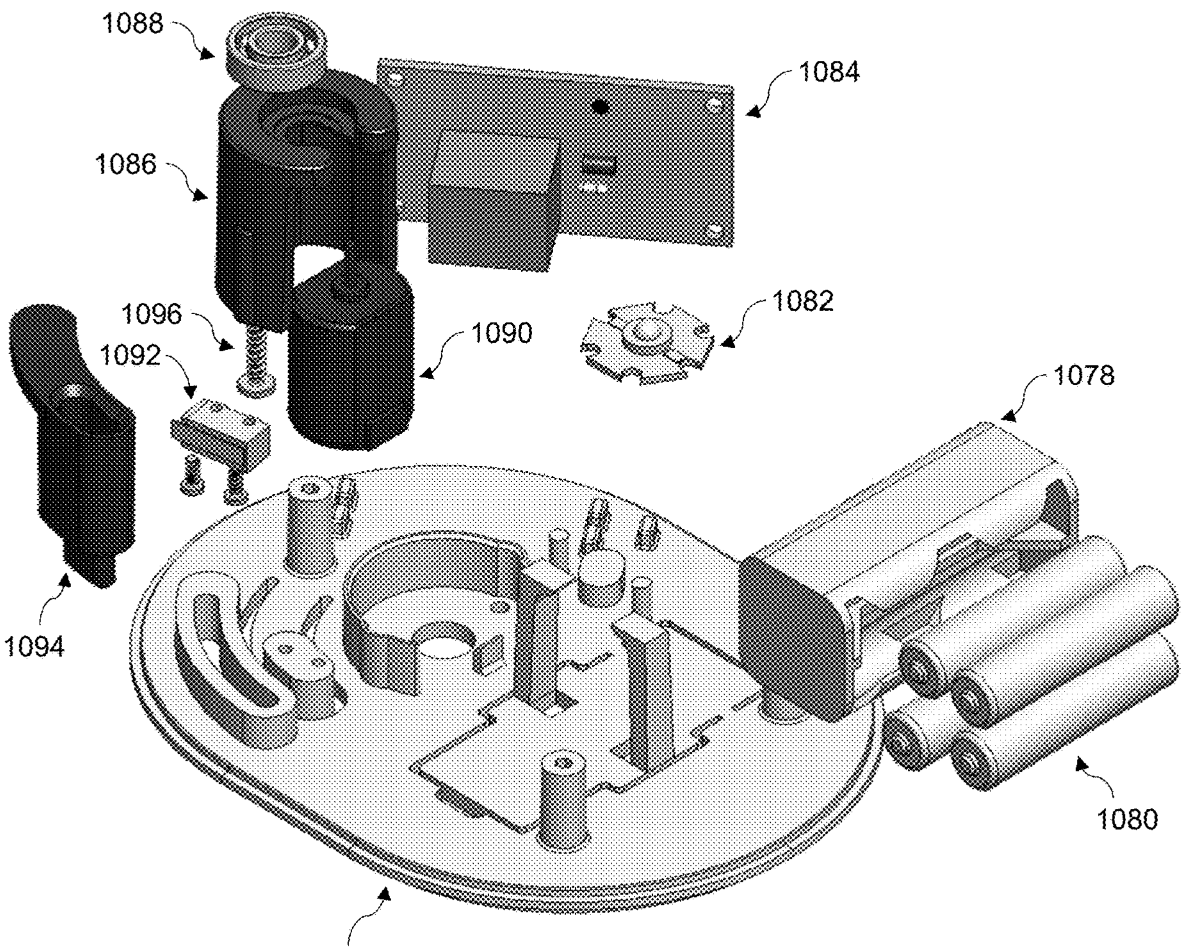
Figure 131A:
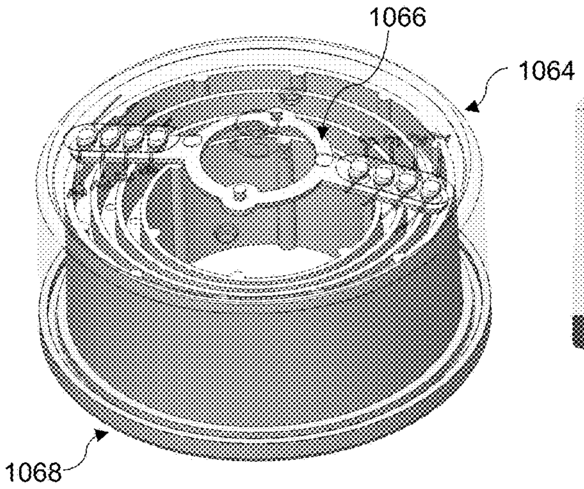
Figure 131B:
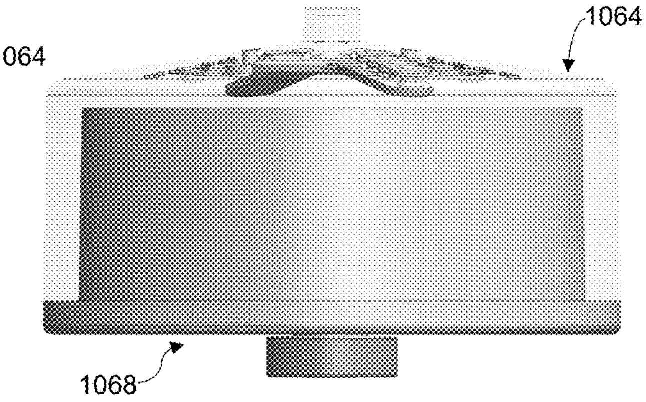
Figure 131C:
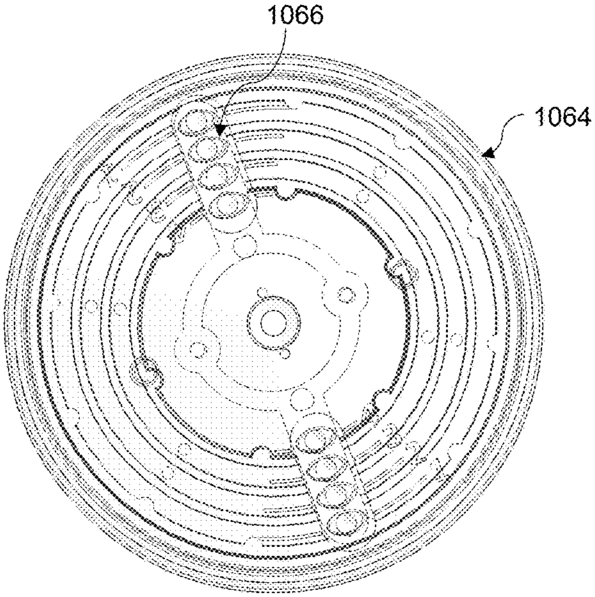
Figure 131D:
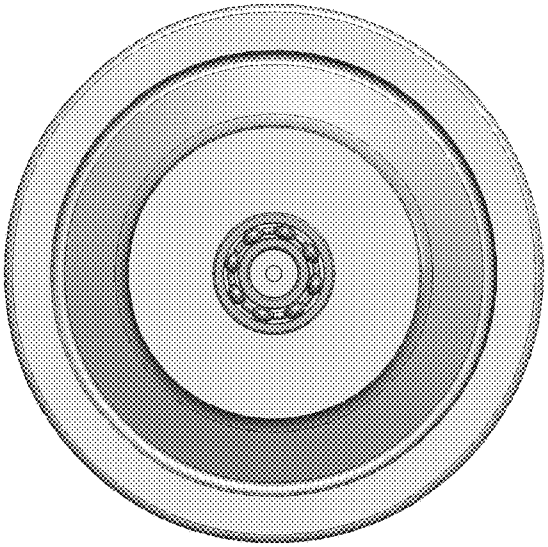
Figure 132A:
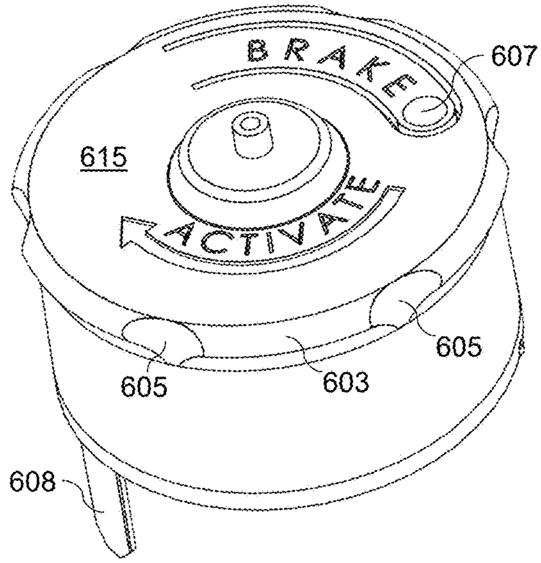
Figure 132B:
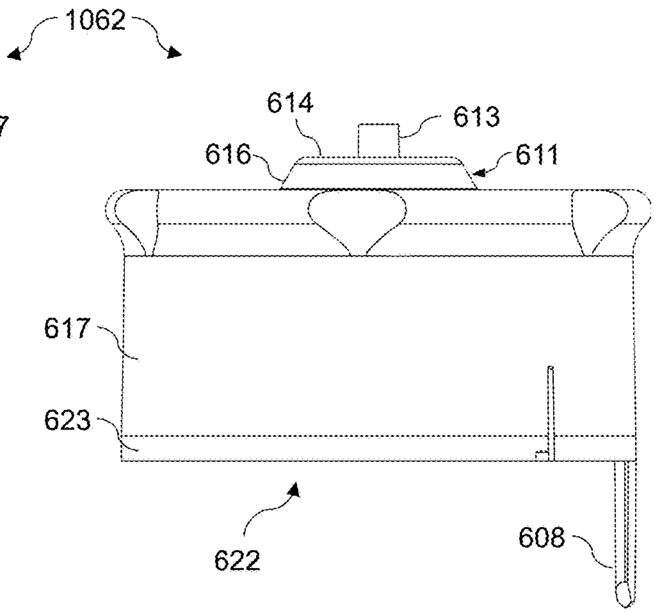
Figure 132C:
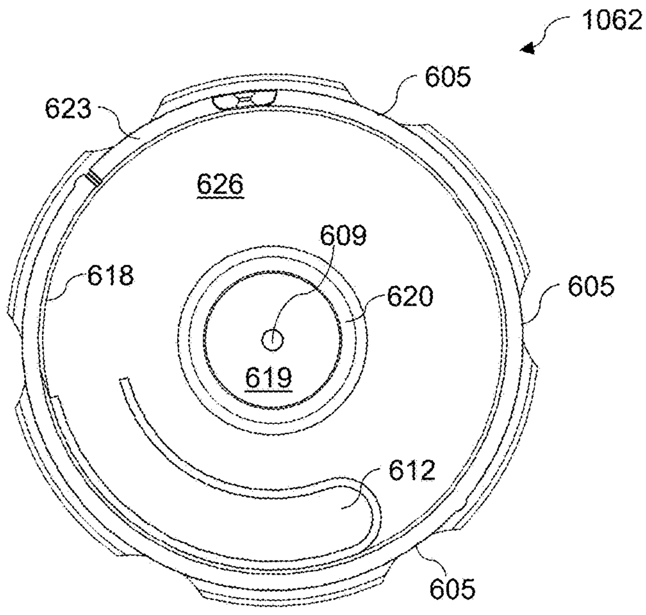
Figure 132D:
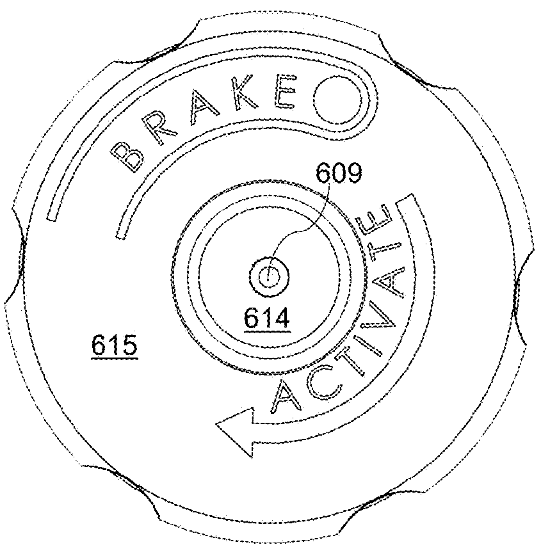
Figure 133A:
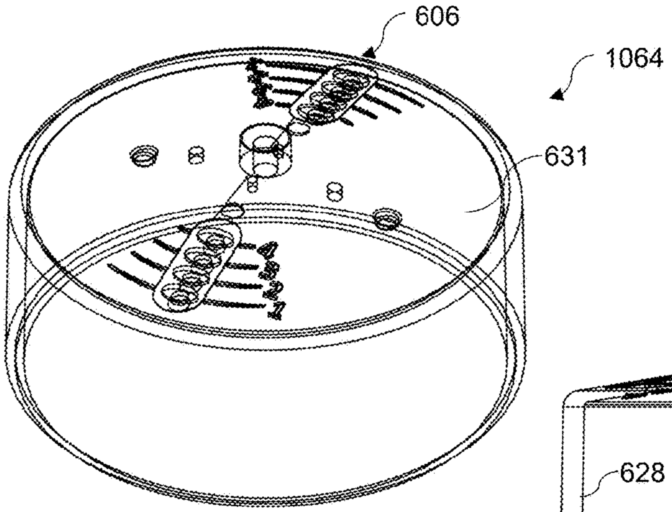
Figure 133B:
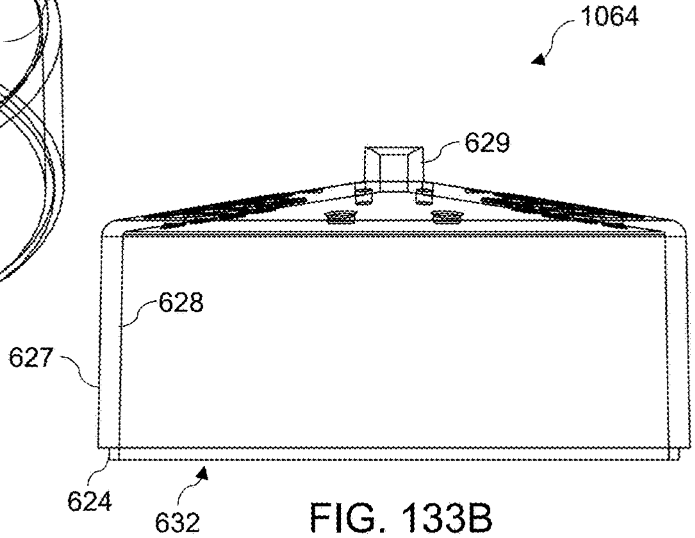
Figure 133C:
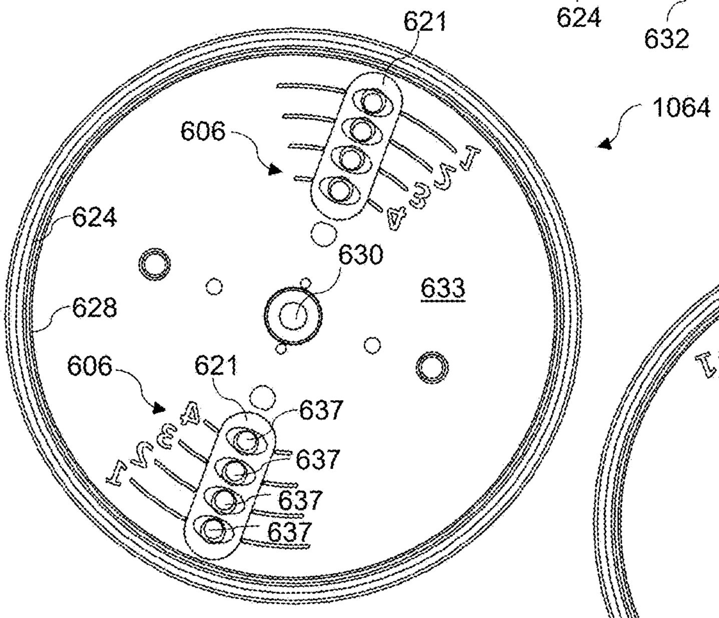
Figure 133D:
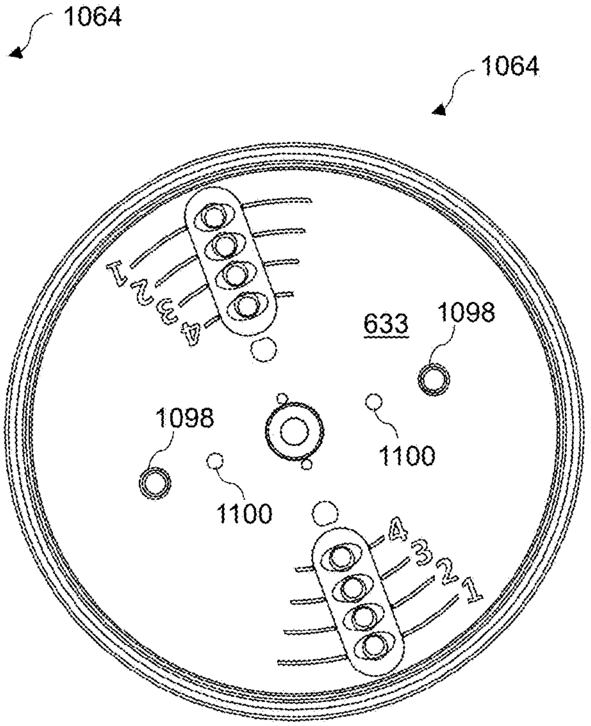
Figure 134A:
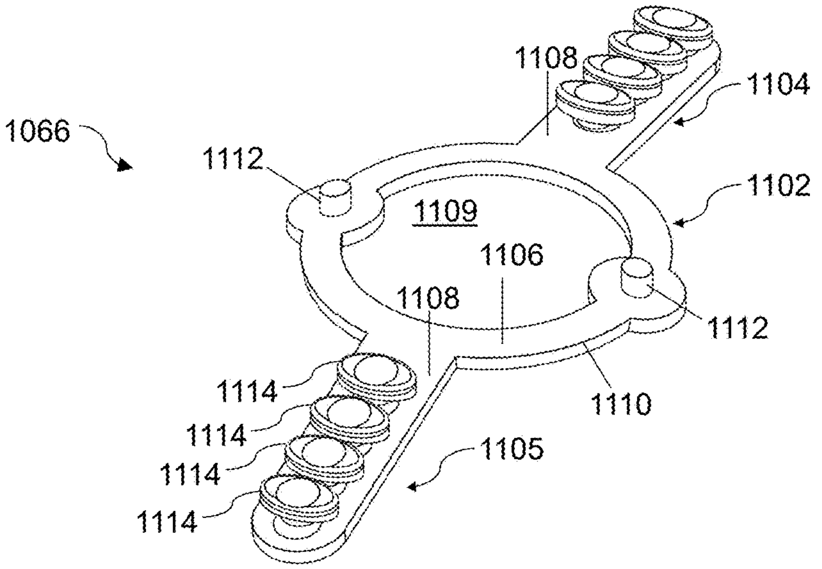
Figure 134B:
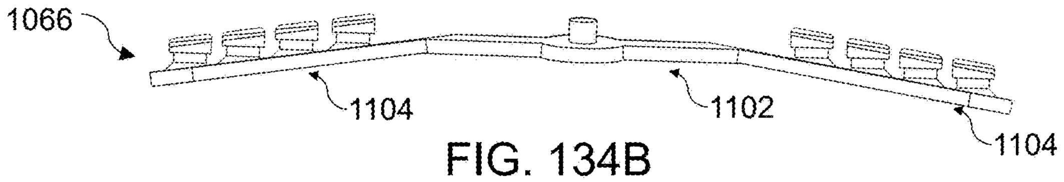
Figure 134C:
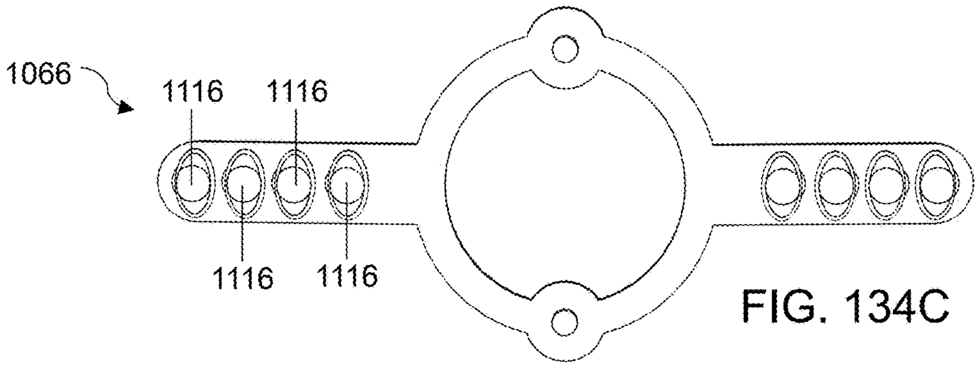
Figure 134D:
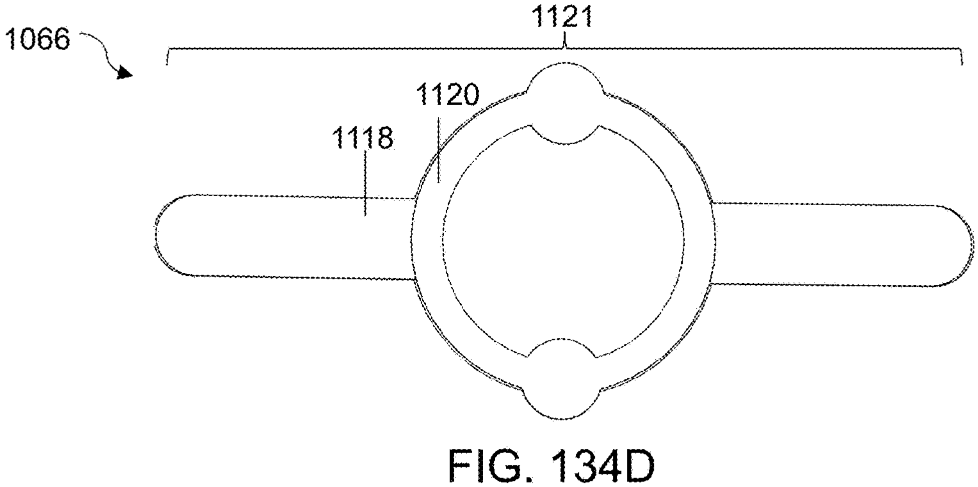
Figure 135A:
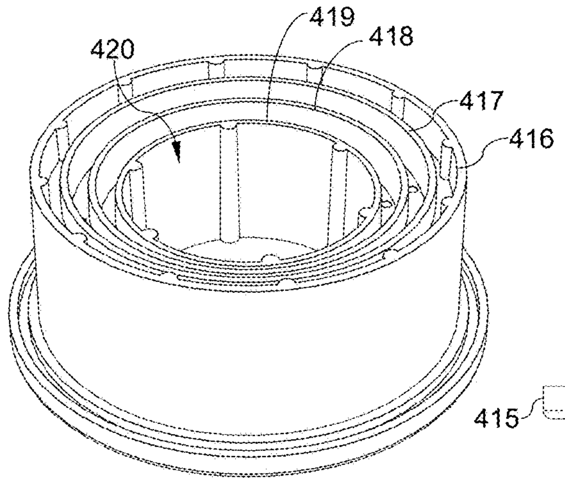
Figure 135B:
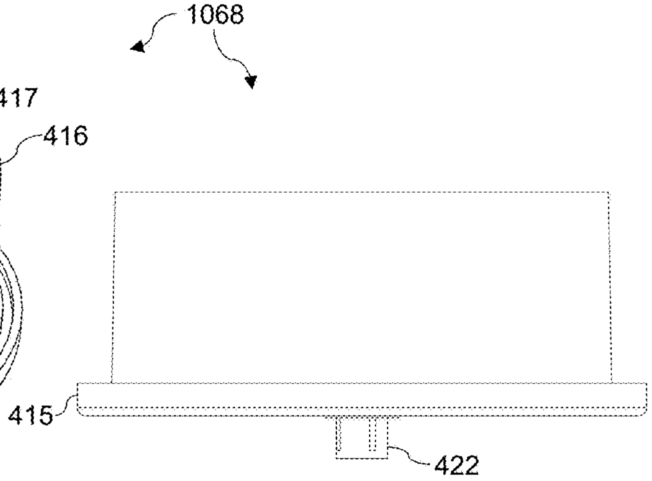
Figure 135C:
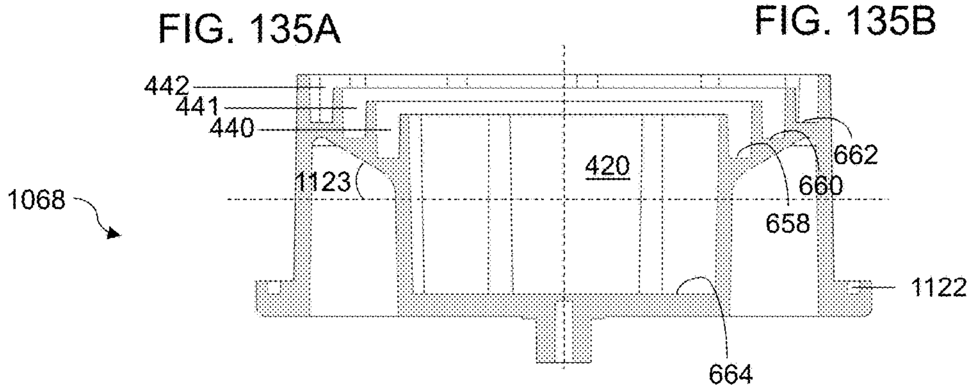
Figure 135D:
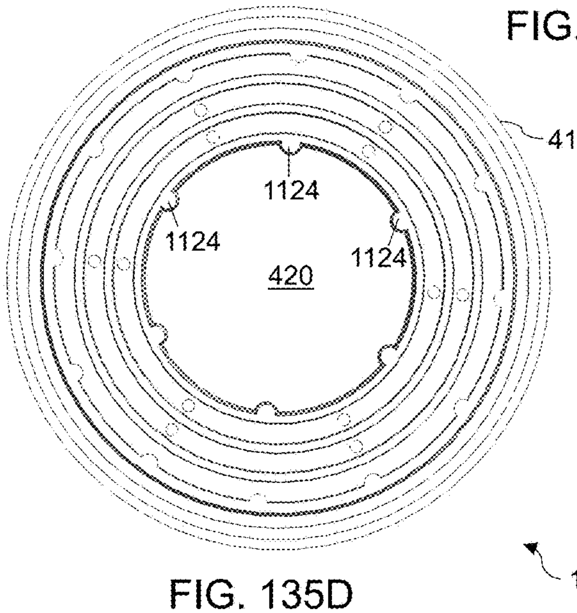
Figure 135E:
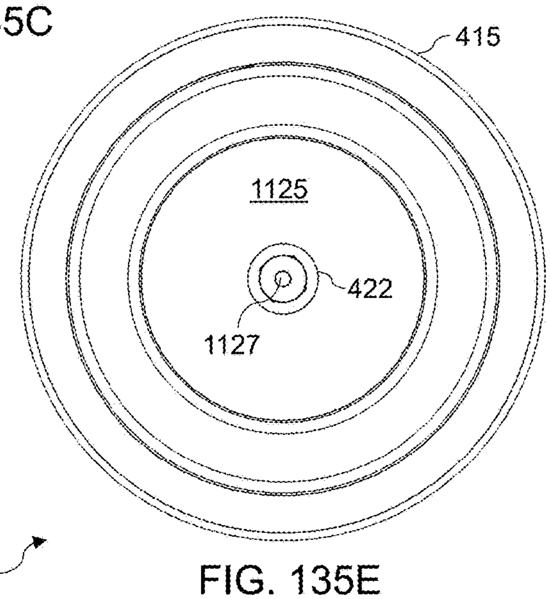
Figure 136A:
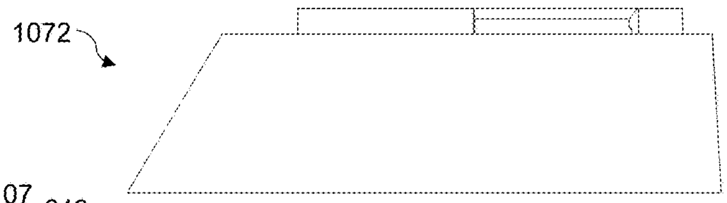
Figure 136B:
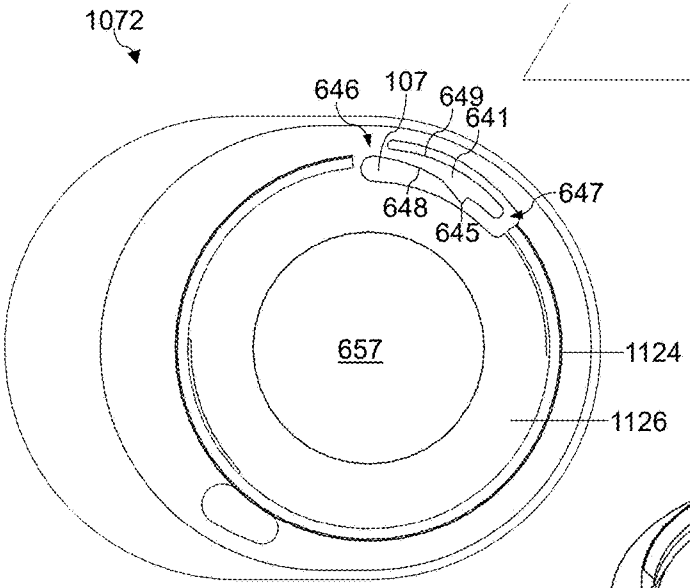
Figure 136C:
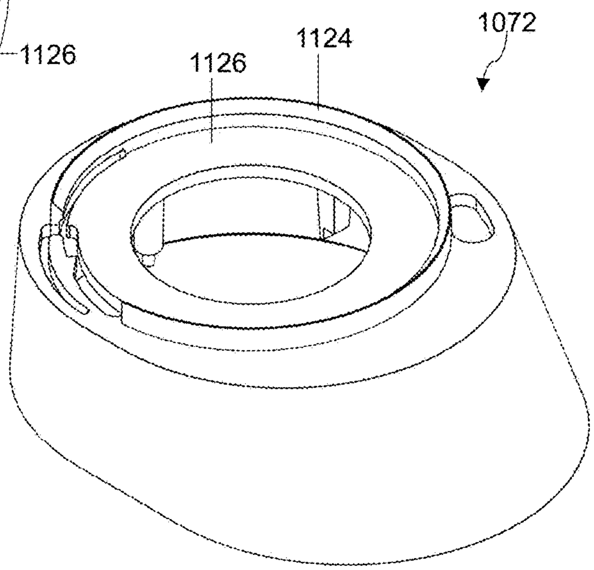
Figure 136D:
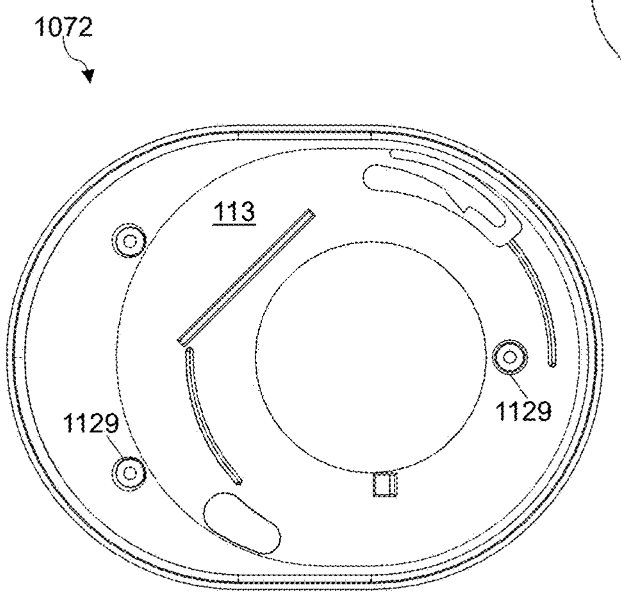
Figure 137A:
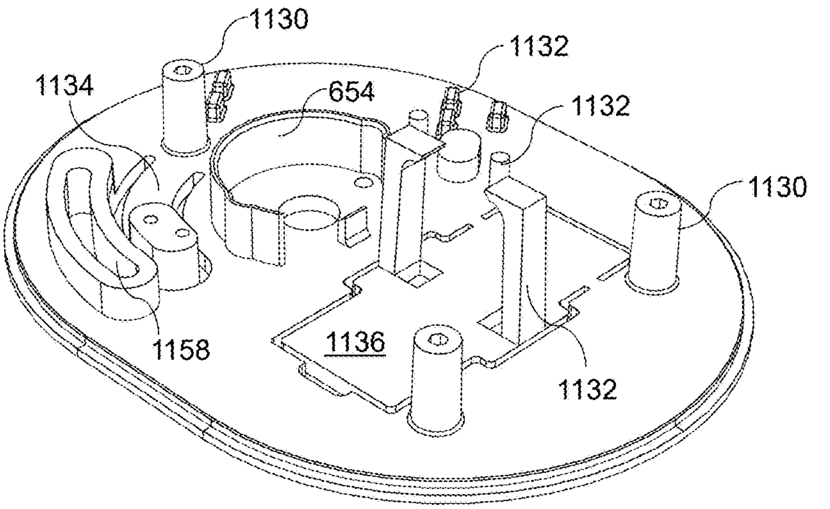
Figure 137B:
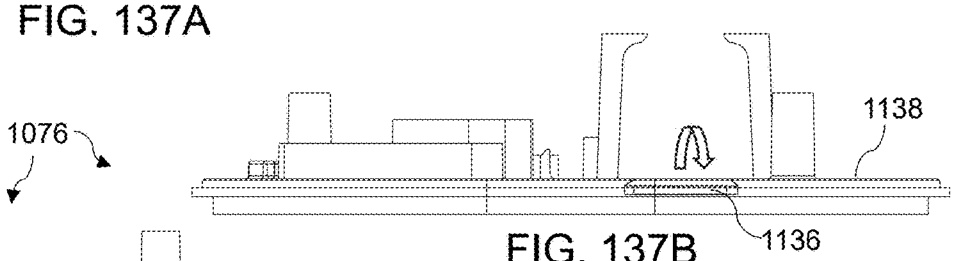
Figure 137C:
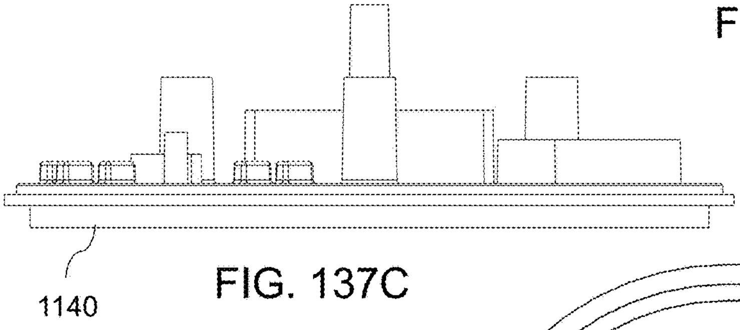
Figure 137D:
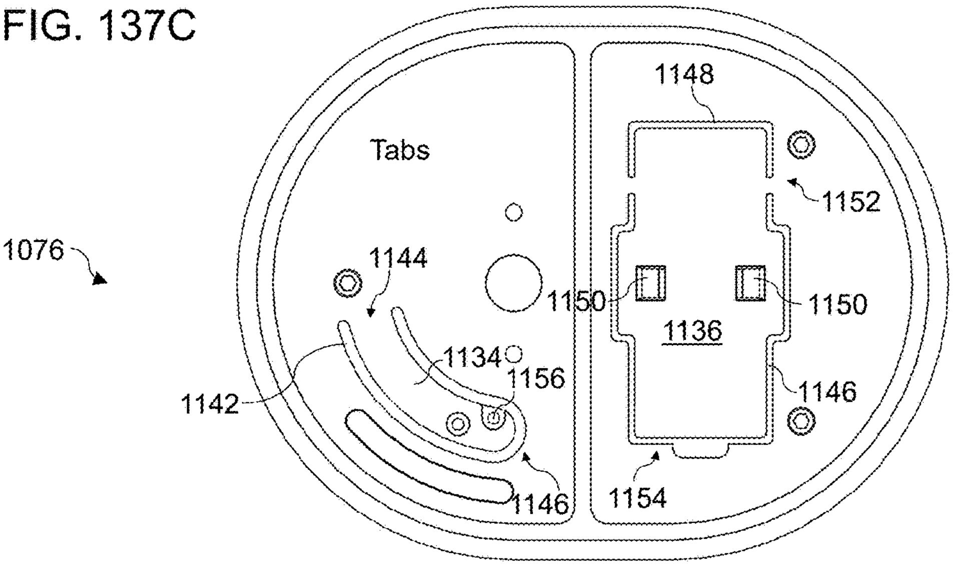
Figure 138A:
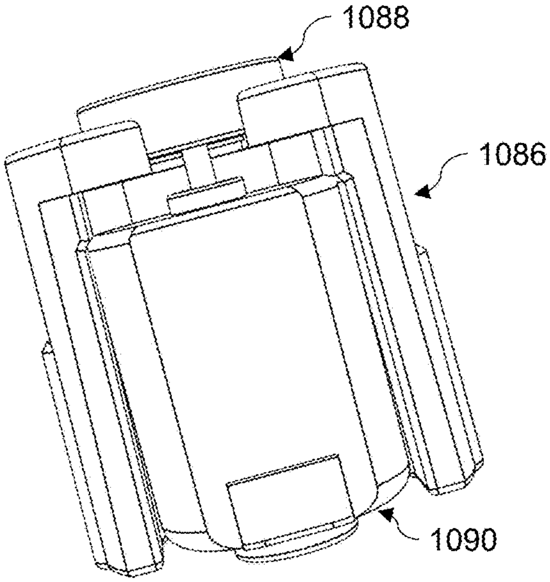
Figure 138B:
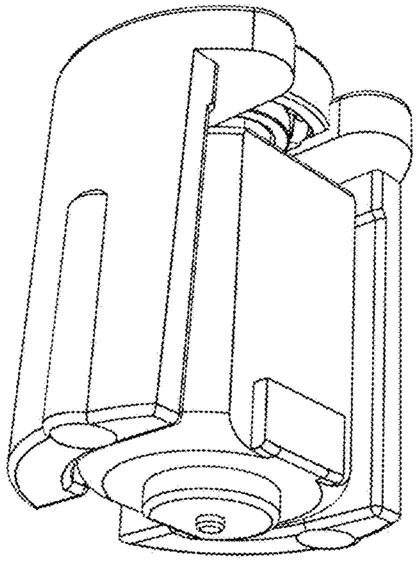
Figure 138C:
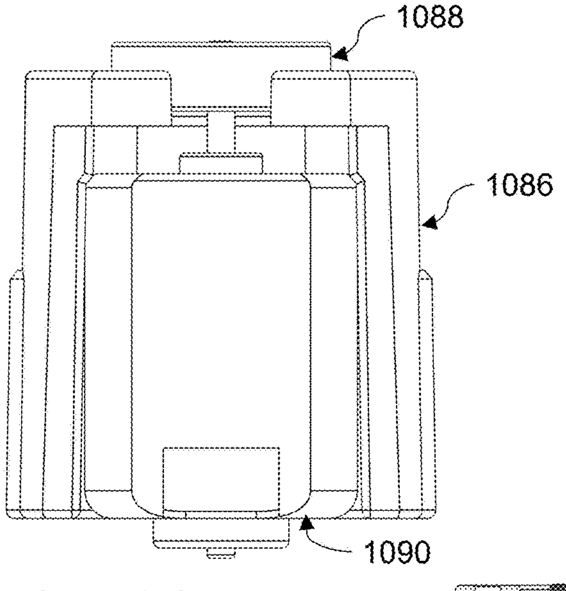
Figure 138D:
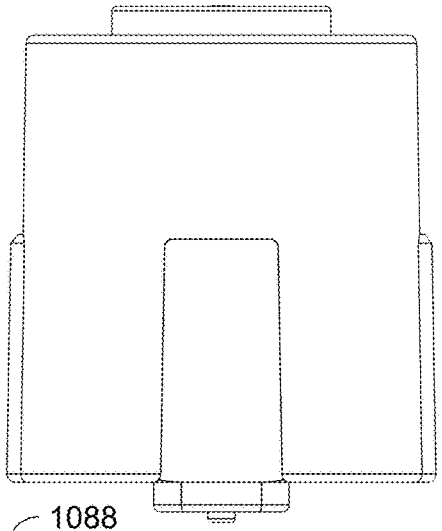
Figure 138E:
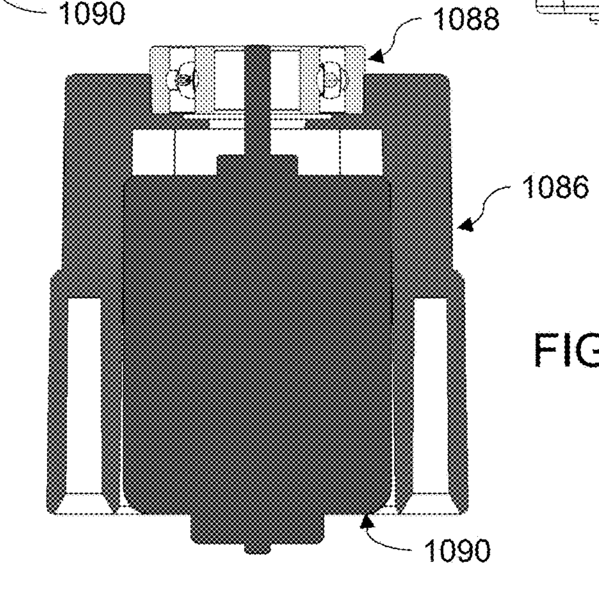
Figure 139A:
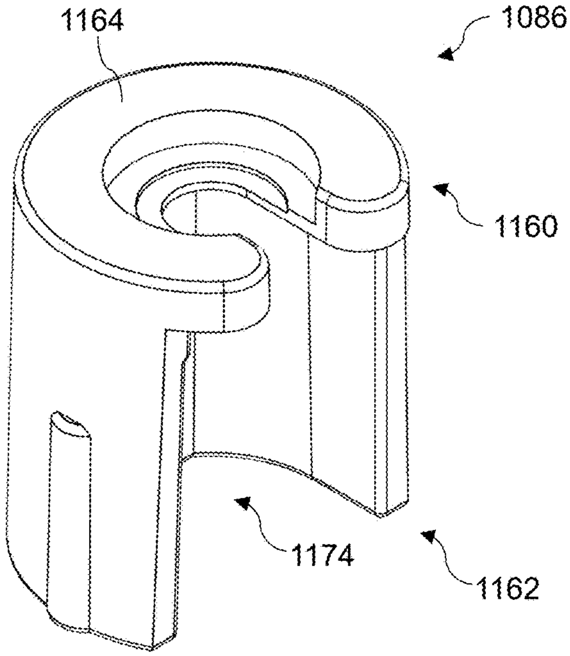
Figure 139B:
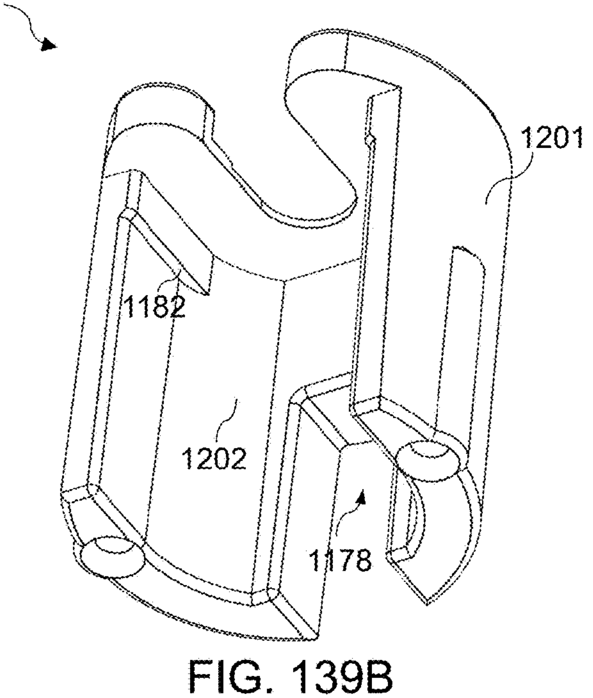
Figure 139C:
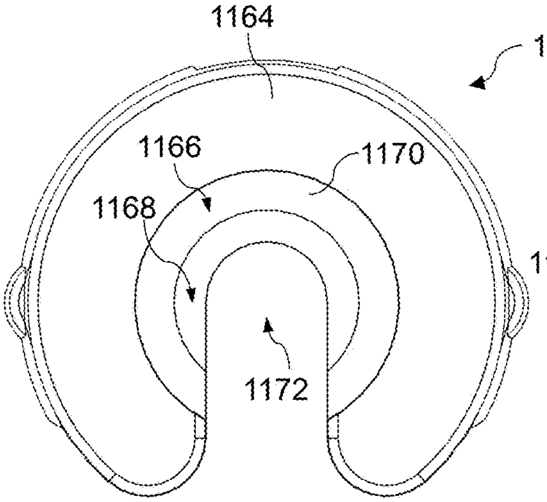
Figure 139D:
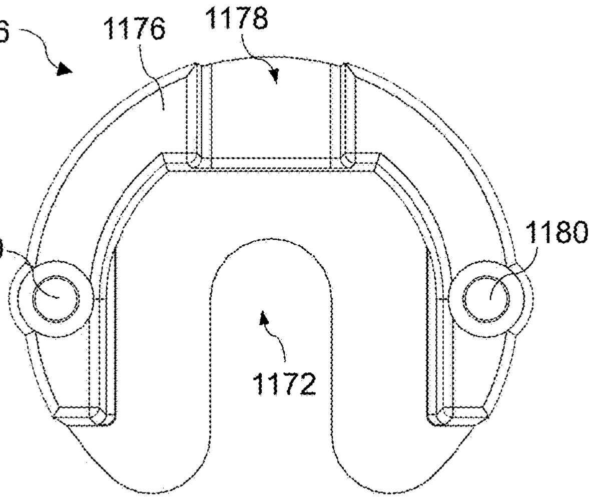
Figure 139E:
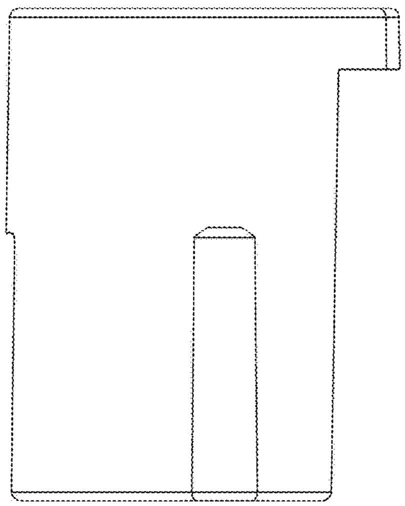
Figure 139F:
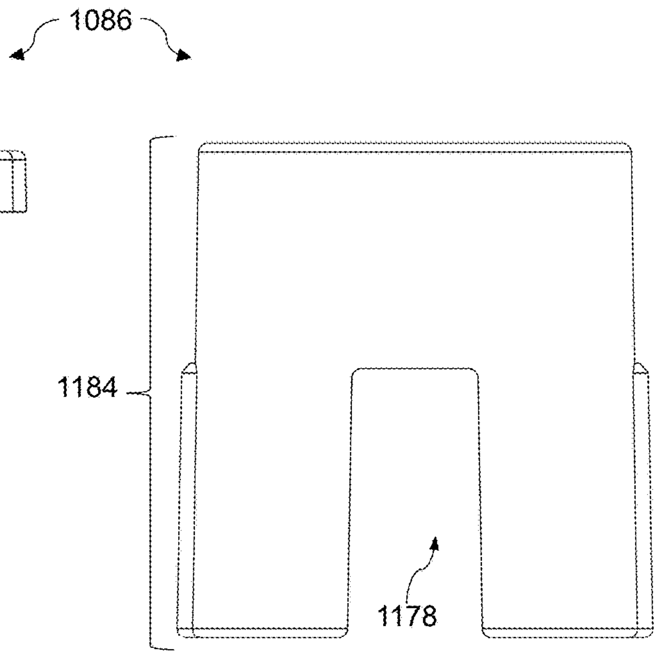
Figure 139G:
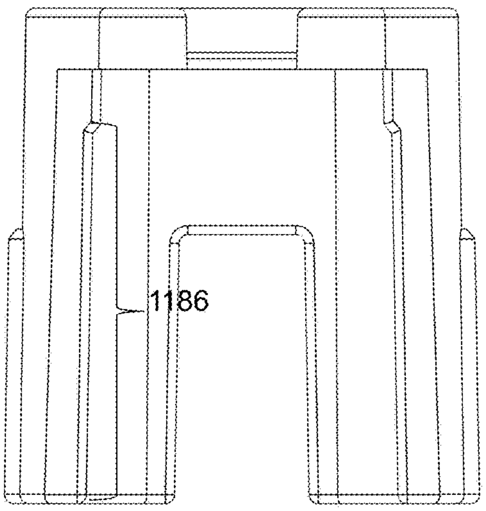
Figure 139H:
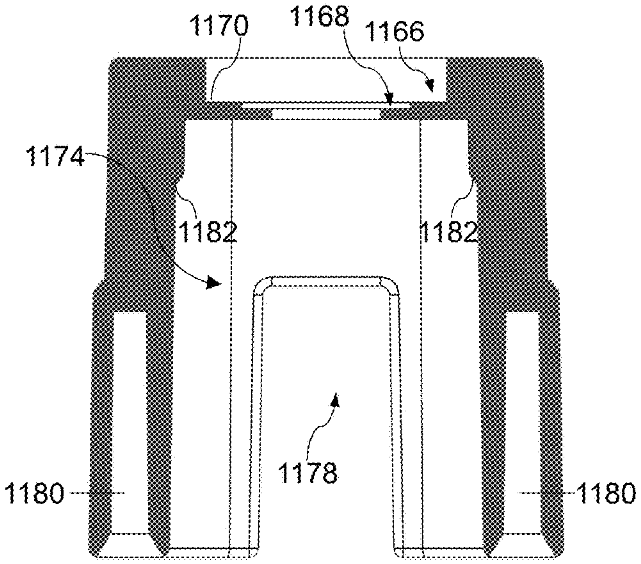
Figure 140A:
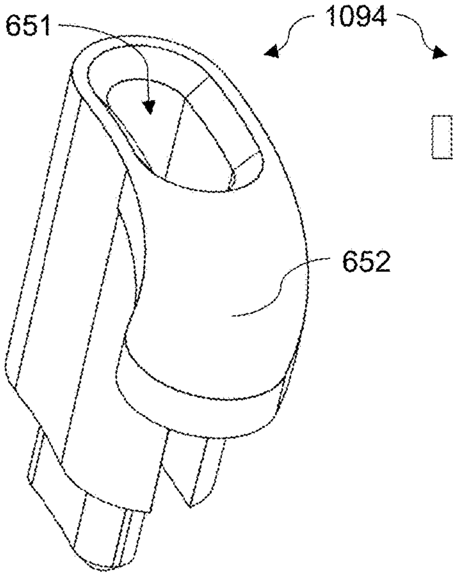
Figure 140B:
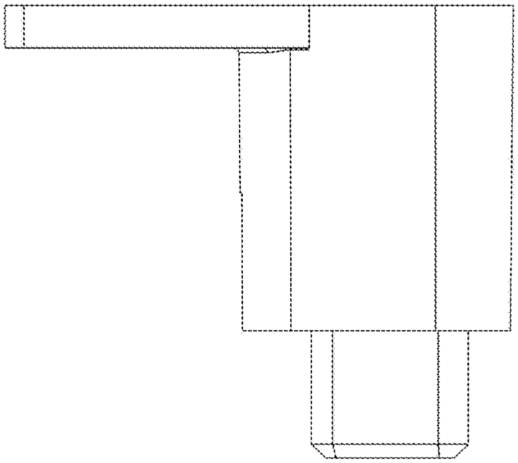
Figure 140C:
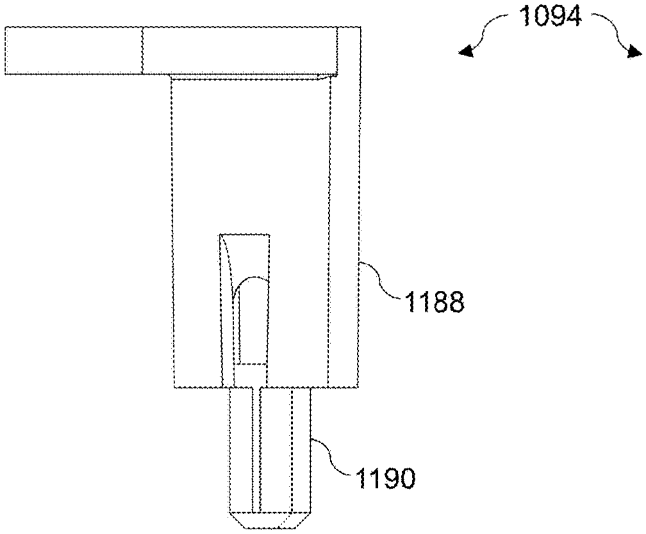
Figure 140D:
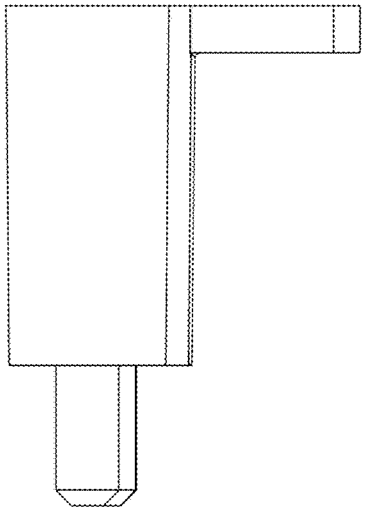
Figure 140E:
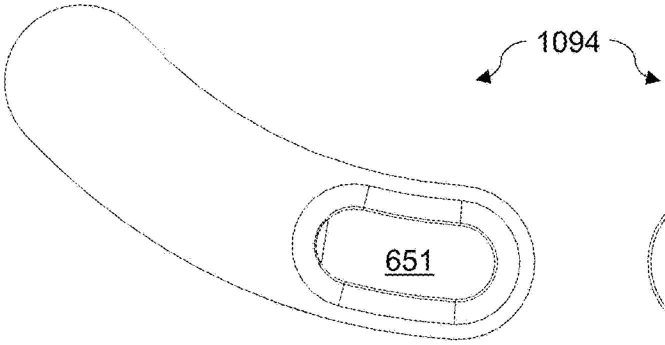
Figure 140F:
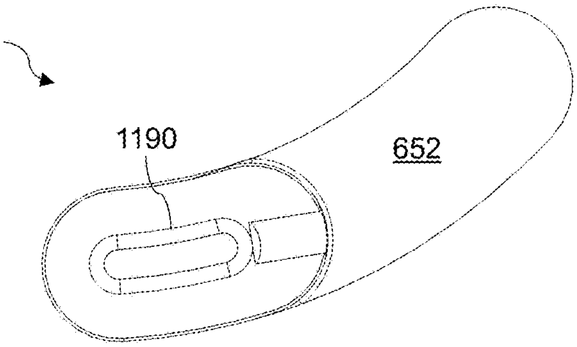
Figure 141A:
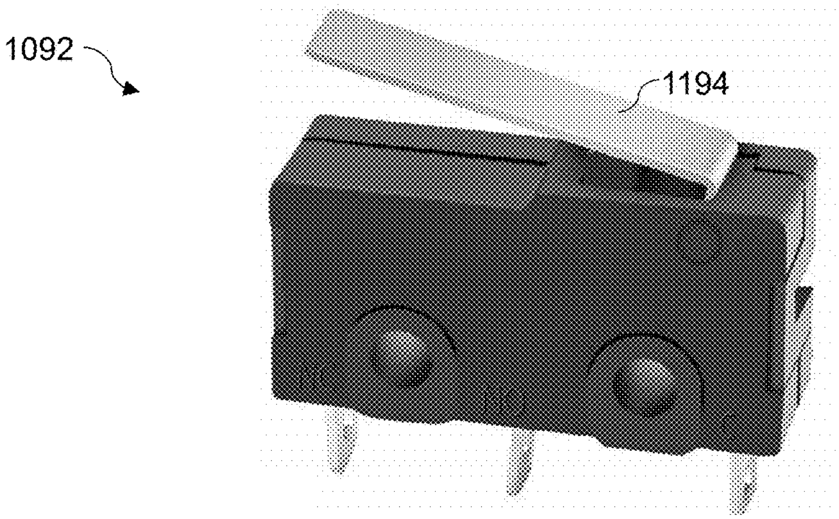
Figure 141B:
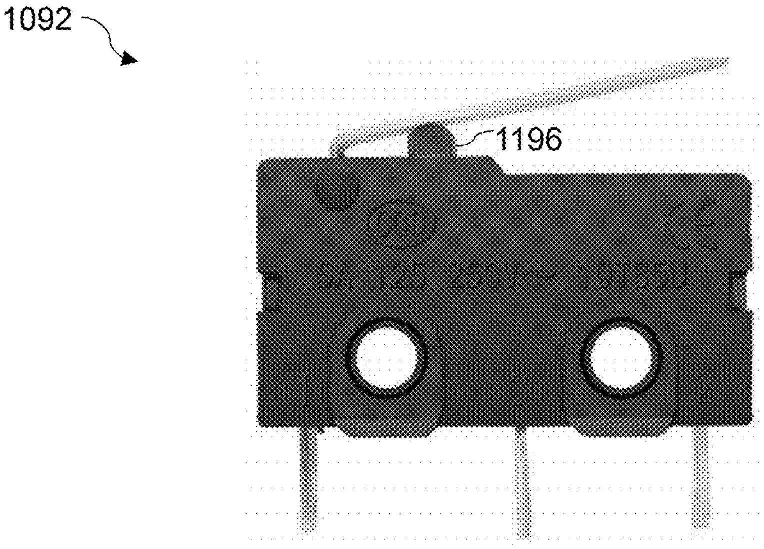
Figure 141C:
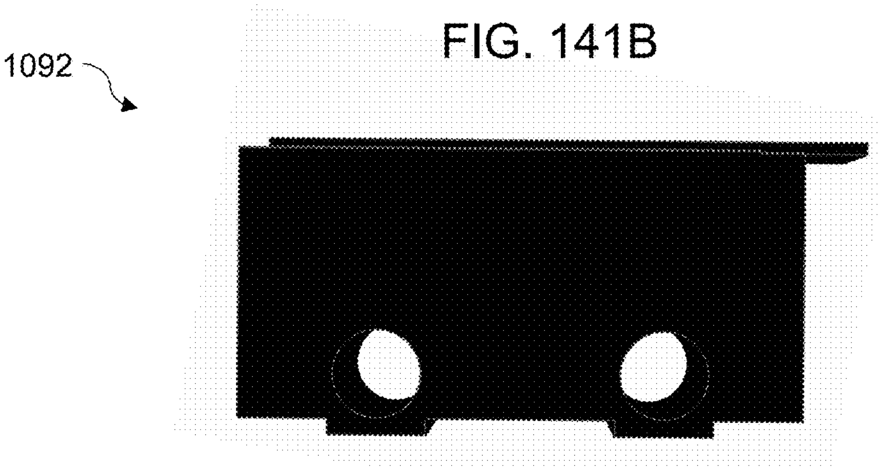
Figure 142A:
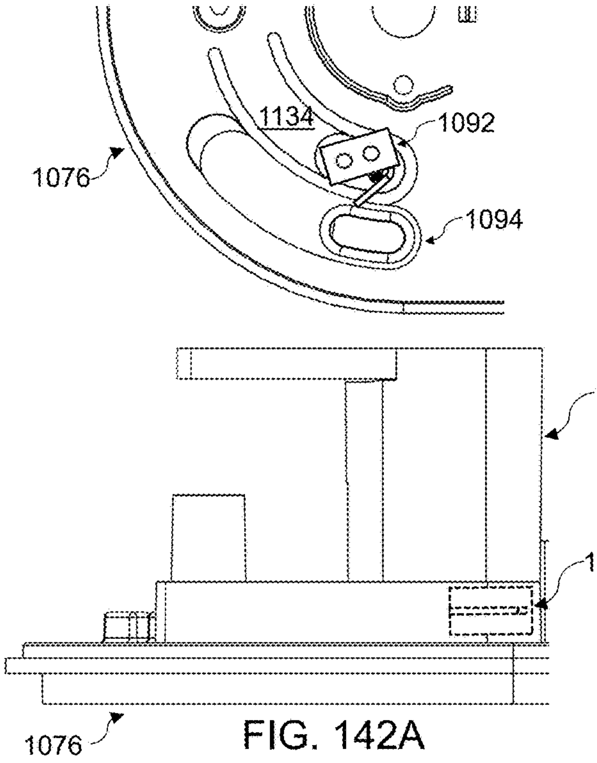
Figure 142B:
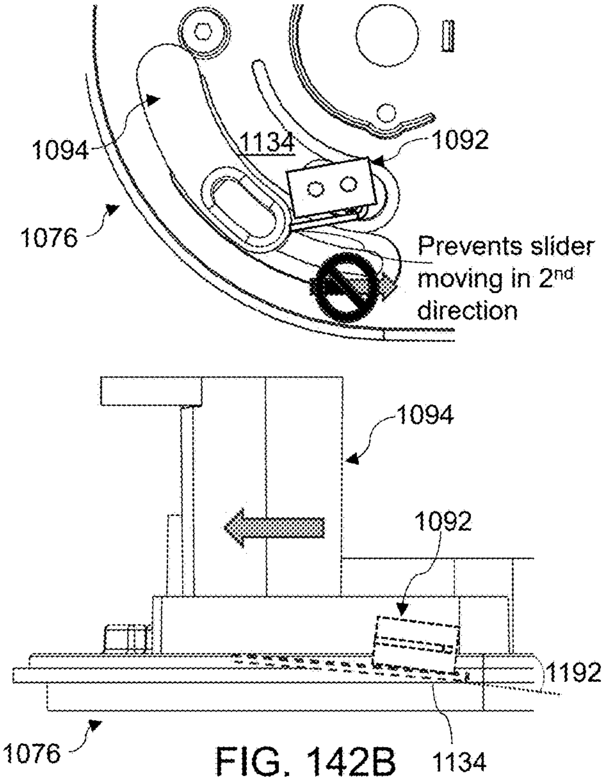
Figure 143A:
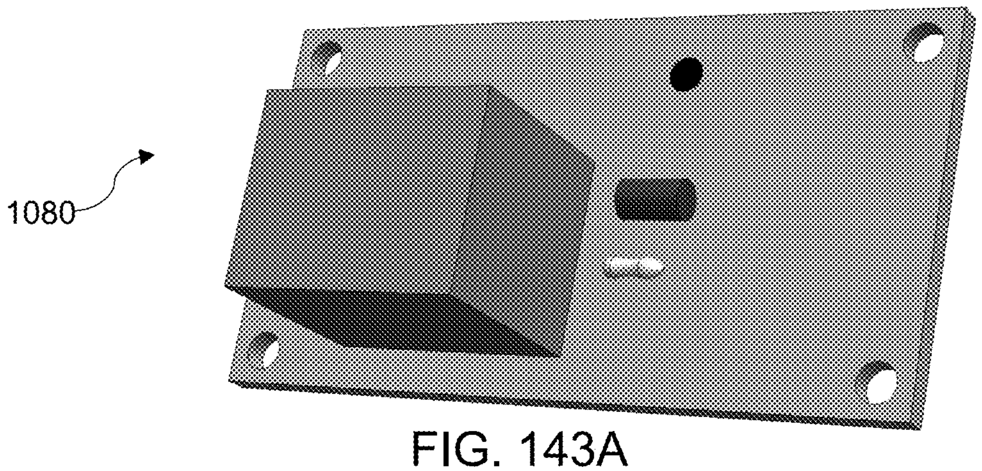
Figure 143B:
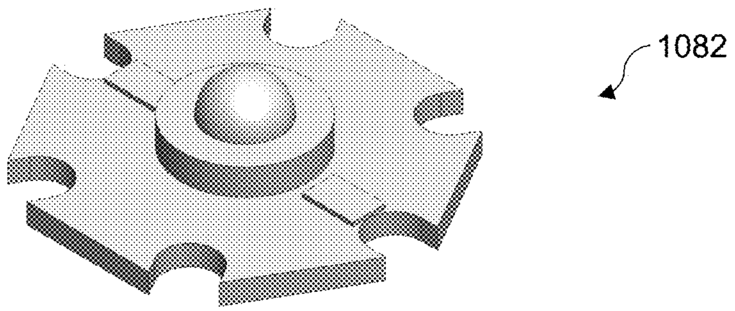
Figure 143C:
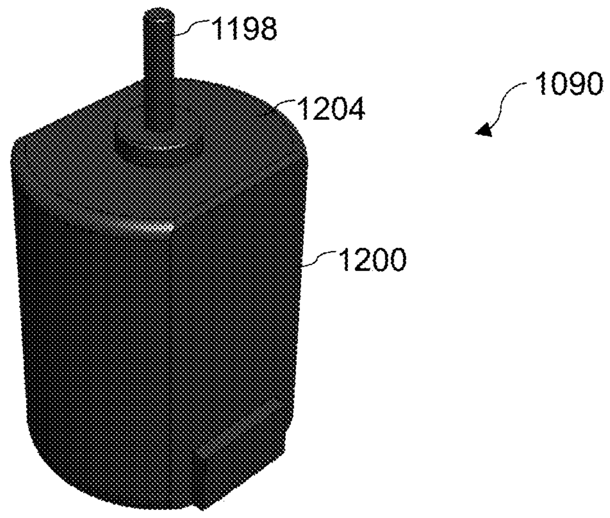

In another embodiment, FIG. 127B discloses an alternative method of isolating MNCs from bone marrow (BM-MNCs) 1038 that comprises the steps of: injecting the bone marrow (BM) aspirate into the sequester device that is pre-laced with a first reagent 1040; diluting the BM aspirate by introducing a 2nd reagent 1042; filtering the diluted BM aspirate 1044; introducing a 3rd reagent to facilitate gradient separation 1046; centrifuging the buffered, diluted BM aspirate at a set time and speed 1048; aspirating/extracting the upper layer band leaving the BM-MNC layer undisturbed 1050; transferring BM-MNC layer to a 2nd sequester device 1052; washing the separated BM-MNC with introduction of 4th reagent by centrifugation at set speed and time 1054; re-suspending the BM-MNC pellet by repeating washing step for increased purity 1056; aspirating/extracting remaining 4th reagent and the MNC pellet from the sequester device 1058. Introduction of the reagents may comprise dispensing via syringe though central luer port disposed on the container cover and/or dispensing via one or more blister modules by compressing the blister. The reagents my comprise digestion enzyme, buffers, thixotropic gels, anticoagulants, density gradient media, dilution media and/or any combination thereof. Centrifugation speed may comprise 200 g to 600 g; 200 g to 400 g; 300 g to 400g. The centrifugation time may comprise 10 minutes to 40 minutes. The first, second and any other subsequent centrifugation cycles may comprise the same or different set times and speed. Filtration step comprises filtering with a filtering ring, the at least one of the first, second, third concentric rings comprises a filtration ring.

Blood is used in conjunction with the devices and methods described however, the devices and methods are applicable for use with bone marrow or other human and/or animal tissue, and/or any colloidal or suspension mixtures.

EXAMPLE EMBODIMENTS

Embodiment 1. A centrifuge comprising: a base container having a rotational mechanism contained therein; a centrifuge container having a bottom plate and a top plate joined by a circumferential sidewall, and a coiled spring connected to the bottom plate; a sequester wheel comprising a plurality of concentric rings, forming at least one channel, connected to a hub; wherein the sequester wheel is engaged with the bottom plate, the coiled spring positioned therebetween, the hub centered with the bottom plate and the top plate within the centrifuge container, defining an axis; and wherein the centrifuge container is engaged with the rotational mechanism and rotatable about the axis.

Embodiment 2. The centrifuge of Embodiment 1, further having a toggle switch pivotally engaged with the bottom plate and extending from a bottom side to a top side of the bottom plate and extending through the sequester wheel.

Embodiment 3. The centrifuge of Embodiment 2, wherein the bottom plate is further comprising tabs for engaging the sequester wheel;

Embodiment 4. The centrifuge as in any of Embodiments 1-3 wherein, the rotational mechanism comprises: a circuit having an internal power supply connected to a switch; wherein the switch is connected to an electrical motor and a solenoid.

Embodiment 5. The centrifuge of Embodiment 4, wherein the circuit is further comprising a circuit board having a timer connected to a relay; and wherein the switch is connected to the electrical motor and the solenoid through the circuit board.

Embodiment 6. A centrifuge comprising: a base container having a rotational mechanism contained therein; a sequester device having a first center, a circumferential outer ring concentric with a plurality of inner tiered concentric rings forming at least one channel, and a container; a centrifuge cover having a top side with a second center and a circumferential sidewall; wherein the centrifuge cover is connected to the sequester device and forming a cylindrical container having an internal space with an outer channel; wherein the cylindrical container is coupled to the rotational mechanism and is rotatable about an axis defined by the first center and the second center.

Embodiment 7. The centrifuge of Embodiment 6 wherein, the rotational mechanism comprises: a circuit having an internal power supply; wherein the power supply is connected to a switch and an electrical motor.

Embodiment 8. The centrifuge of Embodiment 7, wherein the circuit further comprises a circuit board with a timer connected to a relay.

Embodiment 9. The centrifuge of Embodiment 6, wherein the top side is conical.

Embodiment 10. The centrifuge of Embodiment 6, further comprising: a protective cover having a top side with a first insertion hole around a third center and a circumferential sidewall extending to a sidewall rim; and an activation tab extending from the sidewall rim away from the top side; wherein the protective cover is engaged with the base container and the rotational mechanism, covering without contacting the centrifuge container.

Embodiment 11. The centrifuge of Embodiment 10, wherein the top side of the centrifuge cover has a second insertion hole around the second center, extending through the centrifuge cover; and wherein the first insertion hole and the second insertion hole are aligned.

Embodiment 12. The centrifuge of Embodiment 11, wherein the first insertion hole is covered by a membrane.

Embodiment 13. The centrifuge of Embodiment 10, wherein the base container further comprises an activation slot through which the activation tab is insertable; and wherein the rotational mechanism further comprises an activation mechanism to which the activation tab is engaged.

Embodiment 14. The centrifuge of Embodiment 13, wherein the activation slot comprises a locking protrusion; and wherein the locking protrusion provides for activation tab motion in a single direction.

Embodiment 15. The centrifuge container of Embodiment 10, wherein the rotational mechanism comprises at least one light source; wherein the cylindrical container further comprises a transparent material; wherein the protective cover further comprises a transparent material; and wherein the light source is visible through the cylindrical container and the protective cover.

Embodiment 16. The centrifuge of Embodiment 15, wherein the cylindrical container further comprises: a plurality of extraction holes through the top side into the cylindrical container and a visual marker on the top side adjacent to the extraction holes.

Embodiment 17. The centrifuge of Embodiment 10, wherein the visual marker is visible through the protective cover.

Embodiment 18. A centrifuge comprising: a base container having a rotational mechanism contained therein; a cylindrical container having a top side with a first center, a bottom side with a second center, a sidewall, and an interior having an anti-coagulant and a thixotropic separation gel therein; wherein the cylindrical container is coupled to the rotational mechanism and is rotatable about an axis defined by the first center and the second center.

Embodiment 19. A centrifuge comprising: a base container having a rotational mechanism connected to an activation switch; a cap assembly having a cap at a first end of an articulated arm, an activation tab at a second end, and an activation handle protruding from the articulated arm; an activation armature; a conical first member positioned within a conical second member having a plurality of openings and positioned within a conical third member; and a base ring; wherein the first member engages the base ring and the base container, the activation armature extends from the base ring to the activation switch within the base container; wherein the second member engages the rotation mechanism above the first member and the third member is positioned above the second member to engage the first member, the second member being rotatable between the first member and the second member; and wherein the cap engages the third member, and the activation tab engages the activation armature, providing a connection between the activation handle and the activation switch for activation of the rotational mechanism.

Embodiment 20. A portable centrifuge comprising: a base, the base comprising a rotational mechanism and at least one light; a sequester device, the sequester device being disposed onto the base, the sequester device including a plurality of concentric rings that are spaced apart to form at least one channel; a container cover, the container cover including at least one injection tube and at least one extraction region, the at least one extraction region including a plurality of extraction holes, the container cover being disposed over the sequester device; and a protective cover, the protective being disposed over the container cover.

Embodiment 21. The portable centrifuge of Embodiment 20, wherein the at least one light is a UV light.

Embodiment 22. The portable centrifuge of Embodiment 21, wherein the UV light comprises emission of wavelengths within the UV-C wavelength for a germicidal effect.

Embodiment 23. The portable centrifuge of Embodiment 22, wherein the UV-C wavelength comprises range of 200 to 300 nanometers.

Embodiment 24. The portable centrifuge of Embodiment 20, wherein the sequester device comprises a coating, the coating is selected from a group consisting of anticoagulants, preservatives, germicidal agents, sterilants, antiseptics, clot activators, separator gels.

Embodiment 25. The portable centrifuge of Embodiment 24, wherein the germicidal agents comprises amotosalen or riboflavin.

Embodiment 26. The portable centrifuge of Embodiment 20, wherein the plurality of concentric rings spaced apart forming at least one channel comprises a coating, the coating is selected from a group consisting of anticoagulants, preservatives, disinfectants, germicidal agents, clot activators, separator gels, pathogen reduction agents or pathogen inactivation agents.

Embodiment 27. The portable centrifuge of Embodiment 20, wherein the sequester device comprises a material, the material is a polymer.

Embodiment 28. The portable centrifuge of Embodiment 26, wherein the polymer is clear or translucent.

Embodiment 29. The portable centrifuge of Embodiment 20, wherein the plurality of extraction holes is aligned with the at least one channel.

Embodiment 30. A portable centrifuge comprising: a base, the base comprising a rotational mechanism, a first light and a second light; a sequester device, the sequester device being disposed onto the base, the sequester device including a plurality of concentric rings that are spaced apart to form at least one channel and a central container; a container cover, the container cover including at least one injection tube and at least one extraction region, the at least one extraction region including a plurality of extraction holes, the container cover being disposed over a portion of the sequester device; and a protective cover, the protective being disposed over the container cover.

Embodiment 31. The portable centrifuge of Embodiment 30, wherein the container cover or the protective cover comprising a third light, the third light coupled to a portion of the container cover or the protective cover.

Embodiment 32. The portable centrifuge of Embodiment 30, wherein the first light or second light comprises a UV light.

Embodiment 33. The portable centrifuge of Embodiment 32, wherein the UV light comprises a wavelength emission within the UV-C wavelength range for a germicidal effect.

Embodiment 34. The portable centrifuge of Embodiment 30, wherein at least a portion of the central container comprising a coating.

Embodiment 35. The portable centrifuge of Embodiment 30, wherein at least a portion of the plurality of concentric rings comprising a coating.

Embodiment 36. The portable centrifuge of Embodiment 30, wherein at least a portion of the plurality of concentric rings and at least a portion of the central container comprising a coating.

Embodiment 37. The portable centrifuge of Embodiment 34, 35 and 36, the coating is selected from a group consisting of anticoagulants, preservatives, germicidal agents, sterilants, antiseptics, clot activators, separator gels.

Embodiment 38. The portable centrifuge of Embodiment 37, wherein the germicidal agents comprises amotosalen or riboflavin.

Embodiment 39. The portable centrifuge of Embodiment 30, wherein the first light or second light comprises a UV light, and at least a portion of the central container comprising a coating.

Embodiment 40. The portable centrifuge of Embodiment 30, wherein the first light or second light comprises a UV light and at least a portion of the plurality of concentric rings comprising a coating.

Embodiment 41. The portable centrifuge of Embodiment 30, wherein the first light or second light comprises a UV light, at least a portion of the central container comprising a coating and at least a portion of the plurality of rings comprising a coating.

Embodiment 42. The portable centrifuge of Embodiment 39, 40 and 41, wherein the UV light comprises a wavelength emission within the UV-A wavelength range.

Embodiment 43. The portable centrifuge of Embodiment 39, 40 and 41, wherein the coating comprises a germicidal agent, the germicidal agent is riboflavin or amotosalen.

Embodiment 44. The portable centrifuge of Embodiment 31, wherein the third light comprises a UV light.

Embodiment 45. The portable centrifuge of Embodiment 40, wherein the UV light comprises a wavelength emission within the UV-C wavelength range for a germicidal effect.

Embodiment 46. The portable centrifuge of Embodiment 30, wherein the third light comprises a UV light, and at least a portion of the central container comprising a coating.

Embodiment 47. The portable centrifuge of Embodiment 30, wherein the third light comprises a UV light and at least a portion of the plurality of concentric rings comprising a coating.

Embodiment 48. The portable centrifuge of Embodiment 30, wherein the third light comprises a UV light, at least a portion of the central container comprising a coating and at least a portion of the plurality of rings comprising a coating.

Embodiment 49. The portable centrifuge of Embodiment 46, 47 and 48, wherein the UV light comprises a wavelength emission within the UV-A wavelength range.

Embodiment 50. The portable centrifuge of Embodiment 46, 47 and 48, wherein the coating comprises a germicidal agent, the germicidal agent is riboflavin or amotosalen.

Embodiment 51. The portable centrifuge of Embodiment 30, wherein the first light or second light comprises a UV light, and the third light comprises a UV light.

Embodiment 52. The portable centrifuge of Embodiment 51, wherein the UV light of the first or second light and the UV light of the third light is the same UV wavelength or different UV wavelengths.

Embodiment 53. The portable centrifuge of Embodiment 51, wherein the UV light of the first or second light and the UV light of the third light comprises a wavelength emission within the UV-C wavelength range for a germicidal effect.

Embodiment 54. The portable centrifuge of Embodiment wherein the first light or second light comprises a UV light, the third light comprises a UV light, and at least a portion of the central container comprising a coating.

Embodiment 55. The portable centrifuge of Embodiment wherein the first light or second light comprises a UV light, the third light comprises a UV light, and at least a portion of the plurality of concentric rings comprising a coating.

Embodiment 56. The portable centrifuge of Embodiment wherein the first light or second light comprises a UV light, the third light comprises a UV light, at least a portion of the plurality of concentric rings comprising a coating and at least a portion of the central container comprising a coating.

Embodiment 57. The portable centrifuge of Embodiment 54, 55 and 56, wherein the UV light comprises a wavelength emission within the UV-A wavelength range.

Embodiment 58. The portable centrifuge of Embodiment 54, 55 and 56, wherein the coating comprises a germicidal agent, the germicidal agent is riboflavin or amotosalen.

Embodiment 59. A method comprising: removing a protective cover from a centrifuge; introducing blood into a centrifuge container; replacing the protective cover of the centrifuge; turning the protective cover to activate the centrifuge; separating the blood into constituent components by rotation of the centrifuge; removing the protective cover from the centrifuge; and removing the blood constituent components.

Embodiment 60. A method comprising: removing a protective cover; introducing blood into a centrifuge container; replacing the protective cover; turning the protective cover to activate the centrifuge; having the blood interact with a thixotropic separation gel and an anti-coagulant; separating the blood into constituent components by activation of the centrifuge; removing the protective cover; and removing the blood constituent components.

Embodiment 61. A method comprising: removing a protective cover from a centrifuge; introducing blood into a centrifuge container; replacing the protective cover on the centrifuge; turning the protective cover to activate the centrifuge; separating the blood into constituent components; removing the protective cover; and removing the blood constituent components.

Embodiment 62. A method comprising: removing a cap assembly; introducing blood into test-tubes; replacing the cap assembly; pressing the activation handle to activate the centrifuge; separating the blood into constituent components by activation of the centrifuge; removing the cap assembly; and removing blood constituent components from the test-tubes.

Embodiment 63. A method of pathogen reduction during a centrifugation cycle comprising the steps of: Preparing a portable centrifuge for a centrifugation cycle, the portable centrifuge comprising at least one UV light, a rotational mechanism, a sequester device and a protective cover; injecting whole blood within at least a portion of the sequester device; activating the rotational mechanism and the at least one UV light by placing the protective cover over at portion of the sequester device; irradiating the whole blood with the at least one UV light while the portable centrifuge is separating the whole blood into constituent components into a plurality of channels within the sequester device; removing the protective cover; and extracting the blood constituent components from the sequester device.

Embodiment 64. A method of pathogen reduction during a centrifugation cycle comprising the steps of: Preparing a portable centrifuge for a centrifugation cycle, the portable centrifuge comprising at least one UV light, a rotational mechanism, a sequester device and a protective cover, at least a portion of the sequester device comprising a coating; injecting whole blood within at least a portion of the sequester device; activating the rotational mechanism and the at least one UV light by placing the protective cover over at portion of the sequester device; irradiating the whole blood with the at least one UV light while the portable centrifuge is separating the whole blood into constituent components into a plurality of channels within the sequester device; removing the protective cover; and extracting the blood constituent components from the sequester device.

Embodiment 65. A method of pathogen reduction during a centrifugation cycle of Embodiment 63 or 64, the at least one UV light comprises a wavelength emission within the UV-C wavelength range for a germicidal effect.

Embodiment 66. A method of pathogen reduction during a centrifugation cycle of Embodiment 64, the at least one UV light comprises a wavelength emission within the UV-A wavelength range for a germicidal effect.

Embodiment 67. A method of pathogen reduction during a centrifugation cycle of Embodiment 64, the coating is selected from a group consisting of anticoagulants, preservatives, germicidal agents, sterilants, antiseptics, clot activators, separator gels.

Embodiment 68. The portable centrifuge of Embodiment 67, wherein the germicidal agents comprises amotosalen or riboflavin.

Embodiment 69. A method of pathogen reduction during a centrifugation cycle of Embodiment 64, the at least one UV light comprises a wavelength emission within the UV-A wavelength range for a germicidal effect and the coating comprises a germicidal agent, the germicidal agent is amotosalen or riboflavin.

Embodiment 70. A convalescent plasma therapy centrifuge comprising: a base, the base comprising a rotational mechanism, a first light and a second light; a sequester device, the sequester device being disposed onto the base, the sequester device including a first concentric ring and a second concentric that are spaced apart to form at least one channel and a central container; a container cover, the container cover including at least one injection tube and at least one extraction region, the at least one extraction region including a plurality of extraction holes, the container cover being disposed over a portion of the sequester device; and a protective cover, the protective being disposed over the container cover.

Embodiment 71. A microfluidic portable centrifuge comprising: a base, the base comprising a rotational mechanism; a sequester device, the sequester device being disposed onto the base, the sequester device including a plurality of concentric rings that are spaced apart to form at least one channel and a central container; a container cover, the container cover including at least one injection tube, at least one extraction region and at least one coagulation module, the at least one extraction region including a plurality of extraction holes, the at least one coagulation module comprising a top surface, a bottom surface, and a microfluidic mechanism, the microfluidic mechanism disposed between the top surface and the bottom surface, the bottom surface including a blood communication port, the container cover being disposed over a portion of the sequester device; and a protective cover, the protective being disposed over the container cover.

Embodiment 72. The microfluidic portable centrifuge of Embodiment 71, wherein the microfluidic mechanism comprises at least one serpentine microchannel.

Embodiment 73. The microfluidic portable centrifuge of Embodiment 71, wherein the microfluidic mechanism comprises a plurality of serpentine microchannels.

Embodiment 74. The microfluidic portable centrifuge of Embodiment 71, wherein the microfluidic mechanism comprises at least one serpentine microchannel and a metering mechanism.

Embodiment 76. The microfluidic portable centrifuge of Embodiment 71, wherein the microfluidic portable centrifuge further comprises a first light and a second light.

Embodiment 77. The microfluidic portable centrifuge of Embodiment 75, wherein the first light or second light comprises a UV light.

Embodiment 78. The microfluidic portable centrifuge of Embodiment 76, wherein the UV light comprises a wavelength emission within the UV-C wavelength range for a germicidal effect.

Embodiment 79. The microfluidic portable centrifuge of Embodiment 72, wherein the at least one serpentine microchannel comprises a coating.

Embodiment 80. A portable centrifuge comprising: a base, the base comprising a rotational mechanism; a sequester device, the sequester device being disposed onto the base, the sequester device comprises a plurality of concentric rings that are spaced apart and tiered to form at least one channel and a central container; and a centrifuge cover, the centrifuge cover disposed over the sequester device to create a liquid impermeable seal.

Embodiment 81. The portable centrifuge of Embodiment 80, wherein the portable centrifuge further comprises at least one light.

Embodiment 82. The portable centrifuge of Embodiment 81, wherein the at least one light comprises a UV light.

Embodiment 83. The portable centrifuge of Embodiment 80, wherein at least a portion of the sequester device comprises a coating.

Embodiment 84. The portable centrifuge of Embodiment 80, wherein the portable centrifuge further comprises at least one UV light and at least a portion of the sequester device comprises a germicidal agent coating.

Embodiment 85. The portable centrifuge of Embodiment 82, 83 or 84, wherein the UV light comprises a wavelength emission within the UV-C wavelength range for a germicidal effect.

Embodiment 86. The portable centrifuge of Embodiment 83, the coating is selected from a group consisting of anticoagulants, preservatives, germicidal agents, sterilants, antiseptics, clot activators, separator gels.

Embodiment 87. The portable centrifuge of Embodiment 84 or 86, wherein the germicidal agent comprises amotosalen or riboflavin.

Embodiment 88. The portable centrifuge of Embodiment 80, wherein the central container comprises a first volume and the at least one channel comprises a second volume, the first volume is larger than the second volume.

Embodiment 89. The portable centrifuge of Embodiment 80, wherein the central container comprises a first volume and the at least one channel comprises a second volume, the first volume and the second volume equals the total volume of extracted blood from a patient, the second volume substantially matches a portion of the total volume determined by multiplying hematocrit with the total volume of extracted blood.

Embodiment 90. The portable centrifuge of Embodiment 80, wherein the at least one cover further comprises an injection port and at least one extraction region.

Embodiment 91. The portable centrifuge of Embodiment 90, wherein the injection port is concentrically aligned with the central container, the at least one extraction region is adjacent to the insertion port, the at least one extraction region comprises at least one extraction hole, the at least one extraction hole aligns with the at least one channel.

Embodiment 92. The portable centrifuge of Embodiment 80, wherein the at least one cover further comprises an opening, the opening is concentrically aligned with the central container, the opening is sized and configured to receive a filter or an eye dispensing mechanism.

Embodiment 93. The portable centrifuge of Embodiment 80, wherein the portable centrifuge further comprises a protective cover, the protective cover is disposed over the centrifuge cover and rotatable from an unlocked position, which the rotational mechanism is not engaged to a locked position that engages the rotational mechanism to initiate rotation.

Embodiment 94. A portable centrifuge for plasma therapy comprising: a base, the base comprising a rotational mechanism; a sequester device, the sequester device being disposed onto the base, the sequester device including a first concentric ring and a second concentric ring that are spaced apart and tiered to form at least one channel and a central container; and a centrifuge cover, the centrifuge cover including an injection port and at least one extraction region, the at least one extraction region including at least one extraction hole, the container cover being disposed over a portion of the sequester device to create a liquid impermeable seal.

Embodiment 95. The portable centrifuge of Embodiment 94, wherein at least a portion of the portable centrifuge is sterilized.

Embodiment 96. The portable centrifuge of Embodiment 94, wherein the portable centrifuge further comprises at least one light.

Embodiment 97. The portable centrifuge of Embodiment 96, wherein the at least one light comprises a UV light.

Embodiment 98. The portable centrifuge of Embodiment 94, wherein at least a portion of the sequester device comprises a coating.

Embodiment 99. The portable centrifuge of Embodiment 94, wherein the portable centrifuge further comprises at least one UV light and at least a portion of the sequester device comprises a germicidal agent coating.

Embodiment 100. The portable centrifuge of Embodiment 97 or 99, wherein the UV light comprises a wavelength emission within the UV-C wavelength range for a germicidal effect.

Embodiment 101. The portable centrifuge of Embodiment 98, the coating is selected from a group consisting of anticoagulants, preservatives, germicidal agents, sterilants, antiseptics, clot activators, separator gels.

Embodiment 102. The portable centrifuge of Embodiment 94, wherein the central container comprises a first volume and the at least one channel comprises a second volume, the first volume is larger than the second volume.

Embodiment 103. The portable centrifuge of Embodiment 94, wherein the central container comprises a first volume and the at least one channel comprises a second volume, the first volume and the second volume equals the total volume of extracted blood from a patient, the second volume substantially matches a portion of the total volume determined by multiplying hematocrit with the total volume of extracted blood.

Embodiment 104. The portable centrifuge of Embodiment 94, wherein the injection port is concentrically aligned with the central container and the at least one extraction hole aligns with the at least one channel.

Embodiment 105. The portable centrifuge of Embodiment 94, wherein the portable centrifuge further comprises a protective cover, the protective cover is disposed over the centrifuge cover and rotatable from an unlocked position, which the rotational mechanism is not engaged to a locked position that engages the rotational mechanism to initiate rotation.

Embodiment 106. A portable centrifuge for ocular disorder therapy comprising: a base, the base comprising a rotational mechanism; a sequester device, the sequester device being disposed onto the base, the sequester device comprises at least one concentric ring that forms a central container and a channel; and a centrifuge cover, the centrifuge cover including an opening that concentrically aligns with the central container of the sequester device, the centrifuge cover disposed over the sequester device to create a liquid impermeable seal.

Embodiment 107. The portable centrifuge of Embodiment 106, wherein the portable centrifuge further comprises at least one light.

Embodiment 108. The portable centrifuge of Embodiment 107, wherein the at least one light comprises a UV light.

Embodiment 109. The portable centrifuge of Embodiment 106, wherein at least a portion of the sequester device comprises a coating.

Embodiment 110. The portable centrifuge of Embodiment 106, wherein the portable centrifuge further comprises at least one UV light and at least a portion of the sequester device comprises a germicidal agent coating.

Embodiment 111. The portable centrifuge of Embodiment 108 or 110, wherein the UV light comprises a wavelength emission within the UV-C wavelength range for a germicidal effect.

Embodiment 112. The portable centrifuge of Embodiment 109, the coating is selected from a group consisting of anticoagulants, preservatives, germicidal agents, sterilants, antiseptics, clot activators, separator gels.

Embodiment 113. The portable centrifuge of Embodiment 110 or 112, wherein the germicidal agent comprises amotosalen or riboflavin.

Embodiment 114. The portable centrifuge of Embodiment 106, wherein the central container comprises a first volume and the channel comprises a second volume, the first volume is larger than the second volume.

Embodiment 115. The portable centrifuge of Embodiment 106, wherein the central container comprises a first volume and the at least one channel comprises a second volume, the first volume and the second volume equals the total volume of extracted blood from a patient, the second volume substantially matches a portion of the total volume determined by multiplying hematocrit with the total volume of extracted blood.

Embodiment 116. The portable centrifuge of Embodiment 106, wherein the central container and the opening is sized and configured to receive a filter or an eye dispensing mechanism.

Embodiment 117. The portable centrifuge of Embodiment 106, wherein the portable centrifuge further comprises a protective cover, the protective cover is disposed over the centrifuge cover and rotatable from an unlocked position, which the rotational mechanism is not engaged to a locked position that engages the rotational mechanism to initiate rotation.

Embodiment 118. The portable centrifuge for isolation of MNC's from peripheral blood comprises: a base, the base comprising a rotational mechanism; a sequester device, the sequester device being disposed onto the base, the sequester device comprises at least one channel, a first cylinder having a first inner diameter and a first outer diameter, and a second cylinder having a second inner diameter, the first inner diameter forms a central container, the first cylinder is disposed within the second inner diameter of the second cylinder, the first cylinder is concentric and tiered to the second cylinder, the at least one channel positioned between the first outer diameter of the first cylinder and the second inner diameter of the second cylinder; a centrifuge cover, the centrifuge cover including a port extending from a top surface of the centrifuge cover, the centrifuge cover disposed over the sequester device to create a liquid impermeable seal; and one or more reagents; the one or more reagents is disposed within the sequester device.

Embodiment 119. The portable centrifuge for isolation of MNC's from peripheral blood comprises: a base, the base comprising a rotational mechanism; a sequester device, the sequester device being disposed onto the base, the sequester device comprises at least one channel, a first ring including an inner diameter that forms a central container, a second ring, the first ring is disposed within the second ring, the first ring is separated from the second ring by the at least one channel, the second ring is concentric and tiered from the first ring; a centrifuge cover, the centrifuge cover including a luer port the centrifuge cover disposed over a portion of the sequester device to create a liquid impermeable seal; and one or more reagents; the one or more reagents is disposed within the sequester device.

Embodiment 120. The portable centrifuge of Embodiment 118 or 119, wherein the portable centrifuge further comprises a protective cover, the protective cover is disposed over the centrifuge cover.

Embodiment 121. The portable centrifuge of Embodiment 118 or 119, wherein the one or more reagents comprises a density gradient media.

Embodiment 122. The portable centrifuge of Embodiment 118 or 119, wherein the one or more reagents comprises a density gradient media and an anticoagulant.

Embodiment 123. The portable centrifuge of Embodiment 121 or 122, wherein density gradient media is disposed within the sequester device comprises being disposed into at least one channel of the sequester device.

Embodiment 124. The portable centrifuge of Embodiment 118 or 119, wherein the portable centrifuge further comprises at least one light.

Embodiment 125. The portable centrifuge of Embodiment 124, wherein the at least one light comprises a UV light.

Embodiment 126. The portable centrifuge of Embodiment 118 or 119, wherein at least a portion of the sequester device comprises a coating.

Embodiment 127. The portable centrifuge of Embodiment 125, wherein the UV light comprises a wavelength emission within the UV-C wavelength range for a germicidal effect.

Embodiment 128. The portable centrifuge of Embodiment 126, wherein the coating is selected from a group consisting of anticoagulants, preservatives, germicidal agents, sterilants, antiseptics, clot activators, separator gels.

Embodiment 129. The portable centrifuge of Embodiment 118 or 119, wherein the luer port is centrally located on a top surface of the centrifuge cover.

Embodiment 130. The portable centrifuge of Embodiment 118 or 119, wherein the centrifuge cover further comprises a at least one extraction region, the at least one extraction region includes at least one extraction hole.

Embodiment 131. The portable centrifuge of Embodiment 130, wherein the centrifuge cover further comprises a second extraction region, the second extraction region comprises at least one extraction hole, the second extraction region is diametrically opposite to the at least one extraction region or spaced 180 degrees apart.

Embodiment 132. The portable centrifuge of Embodiment 130 or 131, wherein the at least one extraction hole aligns with the at least one channel.

Embodiment 133. The portable centrifuge for isolation of MNC's from bone marrow comprises: a base, the base comprising a rotational mechanism; a sequester device, the sequester device being disposed onto the base, the sequester device comprises a first channel, a second channel, a first cylinder, a second cylinder and a third cylinder, the first cylinder having a first inner diameter and a first outer diameter, the first inner diameter forms a central container, the second cylinder having a second inner diameter and second outer diameter, and the third cylinder having a third inner diameter and third outer diameter, the second cylinder is disposed within the third inner diameter of the third cylinder, the second channel is positioned between the third inner diameter of the third cylinder and the second outer diameter of the second cylinder, the first cylinder is disposed within the second inner diameter of the second cylinder, the first channel is positioned between the second inner diameter of the second cylinder and the first outer diameter of the first cylinder, the first, second and third cylinder are concentric to each other and tiered; a centrifuge cover, the centrifuge cover including a luer port and at least one opening, the centrifuge cover disposed over the sequester device to create a liquid impermeable seal; and one or more blister modules, the one or more blister modules removably connected to the to the centrifuge cover, the one or more blister modules comprise a frangible base and a chamber, the chamber includes at least one reagent, the chamber is movable from a first position that is uncompressed and filled with the at least one reagent to a second position, which the chamber is compressed to break the frangible base allowing the at least one reagent to be in fluid communication with the at least one opening and dispense the at least one reagent into the sequester device.

Embodiment 134. The portable centrifuge for isolation of MNC's from bone marrow comprises: a base, the base comprising a rotational mechanism; a sequester device, the sequester device being disposed onto the base, the sequester device comprises a first channel, a second channel, a first ring, a second ring, and a third ring, the second ring is disposed within the third ring and separated by the second channel, the first ring is disposed within the second ring and separated by the first channel, the first ring including an inner diameter that forms a central container, the first, second and third ring are concentric and tiered; a centrifuge cover, the centrifuge cover including a luer port and at least one opening, the centrifuge cover disposed over a portion of the sequester device to create a liquid impermeable seal; and one or more blister modules, the one or more blister modules removably connected to the to the centrifuge cover, the one or more blister modules comprise a frangible base and a chamber, the chamber includes at least one reagent, the chamber is movable from a first position that is uncompressed and filled with the at least one reagent to a second position, which the chamber is compressed to break the frangible base allowing the at least one reagent to be in fluid communication with the at least one opening of the centrifuge cover and dispense the at least one reagent into the sequester device.

Embodiment 135. The portable centrifuge of Embodiment 133 or 134, wherein the portable centrifuge further comprises a protective cover, the protective cover is disposed over the centrifuge cover.

Embodiment 136. The portable centrifuge of Embodiment 133 or 134, wherein each of the one or more blister modules are adjacent to the luer port and positioned diametrically opposite and/or spaced 180 degrees apart.

Embodiment 137. The portable centrifuge of Embodiment 133 or 134, wherein the at least one reagent comprises at least one of a density gradient media, anticoagulant, thixotropic gel, buffer, dilution media, and/or any combination thereof.

Embodiment 138. The portable centrifuge of Embodiment 133 or 134, wherein the at least one reagent is dispensed into the sequester device comprises dispensing into the central container of the first ring of the sequester device.

Embodiment 139. The portable centrifuge of Embodiment 133 or 134, wherein the portable centrifuge further comprises at least one light.

Embodiment 140. The portable centrifuge of Embodiment 139, wherein the at least one light comprises a UV light.

Embodiment 141. The portable centrifuge of Embodiment 133 or 134, wherein at least a portion of the sequester device comprises a coating.

Embodiment 142. The portable centrifuge of Embodiment 140, wherein the UV light comprises a wavelength emission within the UV-C wavelength range for a germicidal effect.

Embodiment 143. The portable centrifuge of Embodiment 141, wherein the coating is selected from a group consisting of anticoagulants, preservatives, germicidal agents, sterilants, antiseptics, clot activators, separator gels.

Embodiment 144. The portable centrifuge of Embodiment 133 or 134, wherein the luer port is centrally located on the top surface of the centrifuge cover.

Embodiment 145. The portable centrifuge of Embodiment 133 or 134, wherein the centrifuge cover further comprises at least one extraction region, the at least one extraction region includes at least one extraction hole.

Embodiment 146. The portable centrifuge of Embodiment 145, wherein the centrifuge cover further comprises a second extraction region, the second extraction region comprises at least one extraction hole, the second extraction region is diametrically opposite to the at least one extraction region or spaced 180 degrees apart.

Embodiment 147. The portable centrifuge of Embodiment 145 or 146, wherein the at least one extraction hole aligns with the at least one channel.

Embodiment 148. The portable centrifuge for isolation of SVF from adipose tissue comprises: a base, the base comprising a rotational mechanism; a sequester device, the sequester device being disposed onto the base, the sequester device comprises a first channel, a second channel, a first ring, a second ring, and a third ring, the second ring is disposed within the third ring and separated by the second channel, the first ring is disposed within the second ring and separated by the first channel, the first ring including an inner diameter that forms a central container, the first, second and third ring are concentric and tiered; a centrifuge cover, the centrifuge cover including a luer port, the centrifuge cover disposed over a portion of the sequester device to create a liquid impermeable seal; and a disaggregation mechanism, the disaggregation mechanism includes a central member, the central member comprises a plurality of facets extending away from an external surface, each of the plurality of facets having a portion of sharp edges.

Embodiment 149. The portable centrifuge of Embodiment 148, wherein the disaggregation mechanism is stationary relative to the sequester device while the rotation mechanism is activated.

Embodiment 150. The portable centrifuge of Embodiment 148, wherein the portable centrifuge further comprises an incubator.

Embodiment 151. The portable centrifuge of Embodiment 148, wherein the portable centrifuge further comprises a one or more blister modules, the one or more blister modules removably connected to the to the centrifuge cover, the one or more blister modules comprise a frangible base and a chamber, the chamber includes at least one reagent, the chamber is movable from a first position that is uncompressed and filled with the at least one reagent to a second position, which the chamber is compressed to break the frangible base allowing the at least one reagent to be in fluid communication with an at least one opening disposed on the centrifuge cover and dispense the at least one reagent into the sequester device.

Embodiment 152. The portable centrifuge of Embodiment 148, wherein the portable centrifuge further comprises an agitation mechanism.

Embodiment 153. The portable centrifuge of Embodiment 148, wherein the portable centrifuge further comprises an incubator and an agitation mechanism.

Embodiment 154. The portable centrifuge of Embodiment 148, wherein the portable centrifuge further comprises an incubator, an agitation mechanism, and one or more blister modules.

Embodiment 155. The portable centrifuge of Embodiment 150, 153, or 154, wherein the incubator comprises a chemical or electrical incubator.

Embodiment 156. The portable centrifuge of Embodiment 152, 153 or 154, wherein the agitation mechanism comprises an oscillation or shaking action.

Embodiment 157. The portable centrifuge of Embodiment 154, wherein the one or more blister modules removably connected to the to the centrifuge cover, the one or more blister modules comprise a frangible base and a chamber, the chamber includes at least one reagent, the chamber is movable from a first position that is uncompressed and filled with the at least one reagent to a second position, which the chamber is compressed to break the frangible base allowing the at least one reagent to be in fluid communication with an at least one opening disposed on the centrifuge cover and dispense the at least one reagent into the sequester device.

Embodiment 158. The portable centrifuge of Embodiment 148, wherein the portable centrifuge further comprises a protective cover, the protective cover is disposed over the centrifuge cover.

Embodiment 159. The portable centrifuge of Embodiment 151 or 157, wherein each of the one or more blister modules are adjacent to the luer port and positioned diametrically opposite and/or spaced 180 degrees apart.

Embodiment 160. The portable centrifuge of Embodiment 151 or 157, wherein the at least one reagent comprises at least one of a density gradient media, anticoagulant, thixotropic gel, buffer, dilution media, and/or any combination thereof.

Embodiment 161. The portable centrifuge of Embodiment 151 or 157, wherein the at least one reagent is dispensed into the sequester device comprises dispensing into the central container of the first ring of the sequester device.

Embodiment 162. The portable centrifuge of Embodiment 148, wherein the portable centrifuge further comprises at least one light.

Embodiment 163. The portable centrifuge of Embodiment 162, wherein the at least one light comprises a UV light.

Embodiment 164. The portable centrifuge of Embodiment 148, wherein at least a portion of the sequester device comprises a coating.

Embodiment 165. The portable centrifuge of Embodiment 163, wherein the UV light comprises a wavelength emission within the UV-C wavelength range for a germicidal effect.

Embodiment 166. The portable centrifuge of Embodiment 164, wherein the coating is selected from a group consisting of anticoagulants, preservatives, germicidal agents, sterilants, antiseptics, clot activators, separator gels.

Embodiment 167. The portable centrifuge of Embodiment 148, wherein the luer port is centrally located on the top surface of the centrifuge cover.

Embodiment 168. The portable centrifuge of Embodiment 148, wherein the centrifuge cover further comprises a at least one extraction region, the at least one extraction region includes at least one extraction hole.

Embodiment 169. The portable centrifuge of Embodiment 168, wherein the centrifuge cover further comprises a second extraction region, the second extraction region comprises at least one extraction hole, the second extraction region is diametrically opposite to the at least one extraction region or spaced 180 degrees apart.

Embodiment 170. The portable centrifuge of Embodiment 168 or 169, wherein the at least one extraction hole aligns with the at least one channel.

Embodiment 171. The portable centrifuge of Embodiment 148, wherein at least one of the first ring, second ring and third ring comprise a filtration cylinder, the filtration cylinder including a mesh size, the mesh size is at least 70 micrometers.

Embodiment 172. The portable centrifuge of Embodiments 134 or 148, wherein at least the first cylinder/ring or second cylinder/ring comprises a filtration cylinder/ring, the filtration cylinder/ring including a mesh size, the mesh size is at least 70 micrometers.

We claim:

1. A portable centrifuge comprises:

a base, the base comprises a rotational mechanism and a longitudinal axis;

a sequester wheel, the sequester wheel disposed onto the base, the sequester wheel comprising a first ring, a second ring, a third ring, a first channel and a second channel, each of the first, second and third rings are concentric to each other, the first channel is disposed between a first ring and a second ring, the second channel is disposed between a second ring and a third ring, the first ring forms an inner container;

a heating mechanism;

one or more disaggregation elements, the one or more disaggregation elements comprises a plurality of sharp cutting teeth or a plurality of sharp cutting flutes; and a cover, the cover comprising an injection port, the cover disposed over the sequester wheel.

2. The portable centrifuge of claim 1, wherein the heating mechanism is disposed onto a portion of the base or a portion of the sequester wheel.

3. The portable centrifuge of claim 1, wherein the first ring or second ring comprises a filtration ring, the filtration ring includes a filtration mesh size of at least 40 micrometers or greater.

4. The portable centrifuge of claim 1, wherein the one or more disaggregation elements are disposed onto at least one surface of the first ring, second ring, or third ring.

5. The portable centrifuge of claim 1, wherein the cover further comprises at least one blister module, the at least one blister module comprises a chamber, a frangible base and at least one reagent, the chamber is movable from a first position that is uncompressed with the chamber filled with the at least one reagent to a second position that is compressed breaking the frangible base to dispense the at least one reagent into the sequester wheel.

6. The portable centrifuge of claim 5, wherein the at least one blister module is removably connected to the cover.

7. The portable centrifuge of claim 5, wherein the at least one reagent comprises an anticoagulant, a density gradient media, or a separation gel.

8. The portable centrifuge of claim 1, wherein the portable centrifuge further comprises a filtration mechanism, the filtration mechanism coupled to the injection port of the cover, the filtration mechanism includes a filtration mesh size of at least 40 micrometer or greater.

9. The portable centrifuge of claim 1, wherein the heating mechanism comprises an electrical heater or a chemical heater.

10. The portable centrifuge of claim 1, wherein at least a portion of the sequester wheel comprises a reagent, the reagent includes an anticoagulant, a separation gel or a density gradient media.

11. The portable centrifuge of claim 1, wherein the portable centrifuge further comprises at least one light, the at least one light comprises a UV light or an LED light.

12. The portable centrifuge of claim 1, wherein the sequester wheel comprises a clear or translucent material.

13. The portable centrifuge of claim 1, wherein the portable centrifuge further comprises a second cover, the second cover is disposed over the cover.

14. The portable centrifuge of claim 1, wherein the one or more disaggregation elements rotates relative to the sequester wheel.

15. A portable centrifuge comprises:

a base, the base comprises a rotational mechanism and a longitudinal axis;

a sequester wheel, the sequester wheel disposed onto the base, the sequester wheel comprising a first ring, a second ring, a third ring, a first channel and a second channel, each of the first, second and third rings are concentric to each other, the first channel is disposed between a first ring and a second ring, the second channel is disposed between a second ring and a third ring, the first ring forms an inner container, at least a portion of the sequester wheel comprises a reagent, the reagent includes an anticoagulant, a separation gel or a density gradient media;

a heating mechanism;

one or more disaggregation elements; and a cover, the cover comprising an injection port, the cover disposed over a portion of the sequester wheel.

16. The portable centrifuge of claim 15, wherein the heating mechanism comprises an electrical heater or a chemical heater.

17. The portable centrifuge of claim 15, wherein the reagent is pre-laced into a portion of the sequester wheel.

18. A portable centrifuge comprises:

a base, the base comprises a rotational mechanism and a longitudinal axis;

a sequester wheel, the sequester wheel disposed onto the base, the sequester wheel comprising a first ring, a second ring, a third ring, a first channel and a second channel, each of the first, second and third rings are concentric to each other, the first channel is disposed between a first ring and a second ring, the second channel is disposed between a second ring and a third ring, the first ring forms an inner container;

a heating mechanism;

one or more disaggregation elements, the one or more disaggregation elements are disposed into the inner container; and a cover, the cover comprising an injection port, the cover disposed over a portion of the sequester wheel.

19. The portable centrifuge of claim 18, wherein the one or more disaggregation elements rotates relative to the sequester wheel.

20. The portable centrifuge of claim 18, wherein the one or more disagreggation elements comprises sharp cutting teeth or sharp cutting flutes.

* * * * *